(12) United States Patent
Satoh et al.

(10) Patent No.: US 7,872,004 B2
(45) Date of Patent: Jan. 18, 2011

(54) 6-(HETEROCYCLYL-SUBSTITUTED BENZYL)-4-OXOQUINOLINE COMPOUND AND USE THEREOF AS HIV INTEGRASE INHIBITOR

(75) Inventors: Motohide Satoh, Takatsuki (JP); Hisateru Aramaki, Takatsuki (JP); Masaki Yamashita, Takatsuki (JP); Masafumi Inoue, Takatsuki (JP); Hiroshi Kawakami, Takatsuki (JP); Hisashi Shinkai, Takatsuki (JP); Hiroshi Nakamura, Takatsuki (JP); Yuji Matsuzaki, Takatsuki (JP); Shuichi Wamaki, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 376 days.

(21) Appl. No.: 11/767,021

(22) Filed: Jun. 22, 2007

(65) Prior Publication Data

US 2008/0207618 A1 Aug. 28, 2008

Related U.S. Application Data

(60) Provisional application No. 60/819,585, filed on Jul. 10, 2006, provisional application No. 60/840,651, filed on Aug. 28, 2006, provisional application No. 60/853,967, filed on Oct. 24, 2006.

(30) Foreign Application Priority Data

| Jun. 23, 2006 | (JP) | ................... 2006-174331 |
| Aug. 11, 2006 | (JP) | ................... 2006-220082 |
| Oct. 5, 2006 | (JP) | ................... 2006-274143 |

(51) Int. Cl.
| A61K 31/5377 | (2006.01) |
| A61K 31/4709 | (2006.01) |
| C07D 413/02 | (2006.01) |
| C07D 215/00 | (2006.01) |

(52) U.S. Cl. ................... 514/235.2; 514/312; 514/314; 544/151; 546/153

(58) Field of Classification Search ................ 544/151; 546/153; 514/235.2, 312, 314
See application file for complete search history.

(56) References Cited

U.S. PATENT DOCUMENTS

| 7,482,454 B2 | 1/2009 | Ledoussal et al. |
| 2005/0239819 A1 | 10/2005 | Satoh et al. |
| 2006/0019906 A1 | 1/2006 | Satoh et al. |
| 2006/0084665 A1 | 4/2006 | Satoh et al. |

FOREIGN PATENT DOCUMENTS

| CA | 2637204 | 8/2007 |
| WO | WO 99/14214 | 3/1999 |
| WO | WO 2004/046115 A1 | 6/2004 |
| WO | WO 2005/087759 A1 | 9/2005 |
| WO | WO 2005/113509 A1 | 12/2005 |
| WO | WO 2006/033422 A1 | 3/2006 |
| WO | WO 2007/090579 | 8/2007 |

OTHER PUBLICATIONS

Morissette et al. Advanced Drug Delivery Reviews 2004, 56, 275-300.*
Vippagunta, Sudha R. "Crystalline Solids." Advanced Drug Delivery Reviews 48(2001): 3-26.*
Written Opinion of the International Search Authority for PCT/JP2007/062579 dated Feb. 3, 2009.
De Clercq, Erik, "New Developments in Anti-HIV Chemotherapy," Biochimica at Biophysica Acta 1587 (2002) 258-275.
Vincent, K.A., et al., "Characterization of Human Immunodefieicny Virus Type I integrase Expressed in *Eschericia coli* and Analysis of Variants with Amino-Terminal Mutations," J. Virol. (1993) 67:425-437.

* cited by examiner

*Primary Examiner*—Kamal A Saeed
*Assistant Examiner*—Samantha L Shterengarts
(74) *Attorney, Agent, or Firm*—Finnegan, Henderson, Farabow, Garrett & Dunner, LLP

(57) ABSTRACT

The present invention relates to a compound represented by the following formula [I]

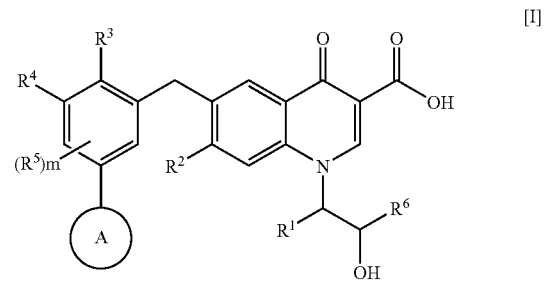

wherein each symbol is as defined in the specification, or a pharmaceutically acceptable salt thereof, or a solvate thereof, and a pharmaceutical composition, an anti-HIV agent and an HIV integrase inhibitor containing such compound. The compound of the present invention has an HIV integrase inhibitory activity, and is useful as an anti-HIV agent, or as an agent for the prophylaxis or treatment of AIDS. In addition, by the combined use with other anti-HIV agents such as a protease inhibitor, a reverse transcriptase inhibitor and the like, it can be a more effective anti-HIV agent. Because it shows integrase-specific high inhibitory activity, the compound can be a pharmaceutical agent safe on human body, which causes only a fewer side effects.

28 Claims, No Drawings

6-(HETEROCYCLYL-SUBSTITUTED BENZYL)-4-OXOQUINOLINE COMPOUND AND USE THEREOF AS HIV INTEGRASE INHIBITOR

This application claims the benefit of JP2006-174331, filed Jun. 23, 2006, and claims the benefit of JP 2006-220082, filed Aug. 11, 2006, and claims the benefit of JP 2006-274143, filed Oct. 5, 2006, and claims the benefit of U.S. Provisional Application No. 60/819,585, filed Jul. 10, 2006, and claims the benefit of U.S. Provisional Application No. 60/840,651, filed Aug. 28, 2006, and claims the benefit of U.S. Provisional Application No. 60/853,967, filed Oct. 24, 2006.

TECHNICAL FIELD

The present invention relates to a novel 4-oxoquinoline compound, or a pharmaceutically acceptable salt thereof, or a solvate thereof, which is useful as an anti-HIV agent. In addition, the present invention relates to a pharmaceutical composition comprising the 4-oxoquinoline compound or a pharmaceutically acceptable salt thereof, or a solvate thereof and a pharmaceutically acceptable carrier; an anti-HIV agent, an HIV integrase inhibitor and the like, which comprise the 4-oxoquinoline compound or a pharmaceutically acceptable salt thereof, or a solvate thereof as an active ingredient; an anti-HIV agent comprising the 4-oxoquinoline compound or a pharmaceutically acceptable salt thereof, or a solvate thereof, in combination with one or more other kinds of anti-HIV active substances; and the like.

BACKGROUND ART

HIV (Human Immunodeficiency Virus (type 1)) belonging to retrovirus is a causative virus of AIDS (Acquired Immunodeficiency Syndrome).

HIV targets CD4 positive cell groups such as helper T cell, macrophage and dendritic cell and destroys these immunocompetent cells to cause immunodeficiency.

Accordingly, a pharmaceutical agent that eradicates HIV in a living organism or suppresses its growth is effective for the prophylaxis or treatment of AIDS.

HIV possesses a bimolecular RNA gene in a shell, which is covered with an envelope protein. The RNA codes for several enzymes (protease, reverse transcriptase, integrase) characteristic of the virus and the like. Translated reverse transcriptase and integrase are present in the shell, and protease is present inside and outside the shell.

HIV contacts and invades a host cell, causes uncoating, and releases a complex of RNA and integrase and the like into the cytoplasm. From the RNA, DNA is transcribed by reverse transcriptase, and a full length double stranded DNA is produced. The DNA moves into the nucleus of the host cell and is incorporated by integrase into the DNA of the host cell. The incorporated DNA is converted to an mRNA by polymerase of the host cell, from which mRNA various proteins necessary for forming a virus are synthesized by HIV protease and the like, and a virus particle is finally formed, which then undergoes budding and its release.

These virus specific enzymes are considered to be essential for the growth of HIV. These enzymes are drawing attention as the target of the development of antiviral agents, and several anti-HIV agents have been already developed.

For example, zidovudine, didanosine, lamivudine and the like have been already on the market as reverse transcriptase inhibitors, and indinavir, nelfinavir and the like as protease inhibitors.

In addition, a multiple drug combination therapy (also often called HAART (highly active antiretroviral therapy)) concurrently using these pharmaceutical agents has been employed. For example, a combined use of three agents of "two reverse transcriptase inhibitors (zidovudine and lamivudine, or tenofovir and emtricitabine)", and "a nonnucleoside transcriptase inhibitor (efavirenz)" or "a protease inhibitor (lopinavir, fosamprenavir or atazanavir) combined with ritonavir" have been clinically applied. Such multiple drug combination therapy is becoming a mainstream of AIDS therapy.

However, some of these pharmaceutical agents are known to cause side effects such as liver function failure, central nervous disorders (e.g., vertigo), and the like. In addition, acquisition of resistance to a pharmaceutical agent causes a problem. Even worse, emergence of an HIV that shows multiple drug resistance in a multiple drug combination therapy has been known.

Under the circumstances, a further development of a novel pharmaceutical agent, particularly a development of an anti-HIV agent based on a new mechanism, has been desired, wherein a development of an anti-HIV agent having an integrase inhibitory activity is expected, because an integrase characteristic of retrovirus is an essential enzyme for the growth of HIV.

Nevertheless, an effective integrase inhibitor has not been found as yet.

The compounds having an integrase inhibitory activity are described in the following.

WO2004/046115 (patent family: US2005/239819) describes the following compound [A] and the like, as an anti-HIV agent having an integrase inhibitory activity (see patent document 1).

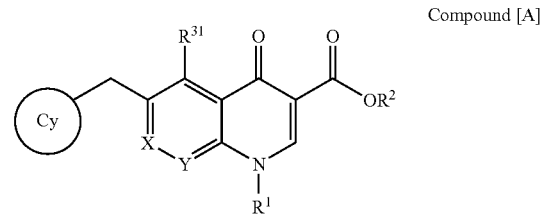

Compound [A]

wherein ring Cy is an optionally substituted $C_{3-10}$ hydrocarbon group or an optionally substituted heterocyclic group; $R^1$ is an optionally substituted $C_{1-10}$ alkyl group, an optionally substituted $C_{3-10}$ carbon ring group or the like; $R^2$ is a hydrogen atom or the like; $R^{31}$ is a hydrogen atom or the like; X is C—$R^{32}$ or a nitrogen atom; and Y is C—$R^{33}$ or a nitrogen atom (wherein $R^{32}$ and $R^{33}$ are independently a hydrogen atom or the like).

WO2004/046115 also describes the following compound [B] and the like, as an anti-HIV agent having an integrase inhibitory activity.

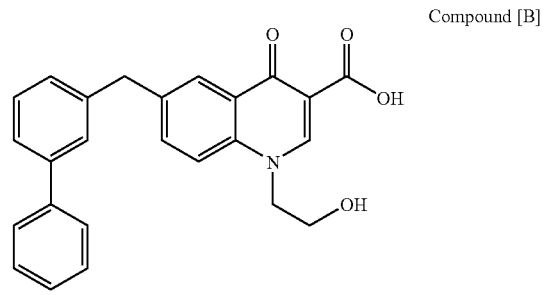

Compound [B]

WO2005/087759 describes the following compound [C] and the like, as an anti-HIV agent having a retroviral integrase inhibitory activity (see patent document 2).

Compound [C]

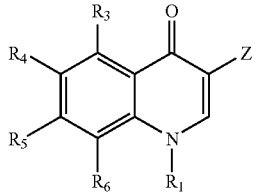

wherein $R_1$ is H, $C_{1-6}$ alkyl or substituted $C_{1-6}$ alkyl; Z is —C(O)OR$_2$ or —C(O)CH$_2$C(O)X; X is a 5 or 6-membered aromatic or heteroaromatic ring or —C(O)OR$_2$; $R_2$ is H or $C_{1-6}$ alkyl; $R_3$, $R_4$, $R_5$ and $R_6$ are each H, halogen, $C_{1-6}$ alkyloxy, —N(R$_8$)(R$_9$), —C(O)CH$_3$, —C(O)CH$_2$C(O)X, —S(O)$_n$—R$_{10}$ wherein n is 0, 1 or 2, heteroalkyl, cycloalkyl, substituted cycloalkyl, heterocycloalkyl, substituted heterocycloalkyl, aryl, substituted aryl, heteroaryl or substituted heteroary; $R_8$ and $R_9$ are each H or $C_{1-2}$ alkyl; and $R_{10}$ is $C_{1-6}$ alkyl or the like, provided that if Z is —C(O)OR$_2$ then at least one of $R_3$, $R_4$, $R_5$ and $R_6$ is —C(O)CH$_2$C(O)X.

In addition, WO2005/113509 (patent family: US2006/019906) describes the following compound [D] and the like, as an anti-HIV agent having an integrase inhibitory activity (see patent document 3).

Compound [D]

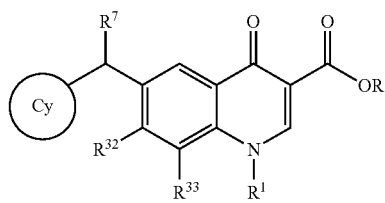

wherein ring Cy is a group selected from the group consisting of

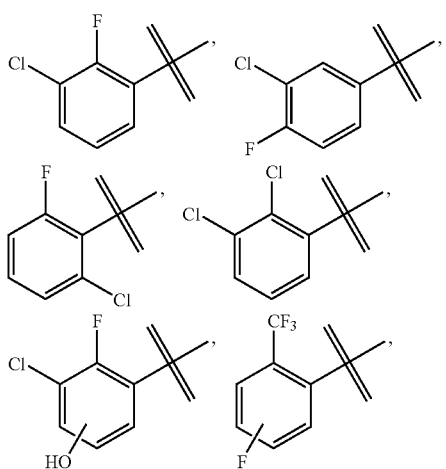

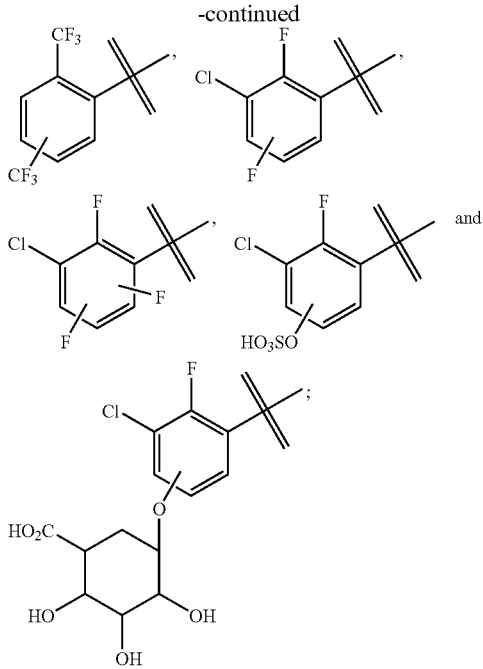

R is a hydrogen atom or the like; $R^1$ is

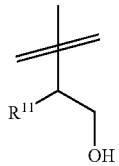

wherein $R^{11}$ is —(C$_m$H$_{2m}$)—OR$^{12}$, —(C$_m$H$_{2m}$)—SR$^{12}$, —(C$_m$H$_{2m}$)—SO$_2$R$^{12}$ (wherein R$^{12}$ is a $C_{1-4}$ alkyl group and m is an integer of 1 to 4), a saturated heterocyclic group, an isopropyl group or a tert-butyl group or the like; $R^{32}$ is a hydrogen atom, an ethyl group, a methoxy group or the like; $R^{33}$ is a hydrogen atom or the like; and $R^7$ is a hydrogen atom or a hydroxyl group.

However, these publications do not disclose a compound having a benzyl group substituted by a heterocyclic group at the 6-position of 4-oxoquinoline ring, or even a description suggestive thereof.

In addition, WO2006/033422 (patent family: US2006/084665) describes the following compound [E] and the like, as an anti-HIV agent having an integrase inhibitory activity (see patent document 4).

Compound [E]

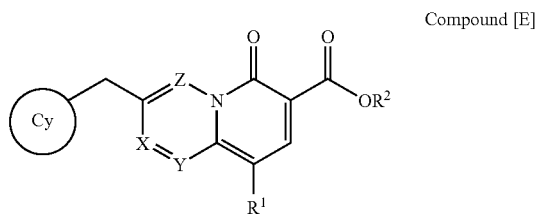

wherein ring Cy is an optionally substituted $C_{3-10}$ carbon ring group or an optionally substituted heterocyclic group; $R^1$ is a hydrogen atom, an optionally substituted $C_{1-10}$ alkyl group or the like; $R^2$ is a hydrogen atom or the like; Z is C—$R^{31}$ or a nitrogen atom wherein $R^{31}$ is a hydrogen atom or the like; X is C—$R^{32}$ or a nitrogen atom; and Y is C—$R^{33}$ or a nitrogen atom wherein $R^{32}$ and $R^{33}$ are each a hydrogen atom or the like.

However, this publication does not include the 4-oxoquinoline compound disclosed in this specification, or even a description suggestive thereof.

patent document 1: WO2004/046115 (page 133, Example 1-88)
patent document 2: WO2005/087759
patent document 3: WO2005/113509
patent document 4: WO2006/033422

DISCLOSURE OF THE INVENTION

From the findings obtained from pharmacological studies and clinical results heretofore, an anti-HIV agent is effective for the prophylaxis or treatment of AIDS, and particularly a compound having an integrase inhibitory activity can be an effective anti-HIV agent.

Therefore, the present invention aims at provision of a compound having an anti-HIV activity, particularly a compound having an integrase inhibitory activity.

The present inventors have conducted intensive studies in an attempt to find a compound having an anti-HIV activity, particularly a compound having an integrase inhibitory activity, and completed the present invention.

That is, the present invention relates to a compound represented by the following formula [I] having an integrase inhibitory activity (sometimes to be abbreviated as compound [I] in the present specification), a pharmaceutically acceptable salt thereof, a solvate thereof and use thereof.

[1] A compound represented by the following formula [I] or a pharmaceutically acceptable salt thereof, or a solvate thereof:

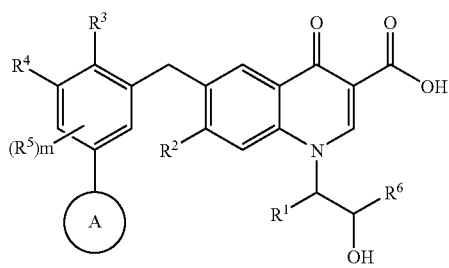

[I]

wherein
ring A is a monocyclic heterocyclic group optionally substituted by 1 to 5 substituents selected from the following group A, wherein the monocyclic heterocyclic group contains, besides carbon atom, at least one hetero atom selected from nitrogen atom, oxygen atom and sulfur atom;
group A is a group consisting of halogen atom, $C_{1-4}$ alkyl group, —$(CH_2)_n$—$OR^{a1}$, —$NR^{a3}R^{a4}$, —$COR^{a2}$ and —$CONR^{a3}R^{a4}$, wherein $R^{a1}$, $R^{a2}$, $R^{a3}$ and $R^{a4}$ are the same or different and each is a hydrogen atom or a $C_{1-4}$ alkyl group, and n is 0 or an integer of 1 to 4;

$R^1$ is a hydrogen atom,
a $C_{1-6}$ alkyl group optionally substituted by 1 to 3 substituents selected from the following group B,
a $C_{3-10}$ carbon ring group optionally substituted by 1 to 5 substituents selected from the above-mentioned group A, or
a heterocyclic group optionally substituted by 1 to 5 substituents selected from the above-mentioned group A,
wherein the heterocyclic group contains, besides carbon atom, at least one hetero atom selected from nitrogen atom, oxygen atom and sulfur atom;
group B is a group consisting of
a $C_{3-10}$ carbon ring group optionally substituted by 1 to 5 substituents selected from the above-mentioned group A,
a heterocyclic group optionally substituted by 1 to 5 substituents selected from the above-mentioned group A,
wherein the heterocyclic group is as defined above,
a halogen atom, cyano group,
—$OR^{b1}$, —$SR^{b1}$, —$NR^{b2}R^{b3}$,
—$CONR^{b2}R^{b3}$, —$SO_2NR^{b2}R^{b3}$, —$COR^{b1}$,
—$NR^{b2}COR^{b1}$, —$SO_2R^{b1}$, —$NR^{b2}SO_2R^{b1}$,
—$COOR^{b1}$, —$NR^{b2}COOR^{b1}$ and —$NR^{b4}CO$—$NR^{2b}R^{b3}$
wherein $R^{b1}$, $R^{b2}$, $R^{b3}$ and $R^{b4}$ are the same or different and each is a hydrogen atom, a $C_{1-4}$ alkyl group, a $C_{3-10}$ carbon ring group optionally substituted by 1 to 5 substituents selected from the above-mentioned group A, or a heterocyclic group optionally substituted by 1 to 5 substituents selected from the above-mentioned group A, wherein the heterocyclic group is as defined above;
$R^2$ is a hydrogen atom, a $C_{1-4}$ alkyl group or —$OR^{11}$, wherein $R^{11}$ is a hydrogen atom or a $C_{1-4}$ alkyl group;
$R^3$ and $R^4$ are the same or different and each is a hydrogen atom, a halogen atom, a $C_{1-4}$ alkyl group or —$OR^{12}$, wherein $R^{12}$ is a hydrogen atom or a $C_{1-4}$ alkyl group;
$R^5$ is each independently, a halogen atom, a $C_{1-4}$ alkyl group or —$OR^{13}$, wherein $R^{13}$ is a hydrogen atom or a $C_{1-4}$ alkyl group;
m is 0, 1 or 2; and
$R^6$ is a hydrogen atom, or $R^1$ and $R^6$ form, together with the carbon atoms bonded thereto, a $C_{3-10}$ cycloalkyl group optionally substituted by 1 to 5 substituents selected from the above-mentioned group A.

[2] The compound of the above-mentioned [1], wherein ring A is a monocyclic heterocyclic group containing at least one nitrogen atom, said monocyclic heterocyclic group is optionally substituted by 1 to 5 substituents selected from group A and bonded, via the nitrogen atom, to the benzene ring, or a pharmaceutically acceptable salt thereof, or a solvate thereof.

[3] The compound of the above-mentioned [2], wherein ring A is a heterocyclic group selected from 1-pyrrolidinyl group, 2-oxopyrrolidin-1-yl group, piperidino group, 2-oxopiperidin-1-yl group, 1-piperazinyl group, morpholino group, thiomorpholino group, 3-oxomorpholin-4-yl group, 1,1-dioxoisothiazolidin-2-yl group, 2-oxooxazolidin-3-yl group and 3-oxopyrazolidin-1-yl group, wherein the heterocyclic group is optionally substituted by 1 to 5 substituents selected from group A, or a pharmaceutically acceptable salt thereof, or a solvate thereof.

[4] The compound of the above-mentioned [3], wherein $R^1$ is a $C_{1-6}$ alkyl group optionally substituted by 1 to 3 substituents selected from group B, and $R^6$ is a hydrogen atom, or a pharmaceutically acceptable salt thereof, or a solvate thereof.

[5] The compound of the above-mentioned [1], wherein $R^2$ is a $C_{1-4}$ alkyl group or —$OR^{11}$, wherein $R^{11}$ is a hydrogen atom or a $C_{1-4}$ alkyl group, or a pharmaceutically acceptable salt thereof, or a solvate thereof.

[6] The compound of the above-mentioned [1], wherein $R^2$ is a hydrogen atom, or a pharmaceutically acceptable salt thereof, or a solvate thereof.

[7] The compound of the above-mentioned [1], wherein $R^3$ and $R^4$ are the same or different and each is a halogen atom, or a pharmaceutically acceptable salt thereof, or a solvate thereof.

[8] The compound of the above-mentioned [1], wherein m is 1, and $R^5$ is a halogen atom, or a pharmaceutically acceptable salt thereof, or a solvate thereof.

[9] The compound of the above-mentioned [1], wherein m is 0, or a pharmaceutically acceptable salt thereof, or a solvate hereof.

[10] The compound of the above-mentioned [1], which is selected from a group consisting of 6-[3-chloro-2-fluoro-5-(morpholin-4-yl)benzyl]-1-((R)-1-ethoxymethyl-2-hydroxyethyl)-7-ethyl-4-oxo-1,4-dihydroquinoline-3-carboxylic acid (Example 1), 6-[3-chloro-2-fluoro-5-(2-oxopyrrolidin-1-yl)benzyl]-1-((S)-1-hydroxymethyl-2-methylpropyl)-7-methoxy-4-oxo-1,4-dihydroquinoline-3-carboxylic acid (Example 2), 6-[3-chloro-2-fluoro-5-(pyrrolidin-1-yl)benzyl]-1-((S)-1-hydroxymethyl-2-methylpropyl)-7-methoxy-4-oxo-1,4-dihydroquinoline-3-carboxylic acid (Example 3), 6-[3-chloro-2-fluoro-5-(2-oxooxazolidin-3-yl)benzyl]-1-((S)-1-hydroxymethyl-2-methylpropyl)-7-methoxy-4-oxo-1,4-dihydroquinoline-3-carboxylic acid (Example 4), 6-[3-chloro-2-fluoro-5-(morpholin-4-yl)benzyl]-1-((S)-1-hydroxymethyl-2-methylpropyl)-7-methoxy-4-oxo-1,4-dihydroquinoline-3-carboxylic acid (Example 5), 6-[3-chloro-2-fluoro-5-(piperidin-1-yl)benzyl]-1-((S)-1-hydroxymethyl-2-methylpropyl)-7-methoxy-4-oxo-1,4-dihydroquinoline-3-carboxylic acid (Example 6), 6-[3-chloro-2-fluoro-5-(2-oxopiperidin-1-yl)benzyl]-1-((S)-1-hydroxymethyl-2-methylpropyl)-7-methoxy-4-oxo-1,4-dihydroquinoline-3-carboxylic acid (Example 7), 6-[3-chloro-2-fluoro-5-((R)-3-hydroxypyrrolidin-1-yl)benzyl]-1-((S)-1-hydroxymethyl-2-methylpropyl)-7-methoxy-4-oxo-1,4-dihydroquinoline-3-carboxylic acid (Example 8), 6-[3-chloro-2-fluoro-5-((S)-3-hydroxypyrrolidin-1-yl)benzyl]-1-((S)-1-hydroxymethyl-2-methylpropyl)-7-methoxy-4-oxo-1,4-dihydroquinoline-3-carboxylic acid (Example 9), 6-[3-chloro-2-fluoro-5-(2-methyl-3-oxopyrazolidin-1-yl)benzyl]-1-((S)-1-hydroxymethyl-2-methylpropyl)-7-methoxy-4-oxo-1,4-dihydroquinoline-3-carboxylic acid (Example 10), 6-[5-(4-acetylpiperazin-1-yl)-3-chloro-2-fluorobenzyl]-1-((S)-1-hydroxymethyl-2-methylpropyl)-7-methoxy-4-oxo-1,4-dihydroquinoline-3-carboxylic acid (Example 11), 6-[3-chloro-5-(3,3-difluoropyrrolidin-1-yl)-2-fluorobenzyl]-1-((S)-1-hydroxymethyl-2-methylpropyl)-7-methoxy-4-oxo-1,4-dihydroquinoline-3-carboxylic acid (Example 12), 6-[3-chloro-2-fluoro-5-((R)-3-fluoropyrrolidin-1-yl)benzyl]-1-((S)-1-hydroxymethyl-2-methylpropyl)-7-methoxy-4-oxo-1,4-dihydroquinoline-3-carboxylic acid (Example 13), 6-[3-chloro-2-fluoro-5-((S)-3-fluoropyrrolidin-1-yl)benzyl]-1-((S)-1-hydroxymethyl-2-methylpropyl)-7-methoxy-4-oxo-1,4-dihydroquinoline-3-carboxylic acid (Example 14), 6-[3-chloro-2-fluoro-5-(morpholin-4-yl)benzyl]-1-((1R,2R)-1-hydroxymethyl-2-methoxypropyl)-7-methoxy-4-oxo-1,4-dihydroquinoline-3-carboxylic acid (Example 15), 6-[3-chloro-2,4-difluoro-5-(morpholin-4-yl)benzyl]-1-((S)-1-hydroxymethyl-2-methylpropyl)-7-methoxy-4-oxo-1,4-dihydroquinoline-3-carboxylic acid (Example 16), 6-[3-chloro-2-fluoro-5-(morpholin-4-yl)benzyl]-1-((S)-1-hydroxymethyl-2,2-dimethylpropyl)-7-methoxy-4-oxo-1,4-dihydroquinoline-3-carboxylic acid (Example 17), 6-[3-chloro-2-fluoro-5-(morpholin-4-yl)benzyl]-7-ethyl-1-((S)-1-hydroxymethyl-2,2-dimethylpropyl)-4-oxo-1,4-dihydroquinoline-3-carboxylic acid (Example 18), 6-[3-chloro-2-fluoro-5-(morpholin-4-yl)benzyl]-1-((R)-1-ethoxymethyl-2-hydroxyethyl)-7-methoxy-4-oxo-1,4-dihydroquinoline-3-carboxylic acid (Example 19), 6-[3-chloro-2-fluoro-5-(morpholin-4-yl)benzyl]-7-ethyl-1-[(R)-2-hydroxy-1-(methoxymethyl)ethyl]-4-oxo-1,4-dihydroquinoline-3-carboxylic acid (Example 20), 6-[3-chloro-5-(1,1-dioxoisothiazolidin-2-yl)-2-fluorobenzyl]-1-((S)-1-hydroxymethyl-2-methylpropyl)-7-methoxy-4-oxo-1,4-dihydroquinoline-3-carboxylic acid (Example 21), 6-[3-chloro-2-fluoro-5-(morpholin-4-yl)benzyl]-1-[(R)-2-hydroxy-1-(methoxymethyl)ethyl]-7-methoxy-4-oxo-1,4-dihydroquinoline-3-carboxylic acid (Example 22), 6-[3-chloro-2-fluoro-5-(morpholin-4-yl)benzyl]-7-ethyl-1-((S)-1-hydroxymethyl-2-methylpropyl)-4-oxo-1,4-dihydroquinoline-3-carboxylic acid (Example 23), 6-[3-chloro-2-fluoro-5-(2-oxopyrrolidin-1-yl)benzyl]-7-ethyl-1-((S)-1-hydroxymethyl-2-methylpropyl)-4-oxo-1,4-dihydroquinoline-3-carboxylic acid (Example 24), 6-[3-chloro-2,4-difluoro-5-(2-oxopyrrolidin-1-yl)benzyl]-1-((S)-1-hydroxymethyl-2-methylpropyl)-7-methoxy-4-oxo-1,4-dihydroquinoline-3-carboxylic acid (Example 25), 6-[3-chloro-2,4-difluoro-5-(2-oxopyrrolidin-1-yl)benzyl]-7-ethyl-1-((S)-1-hydroxymethyl-2-methylpropyl)-4-oxo-1,4-dihydroquinoline-3-carboxylic acid (Example 26), 6-[3-chloro-2-fluoro-5-(thiomorpholin-4-yl)benzyl]-1-((S)-1-hydroxymethyl-2-methylpropyl)-7-methoxy-4-oxo-1,4-dihydroquinoline-3-carboxylic acid (Example 27), 6-[3-chloro-2-fluoro-5-(morpholin-4-yl)benzyl]-1-((1R,2S)-1-hydroxymethyl-2-methoxypropyl)-7-methoxy-4-oxo-1,4-dihydroquinoline-3-carboxylic acid (Example 28), 6-[3-chloro-2-fluoro-5-(morpholin-4-yl)benzyl]-1-((S)-1-hydroxymethyl-3-methoxypropyl)-7-methoxy-4-oxo-1,4-dihydroquinoline-3-carboxylic acid (Example 29), 6-[3-chloro-2-fluoro-5-(4-hydroxypiperidin-1-yl)benzyl]-1-((S)-1-hydroxymethyl-2-methylpropyl)-7-methoxy-4-oxo-1,4-dihydroquinoline-3-carboxylic acid (Example 32), 6-[3-chloro-2-fluoro-5-(morpholin-4-yl)benzyl]-7-ethyl-1-((1R,2R)-1-hydroxymethyl-2-methoxypropyl)-4-oxo-1,4-dihydroquinoline-3-carboxylic acid (Example 34), 6-[3-chloro-2-fluoro-5-(morpholin-4-yl)benzyl]-7-ethyl-1-((1R,2S)-1-hydroxymethyl-2-methoxypropyl)-4-oxo-1,4-dihydroquinoline-3-carboxylic acid (Example 35), 6-[3-chloro-2-fluoro-5-(pyridin-2-yl)benzyl]-1-((S)-1-hydroxymethyl-2-methylpropyl)-7-methoxy-4-oxo-1,4-dihydroquinoline-3-carboxylic acid (Example 36), 6-[3-chloro-2-fluoro-5-(thiazol-2-yl)benzyl]-1-((S)-1-hydroxymethyl-2-methylpropyl)-7-methoxy-4-oxo-1,4-dihydroquinoline-3-carboxylic acid (Example 37), 6-[3-chloro-2-fluoro-5-(morpholin-4-yl)benzyl]-1-[(1R,2R)-2-ethoxy-1-(hydroxymethyl)propyl]-7-ethyl-4-oxo-1,4-dihydroquinoline-3-carboxylic acid (Example 38), 6-[3-chloro-2-fluoro-5-(2-oxopyrrolidin-1-yl)benzyl]-1-((R)-1-ethoxymethyl-2-hydroxyethyl)-7-methoxy-4-oxo-1,4-dihydroquinoline-3-carboxylic acid (Example 39), 6-[3-chloro-2-fluoro-5-(2-oxopyrrolidin-1-yl)benzyl]-1-[(1R,2R)-2-ethoxy-1-(hydroxymethyl)propyl]-7-ethyl-4-oxo-1,4-dihydroquinoline-3-carboxylic acid (Example 40), 6-[3-chloro-2-fluoro-5-(2-oxopyrrolidin-1-yl)benzyl]-7-ethyl-1-((1R,2R)-1-hydroxymethyl-2-methoxypropyl)-4-oxo-1,4-dihydroquinoline-3-carboxylic acid (Example 41), 6-[3-chloro-2-fluoro-5-(morpholin-4-yl)benzyl]-1-((R)-1-hydroxymethyl-2-methoxy-2-methylpropyl)-7-methoxy-4-oxo-1,4-dihydroquinoline-3-carboxylic acid (Example 42), 6-[3-chloro-2-fluoro-5-(morpholin-4-yl)benzyl]-7-ethyl-1-((R)-1-hydroxymethyl-2-methoxy-2-methylpropyl)-4-oxo-1,4-dihydroquinoline-3-carboxylic acid (Example 43), 6-[3-chloro-2-fluoro-5-(morpholin-4-yl)benzyl]-7-ethyl-1-((S)-1-hydroxymethyl-3-methoxypropyl)-4-oxo-1,4-dihydroquinoline-3-carboxylic acid (Example 44), 6-[3-chloro-2-fluoro-5-(2-oxopyrrolidin-1-yl)benzyl]-1-((S)-1-hydroxymethyl-2,2-dimethylpropyl)-7-methoxy-4-oxo-1,4-dihydroquinoline-3-carboxylic acid (Example 45), 6-[3-chloro-2,4-difluoro-5-(2-oxopyrrolidin-1-yl)benzyl]-1-((S)-1-hydroxymethyl-2,2-dimethylpropyl)-7-methoxy-4-oxo-1,4-dihydroquinoline-3-carboxylic acid (Example 46), 6-[3-chloro-2-fluoro-5-(2-oxopyrrolidin-1-yl)benzyl]-1-((S)-1-hydroxymethyl-3-methoxypropyl)-7-methoxy-4-oxo-1,4-dihydroquinoline-3-carboxylic acid (Example 47), 6-[3-chloro-2-fluoro-5-(2-oxopyrrolidin-1-yl)benzyl]-1-((1R,2R)-1-hydroxymethyl-2-methoxypropyl)-7-methoxy-4-oxo-1,4-dihydroquinoline-3-carboxylic acid (Example 48), 6-[3-chloro-2,4-difluoro-5-(morpholin-4-yl)benzyl]-1-((S)-1-hydroxymethyl-2,2-dimethylpropyl)-7-methoxy-4-oxo-1,4-dihydroquinoline-3-carboxylic acid (Example 49), 6-[3-chloro-2-fluoro-5-(morpholin-4-yl)benzyl]-1-[(1R,2R)-2-ethoxy-1-(hydroxymethyl)propyl]-7-methoxy-4-oxo-1,4-dihydroquinoline-3-carboxylic acid (Example 50), 6-[3-chloro-2-fluoro-5-(2-oxopyrrolidin-1-yl)benzyl]-1-((S)-1-hydroxymethyl-2,2-dimethylpropyl)-4-oxo-1,4-dihydroquinoline-3-carboxylic acid (Example 51), 6-[3-chloro-2-fluoro-5-(2-oxopyrrolidin-1-yl)benzyl]-7-ethyl-1-((S)-1-hydroxymethyl-2,2-dimethylpropyl)-4-oxo-1,4-dihydroquinoline-3-carboxylic acid (Example 52), 6-[3-chloro-2-fluoro-5-(morpholin-4-yl)benzyl]-1-((S)-1-hydroxymethyl-2,2-dimethylpropyl)-4-oxo-1,4-dihydroquinoline-3-carboxylic acid (Example 53), 6-[3-chloro-2,4-difluoro-5-(2-oxopyrrolidin-1-yl)benzyl]-1-((S)-1-hydroxymethyl-2,2-dimethylpropyl)-4-oxo-1,4-dihydroquinoline-3-carboxylic acid (Example 54), 6-[3-chloro-2,4-difluoro-5-(2-oxopyrrolidin-1-yl)benzyl]-7-ethyl-1-((S)-1-hydroxymethyl-2,2-dimethylpropyl)-4-oxo-1,4-dihydroquinoline-3-carboxylic acid (Example 55), 6-[3-chloro-2,4-difluoro-5-(morpholin-4-yl)benzyl]-1-((S)-1-hydroxymethyl-2,2-dimethylpropyl)-4-oxo-1,4-dihydroquinoline-3-carboxylic acid (Example 56), 6-[3-chloro-2-fluoro-5-(5-methyl-1,2,4-oxadiazol-3-yl)benzyl]-1-((S)-1-hydroxymethyl-2-methylpropyl)-7-methoxy-4-oxo-1,4-dihydroquinoline-3-carboxylic acid (Example 57)

6-[3-chloro-2,4-difluoro-5-(3-oxomorpholin-4-yl)benzyl]-1-((S)-1-hydroxymethyl-2,2-dimethylpropyl)-4-oxo-1,4-dihydroquinoline-3-carboxylic acid (Example 58), and 6-[3-chloro-2,4-difluoro-5-(morpholin-4-yl)benzyl]-1-((R)-1-hydroxymethyl-2,2-dimethylpropyl)-4-oxo-1,4-dihydroquinoline-3-carboxylic acid (Example 59), or a pharmaceutically acceptable salt thereof, or a solvate thereof.

[11] A pharmaceutical composition comprising the compound of any one of the above-mentioned [1] to [10] or a pharmaceutically acceptable salt thereof, or a solvate thereof, and a pharmaceutically acceptable carrier.

[12] An anti-HIV agent comprising the compound of any one of the above-mentioned [1] to [10] or a pharmaceutically acceptable salt thereof, or a solvate thereof, as an active ingredient.

[13] An HIV integrase inhibitor comprising the compound of any one of the above-mentioned [1] to [10] or a pharmaceutically acceptable salt thereof, or a solvate thereof, as an active ingredient.

[14] An anti-HIV agent comprising the compound of any one of the above-mentioned [1] to [10] or a pharmaceutically acceptable salt thereof, or a solvate thereof, in combination with one or more other kinds of anti-HIV active substances.

[15] Use of the compound of any one of the above-mentioned [1] to [10] or a pharmaceutically acceptable salt thereof, or a solvate thereof, for the production of an anti-HIV agent.

[16] Use of the compound of any one of the above-mentioned [1] to [10] or a pharmaceutically acceptable salt thereof, or a solvate thereof, for the production of an HIV integrase inhibitor.

[17] A method for the prophylaxis or treatment of an HIV infectious disease in a mammal, which comprises administering an effective amount of the compound of any one of the above-mentioned [1] to [10] or a pharmaceutically acceptable salt thereof, or a solvate thereof, to said mammal.

[18] The method of the above-mentioned [17], which further comprises administering an effective amount of one or more other kinds of anti-HIV active substances to the mammal.

[19] A method for inhibiting HIV integrase in a mammal, which comprises administering an effective amount of the compound of any one of the above-mentioned [1] to [10] or a pharmaceutically acceptable salt thereof, or a solvate thereof, to said mammal.

[20] An anti-HIV composition comprising the compound of any one of the above-mentioned [1] to [10] or a pharmaceutically acceptable salt thereof, or a solvate thereof, and a pharmaceutically acceptable carrier.

[21] A pharmaceutical composition for inhibiting HIV integrase, comprising the compound of any one of the above-mentioned [1] to [10] or a pharmaceutically acceptable salt thereof, or a solvate thereof, and a pharmaceutically acceptable carrier.

The compounds of the present invention show a high inhibitory activity against HIV integrase.

Therefore, these compounds can be pharmaceutical agents effective for, for example, the prophylaxis or treatment of AIDS, as integrase inhibitors, antiviral agents, anti-HIV agents and the like, having an HIV integrase inhibitory activity. In addition, by a combined use with other anti-HIV agent(s) such as protease inhibitor, reverse transcriptase inhibitor and the like, they can be more effective anti-HIV agents. Furthermore, having high inhibitory activity specific for integrase, they can be pharmaceutical agents safe for human body with a fewer side effects.

BEST MODE FOR EMBODYING THE INVENTION

The definitions of respective substituents, respective symbols and respective moieties used in the present specification are as follows.

The "halogen atom" is a fluorine atom, a chlorine atom, a bromine atom or an iodine atom, preferably a fluorine atom, a chlorine atom or a bromine atom.

The "$C_{1-4}$ alkyl group" is a straight chain or branched chain alkyl group having 1 to 4 carbon atoms, and specifically, methyl group, ethyl group, propyl group, isopropyl group, butyl group, isobutyl group, sec-butyl group and tert-butyl group can be mentioned.

The "$C_{1-6}$ alkyl group" is a straight chain or branched chain alkyl group having 1 to 6 carbon atoms, and specifically, methyl group, ethyl group, propyl group, isopropyl group, butyl group, isobutyl group, sec-butyl group, tert-butyl group, pentyl group, isopentyl group, 1-methylbutyl group, 1-ethylpropyl group, 2-ethylpropyl group, 2,2-dimethylpropyl group, 1,2-dimethylpropyl group, tert-pentyl group, hexyl group, isohexyl group, 1-methylpentyl group, 1,1-dimethylbutyl group, 1,2-dimethylbutyl group, 1,3-dimethylbutyl group, 1-ethylbutyl group, 1-ethyl-1-methylpropyl group, 1-ethyl-2-methylpropyl group, 1,1,2-trimethylpropyl group, 1,2,2-trimethylpropyl group and the like can be mentioned.

The "$C_{3-10}$ cycloalkyl group" is a cycloalkyl group having 3 to 10 carbon atoms, preferably 3 to 6, and specifically, cyclopropyl group, cyclobutyl group, cyclopentyl group, cyclohexyl group, cycloheptyl group, cyclooctyl group, cyclononyl group and cyclodecyl group can be mentioned.

The "$C_{3-10}$ carbon ring group" is a saturated or unsaturated cyclic hydrocarbon group having 3 to 10 carbon atoms, and means aryl group, cycloalkyl group, cycloalkenyl group, or a fused ring thereof.

As the "aryl group", specifically, phenyl group, naphthyl group, pentalenyl group, azulenyl group and the like can be mentioned, preferably phenyl group and naphthyl group, particularly preferably phenyl group.

As the "cycloalkyl group", specifically, cyclopropyl group, cyclobutyl group, cyclopentyl group, cyclohexyl group, cycloheptyl group, cyclooctyl group, adamantyl group, norbornanyl group and the like can be mentioned, preferably cyclopropyl group, cyclobutyl group, cyclopentyl group and cyclohexyl group.

The "cycloalkenyl group" contains at least one, preferably 1 or 2, double bonds, and specifically cyclopropenyl group, cyclobutenyl group, cyclopentenyl group, cyclopentadienyl group, cyclohexenyl group, cyclohexadienyl group (2,4-cyclohexadien-1-yl group, 2,5-cyclohexadien-1-yl group etc.), cycloheptenyl group, cyclooctenyl group and the like can be mentioned.

As the fused ring of these "aryl group", "cycloalkyl group" or "cycloalkenyl group", specifically, indenyl group, indanyl group, 1,4-dihydronaphthyl group, 1,2,3,4-tetrahydronaphthyl group (1,2,3,4-tetrahydro-2-naphthyl group, 5,6,7,8-tetrahydro-2-naphthyl group etc.), perhydronaphthyl group and the like can be mentioned. It is preferably a fused ring of phenyl group and the other ring, more preferably indenyl group, indanyl group, 1,4-dihydronaphthyl group, 1,2,3,4-tetrahydronaphthyl group and the like, particularly preferably indanyl group.

The "$C_{3-10}$ carbon ring group optionally substituted by 1 to 5 substituents selected from group A" is the above-defined "$C_{3-10}$ carbon ring group" optionally substituted by 1 to 5, preferably 1 to 3, substituents selected from the below-defined "group A", and includes an unsubstituted "$C_{3-10}$ carbon ring group".

The "group A" is a group consisting of the above-defined "halogen atom", the above-defined "$C_{1-4}$ alkyl group", —(CH$_2$)$_n$—OR$^{a1}$, —NR$^{a3}$R$^{a4}$, —COR$^{a2}$ and —CONR$^{a3}$R$^{a4}$, wherein R$^{a1}$, R$^{a2}$, R$^{a3}$ and R$^{a4}$ are the same or different and each is a hydrogen atom or the above-defined "$C_{1-4}$ alkyl group", and n is 0 or an integer of 1 to 4.

As the "—(CH$_2$)$_n$—OR$^{a1}$", specifically, hydroxy group, methoxy group, ethoxy group, propoxy group, isopropoxy group, tert-butoxy group, hydroxymethyl group, methoxymethyl group, 2-(methoxy)ethyl group and the like can be mentioned.

As the "—NR$^{a3}$R$^{a4}$", specifically, amino group, methylamino group, ethylamino group, propylamino group, isopropylamino group, tert-butylamino group, dimethylamino group, diethylamino group, N-ethyl-N-methylamino group, N-methyl-N-propylamino group, N-isopropyl-N-methylamino group and the like can be mentioned.

As the "—COR$^{a2}$", specifically, formyl group, acetyl group, propionyl group, butyryl group, isobutyryl group, 2,2-dimethylpropionyl group and the like can be mentioned.

As the "—CONR$^{a3}$R$^{a4}$", specifically, carbamoyl group, methylcarbamoyl group, ethylcarbamoyl group, propylcarbamoyl group, isopropylcarbamoyl group, tert-butylcarbamoyl group, dimethylcarbamoyl group, diethylcarbamoyl group, N-ethyl-N-methylcarbamoyl group and the like can be mentioned.

As the "$C_{3-10}$ carbon ring group optionally substituted by 1 to 5 substituents selected from group A", specifically, phenyl group, naphthyl group, 2-fluorophenyl group, 2-chlorophenyl group, 2-bromophenyl group, 3-fluorophenyl group, 3-chlorophenyl group, 3-bromophenyl group, 4-fluorophenyl group, 2-methylphenyl group, 3-methylphenyl group, 4-methylphenyl group, 2-ethylphenyl group, 3-ethylphenyl group, 2-isopropylphenyl group, 3-isopropylphenyl group, 2-hydroxyphenyl group, 3-hydroxyphenyl group, 4-hydroxyphenyl group, 2-methoxyphenyl group, 3-methoxyphenyl group, 2-ethoxyphenyl group, 3-ethoxyphenyl group, 2-propoxyphenyl group, 3-propoxyphenyl group, 2-aminophenyl group, 3-aminophenyl group, 2-(methylamino)phenyl group, 3-(methylamino)phenyl group, 2-(dimethylamino)phenyl group, 3-(dimethylamino)phenyl group, 2-(diethylamino)phenyl group, 2-(N-ethyl-N-methylamino)phenyl group, 2-(N-isopropyl-N-methylamino)phenyl group, 2-acetylphenyl group, 3-acetylphenyl group, 2-(carbamoyl)phenyl group, 3-(carbamoyl)phenyl group, 2-(methylcarbamoyl)phenyl group, 3-(methylcarbamoyl)phenyl group, 2-(dimethylcarbamoyl)phenyl group, 3-(dimethylcarbamoyl)phenyl group, 2,3-difluorophenyl group, 2,3-dichlorophenyl group, 3,4-dichlorophenyl group, 2,3-dibromophenyl group, 2,4-difluorophenyl group, 2,4-dichlorophenyl group, 2,5-dichlorophenyl group, 2,6-dichlorophenyl group, 2-chloro-3-fluorophenyl group, 2-chloro-4-fluorophenyl group, 2-chloro-5-fluorophenyl group, 2-chloro-6-fluorophenyl group, 3-chloro-2-fluorophenyl group, 5-chloro-2-fluorophenyl group, 5-bromo-2-chlorophenyl group, 2-chloro-3-methylphenyl group, 2-chloro-5-methylphenyl group, 3-chloro-2-methylphenyl group, 2-chloro-3-hydroxyphenyl group, 2-chloro-5-hydroxyphenyl group, 2-chloro-3-methoxyphenyl group, 2-chloro-5-methoxyphenyl group, 3-chloro-2-methoxyphenyl group, 2-chloro-3-aminophenyl group, 2-chloro-5-aminophenyl group, 2-chloro-3-(methylamino) phenyl group, 2-chloro-5-(methylamino)phenyl group, 2-chloro-3-(dimethylamino)phenyl group, 2-chloro-5-(dimethylamino)phenyl group, 2,3,4-trifluorophenyl group, 2-chloro-3,4-difluorophenyl group, 2-chloro-3,5-difluorophenyl group, 2-chloro-3,6-difluorophenyl group, 2-chloro-4,5-difluorophenyl group, 2-chloro-4,6-difluorophenyl group, 3-chloro-2,4-difluorophenyl group, 3-chloro-2,5-difluorophenyl group, 3-chloro-2,6-difluorophenyl group, 2,3-dichloro-4-fluorophenyl group, 2-chloro-3,5,6-trifluorophenyl group, 3-chloro-2,4,5-trifluorophenyl group, 3-chloro-2,4,6-trifluorophenyl group, 2,3-dichloro-4,5,6-trifluorophenyl group, 3,5-dichloro-3,4,6-trifluorophenyl group, 2,6-dichloro-3,4,5-trifluorophenyl group, perfluorophenyl group, cyclopropyl group, cyclobutyl group, cyclopentyl group, cyclohexyl group, 2-hydroxycyclopropyl group, 2-hydroxycyclobutyl group, 3-hydroxycyclobutyl group, 2-hydroxycyclopentyl group, 3-hydroxycyclopentyl group, 2-hydroxycyclohexyl group, 3-hydroxycyclohexyl group, 4-hydroxycyclohexyl group, 4-indanyl group, 1-inden-4-yl group and the like can be mentioned.

The "heterocyclic group" is a saturated or unsaturated (including partially unsaturated and completely unsaturated) monocyclic 4 to 6-membered (preferably 5-membered or 6-membered) heterocyclic group containing, besides carbon atom, at least one, preferably 1 to 4, hetero atoms selected from nitrogen atom, oxygen atom and sulfur atom, a fused ring of these heterocycles, or a fused ring of these heterocycle and $C_{3-10}$ carbon ring selected from benzene, cyclopentane and cyclohexane.

As the "saturated monocyclic heterocyclic group", azetidinyl group, pyrrolidinyl group, tetrahydrofuryl group, tetrahydrothienyl group, imidazolidinyl group, pyrazolidinyl group, 1,3-dioxolanyl group, 1,3-oxathiolanyl group, oxazolidinyl group, isoxazolidinyl group, thiazolidinyl group, isothiazolidinyl group, piperidinyl group, piperazinyl group, tetrahydropyranyl group, tetrahydrothiopyranyl group, dioxanyl group, morpholinyl group, 3-oxomorpholinyl group, thiomorpholinyl group, 2-oxoazetidinyl group, 2-oxopyrrolidinyl group, 3-oxopyrazolidinyl group, 2-oxooxazolidinyl group, 1,1-dioxoisothiazolidinyl group, 2-oxopiperidinyl group, 4-oxopiperidinyl group, 2,6-dioxopiperidinyl group and the like can be mentioned.

As the "unsaturated monocyclic heterocyclic group", pyrrolyl group, furyl group, thienyl group, imidazolyl group, 1,2-dihydro-2-oxoimidazolyl group, pyrazolyl group, oxazolyl group, isoxazolyl group, thiazolyl group, isothiazolyl group, 1,2,4-triazolyl group, 1,2,3-triazolyl group, tetrazolyl group, 1,3,4-oxadiazolyl group, 1,2,4-oxadiazolyl group, 1,3,4-thiadiazolyl group, 1,2,4-thiadiazolyl group, furazanyl group, pyridyl group, pyrimidinyl group, 3,4-dihydro-4-oxopyrimidinyl group, pyridazinyl group, pyrazinyl group, 1,3,5-triazinyl group, imidazolinyl group, pyrazolinyl group, oxazolinyl group (2-oxazolinyl group, 3-oxazolinyl group, 4-oxazolinyl group), isoxazolinyl group, thiazolinyl group, isothiazolinyl group, pyranyl group, 2-oxopyranyl group, 2-oxo-2,5-dihydrofuranyl group, 1,1-dioxo-1H-isothiazolyl group and the like can be mentioned.

As the "fused heterocyclic group", indolyl group (e.g., 2-indolyl group, 3-indolyl group, 4-indolyl group, 7-indolyl group etc.), isoindolyl group, 1,3-dihydro-1,3-dioxoisoindolyl group, benzofuranyl group (e.g., 2-benzofuranyl group, 4-benzofuranyl group, 7-benzofuranyl group etc.), indazolyl group, isobenzofuranyl group, benzothienyl group (e.g., 2-benzothienyl group, 4-benzothienyl group, 7-benzothienyl group etc.), benzoxazolyl group (e.g., 2-benzoxazolyl group, 4-benzoxazolyl group, 7-benzoxazolyl group etc.), benzimidazolyl group (e.g., 2-benzimidazolyl group, 4-benzimidazolyl group, 7-benzimidazolyl group etc.), benzothiazolyl group (e.g., 2-benzothiazolyl group, 4-benzothiazolyl group, 7-benzothiazolyl group etc.), indolizinyl group, quinolyl group, isoquinolyl group, 1,2-dihydro-2-oxoquinolyl group, quinazolinyl group, quinoxalinyl group, cinnolinyl group, phthalazinyl group, quinolizinyl group, purinyl group, pteridinyl group, indolinyl group, isoindolinyl group, 5,6,7,8-tetrahydroquinolyl group, 1,2,3,4-tetrahydroquinolyl group, 2-oxo-1,2,3,4-tetrahydroquinolyl group, benzo[1,3]dioxolyl group, 3,4-methylenedioxypyridyl group, 4,5-ethylenedioxypyrimidinyl group, chromenyl group, chromanyl group, isochromanyl group and the like can be mentioned. It is preferably a fused ring of monocyclic 5-membered or 6-membered heterocycle and benzene ring.

As the "heterocyclic group optionally substituted by 1 to 5 substituents selected from group A" is the above-defined "heterocyclic group" optionally substituted by 1 to 5, preferably 1 to 3, substituents selected from the above-defined "group A", and includes an unsubstituted "heterocyclic group".

As the "heterocyclic group", preferably a monocyclic heterocyclic group containing 1 or 2 hetero atoms, or a heterocyclic group which is a fused ring thereof with a benzene ring.

As the "heterocyclic group optionally substituted by 1 to 5 substituents selected from group A", specifically, 1-pyrrolidinyl group, 2-pyrrolidinyl group, 3-pyrrolidinyl group, 1-piperidinyl group, 2-piperidinyl group, 3-piperidinyl group, 4-piperidinyl group, morpholino group, 1-pyrrolyl group, 2-pyrrolyl group, 3-pyrrolyl group, 2-furyl group, 3-furyl group, 2-thienyl group, 3-thienyl group, 4,5-dichlorothiophen-3-yl group, 2-oxo-2,5-dihydrofuran-3-yl group, 1,1-dioxo-1H-isothiazol-5-yl group, 4-methylthiazol-5-yl group, 1-imidazolyl group, 2-imidazolyl group, 3-imidazolyl group, 4-imidazolyl group, 1-pyrazolyl group, 3-pyrazolyl group, 4-pyrazolyl group, 2-oxazolyl group, 3-isoxazolyl group, 2-thiazolyl group, 3-isothiazolyl group, 2-pyridyl group, 3-fluoropyridin-2-yl group, 3-chloropyridin-2-yl group, 3-chloro-4-fluoropyridin-2-yl group, 3,5-dichloropyridin-2-yl group, 3-pyridyl group, 2-fluoropyridin-3-yl group, 2-chloropyridin-3-yl group, 2-chloro-4-fluoropyridin-3-yl group, 2-chloro-5-fluoropyridin-3-yl group, 2,5-dichloropyridin-3-yl group, 2-chloro-6-fluoropyridin-3-yl group, 2,6-dichloropyridin-3-yl group, 4-pyridyl group, 2-fluoropyridin-4-yl group, 2-chloropyridin-4-yl group, 2-chloro-3-fluoropyridin-4-yl group, 2,3-difluoropyridin-4-yl group, 2,3-dichloropyridin-4-yl group, 2,5-dichloropyridin-4-yl group, 2-chloro-6-fluoropyridin-4-yl group, 2,6-dichloropyridin-4-yl group, 2-chloro-3,6-difluoropyridin-4-yl group, 2-chloro-3,5-difluoropyridin-4-yl group, 2,3,6-trifluoropyridin-4-yl group, 2,3,5,6-tetrafluoropyridin-4-yl group, 2-indolyl group, 3-indolyl group, 4-indolyl group, 7-indolyl group, 2-benzofuranyl group, 4-benzofuranyl group, 7-benzofuranyl group, 2-benzothienyl group, 4-benzothienyl group, 7-benzothienyl group, 2-benzimidazolyl group, 4-benzimidazolyl group, 2-benzoxazolyl group, 4-benzoxazolyl group, 7-benzoxazolyl group, 2-benzothiazolyl group, 4-benzothiazolyl group, 7-benzothiazolyl group, 2-benzo[1,3]dioxolyl group, 4-benzo[1,3]dioxolyl group, 5-benzo[1,3]dioxolyl group, tetrahydropyran-2-yl group and the like can be mentioned.

The "$C_{1-6}$ alkyl group optionally substituted by 1 to 3 substituents selected from group B" is the above-defined "$C_{1-6}$ alkyl group" optionally substituted by 1 to 3 substituents selected from the below-defined "group B", and includes an unsubstituted "$C_{1-6}$ alkyl group".

The "group B" is a group consisting of the above-defined "$C_{3-10}$ carbon ring group optionally substituted by 1 to 5 substituents selected from group A", the above-defined "heterocyclic group optionally substituted by 1 to 5 substituents selected from group A", the above-defined "halogen atom", cyano group,
—$OR^{b1}$, —$SR^{b1}$, —$NR^{b2}R^{b3}$,
—$CONR^{b2}R^{b3}$, —$SO_2NR^{b2}R^{b3}$, —$COR^{b1}$,
—$NR^{b2}COR^{b1}$, —$SO_2R^{b1}$, —$NR^{b2}SO_2R^{b1}$,
—$COOR^{b1}$, —$NR^{b2}COOR^{b1}$ and —$NR^{b4}CO—NR^{b2}R^{b3}$.

$R^{b1}$, $R^{b2}$, $R^{b3}$ and $R^{b4}$ are the same or different and each is a hydrogen atom, the above-defined "$C_{1-4}$ alkyl group", the above-defined "$C_{3-10}$ carbon ring group optionally substituted by 1 to 5 substituents selected from group A", or the above-defined "heterocyclic group optionally substituted by 1 to 5 substituents selected from group A".

As the "—$OR^{b1}$", specifically, hydroxy group, methoxy group, ethoxy group, propoxy group, isopropoxy group, butoxy group, isobutoxy group, sec-butoxy group, tert-butoxy group, phenoxy group, pyridin-2-yloxy group, tetrahydropyran-2-yloxy group and the like can be mentioned.

As the "—$SR^{b1}$", specifically, mercapto group, methylsulfanyl group, ethylsulfanyl group, propylsulfanyl group, isopropylsulfanyl group, tert-butylsulfanyl group and the like can be mentioned.

As the "—$NR^{b2}R^{b3}$", specifically, amino group, methylamino group, ethylamino group, propylamino group, isopropylamino group, tert-butylamino group, dimethylamino group, diethylamino group, N-ethyl-N-methylamino group, N-methyl-N-propylamino group, N-isopropyl-N-methylamino group, phenylamino group, pyridin-2-ylamino group, N-methyl-N-phenylamino group and the like can be mentioned.

As the "—$CONR^{b2}R^{b3}$", specifically, carbamoyl group, methylcarbamoyl group, ethylcarbamoyl group, propylcarbamoyl group, isopropylcarbamoyl group, tert-butylcarbamoyl group, dimethylcarbamoyl group, diethylcarbamoyl group, N-ethyl-N-methylcarbamoyl group, phenylcarbamoyl group and the like can be mentioned.

As the "—$SO_2NR^{b2}R^{b3}$", specifically, sulfamoyl group, ethylsulfamoyl group, ethylsulfamoyl group, propylsulfamoyl group, isopropylsulfamoyl group, tert-butylsulfamoyl group, dimethylsulfamoyl group, diethylsulfamoyl group, N-ethyl-N-methylsulfamoyl group, phenylsulfamoyl group and the like can be mentioned.

As the "—$COR^{b1}$", specifically, formyl group, acetyl group, propionyl group, butyryl group, isobutyryl group, 2,2-dimethylpropionyl group, benzoyl group, pyrrolidin-1-ylcarbonyl group, 2-fluoropyrrolidin-1-ylcarbonyl group, 2-oxopyrrolidin-1-ylcarbonyl group, piperidinocarbonyl group, 4-oxopiperidin-1-ylcarbonyl group, 2,6-dimethylpiperidin-1-ylcarbonyl group, piperazin-1-ylcarbonyl group, morpholinocarbonyl group and the like can be mentioned.

As the "—$NR^{b2}COR^{b1}$", specifically, formylamino group, acetylamino group, propionylamino group, butyrylamino group, isobutyrylamino group, 2,2-dimethylpropionylamino group, N-acetyl-N-methylamino group, benzoylamino group, pyrrolidin-1-ylcarbonylamino group, 2-fluoropyrrolidin-1-ylcarbonylamino group, 2-oxopyrrolidin-1-ylcarbonylamino group, piperidinocarbonylamino group, 4-oxopiperidin-1-ylcarbonylamino group, 2,6-dimethylpiperidin-1-ylcarbonylamino group, piperazin-1-ylcarbonylamino group, morpholinocarbonylamino group and the like can be mentioned.

As the "—$SO_2R^{b1}$", specifically, methylsulfonyl group, ethylsulfonyl group, propylsulfonyl group, isopropylsulfonyl group, tert-butylsulfonyl group and the like can be mentioned.

As the "—$NR^{b2}SO_2R^{b1}$", specifically, methylsulfonylamino group, ethylsulfonylamino group, propylsulfonylamino group, isopropylsulfonylamino group, tert-butylsulfonylamino group, N-methyl-N-(methylsulfonyl)amino group and the like can be mentioned.

As the "—$COOR^{b1}$", specifically, carboxyl group, methoxycarbonyl group, ethoxycarbonyl group, propoxycarbonyl group, isopropoxycarbonyl group, tert-butoxycarbonyl group and the like can be mentioned.

As the "—$NR^{b2}COOR^{b1}$", specifically, methoxycarbonylamino group, ethoxycarbonylamino group, propoxycarbonylamino group, isopropoxycarbonylamino group, tert-butoxycarbonylamino group, N-(tert-butoxycarbonyl)-N-methylamino group and the like can be mentioned.

As the "—$NR^{b4}CO—NR^{b2}R^{b3}$", specifically, ureido group, 3-methylureido group, 3-ethylureido group, 1,3-dimethylureido group and the like can be mentioned.

As the "$C_{1-6}$ alkyl group optionally substituted by 1 to 3 substituents selected from group B", specifically, methyl group, ethyl group, propyl group, isopropyl group, butyl group, isobutyl group, sec-butyl group, tert-butyl group, pentyl group, isopentyl group, 1-methylbutyl group, 1-ethylpropyl group, 2-ethylpropyl group, 2,2-dimethylpropyl group, 1,2-dimethylpropyl group, tert-pentyl group, hexyl group, isohexyl group, 1-methylpentyl group, 1,1-dimethylbutyl group, 1,2-dimethylbutyl group, 1,3-dimethylbutyl group, 1-ethylbutyl group, 1-ethyl-1-methylpropyl group, 1-ethyl-2-methylpropyl group, 1,1,2-trimethylpropyl group, 1,2,2-trimethylpropyl group, fluoromethyl group, trifluoromethyl group, 1-chloroethyl group, 2-fluoroethyl group, 2-chloroethyl group, 3-fluoropropyl group, 2-chloropropyl group, 2,2,2-trifluoroethyl group, hydroxymethyl group, methoxymethyl group, ethoxymethyl group, propoxymethyl group, isopropoxymethyl group, butoxymethyl group, isobutoxymethyl group, sec-butoxymethyl group, tert-butoxymethyl group, phenoxymethyl group, pyridin-2-yloxymethyl group, 1-hydroxyethyl group, 2-hydroxyethyl group, 1-methoxyethyl group, 2-methoxyethyl group, 1-ethoxyethyl group, 2-ethoxyethyl group, 1-methoxy-1-methylethyl group, 2-propoxyethyl group, 2-isopropoxyethyl group, 2-butoxyethyl group, 2-isobutoxyethyl group, 2-sec-butoxyethyl group, 2-tert-butoxyethyl group, 2-phenoxyethyl group, 2-(pyridin-2-yloxy)ethyl group, 2-hydroxypropyl group, 2-hydroxy-1-methylethyl group, 2-hydroxy-1,1-dimethylethyl group, 1-(hydroxymethyl)propyl group, 3-hydroxypropyl group, 2-hydroxybutyl group, 4-hydroxybutyl group, 2-hydroxypentyl group, 5-hydroxypentyl group, 2,3-dihydroxypropyl group, 2,3-dihydroxybutyl group, 2-hydroxy-1-(hydroxymethyl)ethyl group, 2-hydroxy-2-methylpropyl group, 1-(hydroxymethyl)butyl group, 1-(hydroxymethyl)-2-methylpropyl group, 1-(hydroxymethyl)-2,2-dimethylpropyl group, 1-(hydroxymethyl)-2-methylbutyl group, 2-hydroxy-1-phenylethyl group, 2-hydroxy-2-phenylethyl group, 1-(hydroxymethyl)-2-phenylethyl group, 1-(hydroxymethyl)-3-methylbutyl group, 3-hydroxy-1-methylpropyl group, 1,1-dimethyl-3-hydroxypropyl group, 1,2-dimethyl-3-hydroxypropyl group, 1-isopropyl-3-hydroxypropyl group, 1-ethyl-3-hydroxypropyl group, 2-hydroxy-1-isopropylpropyl group, 1-ethyl-1-(hydroxymethyl)propyl group, 1,1-dimethyl-2-hydroxypropyl group, 1,2-dimethyl-2-hydroxypropyl group, 1-ethyl-2-hydroxypropyl group, 4-hydroxy-1-methylbutyl group, 1-(hydroxymethyl)pentyl group, aminomethyl group, (methylamino)methyl group, (ethylamino)methyl group, (dimethylamino)methyl group, (N-ethyl-N-methylamino)methyl group, 1-aminoethyl group, 2-aminoethyl group, 1-(methylamino)ethyl group, 2-(methylamino)ethyl group, 1-(ethylamino)ethyl group, 2-(ethylamino)ethyl group, 2-(dimethylamino)ethyl group, methylsulfanylmethyl group, 2-(methylsulfanyl)ethyl group, carboxymethyl group, 2-carboxyethyl group, 2-carboxypropyl group, 3-carboxypropyl group, carbamoylmethyl group, 2-(carbamoyl)ethyl group, methylcarbamoylmethyl group, dimethylcarbamoylmethyl group, 2-(phenylcarbamoyl)ethyl group, 2-oxopropyl group, methylsulfonylmethyl group, 2-(methylsulfonyl)ethyl group, sulfamoylmethyl group, methylsulfamoylmethyl group, dimethylsulfamoylmethyl group, tert-butylsulfamoylmethyl group, 2-(acetylamino)ethyl group, 2-(methylsulfonylamino)ethyl group, 2-(ethoxycarbonylamino)ethyl group, benzyl group, phenethyl group, 3-phenylpropyl group, 4-phenylbutyl group, 3,4-dichlorobenzyl group, 2-hydroxy-2-phenylethyl group, cyclopentylmethyl group, cyclohexylmethyl group, 2-cyclohexylethyl group, 1-cyclohexyl-2-hydroxyethyl group, 1-cyclohexylmethyl-2-hydroxyethyl group, phenylcarbamoylmethyl group, 2-(pyridin-2-yl)ethyl group, 2-(imidazol-1-yl)ethyl group, 2-(benzothiophen-2-yl)ethyl group, 2-morpholinoethyl group, 2-(4-methylthiazolin-5-yl)ethyl group, 1-carboxyethyl group, 1-(carbamoyl)ethyl group, 1-carboxy-2-methylpropyl group, 1-(carbamoyl)-2-methylpropyl group, 2-hydroxy-1-(hydroxymethyl)propyl group, 1-(hydroxymethyl)-2-mercaptoethyl group, 1-(hydroxymethyl)-3-(methylsulfanyl)propyl group, 2-carboxy-1-(hydroxymethyl)ethyl group, 2-carbamoyl-1-(hydroxymethyl)ethyl group, 2-(indol-3-yl)-1-(hydroxymethyl)ethyl group, 2-(imidazol-4-yl)-1-(hydroxymethyl)ethyl group, 2-(4-hydroxyphenyl)-1-(hydroxymethyl)ethyl group, 3-carbamoyl-1-(hydroxymethyl)propyl group, 5-amino-1-(hydroxymethyl)pentyl group, 2-(tetrahydropyran-2-yloxy)ethyl group, acetylaminomethyl group, methylsulfonylaminomethyl group, methoxycarbonylaminomethyl group, sulfamoylmethyl group, (tert-butoxycarbonylamino)methyl group, (2,2-dimethylpropionylamino)methyl group, (N-tert-butoxycarbonyl-N-methylamino)methyl group, propionylaminomethyl group, butyrylaminomethyl group, isobutyrylaminomethyl group, benzoylaminomethyl group, ethoxycarbonylaminomethyl group, (morpholinocarbonylamino)methyl group, (3-methylureido)methyl group, (3-ethylureido)methyl group and the like can be mentioned.

As the $R^1$, preferably, methyl group, ethyl group, propyl group, isopropyl group, tert-butyl group, methoxymethyl group, ethoxymethyl group, 1-methoxyethyl group, 2-methoxyethyl group, 1-ethoxyethyl group, 1-methoxy-1-methylethyl group and the like can be mentioned.

The "$C_{3-10}$ cycloalkyl group optionally substituted by 1 to 5 substituents selected from group A", which is formed by $R^1$ and $R^6$ together with the carbon atoms bonded thereto, is the above-defined "$C_{3-10}$ cycloalkyl group" optionally substituted by 1 to 5, preferably 1 to 3, substituents selected from the above-defined "group A", and includes an unsubstituted "$C_{3-10}$ cycloalkyl group".

As the "$C_{3-10}$ cycloalkyl group optionally substituted by 1 to 5 substituents selected from group A", specifically, cyclopropyl group, cyclobutyl group, cyclopentyl group, cyclohexyl group, cycloheptyl group, cyclooctyl group, cyclononyl group, cyclodecyl group and the like can be mentioned.

The "monocyclic heterocyclic group" of the "monocyclic heterocyclic group optionally substituted by 1 to 5 substituents selected from group A" is a saturated or unsaturated (including partially unsaturated and completely unsaturated) monocyclic 4- to 6-membered (preferably 5-membered or 6-membered) heterocyclic group containing besides carbon atom, at least one, preferably 1 to 4 hetero atoms selected from nitrogen atom, oxygen atom and sulfur atom.

As the "monocyclic heterocyclic group", specifically, the following heterocyclic group can be mentioned.

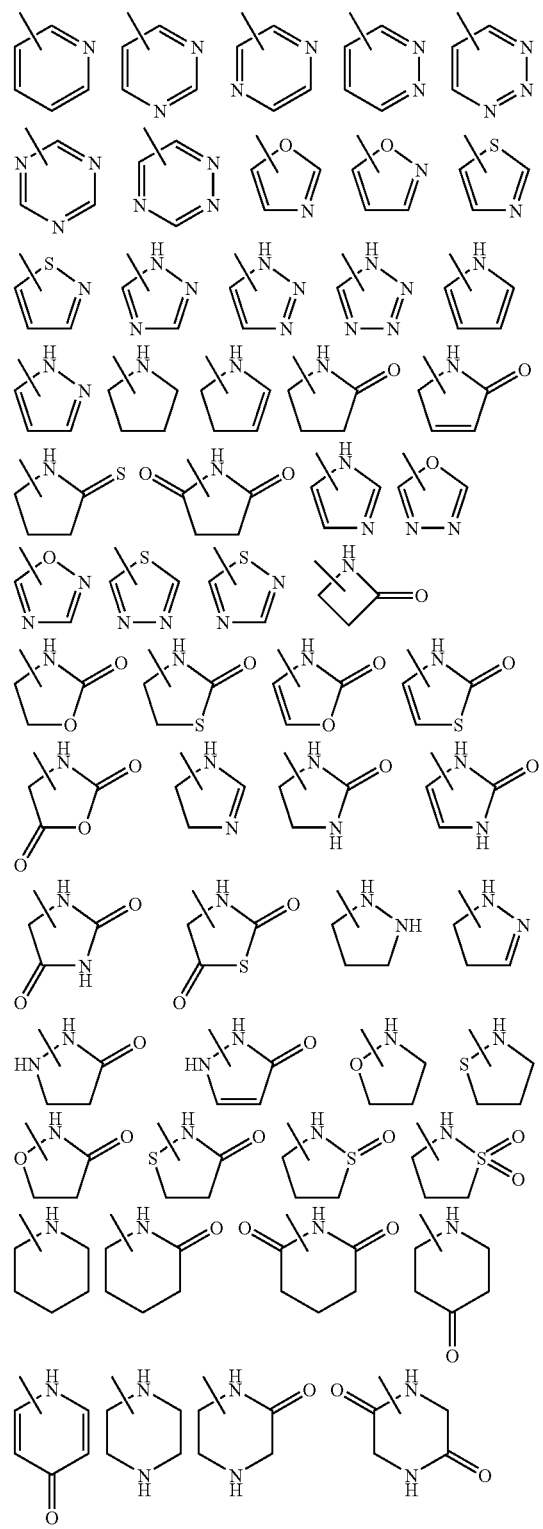

-continued

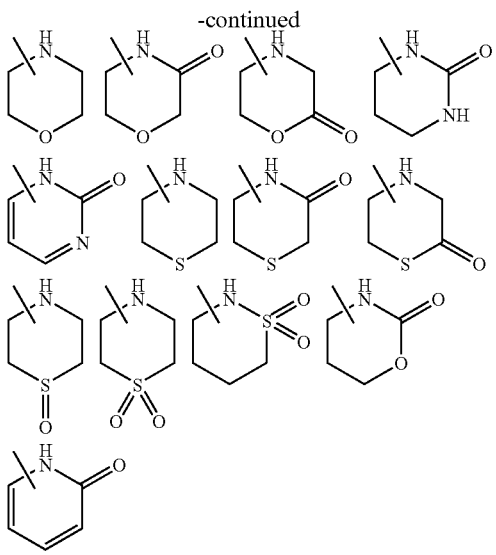

The "monocyclic heterocyclic group optionally substituted by 1 to 5 substituents selected from group A" is the above-defined "monocyclic heterocyclic group" optionally substituted by 1 to 5, preferably 1 to 3, substituents selected from the above-defined "group A", and includes an unsubstituted "monocyclic heterocyclic group".

As the "monocyclic heterocyclic group optionally substituted by 1 to 5 substituents selected from group A" for ring A, specifically, 1-pyrrolidinyl group, 2-oxopyrrolidin-1-yl group, 3-hydroxypyrrolidin-1-yl group, 3-fluoropyrrolidin-1-yl group, 3,3-difluoropyrrolidin-1-yl group, piperidino group, 2-oxopiperidin-1-yl group, 4-hydroxypiperidin-1-yl group, 1-piperazinyl group, 4-methylpiperazin-1-yl group, 4-acetylpiperazin-1-yl group, morpholino group, 3-oxomorpholin-4-yl group, thiomorpholino group, 1,1-dioxoisothiazolidin-2-yl group, 2-oxooxazolidin-3-yl group, 3-oxopyrazolidin-1-yl group, 2-methyl-3-oxopyrazolidin-1-yl group, 2-pyridyl group, 2-thiazolyl group, 1,2,4-oxadiazol-3-yl group, 5-methyl-1,2,4-oxadiazol-3-yl group and the like can be mentioned.

Ring A is preferably a monocyclic heterocyclic group containing at least one nitrogen atom, said monocyclic heterocyclic group is optionally substituted by 1 to 5 substituents selected from group A and bonded, via the nitrogen atom, to the benzene ring represented by

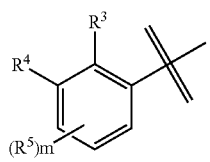

in the formula [I].

As ring A, a heterocyclic group selected from 1-pyrrolidinyl group, 2-oxopyrrolidin-1-yl group, piperidino group, 2-oxopiperidin-1-yl group, 1-piperazinyl group, morpholino group, 3-oxomorpholin-4-yl group, thiomorpholino group, 1,1-dioxoisothiazolidin-2-yl group, 2-oxooxazolidin-3-yl group and 3-oxopyrazolidin-1-yl group, wherein the heterocyclic group is optionally substituted by 1 to 5 substituents selected from group A, is more preferable. For ring A, a heterocyclic group selected from 2-oxopyrrolidin-1-yl group, 2-oxopiperidin-1-yl group, morpholino group and 3-oxomorpholin-4-yl group, wherein the heterocyclic group is optionally substituted by 1 to 5 substituents selected from group A, is further more preferable.

As ring A, one of the most preferable embodiment is 2-oxopyrrolidin-1-yl group, the other most preferable embodiment is morpholino group.

As another preferable embodiment for ring A, a heterocyclic group selected from 1-pyrrolidinyl group, 2-oxopyrrolidin-1-yl group, piperidino group, 2-oxopiperidin-1-yl group, 1-piperazinyl group, morpholino group, 3-oxomorpholin-4-yl group, thiomorpholino group, 1,1-dioxoisothiazolidin-2-yl group, 2-oxooxazolidin-3-yl group, 3-oxopyrazolidin-1-yl group, 2-pyridyl group, 2-thiazolyl group and 1,2,4-oxadiazol-3-yl group, wherein the heterocyclic group is optionally substituted by 1 to 5 substituents selected from group A can be mentioned.

As the group A for ring A, halogen atom, a $C_{1-4}$ alkyl group, —$OR^{a1}$ and —$COR^{a2}$, wherein $R^{a1}$ and $R^{a2}$ are the same or different and each is a hydrogen atom or a $C_{1-4}$ alkyl group are preferable.

Preferably, $R^1$ is a $C_{1-6}$ alkyl group optionally substituted by 1 to 3 substituents selected from group B, and $R^6$ is a hydrogen atom. More preferably, $R^1$ is a $C_{1-6}$ alkyl group optionally substituted by 1 to 3 of —$OR^{b1}$, wherein $R^{b1}$ is a hydrogen atom or a $C_{1-4}$ alkyl group, and $R^6$ is a hydrogen atom.

$R^2$ is preferably, a $C_{1-4}$ alkyl group or —$OR^{11}$, wherein $R^{11}$ is a hydrogen atom or a $C_{1-4}$ alkyl group. As another preferable embodiment for $R^2$, a hydrogen atom can be mentioned.

Preferably, $R^3$ and $R^4$ are the same or different and each is a halogen atom. More preferably, $R^3$ is a fluorine atom and $R^4$ is a chlorine atom.

m is preferably 0 or 1, more preferably 1. When m is 1, then $R^5$ is preferably a halogen atom, more preferably a fluorine atom.

As the group represented by the formula

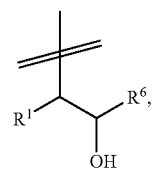

preferably

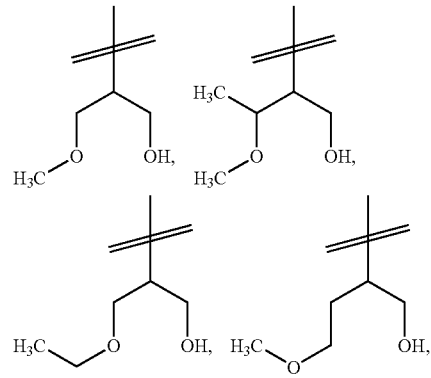

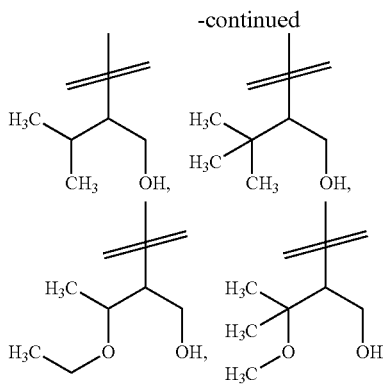

and the like, can be mentioned. When R¹ is other than a hydrogen atom, then R¹ is preferably a group having a configuration represented by

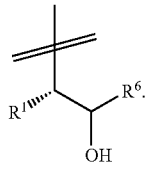

As a compound represented by the formula [I] or a pharmaceutically acceptable salt thereof, the following compounds are preferable.

6-[3-chloro-2-fluoro-5-(morpholin-4-yl)benzyl]-1-((R)-1-ethoxymethyl-2-hydroxyethyl)-7-ethyl-4-oxo-1,4-dihydroquinoline-3-carboxylic acid (Example 1), 6-[3-chloro-2-fluoro-5-(2-oxopyrrolidin-1-yl)benzyl]-1-((S)-1-hydroxymethyl-2-methylpropyl)-7-methoxy-4-oxo-1,4-dihydroquinoline-3-carboxylic acid (Example 2), 6-[3-chloro-2-fluoro-5-(pyrrolidin-1-yl)benzyl]-1-((S)-1-hydroxymethyl-2-methylpropyl)-7-methoxy-4-oxo-1,4-dihydroquinoline-3-carboxylic acid (Example 3), 6-[3-chloro-2-fluoro-5-(2-oxooxazolidin-3-yl)benzyl]-1-((S)-1-hydroxymethyl-2-methylpropyl)-7-methoxy-4-oxo-1,4-dihydroquinoline-3-carboxylic acid (Example 4), 6-[3-chloro-2-fluoro-5-(morpholin-4-yl)benzyl]-1-((S)-1-hydroxymethyl-2-methylpropyl)-7-methoxy-4-oxo-1,4-dihydroquinoline-3-carboxylic acid (Example 5), 6-[3-chloro-2-fluoro-5-(piperidin-1-yl)benzyl]-1-((S)-1-hydroxymethyl-2-methylpropyl)-7-methoxy-4-oxo-1,4-dihydroquinoline-3-carboxylic acid (Example 6), 6-[3-chloro-2-fluoro-5-(2-oxopiperidin-1-yl)benzyl]-1-((S)-1-hydroxymethyl-2-methylpropyl)-7-methoxy-4-oxo-1,4-dihydroquinoline-3-carboxylic acid (Example 7), 6-[3-chloro-2-fluoro-5-((R)-3-hydroxypyrrolidin-1-yl)benzyl]-1-((S)-1-hydroxymethyl-2-methylpropyl)-7-methoxy-4-oxo-1,4-dihydroquinoline-3-carboxylic acid (Example 8), 6-[3-chloro-2-fluoro-5-((S)-3-hydroxypyrrolidin-1-yl)benzyl]-1-((S)-1-hydroxymethyl-2-methylpropyl)-7-methoxy-4-oxo-1,4-dihydroquinoline-3-carboxylic acid (Example 9), 6-[3-chloro-2-fluoro-5-(2-methyl-3-oxopyrazolidin-1-yl)benzyl]-1-((S)-1-hydroxymethyl-2-methylpropyl)-7-methoxy-4-oxo-1,4-dihydroquinoline-3-carboxylic acid (Example 10), 6-[5-(4-acetylpiperazin-1-yl)-3-chloro-2-fluorobenzyl]-1-((S)-1-hydroxymethyl-2-methylpropyl)-7-methoxy-4-oxo-1,4-dihydroquinoline-3-carboxylic acid (Example 11), 6-[3-chloro-5-(3,3-difluoropyrrolidin-1-yl)-2-fluorobenzyl]-1-((S)-1-hydroxymethyl-2-methylpropyl)-7-methoxy-4-oxo-1,4-dihydroquinoline-3-carboxylic acid (Example 12), 6-[3-chloro-2-fluoro-5-((R)-3-fluoropyrrolidin-1-yl)benzyl]-1-((S)-1-hydroxymethyl-2-methylpropyl)-7-methoxy-4-oxo-1,4-dihydroquinoline-3-carboxylic acid (Example 13), 6-[3-chloro-2-fluoro-5-((S)-3-fluoropyrrolidin-1-yl)benzyl]-1-((S)-1-hydroxymethyl-2-methylpropyl)-7-methoxy-4-oxo-1,4-dihydroquinoline-3-carboxylic acid (Example 14), 6-[3-chloro-2-fluoro-5-(morpholin-4-yl)benzyl]-1-((1R,2R)-1-hydroxymethyl-2-methoxypropyl)-7-methoxy-4-oxo-1,4-dihydroquinoline-3-carboxylic acid (Example 15), 6-[3-chloro-2,4-difluoro-5-(morpholin-4-yl)benzyl]-1-((S)-1-hydroxymethyl-2-methylpropyl)-7-methoxy-4-oxo-1,4-dihydroquinoline-3-carboxylic acid (Example 16), 6-[3-chloro-2-fluoro-5-(morpholin-4-yl)benzyl]-1-((S)-1-hydroxymethyl-2,2-dimethylpropyl)-7-methoxy-4-oxo-1,4-dihydroquinoline-3-carboxylic acid (Example 17), 6-[3-chloro-2-fluoro-5-(morpholin-4-yl)benzyl]-7-ethyl-1-((S)-1-hydroxymethyl-2,2-dimethylpropyl)-4-oxo-1,4-dihydroquinoline-3-carboxylic acid (Example 18), 6-[3-chloro-2-fluoro-5-(morpholin-4-yl)benzyl]-1-((R)-1-ethoxymethyl-2-hydroxyethyl)-7-methoxy-4-oxo-1,4-dihydroquinoline-3-carboxylic acid (Example 19), 6-[3-chloro-2-fluoro-5-(morpholin-4-yl)benzyl]-7-ethyl-1-[(R)-2-hydroxy-1-(methoxymethyl)ethyl]-4-oxo-1,4-dihydroquinoline-3-carboxylic acid (Example 20), 6-[3-chloro-5-(1,1-dioxoisothiazolidin-2-yl)-2-fluorobenzyl]-1-((S)-1-hydroxymethyl-2-methylpropyl)-7-methoxy-4-oxo-1,4-dihydroquinoline-3-carboxylic acid (Example 21), 6-[3-chloro-2-fluoro-5-(morpholin-4-yl)benzyl]-1-[(R)-2-hydroxy-1-(methoxymethyl)ethyl]-7-methoxy-4-oxo-1,4-dihydroquinoline-3-carboxylic acid (Example 22), 6-[3-chloro-2-fluoro-5-(morpholin-4-yl)benzyl]-7-ethyl-1-((S)-1-hydroxymethyl-2-methylpropyl)-4-oxo-1,4-dihydroquinoline-3-carboxylic acid (Example 23), 6-[3-chloro-2-fluoro-5-(2-oxopyrrolidin-1-yl)benzyl]-7-ethyl-1-((S)-1-hydroxymethyl-2-methylpropyl)-4-oxo-1,4-dihydroquinoline-3-carboxylic acid (Example 24), 6-[3-chloro-2,4-difluoro-5-(2-oxopyrrolidin-1-yl)benzyl]-1-((S)-1-hydroxymethyl-2-methylpropyl)-7-methoxy-4-oxo-1,4-dihydroquinoline-3-carboxylic acid (Example 25), 6-[3-chloro-2,4-difluoro-5-(2-oxopyrrolidin-1-yl)benzyl]-7-ethyl-1-((S)-1-hydroxymethyl-2-methylpropyl)-4-oxo-1,4-dihydroquinoline-3-carboxylic acid (Example 26), 6-[3-chloro-2-fluoro-5-(thiomorpholin-4-yl)benzyl]-1-((S)-1-hydroxymethyl-2-methylpropyl)-7-methoxy-4-oxo-1,4-dihydroquinoline-3-carboxylic acid (Example 27), 6-[3-chloro-2-fluoro-5-(morpholin-4-yl)benzyl]-1-((1R,2S)-1-hydroxymethyl-2-methoxypropyl)-7-methoxy-4-oxo-1,4-dihydroquinoline-3-carboxylic acid (Example 28), 6-[3-chloro-2-fluoro-5-(morpholin-4-yl)benzyl]-1-((S)-1-hydroxymethyl-3-methoxypropyl)-7-methoxy-4-oxo-1,4-dihydroquinoline-3-carboxylic acid (Example 29), 6-[3-chloro-2-fluoro-5-(2-oxopyrrolidin-1-yl)benzyl]1-[(R)-2-hydroxy-1-(methoxymethyl)ethyl]-7-methoxy-4-oxo-1,4-dihydroquinoline-3-carboxylic acid (Reference example 30), 6-[3-chloro-2,4-difluoro-5-(2-oxopyrrolidin-1-yl)benzyl]-1-[(R)-2-hydroxy-1-(methoxymethyl)ethyl]-7-methoxy-4-oxo-1,4-dihydroquinoline-3-carboxylic acid (Reference example 31), 6-[3-chloro-2-fluoro-5-(4-hydroxypiperidin-1-yl)benzyl]-1-((S)-1-hydroxymethyl-2-methylpropyl)-7-methoxy-4-oxo-1,4-dihydroquinoline-3-carboxylic acid (Example 32), 6-[3-chloro-2-fluoro-5-(4-methylpiperazin-1-yl)benzyl]-1-((S)-1-hydroxymethyl-2-methylpropyl)-7-methoxy-4-oxo-1,4-dihydroquinoline-3-carboxylic acid (Reference example 33), 6-[3-chloro-2-fluoro-5-(morpholin-4-yl)benzyl]-7-ethyl-1-((1R,2R)-1-hydroxymethyl-2-methoxypropyl)-4-oxo-1,4-dihydroquinoline-3-carboxylic acid (Example 34), 6-[3-chloro-2-fluoro-5-(morpholin-4-yl)benzyl]-7-ethyl-1-((1R,2S)-1-hydroxymethyl-2-methoxypropyl)-4-oxo-1,4-dihydroquinoline-3-carboxylic acid (Example 35), 6-[3-chloro-2-fluoro-5-(pyridin-2-yl)benzyl]-1-((S)-1-hydroxymethyl-2-methylpropyl)-7-methoxy-4-oxo-1,4-dihydroquinoline-3-carboxylic acid (Example 36), 6-[3-chloro-2-fluoro-5-(thiazol-2-yl)benzyl]-1-((S)-1-hydroxymethyl-2-methylpropyl)-7-methoxy-4-oxo-1,4-dihydroquinoline-3-carboxylic acid (Example 37), 6-[3-chloro-2-fluoro-5-(morpholin-4-yl)benzyl]-1-[(1R,2R)-2-ethoxy-1-(hydroxymethyl)propyl]-7-ethyl-4-oxo-1,4-dihydroquinoline-3-carboxylic acid (Example 38), 6-[3-chloro-2-fluoro-5-(2-oxopyrrolidin-1-yl)benzyl]-1-((R)-1-ethoxymethyl-2-hydroxyethyl)-7-methoxy-4-oxo-1,4-dihydroquinoline-3-carboxylic acid (Example 39), 6-[3-chloro-2-fluoro-5-(2-oxopyrrolidin-1-yl)benzyl]-1-[(1R,2R)-2-ethoxy-1-(hydroxymethyl)propyl]-7-ethyl-4-oxo-1,4-dihydroquinoline-3-carboxylic acid (Example 40), 6-[3-chloro-2-fluoro-5-(2-oxopyrrolidin-1-yl)benzyl]-7-ethyl-1-((1R,2R)-1-hydroxymethyl-2-methoxypropyl)-4-oxo-1,4-dihydroquinoline-3-carboxylic acid (Example 41), 6-[3-chloro-2-fluoro-5-(morpholin-4-yl)benzyl]-1-((R)-1-hydroxymethyl-2-methoxy-2-methylpropyl)-7-methoxy-4-oxo-1,4-dihydroquinoline-3-carboxylic acid (Example 42), 6-[3-chloro-2-fluoro-5-(morpholin-4-yl)benzyl]-7-ethyl-1-((R)-1-hydroxymethyl-2-methoxy-2-methylpropyl)-4-oxo-1,4-dihydroquinoline-3-carboxylic acid (Example 43), 6-[3-chloro-2-fluoro-5-(morpholin-4-yl)benzyl]-7-ethyl-1-((S)-1-hydroxymethyl-3-methoxypropyl)-4-oxo-1,4-dihydroquinoline-3-carboxylic acid (Example 44), 6-[3-chloro-2-fluoro-5-(2-oxopyrrolidin-1-yl)benzyl]-1-((S)-1-hydroxymethyl-2,2-dimethylpropyl)-7-methoxy-4-oxo-1,4-dihydroquinoline-3-carboxylic acid (Example 45), 6-[3-chloro-2,4-difluoro-5-(2-oxopyrrolidin-1-yl)benzyl]-1-((S)-1-hydroxymethyl-2,2-dimethylpropyl)-7-methoxy-4-oxo-1,4-dihydroquinoline-3-carboxylic acid (Example 46), 6-[3-chloro-2-fluoro-5-(2-oxopyrrolidin-1-yl)benzyl]-1-((S)-1-hydroxymethyl-3-methoxypropyl)-7-methoxy-4-oxo-1,4-dihydroquinoline-3-carboxylic acid (Example 47), 6-[3-chloro-2-fluoro-5-(2-oxopyrrolidin-1-yl)benzyl]-1-((1R,2R)-1-hydroxymethyl-2-methoxypropyl)-7-methoxy-4-oxo-1,4-dihydroquinoline-3-carboxylic acid (Example 48), 6-[3-chloro-2,4-difluoro-5-(morpholin-4-yl)benzyl]-1-((S)-1-hydroxymethyl-2,2-dimethylpropyl)-7-methoxy-4-oxo-1,4-dihydroquinoline-3-carboxylic acid (Example 49), 6-[3-chloro-2-fluoro-5-(morpholin-4-yl)benzyl]-1-[(1R,2R)-2-ethoxy-1-(hydroxymethyl)propyl]-7-methoxy-4-oxo-1,4-dihydroquinoline-3-carboxylic acid (Example 50), 6-[3-chloro-2-fluoro-5-(2-oxopyrrolidin-1-yl)benzyl]-1-((S)-1-hydroxymethyl-2,2-dimethylpropyl)-4-oxo-1,4-dihydroquinoline-3-carboxylic acid (Example 51), 6-[3-chloro-2-fluoro-5-(2-oxopyrrolidin-1-yl)benzyl]-7-ethyl-1-((S)-1-hydroxymethyl-2,2-dimethylpropyl)-4-oxo-1,4-dihydroquinoline-3-carboxylic acid (Example 52), 6-[3-chloro-2-fluoro-5-(morpholin-4-yl)benzyl]-1-((S)-1-hydroxymethyl-2,2-dimethylpropyl)-4-oxo-1,4-dihydroquinoline-3-carboxylic acid (Example 53), 6-[3-chloro-2,4-difluoro-5-(2-oxopyrrolidin-1-yl)benzyl]-1-((S)-1-hydroxymethyl-2,2-dimethylpropyl)-4-oxo-1,4-dihydroquinoline-3-carboxylic acid (Example 54), 6-[3-chloro-2,4-difluoro-5-(2-oxopyrrolidin-1-yl)benzyl]-7-ethyl-1-((S)-1-hydroxymethyl-2,2-dimethylpropyl)-4-oxo-1,4-dihydroquinoline-3-carboxylic acid (Example 55), 6-[3-chloro-2,4-difluoro-5-(morpholin-4-yl)benzyl]-1-((S)-1-hydroxymethyl-2,2-dimethylpropyl)-4-oxo-1,4-dihydroquinoline-3-carboxylic acid (Example 56), 6-[3-chloro-2-fluoro-5-(5-methyl-1,2,4-oxadiazol-3-yl)benzyl]-1-((S)-1-hydroxymethyl-2-methylpropyl)-7-methoxy-4-oxo-1,4-dihydroquinoline-3-carboxylic acid (Example 57)

6-[3-chloro-2,4-difluoro-5-(3-oxomorpholin-4-yl)benzyl]-1-((S)-1-hydroxymethyl-2,2-dimethylpropyl)-4-oxo-1,4-dihydroquinoline-3-carboxylic acid (Example 58), 6-[3-chloro-2,4-difluoro-5-(morpholin-4-yl)benzyl]-1-((R)-1-hydroxymethyl-2,2-dimethylpropyl)-4-oxo-1,4-dihydroquinoline-3-carboxylic acid (Example 59).

The "pharmaceutically acceptable salt" may be any salt as long as it forms a nontoxic salt with a compound represented by the above-mentioned formula [I]. Examples thereof include a salt with an inorganic acid, a salt with an organic acid, a salt with an inorganic base, a salt with an organic base, a salt with an amino acid and the like.

As the salt with an inorganic acid, for example, salts with hydrochloric acid, nitric acid, sulfuric acid, phosphoric acid, hydrobromic acid and the like can be mentioned.

As the salt with an organic acid, for example, salts with oxalic acid, malonic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like can be mentioned.

As the salt with an inorganic base, for example, sodium salt, potassium salt, calcium salt, magnesium salt, ammonium salt and the like can be mentioned.

As the salt with an organic base, for example, salts with methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, morpholine, meglumine and the like can be mentioned.

As the salt with an amino acid, for example, salts with lysine, arginine, aspartic acid, glutamic acid and the like can be mentioned.

Each salt can be obtained by reacting a compound represented by the formula [I] with an inorganic base, an organic base, an inorganic acid, an organic acid or an amino acid according to a method known per se.

In the present invention, a pharmaceutically acceptable salt of a compound represented by the formula [I] is preferably a sodium salt or a potassium salt.

The "solvate" is a compound represented by the formula [I] or a pharmaceutically acceptable salt thereof, with which a molecule of a solvent is coordinated, and also encompasses hydrates (also referred to as water-containing compound). The solvate is preferably a pharmaceutically acceptable solvate, such as a monohydrate, a 1/2 hydrate, a dihydrate, a monohydrate of sodium salt, a monomethanolate, a monoethanolate, a monoacetonitrilate, a 2/3 ethanolate of dihydrochloride of the compound represented by the formula [I] and the like.

A solvate of a compound represented by the formula [I] or a pharmaceutically acceptable salt thereof can be obtained according to a method known per se.

In addition, there are various isomers of a compound represented by the above-mentioned formula [I]. For example, when an asymmetric carbon atom is present, an enantiomer and a diastereomer can be present as stereoisomers based thereon. Accordingly, all of such isomers and mixtures thereof are encompassed in the scope of the present invention. As the compound of the present invention, one isolated and purified from various isomers, by-products, metabolites or prodrugs is preferable, and one having a purity of not less than 90% is preferable and one having a purity of not less than 95% is more preferable.

A compound represented by the formula [I] may be a crystal or an amorphous form.

In addition, a compound represented by the formula [I] may be labeled with an isotope (e.g., $^3H$, $^{14}C$, $^{35}S$ etc.).

In the present invention, a prodrug of a compound represented by the formula [I] can also be a useful pharmaceutical agent.

By the "prodrug" is meant a derivative of the compound of the present invention, which has a chemically or metabolically decomposable group and which, after administration to a body, restores to the original compound to show its inherent efficacy, including a complex and a salt, not involving a covalent bond.

The prodrug is utilized, for example, for improving absorption by oral administration or targeting of a target site.

As the site to be modified, highly reactive functional groups in the compound of the present invention, such as hydroxyl group, carboxyl group, amino group, thiol group and the like, are mentioned.

Examples of the hydroxyl-modifying group include acetyl group, propionyl group, isobutyryl group, pivaloyl group, benzoyl group, 4-methylbenzoyl group, dimethylcarbamoyl group, sulfo group and the like. Examples of the carboxyl-modifying group include ethyl group, pivaloyloxymethyl group, 1-(acetyloxy)ethyl group, 1-(ethoxycarbonyloxy) ethyl group, 1-(cyclohexyloxycarbonyloxy)ethyl group, carboxymethyl group, (5-methyl-2-oxo-1,3-dioxol-4-yl)methyl group, phenyl group, o-tolyl group and the like. Examples of the amino-modifying group include hexylcarbamoyl group, 3-methylthio-1-(acetylamino)propylcarbonyl group, 1-sulfo-1-(3-ethoxy-4-hydroxyphenyl)methyl group, (5-methyl-2-oxo-1,3-dioxol-4-yl)methyl group and the like.

The compound of the present invention can be administered to a mammal (human, mouse, rat, hamster, rabbit, cat, dog, bovine, sheep, monkey etc.) and the like as an anti-HIV agent or composition, an integrase inhibitor, an antiviral agent and the like.

When the compound of the present invention is used as a pharmaceutical composition or preparation, it is generally admixed with pharmaceutically acceptable carriers, excipients, diluents, extending agents, disintegrants, stabilizers, preservatives, buffers, emulsifiers, flavoring agents, colorants, sweetening agents, thickeners, correctives, solubilizing agents, and other additives, that are known per se, such as water, vegetable oil, alcohol (e.g., ethanol, benzyl alcohol etc.), polyethylene glycol, glycerol triacetate, gelatin, carbohydrate (e.g., lactose, starch etc.), magnesium stearate, talc, lanolin, petrolatum and the like, formed into tablet, pill, powder, granule, suppository, injection, eye drop, liquid, capsule, troche, aerosol, elixir, suspension, emulsion, syrup and the like by a conventional method, and administered systemically or topically, and orally or parenterally.

While the dose varies depending on age, body weight, symptom, treatment effect, administration method and the like, it is generally 0.01 mg to 1 g once for an adult, which is given once to several times a day orally or in a dosage form of an injection such as intravenous injection and the like.

An anti-HIV agent is generally required to sustain its effect for a long time, so that can be effective not only for temporal suppression of viral growth but also prohibition of viral regrowth. This means that a prolonged administration is necessary and that a high single dose may be frequently inevitable to sustain effect for a longer period through the night. Such prolonged and high dose administration increases the risk of causing side effects.

In view of this, one of the preferable embodiments of the compound of the present invention is such compound permitting high absorption by oral administration, and such compound capable of maintaining blood concentration of the administered compound for an extended period of time.

In addition to the above-mentioned, as preferable embodiments of the compound of the present invention, a compound having fine pharmacological activity (e.g., a compound having strong HIV integrase inhibitory activity, a compound having high anti-HIV activity), a compound having fine bioavailability (e.g., a compound having high cell membrane permeability, a compound stable to metabolic enzyme, a compound with low binding ability to protein and the like), a highly safe compound (e.g., a compound showing low P450 (CYP)-inhibitory activity and the like) and the like can be mentioned.

Of the compounds of the present invention, a compound having high pharmacological activity (concretely, $IC_{50}$ of HIV integrase inhibitory activity is less than 0.1 µM, preferably less than 0.01 µM) and high oral absorption, whose blood concentration is maintained for a long time after administration, is more preferable.

Using the above-mentioned compound, dose and/or frequency of administration of the compound of the present invention to human are/is expected to be decreased. Preferable administration frequency is not more than twice a day, more preferably, not more than once a day (e.g., once a day, once in two days, etc.).

The novel 4-oxoquinoline compound of the present invention can be used for the improvement of viremia due to HIV and/or maintenance of improved condition thereof, treatment of virus infections, particularly, an HIV infectious disease and/or maintenance of improved condition thereof.

As an index of the "treatment", "improvement" or "effect", a decrease in the virus level or HIV RNA level in the body, particularly in blood, can be used.

By the "prophylaxis of AIDS" is meant, for example, administration of a pharmaceutical agent to an individual who tested HIV positive but has not yet developed the disease state of AIDS; administration of a pharmaceutical agent to an individual who shows an improved disease state of AIDS after treatment but who carries HIV still to be eradicated and whose relapse of AIDS is worried; administration of a pharmaceutical agent before infection with HIV out of a fear of possible infection; and the like.

Examples of the "other anti-HIV agents" and "other anti-HIV active substances" to be used for a multiple drug combination therapy include an anti-HIV antibody or other antibody, an HIV vaccine or other vaccine, immunostimulants such as interferon, interferon agonist and the like, a ribozyme against HIV, an HIV antisense drug, an HIV reverse transcriptase inhibitor, an HIV protease inhibitor, an HIV integrase inhibitor, an inhibitor of attachment between a receptor (CD4, CXCR4, CCR5 and the like) of a host cell recognized by virus and the virus (CCR5 antagonist and the like), a DNA polymerase inhibitor or DNA synthesis inhibitor, a pharmaceutical agent acting on HIVp24, an HIV fusion inhibitor, an IL-2 agonist or antagonist, a TNF-α antagonist, an α-glucosidase inhibitor, a purine nucleoside phosphorylase inhibitor, an apoptosis agonist or inhibitor, a cholinesterase inhibitor, an immunomodulator and the like can be mentioned.

Specific examples of the HIV reverse transcriptase inhibitor include Retrovir® (zidovudine), Epivir® (lamivudine), Zerit® (sanilvudine), Videx® (didanosine), Hivid® (zalcitabine), Ziagen® (abacavir sulfate), Viramune® (nevirapine), Stocrin® (efavirenz), Rescriptor® (delavirdine mesylate), Combivir® (zidovudine+lamivudine), Trizivir® (abacavir sulfate+lamivudine+zidovudine), Coactinon® (emivirine), Phosphonovir®, Coviracil®, alovudine (3'-fluoro-3'-deoxythymidine), Thiovir (thiophosphonoformic acid), Capravirin (5-[(3,5-dichlorophenyl)thio]-4-isopropyl-1-(4-pyridylmethyl)imidazole-2-methanol carbamic acid), Tenofovir disoproxil fumarate ((R)-[[2-(6-amino-9H-purin-9-yl)-1-methylethoxy]methyl]phosphonic acid bis(isopropoxycarbonyloxymethyl)ester fumarate), DPC-083 ((45)-6-chloro-4-[(1E)-cyclopropylethenyl]-3,4-dihydro-4-trifluoromethyl-2(1H)-quinazolinone), DPC-961 ((4S)-6-chloro-4-(cyclopropylethynyl)-3,4-dihydro-4-(trifluoromethyl)-2(1H)-quinazolinone), DAPD ((−)-β-D-2,6-diaminopurine dioxolane), Immunocal, MSK-055, MSA-254, MSH-143, NV-01, TMC-120, DPC-817, GS-7340, TMC-125, SPD-754, D-A4FC, capravirine, UC-781, emtricitabine, alovudine, Phosphazid, BCH-10618, DPC-083, Etravirine, BCH-13520, MIV-210, Abacavir sulfate/lamivudine, GS-7340, GW-5634, GW-695634 and the like, wherein (R) means a registered trademark (hereinafter the same) and the names of other pharmaceutical agents are general names.

Specific examples of the HIV protease inhibitor include Crixivan® (indinavir sulfate ethanolate), saquinavir, Invirase® (saquinavir mesylate), Norvir® (ritonavir), Viracept® (nelfinavir mesylate), lopinavir, Prozei® (amprenavir), Kaletra® (ritonavir+lopinavir), mozenavir dimesylate ([4R-(4α,5α,6β)]-1,3-bis[(3-aminophenyl)methyl]-hexahydro-5,6-dihydroxy-4,7-bis(phenylmethyl)-2H-1,3-diazepin-2-one dimethanesulfonate), tipranavir (3'-[(1R)-1-[(6R)-5,6-dihydro-4-hydroxy-2-oxo-6-phenylethyl-6-propyl-2H-pyran-3-yl]propyl]-5-(trifluoromethyl)-2-pyridinesulfonamide), lasinavir (N-[5(S)-(tert-butoxycarbonylamino)-4(S)-hydroxy-6-phenyl-2(R)-(2,3,4-trimethoxybenzyl)hexanoyl]-L-valine 2-methoxyethylenamide), KNI-272 ((R)—N-tert-butyl-3-[(2S,3S)-2-hydroxy-3-N-[(R)-2-N-(isoquinolin-5-yloxy-acetyl)amino-3-methylthiopropanoyl]amino-4-phenylbutanoyl]-5,5-dimethyl-1,3-thiazolidine-4-carboxamide), GW-433908, TMC-126, DPC-681, buckminsterfullerene, MK-944A (MK944 (N-(2(R)-hydroxy-1(S)-indanyl)-2(R)-phenylmethyl-4(S)-hydroxy-5-[4-(2-benzo[b]furanylmethyl)-2(S)-(tert-butylcarbamoyl)piperazin-1-yl]pentanamide)+indinavir sulfate), JE-2147 ([2(S)-oxo-4-phenylmethyl-3(S)-[(2-methyl-3-oxy)phenylcarbonylamino]-1-oxabutyl]-4-[(2-methylphenyl)methylamino]carbonyl-4(R)-5,5-dimethyl-1,3-thiazole), BMS-232632 (dimethyl (3S,8S,9S,12S)-3,12-bis(1,1-dimethylethyl)-8-hydroxy-4,11-dioxo-9-(phenylmethyl)-6-[[4-(2-pyridinyl)phenyl]methyl]-2,5,6,10,13-pentaazatetradecanedicarboxylate), DMP-850 ((4R,5S,6S,7R)-1-(3-amino-1H-indazol-5-ylmethyl)-4,7-dibenzyl-3-butyl-5,6-dihydroxyperhydro-1,3-diazepin-2-one), DMP-851, RO-0334649, Nar-DG-35, R-944, VX-385, TMC-114, Tipranavir, Fosamprenavir sodium, Fosamprenavir calcium, Darunavir, GW-0385, R-944, RO-033-4649 and AG-1859 and the like.

The HIV integrase inhibitor is exemplified by S-1360, L-870810 and the like, the DNA polymerase inhibitor or DNA synthesis inhibitor is exemplified by Foscavir®, ACH-126443 (L-2',3'-didehydro-dideoxy-5-fluorocytidine), entecavir ((1S,3S,4S)-9-[4-hydroxy-3-(hydroxymethyl)-2-methylenecyclopentyl]guanine), calanolide A ([10R-(10α,11β,12α)]-11,12-dihydro-12-hydroxy-6,6,10,11-tetramethyl-4-propyl-2H,6H,10H-benzo[1,2-b:3,4-b':5,6-b"]tripyran-2-one), calanolide B, NSC-674447 (1,1'-azobisformamide), Iscador (viscum alubm extract), Rubitecan and the like, the HIV antisense drug is exemplified by HGTV-43, GEM-92 and the like, the anti-HIV antibody or other antibody is exemplified by NM-01, PRO-367, KD-247, Cytolin®, TNX-355 (CD4 antibody), AGT-1, PRO-140 (CCR5 antibody), Anti-CTLA-4MAb and the like, the HIV vaccine or other vaccine is exemplified by ALVAC®, AIDSVAX®, Remune®, HIV gp41 vaccine, HIV gp120 vaccine, HIV gp140 vaccine, HIV gp160 vaccine, HIV p17 vaccine, HIV p24 vaccine, HIV p55 vaccine, AlphaVax Vector System, canarypox gp160 vaccine, AntiTat, MVA-F6 Nef vaccine, HIV rev vaccine, C4-V3 peptide, p2249f, VIR-201, HGP-30W, TBC-3B, PARTICLE-3B, Antiferon (interferon-α vaccine) and the like, the interferon or interferon agonist is exemplified by Sumiferon®, MultiFeron®, interferon-τ, Reticulose, human leukocyte interferon α and the like, the CCR5 antagonist is exemplified by SCH-351125 and the like, the pharmaceutical agent acting on HIV p24 is exemplified by GPG-NH2 (glycyl-prolyl-glycinamide) and the like, the HIV fusion inhibitor is exemplified by FP-21399 (1,4-bis[3-[(2,4-dichlorophenyl)carbonylamino]-2-oxo-5,8-disodium sulfonyl]naphthyl-2,5-dimethoxyphenyl-1,4-dihydrazone), T-1249, Synthetic Polymeric Construction No3, pentafuside, FP-21399, PRO-542, Enfuvirtide and the like, the IL-2 agonist or antagonist is exemplified by interleukin-2, Imunace®, Proleukin®, Multikine®, Ontak® and the like, the TNF-α antagonist is exemplified by Thalomid® (thalidomide), Remicade® (infliximab), curdlan sulfate, the α-glucosidase inhibitor is exemplified by Bucast® and the like, the purine nucleoside phosphorylase inhibitor is exemplified by peldesine (2-amino-4-oxo-3H,5H-7-[(3-pyridyl)methyl]pyrrolo[3,2-d]pyrimidine) and the like, the apoptosis agonist or inhibitor is exemplified by Arkin Z®, Panavir®, Coenzyme Q10 (2-deca(3-methyl-2-butenylene)-5,6-dimethoxy-3-methyl-p-benzoquinone) and the like, the cholinesterase inhibitor is exemplified by Cognex® and the like, and the immunomodulator is exemplified by Immunox®, Prokine®, Met-enkephalin (6-de-L-arginine-7-de-L- arginine-8-de-L-valinamide-adrenorphin), WF-10 (10-fold dilute tetrachlorodecaoxide solution), Perthon, PRO-542, SCH-D, UK-427857, AMD-070, AK-602 and the like.

In addition, Neurotropin®, Lidakol®, Ancer 20®, Ampligen®, Anticort®, Inactivin®, PRO-2000, Rev M10 gene, HIV specific cytotoxic T cell (CTL immunotherapy, ACTG protocol 080 therapy, CD4-ζ gene therapy), SCA binding protein, RBC-CD4 complex, Motexafin gadolinium, GEM-92, CNI-1493, (±)-FTC, Ushercell, D2S, BufferGel®, VivaGel®, Glyminox vaginal gel, sodium lauryl sulfate, 2F5, 2F5/2G12, VRX-496, Ad5gag2, BG-777, IGIV-C, BILR-255 and the like are exemplified.

As the "other anti-HIV agents" and "other anti-HIV activity substances" to be used for a multiple drug combination therapy with the compound of the present invention, preferred are an HIV reverse transcriptase inhibitor and an HIV protease inhibitor. Two or three, or even a greater number of pharmaceutical agents can be used in combination, wherein a combination of pharmaceutical agents having different action mechanisms is one of the preferable embodiments. In addition, selection of pharmaceutical agents free of side effect duplication is preferable.

Specific examples of the combination of pharmaceutical agents include a combination of a group consisting of efavirenz, tenofovir, emtricitabine, indinavir, nelfinavir, atazanavir, ritonavir+indinavir, ritonavir+lopinavir, ritonavir+saquinavir, didanosine+lamivudine, zidovudine+didanosine, stavudine+didanosine, zidovudine+lamivudine, stavudine+lamivudine and tenofovir+emtricitabine, and the compound [I] of the present invention (Guidelines for the Use of Antiretroviral Agents in HIV-Infected Adults and Adolescents. Aug. 13, 2001). Particularly preferred is a combined use of two agents with efavirenz, indinavir, nelfinavir, tenofovir, emtricitabine, zidovudine or lamivudine, and a combined use of three agents with zidovudine+lamivudine, tenofovir+lamivudine, tenofovir+zidovudine, tenofovir+efavirenz, tenofovir+nelfinavir, tenofovir+indinavir, tenofovir+emtricitabine, emtricitabine+lamivudine, emtricitabine+zidovudine, emtricitabine+efavirenz, emtricitabine+nelfinavir, emtricitabine+indinavir, nelfinavir+lamivudine, nelfinavir+zidovudine, nelfinavir+efavirenz, nelfinavir+indinavir, efavirenz+lamivudine, efavirenz+zidovudine or efavirenz+indinavir.

In the case of combined administration, the compound of the present invention can be administered simultaneously with a pharmaceutical agent to be used in combination (hereinafter combination drug) or administered at certain time intervals. In the case of combined administration, a pharmaceutical composition containing the compound of the present invention and a combination drug can be administered. Alternatively, a pharmaceutical composition containing the compound of the present invention and a pharmaceutical composition containing a combination drug may be administered separately. The administration route of the compound of the present invention and that of the combination drug may be the same or different.

In the case of a combined administration, the compound of the present invention can be administered once a day or several times a day in a single dose of 0.01 mg to 1 g, or may be administered at a smaller dose. The combination drug can be administered at a dose generally used for the prevention or treatment of an HIV infectious disease, for example, at a single dose of 0.01 mg to 0.3 g. Alternatively, it may be administered in a smaller dose.

Some examples of the production method of the compound used for embodiment of the present invention are shown in the following. However, the production method of the compound of the present invention is not limited to these examples.

Even in the absence of description in the production method, efficient production can be afforded by designs such as introducing, where necessary, a protecting group into a functional group followed by deprotection in a subsequent step; subjecting a functional group to each step as a precursor and converting the group to a desired functional group in a suitable step; exchanging the order of respective production methods and steps; and the like.

The work-up treatment in each step can be applied by a typical method, wherein isolation and purification is performed by selecting or combining conventional methods, as necessary, such as crystallization, recrystallization, distillation, partitioning, silica gel chromatography, preparative HPLC and the like.

Production Method 1

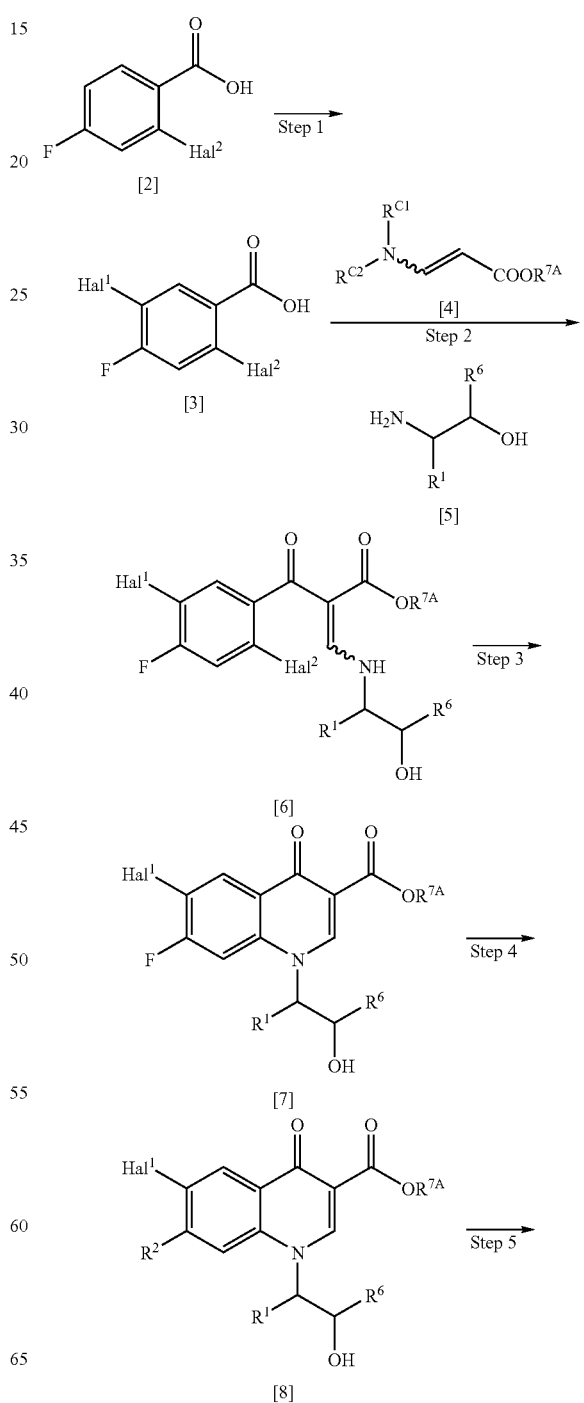

-continued

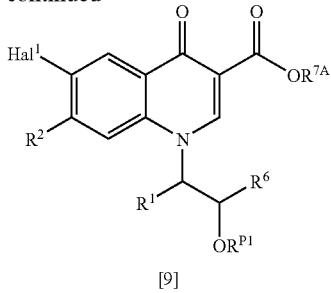

[9]

wherein $Hal^1$ is a halogen atom, preferably a bromine atom or an iodine atom, $Hal^2$ is a halogen atom, preferably a fluorine atom or a chlorine atom, $R^{C1}$ and $R^{C2}$ are the same or different each is a $C_{1-4}$ alkyl group such as methyl group, ethyl group and the like, $R^{7A}$ is a carboxyl-protecting group such as a $C_{1-4}$ alkyl group (e.g., methyl group, ethyl group etc.), benzyl group and the like, $R^{P1}$ is a hydroxyl-protecting group such as acetyl group, methoxycarbonyl group, methoxymethyl group, methoxyethoxymethyl group, trimethylsilyl group, tert-butyldimethylsilyl group, tert-butyldiphenylsilyl group and the like, and the other symbols are as defined above.

Step 1

Compound [3] can be obtained from compound [2] by conventional halogenation.

For example, compound [3] can be obtained by reacting compound [2] with a halogenating agent such as bromine, N-bromosuccinimide, N-iodosuccinimide and the like under cooling to heating in a solvent such as trifluoromethanesulfonic acid, acetic acid, concentrated sulfuric acid, dimethylformamide and the like.

Step 2

An acid halide can be obtained from compound [3] according to a conventional method, for example, by reacting compound [3] with a halogenating agent such as oxalyl chloride, thionyl chloride and the like under cooling to heating in a solvent such as a hydrocarbon solvent (e.g., toluene, xylene etc.); a halogenated hydrocarbon solvent (e.g., dichloromethane, chloroform, carbon tetrachloride, 1,2-dichloroethane etc.); an ester solvent (e.g., ethyl acetate, etc.) and the like.

For example, when thionyl chloride is used as a halogenating agent, a catalytic amount of dimethylformamide can be added.

Compound [6] can be obtained by reacting the acid halide with compound [4] in a solvent, at room temperature to under heating, in the presence of a base such as triethylamine, diisopropylethylamine, potassium carbonate, pyridine and the like, and reacting the resulting compound with compound [5] at room temperature to under heating. Compound [6] may be E form, Z form, or a mixture thereof.

As the solvent, a hydrocarbon solvent such as benzene, toluene, hexane, xylene and the like; a halogenated hydrocarbon solvent such as dichloromethane, chloroform, carbon tetrachloride, 1,2-dichloroethane and the like; an ether solvent such as 1,4-dioxane, diethyl ether, 1,2-dimethoxyethane, tetrahydrofuran and the like; a polar solvent such as acetonitrile and the like; an ester solvent such as ethyl acetate and the like; a mixed solvent thereof and the like can be mentioned.

Alternatively, compound [6] can also be obtained by reacting the acid halide with ethyl malonate and dimethylformamide dimethyl acetal in two steps instead of compound [4], and reacting the resulting compound with compound [5].

Step 3

Compound [7] can be obtained by subjecting compound [6] to cyclization in the presence of a base such as sodium carbonate, potassium carbonate, sodium hydroxide, potassium hydroxide, lithium hydroxide, potassium tert-butoxide, sodium hydride, potassium hydride and the like in a solvent.

As one of preferable production methods, compound [7] can be obtained by subjecting compound [6] to cyclization at room temperature to under heating in a solvent in the presence of 1,8-diazabicyclo[5.4.0]-7-undecene.

As the solvent, a hydrocarbon solvent such as benzene, toluene, hexane, xylene and the like; a halogenated hydrocarbon solvent such as dichloromethane, chloroform, carbon tetrachloride, 1,2-dichloroethane and the like; an ether solvent such as 1,4-dioxane, diethyl ether, 1,2-dimethoxyethane, tetrahydrofuran and the like; a polar solvent such as dimethylformamide, dimethyl sulfoxide, acetonitrile and the like; a mixed solvent thereof and the like can be mentioned.

Step 4

Compound [8] can be obtained by subjecting compound [7] to alkoxylation reaction to introduce $R^2$ according to a conventional method.

For example, when $R^2$ is —$OR^{11'}$ (wherein $R^{11'}$ is a $C_{1-4}$ alkyl group), compound [8] can be obtained by reacting compound [7] with a metal alkoxide under heating in an alcohol solvent such as methanol, ethanol, propanol, butanol and the like.

A solvent and a metal alkoxide corresponding to the desired alkoxy group are to be selected. When $R^2$ is methoxy group, the reaction can be carried out with sodium methoxide or potassium methoxide in methanol solvent. When $R^2$ is ethoxy group, the reaction can be carried out with sodium ethoxide or potassium ethoxide in ethanol solvent.

Compound [8] can also be obtained, without this step, by using a compound wherein the fluorine atom of compound [2] or compound [3] is replaced by $R^2$.

Step 5

Compound [9] can be obtained by introducing a protecting group to the hydroxyl group of compound [8] according to a conventional method.

Alternatively, compound [9] can be also obtained by introducing a protecting group to the hydroxyl group of compound [6] according to a conventional method, subjecting the resulting compound to cyclization in the same manner as in Step 3, and subjecting the resulting compound to alkoxylation in the same manner as in Step 4.

For example, when $R^{P1}$ is a tert-butyldimethylsilyl group, compound [8] can be reacted with tert-butyldimethylsilyl chloride in dimethylformamide or toluene solvent in the presence of imidazole at room temperature.

When $R^{P1}$ is methoxycarbonyl group, compound [8] can be reacted with methyl chlorocarbonate in chloroform solvent in the presence of pyridine under cooling to room temperature.

In the present production method, compound [3], compound [6], compound [7], compound [8] and compound [9] wherein $R^2$ is a hydrogen atom or methoxy group can be also obtained using a compound wherein the fluorine atom of compound [2] is replaced by a hydrogen atom or methoxy group, instead of compound [2].

Production Method 2

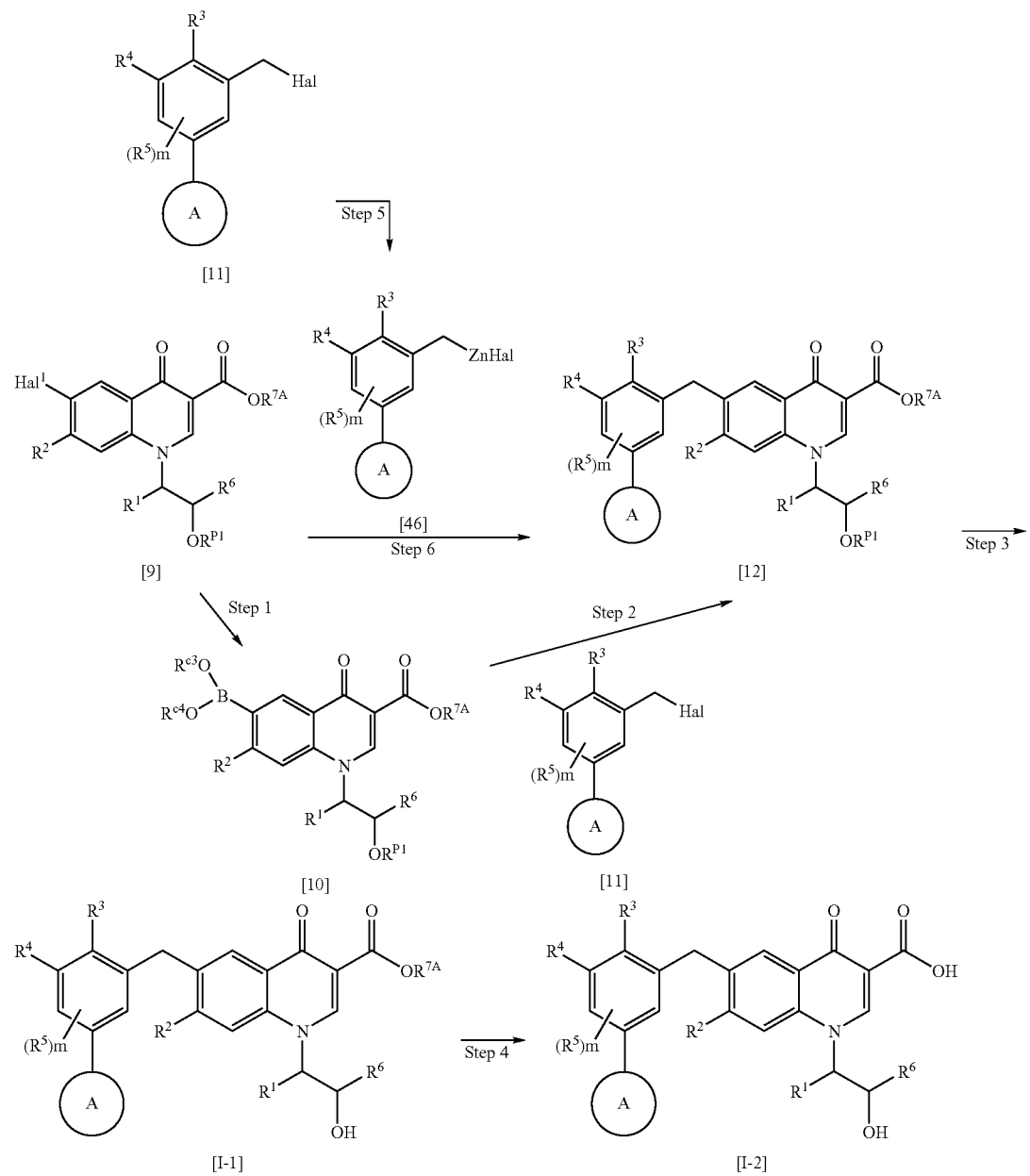

wherein Hal is a halogen atom such as a chlorine atom, a bromine atom and the like, —B(OR$^{C3}$)(OR$^{C4}$) is —B(OH)$_2$, —B(OCH$_3$)$_2$, —B(OCH(CH$_3$)$_2$)$_2$, 4,4,5,5-tetramethyl-1,3,2-dioxaborolan-2-yl group, 5,5-dimethyl-1,3,2-dioxaborinan-2-yl group and the like, and the other symbols are as defined above.

Step 1

Compound [10] can be obtained by reacting compound [9] with pinacolborane, boric acid ester or diboron ester in the presence of a base and a catalyst under argon or nitrogen atmosphere and under heating.

As the diboron ester, bis(neopentylglycolato)diboron, bis(pinacolato)diboron and the like can be mentioned.

As the catalyst, a palladium catalyst such as Pd(PPh$_3$)$_4$, PdCl$_2$(dppb), PdCl$_2$(dppf), PdCl$_2$(dppf)CH$_2$Cl$_2$, PdCl$_2$(PPh$_3$)$_2$, Pd (OAc)$_2$, PdCl$_2$, palladium black, palladium-carbon, and the like can be mentioned.

As the base, generally, ethylenediamine, sodium carbonate, barium hydroxide, potassium phosphate, cesium carbonate, sodium hydrogen carbonate, sodium tert-butoxide, potassium tert-butoxide, triethylamine, potassium acetate and the like can be mentioned.

As a ligand, triphenylphosphine, tri(2-tolyl)phosphine, 2-(dicyclohexylphosphino)biphenyl and the like can be added.

Alternatively, compound [9] can be reacted with boric acid ester such as triisopropyl borate, trimethyl borate and the like, in the presence of n-butyllithium.

As the solvent, dimethyl sulfoxide, 1,4-dioxane, tetrahydrofuran, toluene, 1,2-dimethoxyethane, water and the like can be mentioned.

Step 2

Compound [12] can be obtained by subjecting compound [10] and compound [11] to Suzuki reaction.

For example, compound [12] can be obtained by reacting compound [10] with compound [11] in a solvent such as dimethylformamide, acetonitrile, an alcohol solvent (e.g., methanol, ethanol etc.), 1,2-dimethoxyethane, tetrahydrofuran, toluene, water, a mixed solvent thereof and the like, in the presence of a catalyst such as a palladium catalyst (e.g., tetrakis(triphenylphosphine)palladium, dichlorobis(triphenylphosphine)palladium(II), palladium acetate-triphenylphosphine etc.), a nickel catalyst (e.g., nickel chloride, 1,3-bis(diphenylphosphino)propane nickel(II) chloride etc.) and in the presence of a base such as sodium carbonate, potassium carbonate, potassium hydrogen carbonate, sodium hydrogen carbonate, potassium phosphate, triethylamine, sodium hydrogen phosphate, cesium carbonate and the like, at room temperature to under heating.

The reactivity may be increased by the addition of lithium chloride and the like.

Step 3

Compound [I-1] can be obtained by eliminating the hydroxyl-protecting group of compound [12] according to a conventional method.

For example, when $R^{P1}$ is acetyl group or methoxycarbonyl group, the deprotection can be carried out by treatment such as heating compound [12] with concentrated hydrochloric acid; heating compound [12] in concentrated ammonia, and the like.

For example, when $R^{P1}$ is tert-butyldimethylsilyl group, the deprotection can be carried out by methods such as treating compound [12] with tetrabutylammonium fluoride in tetrahydrofuran at room temperature; treating compound [12] with sodium hydroxide in tetrahydrofuran; treating compound [12] with acetic acid-water-tetrahydrofuran at room temperature to under heating, and the like.

When $R^{P1}$ is acetyl group or methoxycarbonyl group, compound [I-2] can be obtained by reacting compound [12] with a base such as sodium hydroxide, potassium hydroxide and the like under heating.

Step 4

Compound [I-2] can be obtained by subjecting compound [I-1] to hydrolysis in a solvent at room temperature to under heating, under basic condition such as with sodium hydroxide, potassium hydroxide, lithium hydroxide and the like or under acidic condition such as with hydrochloric acid, sulfuric acid and the like.

As the solvent, an alcohol solvent such as methanol, ethanol, n-propanol, isopropanol and the like; a hydrocarbon solvent such as benzene, toluene, hexane, xylene and the like; an ether solvent such as 1,4-dioxane, diethyl ether, 1,2-dimethoxyethane, tetrahydrofuran and the like; water; a mixed solvent thereof and the like can be mentioned.

Step 5

Compound [46] can be obtained by reacting 1,2-dibromoethane with zinc powder in a solvent under heating, reacting the resulting compound with trimethylsilyl chloride, and adding a solution of compound [11] to the reaction mixture to allow reaction.

As the solvent, an ether solvent such as 1,4-dioxane, 1,2-dimethoxyethane, tetrahydrofuran etc.; a hydrocarbon solvent such as benzene, toluene, hexane, xylene, etc.; and the like can be mentioned.

Step 6

Compound [12] can be obtained by reacting compound [46] with compound [9] under cooling to heating in a solvent in the presence of a catalyst and, where necessary, in the presence of a ligand such as triphenylphosphine, tri(2-furyl)phosphine and the like.

As the catalyst, a palladium catalyst such as bis(dibenzylideneacetone)palladium, tris(dibenzylideneacetone)dipalladium, dichlorobis(triphenylphosphine)palladium, dichlorobis(benzonitrile)palladium, dichloroethylenediaminepalladium, palladium acetate, tetrakis(triphenylphosphine)palladium and the like; a nickel catalyst and the like can be mentioned.

As the solvent, an ether solvent such as 1,4-dioxane, 1,2-dimethoxyethane, tetrahydrofuran, etc.; a hydrocarbon solvent such as benzene, toluene, hexane, xylene, etc.; and the like can be mentioned.

Production Method 3

Production example of compound [11]

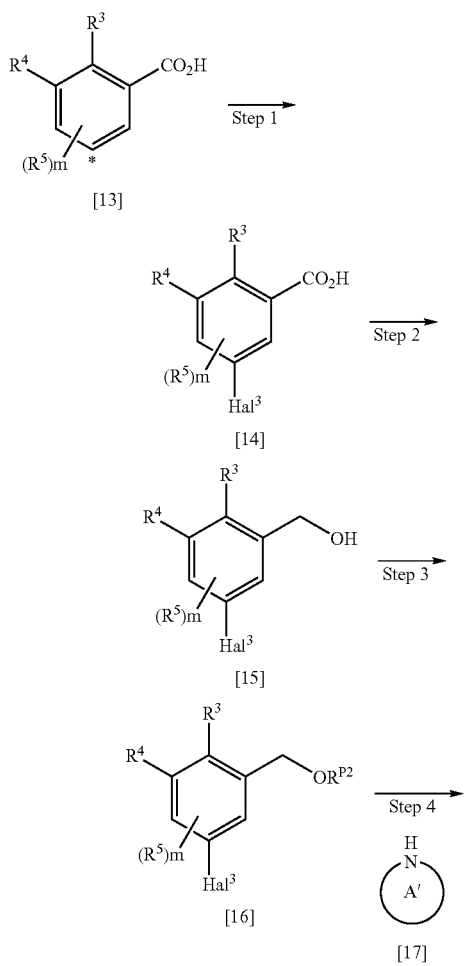

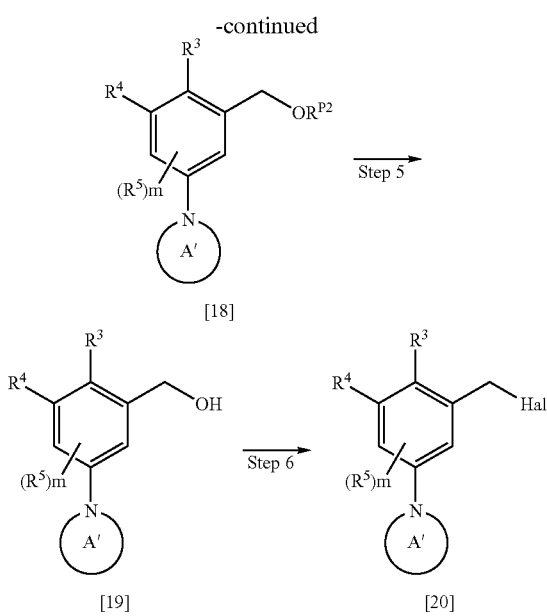

wherein Hal³ is a halogen atom, preferably a bromine atom or an iodine atom, $R^{P2}$ is a hydroxyl-protecting group such as acetyl group, methoxycarbonyl group, methoxymethyl group, methoxyethoxymethyl group, trimethylsilyl group, tert-butyldimethylsilyl group, tert-butyldiphenylsilyl group and the like, ring A' is ring A containing NH as a ring-constituting component, such as pyrrolidine, piperidine, piperazine, morpholine, thiomorpholine, isothiazolidine, oxazolidine, pyrazolidine and the like, and the other symbols are as defined above, provided that substituent $R^5$ should not be bonded to the position of *.

Step 1

In the same manner as in Step 1 of production method 1, compound [14] can be obtained by halogenating compound [13] according to a conventional method.

Step 2

Compound [15] can be obtained by reducing compound [14] according to a conventional method.

For example, compound [15] can be obtained by reacting compound [14] under cooling to heating in a solvent such as tetrahydrofuran and the like, in the presence of a reducing agent such as lithium aluminum hydride, sodium borohydride, borane-tetrahydrofuran complex and the like.

The reduction can be also carried out by a method via a mixed acid anhydride, or a method via an acid halide.

Step 3

In the same manner as in Step 5 of production method 1, compound [16] can be obtained by introducing a protecting group to the hydroxyl group of compound [15] according to a conventional method.

Step 4

Compound [18] can be obtained by reacting compound [16] with compound [17].

For example, Compound [18] can be obtained by reacting compound [16] with compound [17] under cooling to heating in a solvent in the presence of a catalyst and a base under argon or nitrogen atmosphere.

As the catalyst, a palladium catalyst such as Pd₂(dba)₃·CHCl₃, tetrakis(triphenylphosphine)palladium, dichlorobis(triphenylphosphine)palladium(II), palladium acetate, etc.; a copper catalyst such as copper, copper(I) chloride, copper(I) bromide, copper(I) iodide, etc.; and the like can be mentioned.

As the base, sodium carbonate, potassium carbonate, potassium hydrogen carbonate, sodium hydrogen carbonate, potassium phosphate, triethylamine, potassium fluoride, cesium fluoride, sodium hydrogen phosphate, cesium carbonate and the like can be mentioned.

When the palladium catalyst is used, as a ligand, triphenylphosphine, 2,2'-bis(diphenylphosphino)-1,1'-binaphthalene and the like can be added. As the solvent, dimethylformamide, acetonitrile, an alcohol solvent (e.g., methanol, ethanol, isopropanol, tert-butanol etc.), 1,4-dioxane, 1,2-dimethoxyethane, tetrahydrofuran, toluene, water, a mixed solvent thereof and the like can be mentioned.

When the copper catalyst is used, as a ligand, ethyleneglycol; $(CH_3)_2N-(CH_2)_2-OH$; a diamine such as $(CH_3)_2N-(CH_2)_2-NH_2$, $(CH_3)_2N-(CH_2)_2-N(CH_3)_2$, $CH_3NH-(CH_2)_2-NHCH_3$ and the like can be used. As the solvent, dimethylformamide, acetonitrile, an alcohol solvent (e.g., methanol, ethanol, isopropanol, tert-butanol etc.), toluene, xylene and the like can be mentioned.

Step 5

In the same manner as in Step 3 of production method 2, compound [19] can be obtained by eliminating the hydroxyl-protecting group of compound [18] according to a conventional method.

Step 6

Compound [20] can be obtained by halogenating the hydroxyl group of compound [19] according to a conventional method.

For example, compound [20] can be obtained by reacting compound [19] with a halogenating agent such as thionyl chloride, phosphorus trichloride, phosphorus tribromide, carbon tetrabromide-triphenylphosphine, N-bromosuccinimide and the like under cooling to room temperature in a solvent.

As the solvent, a halogenated hydrocarbon solvent such as dichloromethane, chloroform, carbon tetrachloride, 1,2-dichloroethane, etc.; an ether solvent such as 1,4-dioxane, diethyl ether, 1,2-dimethoxyethane, tetrahydrofuran, etc.; and the like can be mentioned.

Production Method 4

Production example of compound [11]

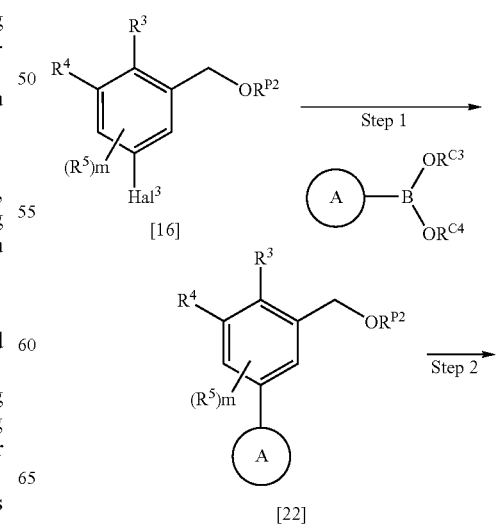

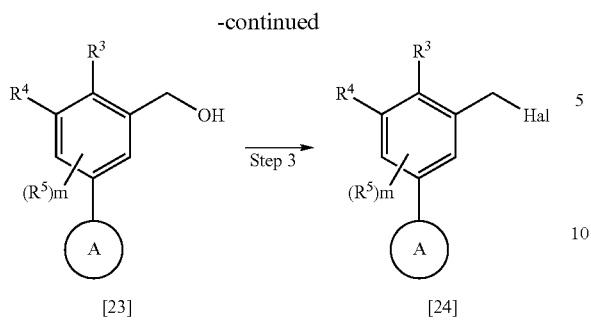

wherein each symbol is as defined above.

Step 1

In the same manner as in Step 2 of production method 2, compound [22] can be obtained by subjecting compound [16] and compound [21] to Suzuki reaction.

Step 2

In the same manner as in Step 3 of production method 2, compound [23] can be obtained by eliminating the hydroxyl-protecting group of compound [22] according to a conventional method.

Step 3

In the same manner as in Step 6 of production method 3, compound [24] can be obtained by halogenating the hydroxyl group of compound [23] according to a conventional method.

Production Method 5

Production example of compound [9] wherein $R^2$ is ethyl group.

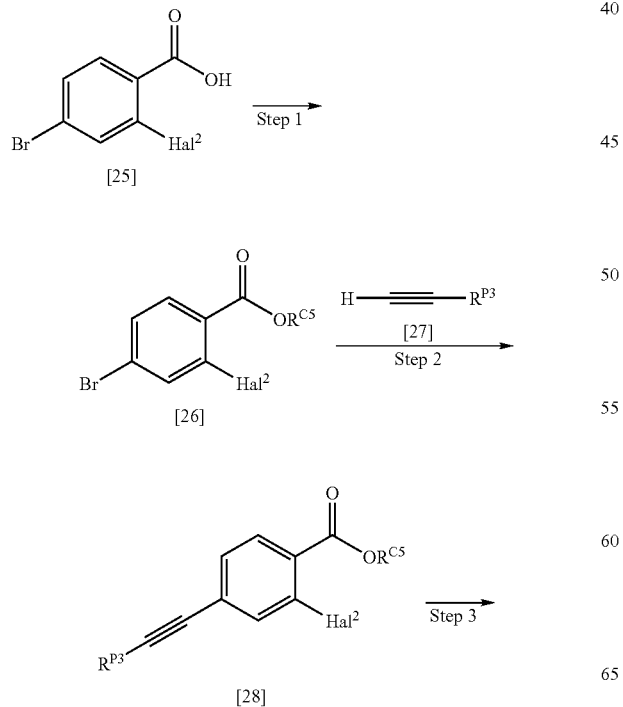

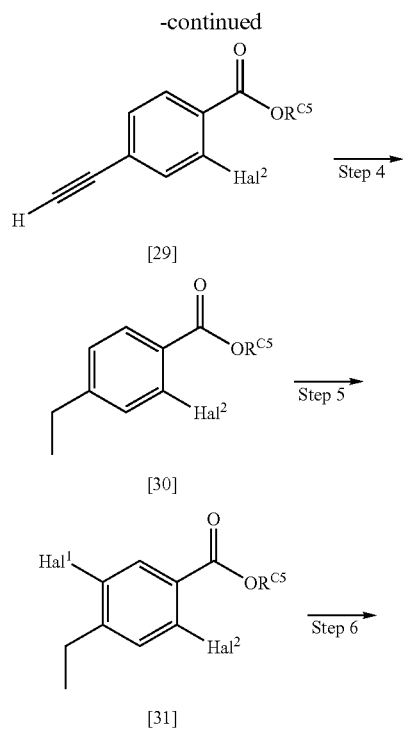

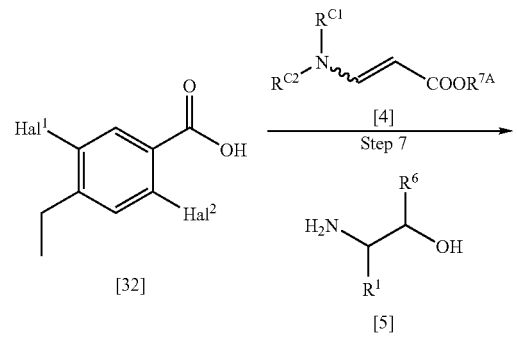

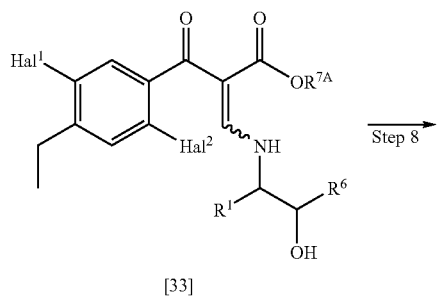

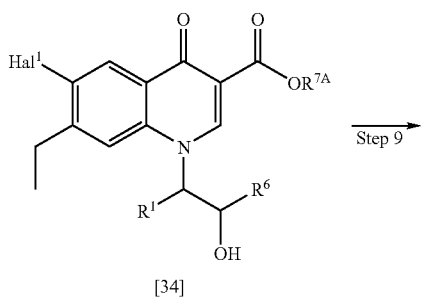

-continued

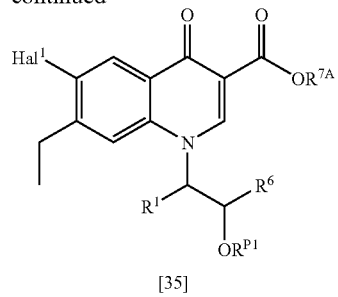

[35]

wherein $R^{C5}$ is a carboxyl-protecting group such as a $C_{1-4}$ alkyl group (e.g., methyl group, ethyl group etc.) and the like, $R^{P3}$ is a protecting group such as trimethylsilyl group, tert-butyldimethylsilyl group, tert-butyldiphenylsilyl group and the like, and the other symbols are as defined above.

Step 1

Compound [26] can be obtained by introducing a protecting group to the carboxyl group of compound [25] according to a conventional method.

For example, compound [26] can be obtained by reacting compound [25] with an alkylating agent such as methyl iodide and the like, in a solvent such as dimethylformamide, tetrahydrofuran, toluene and the like, in the presence of a base such as sodium carbonate, potassium carbonate, sodium hydride, potassium hydride and the like.

Step 2

Compound [28] can be obtained by reacting compound [26] with compound [27] at room temperature to under heating in a solvent such as dimethylformamide, acetonitrile, 1,4-dioxane, 1,2-dimethoxyethane, tetrahydrofuran, toluene, water and the like, in the presence of a catalyst such as a palladium catalyst (e.g., tetrakis(triphenylphosphine)palladium, dichlorobis(triphenylphosphine)palladium(II), palladium acetate-triphenylphosphine and the like), a copper catalyst (e.g., copper(I) iodide and the like) or a mixture thereof and in the presence of a base such as potassium carbonate, potassium hydrogen carbonate, sodium hydrogen carbonate, potassium phosphate, triethylamine and the like.

Step 3

Compound [29] can be obtained by eliminating the protecting group $R^{P3}$ of compound [28] according to a conventional method.

For example, when $R^{P3}$ is trimethylsilyl group, tert-butyldimethylsilyl group or tert-butyldiphenylsilyl group, compound [29] can be obtained by methods such as treating compound [28] with tetrabutylammonium fluoride in tetrahydrofuran under cooling to room temperature; treating compound [28] with sodium hydroxide in tetrahydrofuran; treating compound [28] with acetic acid-water-tetrahydrofuran at room temperature to under heating and the like.

Step 4

Compound [30] can be obtained by reducing compound [29] according to a conventional method such as catalytic reduction under hydrogen atmosphere, and the like.

For example, compound [30] can be obtained by reacting compound [29] in a solvent such as tetrahydrofuran, methanol, ethyl acetate, a mixed solvent thereof and the like, in the presence of a catalyst such as palladium-carbon and the like under hydrogen atmosphere at room temperature.

Step 5

In the same manner as in Step 1 of production method 1, compound [31] can be obtained by halogenating compound [30] according to a conventional method.

Step 6

In the same manner as in Step 4 of production method 2, compound [32] can be obtained by eliminating the carboxyl-protecting group of compound [31] according to a conventional method.

Step 7

In the same manner as in Step 2 of production method 1, compound [33] can be obtained by reacting compound [32] with compound [4], and reacting the resulting compound with compound [5].

Step 8

In the same manner as in Step 3 of production method 1, compound [34] can be obtained by subjecting compound [33] to cyclization.

Step 9

In the same manner as in Step 5 of production method 1, compound [35] can be obtained by introducing a protecting group to the hydroxyl group of compound [34].

Production Method 6

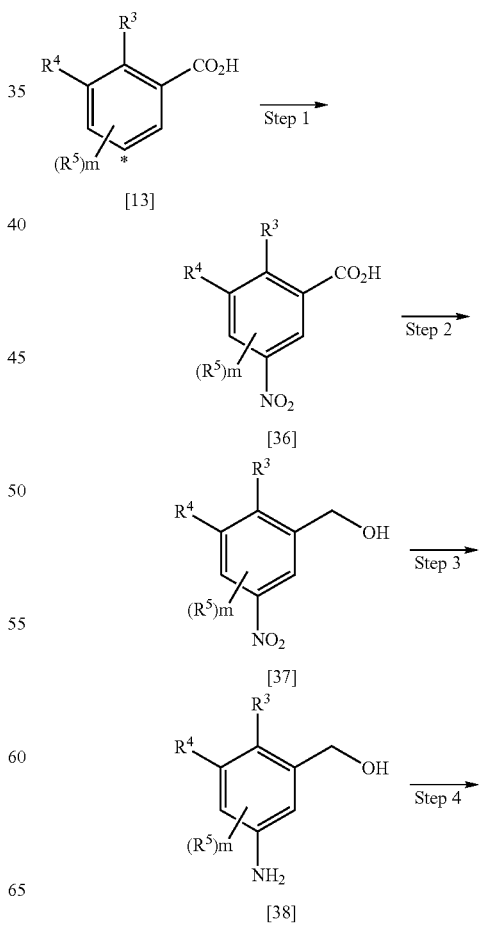

-continued

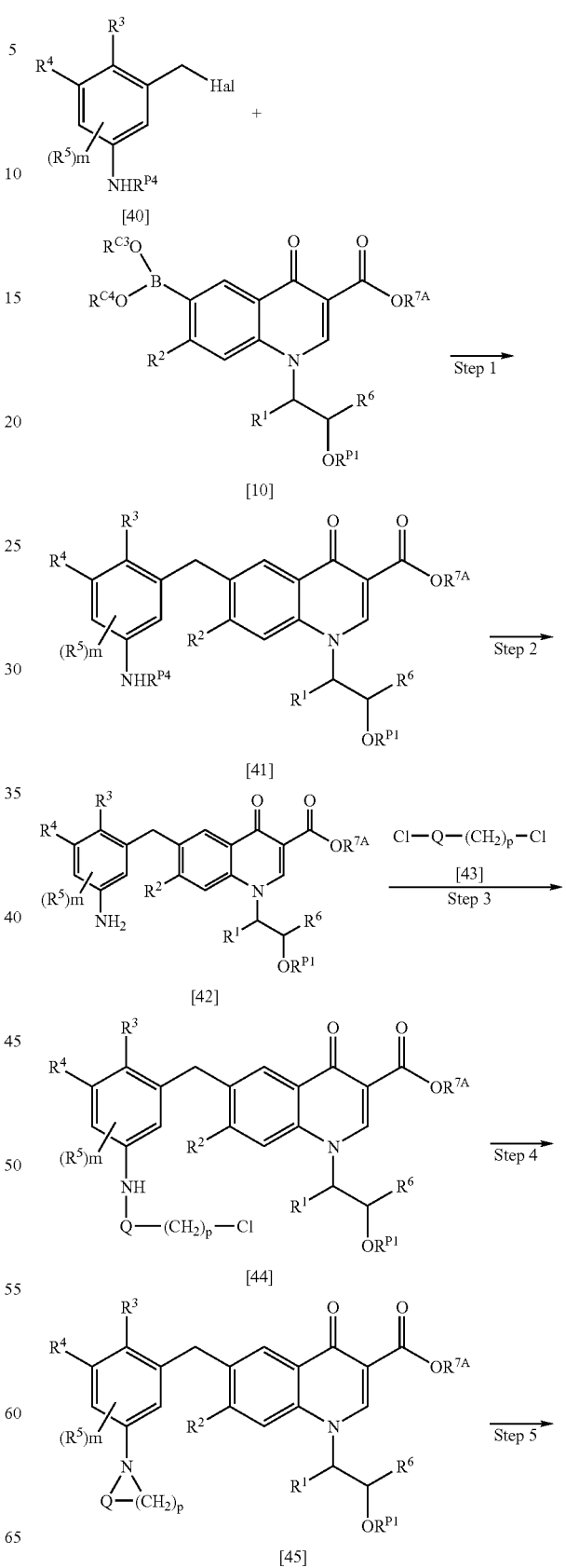

Production Method 7 wherein $R^{P4}$ is an amino-protecting group such as benzoyl group, tert-butyl group, tert-butylcarbonyl group, tert-butoxycarbonyl group and the like, and the other symbols are as defined above, provided that substituent $R^5$ should not be bonded to the position of *.

Step 1

Compound [36] can be obtained by nitrating compound [13] according to a conventional method.

For example, compound [36] can be obtained by nitrating compound [13] with a nitrating agent (e.g., nitric acid, fuming nitric acid, a mixed acid of concentrated nitric acid and concentrated sulfuric acid, and the like), under cooling to room temperature.

Step 2

In the same manner as in Step 2 of production method 3, compound [37] can be obtained by reducing compound [36] according to a conventional method.

Step 3

Compound [38] can be obtained according to a conventional method such as by reducing compound [37] with zinc or iron under neutral or alkaline condition; with iron and an acid; with tin or tin(II) chloride and concentrated hydrochloric acid; with an alkali sulfide; with hydrosulfite under alkaline condition, and the like, by subjecting compound [37] to catalytic reduction under hydrogen atmosphere, and the like.

For example, compound [38] can be obtained by reacting compound [37] with reduced iron and ammonium chloride in a solvent such as ethanol, tetrahydrofuran, water, a mixed solvent thereof and the like, at room temperature to under heating. Alternatively, compound [38] can be obtained by adding acetic acid and zinc powder to compound [37] under cooling to allow reaction at room temperature. Alternatively, compound [38] can be obtained by reacting compound [37] in the presence of a catalyst such as palladium-carbon and the like, in a solvent such as tetrahydrofuran, methanol, ethyl acetate, a mixed solvent thereof and the like, under hydrogen atmosphere at room temperature.

Step 4

Compound [39] can be obtained by introducing a protecting group to the amino group of compound [38] according to a conventional method.

For example, when $R^{P4}$ is tert-butoxycarbonyl group, compound [39] can be obtained by reacting compound [38] with di-tert-butyl dicarbonate at room temperature to under heating in a solvent such as tetrahydrofuran and the like.

Step 5

In the same manner as in Step 6 of production method 3, compound [40] can be obtained by halogenating the hydroxyl group of compound [39] according to a conventional method.

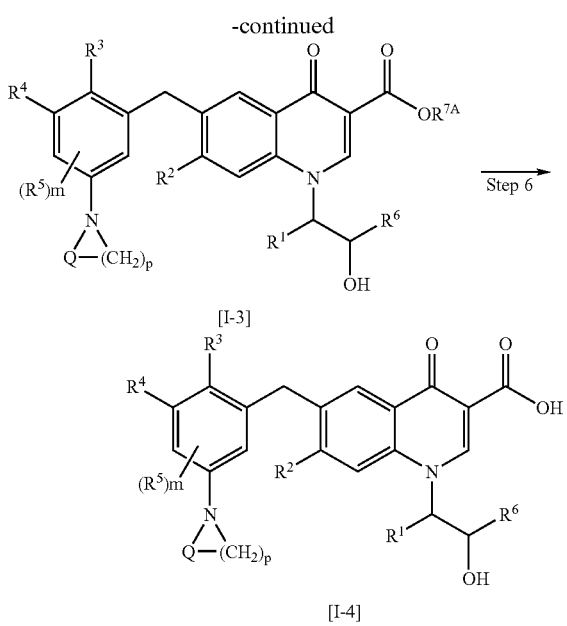

[I-3]

[I-4]

wherein Q is —CO—, —COO— or —SO₂—, p is an integer of 2 to 4, and the other symbols are as defined above.

Step 1

In the same manner as in Step 2 of production method 2, compound [41] can be obtained by subjecting compound [10] and compound [40] to Suzuki reaction.

Step 2

Compound [42] can be obtained by eliminating the amino-protecting group of compound [41] according to a conventional method.

For example, when $R^{P4}$ is tert-butoxycarbonyl group, the deprotection can be carried out by methods such as treating compound [41] in ethyl acetate with a solution of hydrochloric acid in ethyl acetate at room temperature; treating compound [41] with hydrochloric acid in tetrahydrofuran at room temperature; treating compound [41] in 1,4-dioxane with a solution of hydrochloric acid in 1,4-dioxane at room temperature; treating a solution of compound [41] in chloroform with trifluoroacetic acid, and the like method.

Step 3

Compound [44] can be obtained by reacting compound [42] with compound [43] under cooling to heating in a solvent such as dimethylformamide, acetonitrile, tetrahydrofuran, dichloromethane, chloroform, ethyl acetate, toluene and the like, in the presence of a base such as triethylamine, potassium carbonate, pyridine, 4-(dimethylamino)pyridine and the like.

Step 4

Compound [45] can be obtained by subjecting compound [44] to cyclization under cooling to heating in a solvent such as dimethylformamide, acetonitrile, tetrahydrofuran, toluene and the like, in the presence of a base such as sodium carbonate, potassium carbonate, triethylamine, potassium tert-butoxide, sodium hydride, potassium hydride and the like.

Step 5

In the same manner as in Step 3 of production method 2, compound [I-3] can be obtained by eliminating the hydroxyl-protecting group of compound [45] according to a conventional method.

Step 6

In the same manner as in Step 4 of production method 2, compound [I-4] can be obtained by eliminating the carboxyl-protecting group of compound [I-3] according to a conventional method.

EXAMPLES

Now, the 4-oxoquinoline compound represented by the formula [I] of the present invention, a pharmaceutically acceptable salt thereof, or a solvate thereof, and a production method thereof are concretely explained by way of Examples, which are not to be construed as limitative.

Example 1

Step 1

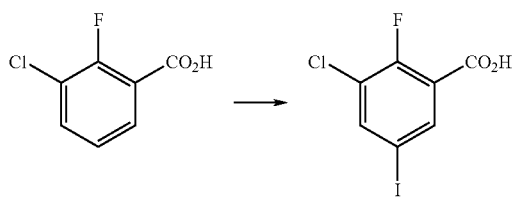

3-Chloro-2-fluorobenzoic acid (25.00 g, 143.21 mmol) was dissolved in concentrated sulfuric acid (100 ml), and N-iodosuccinimide (32.20 g, 143.21 mmol) was portionwise added at 5° C. or below. After the completion of addition, the mixture was stirred at the same temperature for 3 hr, and at room temperature for 13 hr. The reaction mixture was poured into ice water (about 500 ml) added with sodium sulfite (14.90 g, 143.19 mmol) and, after stirring, the precipitated solid was collected by filtration and washed with water. The obtained solid was dried under reduced pressure at 65° C. for 8 hr to give the object compound (41.02 g, yield 95%) as a pale-brown solid.

$^{1}$H NMR (DMSO-$d_6$ 400 MHz) (δ) ppm: 8.06 (1H, dd, J=6.1, 2.2 Hz), 8.22 (1H, dd, J=6.4, 2.2 Hz)

MS (ESI): M– 299

Step 2

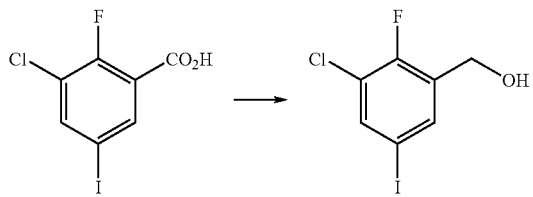

The compound (2.00 g, 6.66 mmol) obtained in Step 1 was dissolved in tetrahydrofuran (10 ml). Under a nitrogen stream, a 1.0 M solution of borane-tetrahydrofuran complex in tetrahydrofuran (20.00 ml, 20.00 mmol) was added dropwise at 0° C. After the completion of the dropwise addition, the mixture was warmed to room temperature, stirred for 2 hr, and heated under reflux for 2 hr. Under ice-cooling, 2N hydrochloric acid (11 ml) was added dropwise to the reaction mixture and, after stirring, the mixture was extracted with ethyl acetate. The organic layer was washed with water, saturated aqueous sodium hydrogen carbonate solution, water and saturated brine in this order, and dried over sodium sulfate. After filtration, the filtrate was concentrated under reduced pressure, and the obtained residue was purified by silica gel chromatography (hexane:ethyl acetate=6:1 to 5:1) to give the object compound (1.70 g, yield 89%) as a white solid.

$^1$H NMR (CDCl$_3$ 400 MHz) (δ) ppm: 1.83-1.84 (1H, m), 4.74-4.76 (2H, m), 7.65-7.70 (2H, m)

Step 3

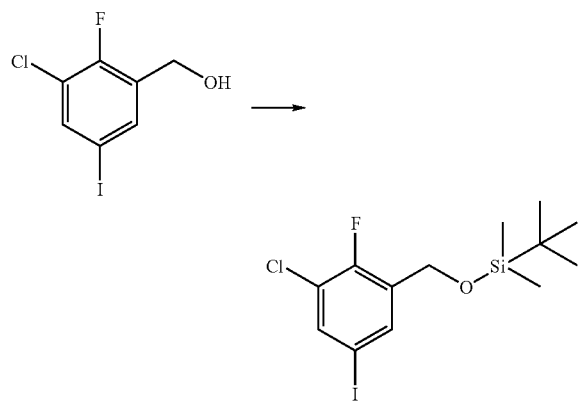

The compound (1.70 g, 5.93 mmol) obtained in Step 2 was dissolved in dimethylformamide (17 ml), imidazole (606 mg, 8.90 mmol) and tert-butyldimethylsilyl chloride (1.07 g, 7.10 mmol) were added, and the mixture was stirred at room temperature for 3 hr. Water was added to the reaction mixture, and the mixture was extracted with ethyl acetate. The organic layer was washed with water and saturated brine in this order, and dried over sodium sulfate. After filtration, the filtrate was concentrated under reduced pressure, and the obtained residue was purified by silica gel chromatography (hexane alone) to give the object compound (2.31 g, yield 97%) as a colorless oil.

$^1$H NMR (CDCl$_3$ 400 MHz) (δ) ppm: 0.12 (6H, s), 0.95 (9H, s), 4.74 (2H, s), 7.60-7.62 (1H, m), 7.68-7.69 (1H, m)

Step 4

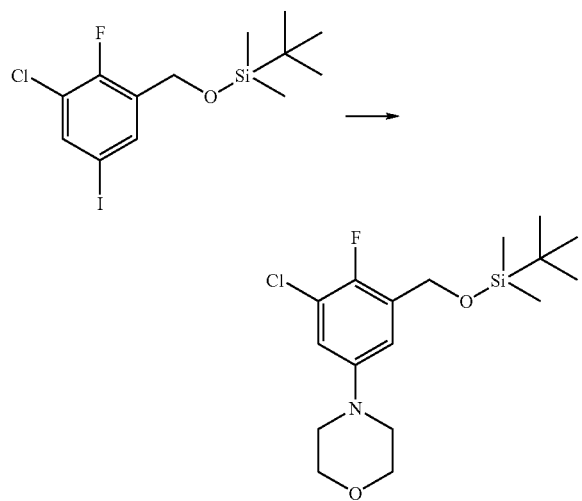

Palladium(II) acetate (448 mg, 2.00 mmol), (±)-2,2'-bis(diphenylphosphino)-1,1'-binaphthalene (2.49 g, 4.00 mmol) and cesium carbonate (9.76 g, 29.96 mmol) were added to 1,4-dioxane (40 ml), and a solution of the compound (8.00 g, 19.96 mmol) obtained in Step 3 and morpholine (2.62 ml, 29.95 mmol) in tert-butanol (40 ml) was added dropwise to the aforementioned mixture (washed with 1,4-dioxane (40 ml)) under an argon stream. The mixture was heated under reflux for 24 hr. After allowing to cool, water was added to the reaction mixture, and the mixture was extracted with ethyl acetate. The organic layer was washed with water and saturated brine in this order, and dried over magnesium sulfate. After filtration, the filtrate was concentrated under reduced pressure, and the obtained residue was purified by silica gel chromatography (hexane:ethyl acetate=8:1) to give the object compound (4.29 g, yield 60%).

$^1$H NMR (CDCl$_3$ 400 MHz) (δ) ppm: 0.12 (6H, s), 0.95 (9H, s), 3.08-3.10 (4H, m), 3.84-3.86 (4H, m), 4.76 (2H, s), 6.79 (1H, dd, J=5.9, 3.1 Hz), 6.95 (1H, dd, J=5.4, 3.1 Hz)

Step 5

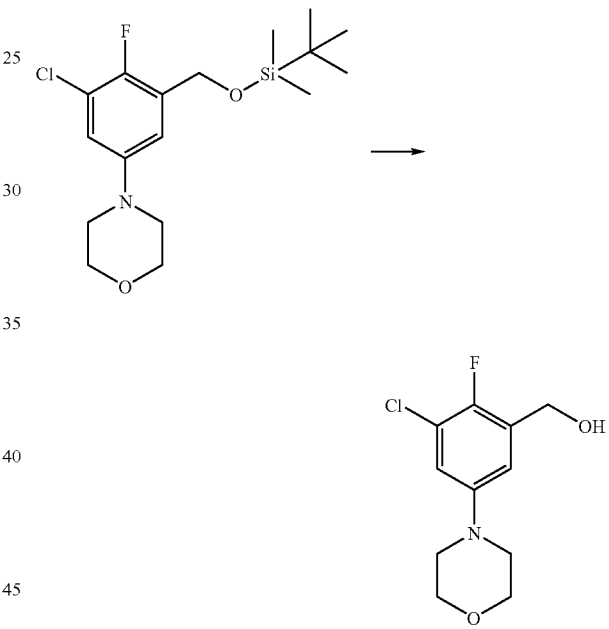

The compound (537 mg, 1.49 mmol) obtained in Step 4 was dissolved in tetrahydrofuran (1 ml), a 1.0 M solution of tetrabutylammonium fluoride in tetrahydrofuran (2.99 ml, 2.99 mmol) was added, and the mixture was stirred at room temperature for 2 hr. Water and ethyl acetate were added to the reaction mixture, the layers were separated, and the organic layer was washed with saturated brine and dried over sodium sulfate. After filtration, the filtrate was concentrated under reduced pressure, and the obtained residue was purified by silica gel chromatography (hexane:ethyl acetate=1:1) to give the object compound (308 mg, yield 84%) as a beige solid.

$^1$H NMR (CDCl$_3$ 300 MHz) (δ) ppm: 1.90 (1H, t, J=6.0 Hz), 3.08-3.12 (4H, m), 3.83-3.86 (4H, m), 4.74 (2H, d, J=6.0 Hz), 6.83 (1H, dd, J=6.0, 3.0 Hz), 6.88 (1H, dd, J=5.3, 3.0 Hz)

MS (ESI): M+ 246

Step 6

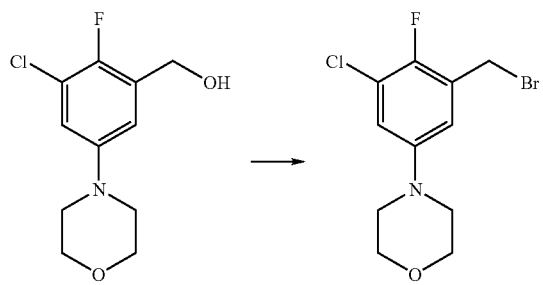

The compound (1.00 g, 4.07 mmol) obtained in Step 5 was dissolved in chloroform (10 ml), and 3 mmol/g triphenylphosphine resin (2.04 g, 6.11 mmol) was added. Furthermore, N-bromosuccinimide (2.03 g, 6.11 mmol) was added under ice-cooling, and the mixture was stirred at room temperature for 40 min. The reaction mixture was filtered and the filtrate was concentrated under reduced pressure. The obtained residue was purified by silica gel chromatography (hexane:ethyl acetate=4:1) to give the object compound (1.10 g, yield 88%) as a white solid.

$^1$H NMR (CDCl$_3$ 400 MHz) (δ) ppm: 3.09-3.11 (4H, m), 3.83-3.86 (4H, m), 4.46 (2H, d, J=1.2 Hz), 6.79 (1H, dd, J=5.4, 3.1 Hz), 6.86 (1H, dd, J=6.0, 3.0 Hz)

Step 7

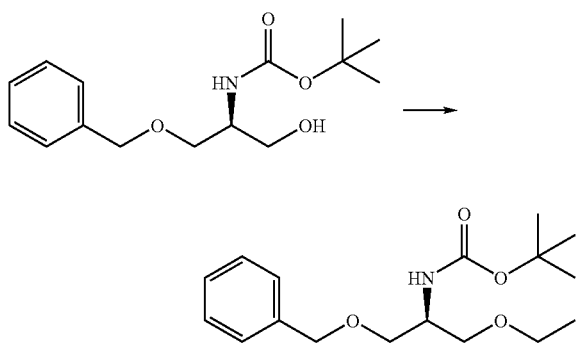

Boc-D-Ser(Bzl)-ol (Boc-O-benzyl-D-serinol) (10.00 g, 35.54 mmol) was dissolved in toluene (50 ml), tetra-n-butylammonium hydrogensulfate (1.28 g, 3.56 mmol), 8N aqueous sodium hydroxide solution (50 ml) and bromoethane (7.96 ml, 106.65 mmol) were added, and the mixture was stirred at room temperature for 20 hr. Bromoethane (2.65 ml, 35.54 mmol) was added, and the mixture was further stirred at room temperature for 3.5 hr. The reaction mixture was extracted with toluene, and the organic layer was washed with saturated brine and dried over magnesium sulfate. After filtration, the filtrate was concentrated under reduced pressure, and the obtained residue was purified by silica gel chromatography (hexane:ethyl acetate=4:1) to give the object compound (10.49 g, yield 95%).

$^1$H NMR (CDCl$_3$ 400 MHz) (δ) ppm: 1.17 (3H, t, J=7.1 Hz), 1.44 (9H, s), 3.49-3.57 (6H, m), 3.90-3.92 (1H, m), 4.53 (2H, s), 4.92-4.94 (1H, m), 7.27-7.37 (5H, m)

Step 8

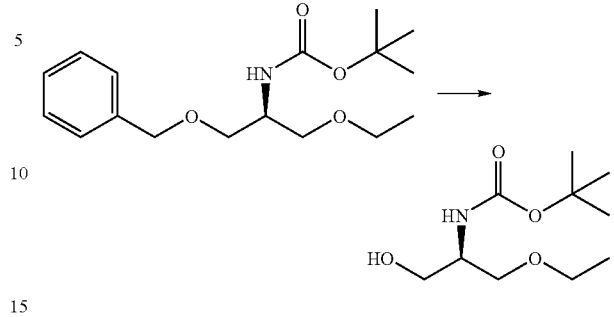

The compound (10.49 g, 33.90 mmol) obtained in Step 7 was dissolved in methanol (100 ml), 4.5% palladium-carbon (1.10 g) was added, hydrogen was added at normal pressure, and the mixture was stirred at room temperature for 1.5 hr. The reaction mixture was filtered through celite, and the filtrate was concentrated under reduced pressure to give a crude product (8.06 g).

$^1$H NMR (CDCl$_3$ 300 MHz) (δ) ppm: 1.20 (3H, t, J=7.2 Hz), 1.46 (9H, s), 2.76-2.78 (1H, m), 3.47-3.84 (7H, m), 5.17-5.22 (1H, m)

Step 9

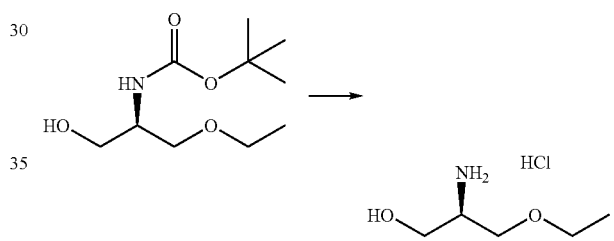

The crude product (8.06 g) obtained in Step 8 was dissolved in 1,4-dioxane (20 ml), 4N hydrochloric acid-1,4-dioxane (34 ml, 136 mmol) was added, and the mixture was stirred at room temperature for 3.5 hr. The reaction mixture was concentrated under reduced pressure to give a crude product (5.86 g).

$^1$H NMR (CDCl$_3$ 400 MHz) (δ) ppm: 1.21 (3H, t, J=7.0 Hz), 3.53-3.61 (2H, m), 3.69-3.71 (3H, m), 3.89-3.94 (2H, m), 8.04 (3H, br s)

MS (ESI): M+ 120 (Free compound)

Step 10

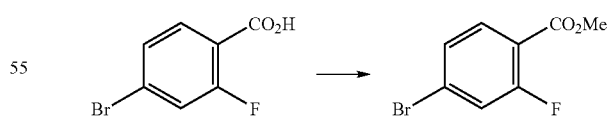

4-Bromo-2-fluorobenzoic acid (25.24 g, 115.24 mmol) was dissolved in dimethylformamide (300 ml), potassium carbonate (23.89 g, 172.86 mmol) was added, iodomethane (9.33 ml, 149.81 mmol) was further added under ice-cooling, and the mixture was stirred at room temperature for 4 hr. The reaction mixture was added to water containing acetic acid (15 ml), and the mixture was extracted three times with ethyl acetate. The organic layer was washed with water (four times) and saturated brine in this order, and dried over sodium sulfate. After filtration, the filtrate was concentrated under reduced pressure to give a crude product (24.90 g) as a pale-yellow solid.

$^1$H NMR (CDCl$_3$ 400 MHz) (δ) ppm: 3.93 (3H, s), 7.33-7.38 (2H, m), 7.82 (1H, dd, J=7.7, 8.6 Hz)

Step 11

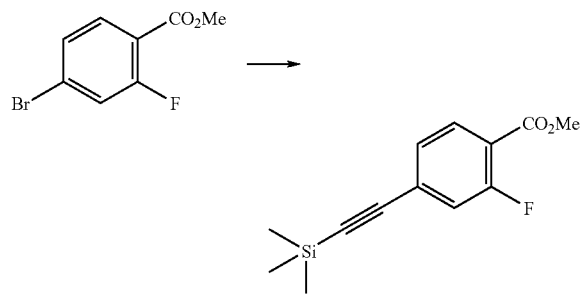

The crude product (2.50 g) obtained in Step 10 was dissolved in 1,4-dioxane (20 ml), triethylamine (20 ml), trimethylsilylacetylene (1.97 ml, 13.95 mmol), dichlorobis(triphenylphosphine)palladium(II) (377 mg, 0.537 mmol) and copper(I) iodide (61 mg, 0.322 mmol) were added in this order, and the mixture was further stirred under heating at 60° C. for 1 hr. After allowing to cool, the reaction mixture was filtered through celite, washed with diethyl ether, and the filtrate was concentrated under reduced pressure. Ethyl acetate and water were added to the obtained residue, the layers were separated, and the aqueous layer was extracted with ethyl acetate. The organic layer was washed with water and saturated brine in this order, and dried over sodium sulfate. After filtration, the filtrate was concentrated under reduced pressure, and the obtained residue was purified by silica gel chromatography (hexane:ethyl acetate=15:1) to give the object compound (3.04 g, yield quantitative, 2 steps) as a yellow oil.

$^1$H NMR (CDCl$_3$ 400 MHz) (δ) ppm: 0.26 (9H, s), 3.93 (3H, s), 7.20-7.28 (2H, m), 7.87 (1H, dd, J=7.7, 7.7 Hz)

Step 12

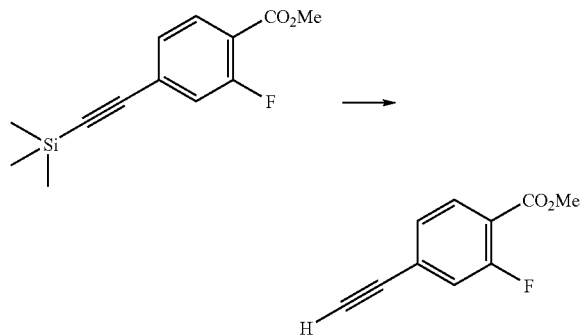

The compound (2.46 g, 9.81=mol) obtained in Step 11 was dissolved in tetrahydrofuran (25 ml). Water (353 μl, 9.61 mmol) and a 1.0 M solution of tetrabutylammonium fluoride in tetrahydrofuran (490 μl, 0.490 mmol) were added at 0° C., and the mixture was stirred at the same temperature for 30 min. Water and ethyl acetate were added to the reaction mixture, and the layers were separated. The organic layer was washed with water (twice) and saturated brine in this order, and dried over sodium sulfate. After filtration, the filtrate was concentrated under reduced pressure, and the obtained residue was purified by silica gel chromatography (hexane:ethyl acetate=10:1) to give the object compound (1.52 g, yield 91%) as a pale-brown solid.

$^1$H NMR (CDCl$_3$ 400 MHz) (δ) ppm: 3.26 (1H, s), 3.94 (3H, s), 7.24-7.33 (2H, m), 7.90 (1H, dd, J=7.8, 7.8 Hz)

Step 13

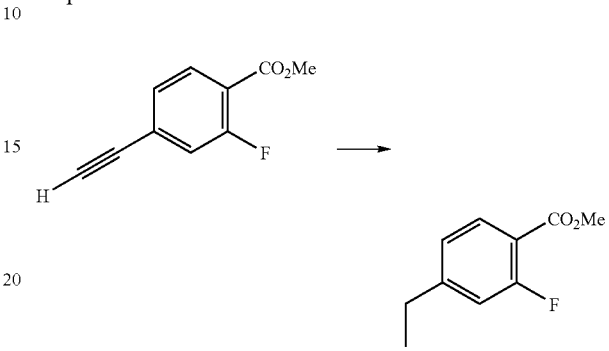

The compound (2.23 g, 12.53 mmol) obtained in Step 12 was dissolved in ethyl acetate (20 ml), 5% palladium-carbon (wet) (200 mg) was added, hydrogen was added at normal pressure, and the mixture was stirred at room temperature for 22 hr. The reaction mixture was filtered through celite, the filtrate was concentrated under reduced pressure, and the obtained residue was purified by silica gel chromatography (hexane:ethyl acetate=20:1 to 15:1) to give the object compound (1.94 g, yield 85%) as a colorless oil.

$^1$H NMR (CDCl$_3$ 400 MHz) (δ) ppm: 1.25 (3H, t, J=7.6 Hz), 2.69 (2H, q, J=7.6 Hz), 3.92 (3H, s), 6.95-7.04 (2H, m), 7.85 (1H, dd, J 7.8, 7.8 Hz)

Step 14

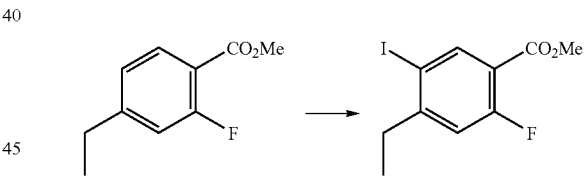

The compound (1.94 g, 10.65 mmol) obtained in Step 13 was dissolved in concentrated sulfuric acid (15 ml), and N-iodosuccinimide (2.40 g, 10.67 mmol) was portionwise added under ice-cooling. The mixture was stirred under ice-cooling for 20 min, and at room temperature for 2 hr. N-iodosuccinimide (120 mg, 0.532 mmol) was added, and the mixture was stirred at room temperature for 30 min. The reaction mixture was poured into ice water containing sodium sulfite (2.0 g, 15.87 mmol) and, after stirring, the mixture was extracted with ethyl acetate. The organic layer was washed with water (three times) and saturated brine in this order, and dried over sodium sulfate. After filtration, the filtrate was concentrated under reduced pressure, and the obtained residue was purified by silica gel chromatography (hexane to hexane:ethyl acetate=15:1) to give the object compound (3.20 g, yield 98%) as a colorless solid.

$^1$H NMR (CDCl$_3$ 400 MHz) (δ) ppm: 1.23 (3H, t, J=7.5 Hz), 2.73 (2H, q, J=7.5 Hz), 3.92 (3H, s), 7.02 (1H, d, J=11.8 Hz), 8.35 (1H, d, J=7.2 Hz)

Step 15

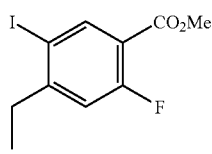

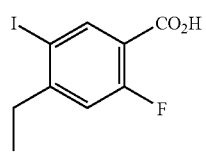

The compound (3.20 g, 10.39 mmol) obtained in Step 14 was dissolved in tetrahydrofuran (10 ml) and methanol (10 ml), 4N aqueous sodium hydroxide solution (5.20 ml, 20.77 mmol) was added, and the mixture was stirred at room temperature for 14 hr. The reaction mixture was concentrated under reduced pressure, 6N hydrochloric acid and ethyl acetate were added to the residue, and the layers were separated. The aqueous layer was extracted with ethyl acetate. The organic layer was washed with water and saturated brine in this order, and dried over magnesium sulfate. After filtration, the filtrate was concentrated under reduced pressure to give a crude product (3.03 g) as a white solid.

$^1$H NMR (CDCl$_3$ 400 MHz) (δ) ppm: 1.25 (3H, t, J=7.5 Hz), 2.76 (2H, q, J=7.5 Hz), 7.06 (1H, d, J=11.8 Hz), 8.44 (1H, d, J=7.2 Hz)

Step 16

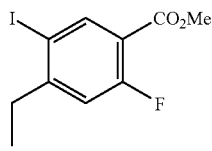

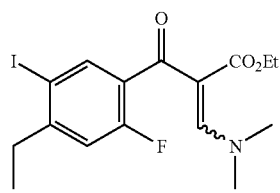

The crude product (2.84 g) obtained in Step 15 was dissolved in toluene (30 ml), thionyl chloride (1.06 ml, 14.49 mmol) and dimethylformamide (catalytic amount) were added, and the mixture was stirred under heating at 100° C. for 2 hr. After allowing to cool, the reaction mixture was concentrated under reduced pressure, and subjected to azeotropic distillation with toluene twice. The obtained residue was dissolved in toluene (15 ml) and the solution was added dropwise to a solution of ethyl 3-(dimethylamino)acrylate (1.45 g, 10.14 mmol) and diisopropylethylamine (2.19 ml, 12.56 mmol) in toluene (15 ml), and the mixture was stirred under heating at 90° C. for 14 hr. After allowing to cool, water was added to the reaction mixture, the layers were separated, and the aqueous layer was extracted with ethyl acetate. The organic layer was washed with water (twice) and saturated brine in this order, and dried over sodium sulfate. After filtration, the filtrate was concentrated under reduced pressure, and the obtained residue was purified by silica gel chromatography (hexane:ethyl acetate=1:1 to 1:2) to give the object compound (2.85 g, yield 70%, 2 steps) as a yellow-brown oil.

$^1$H NMR (CDCl$_3$ 400 MHz) (δ) ppm: 0.96 (3H, t, J=7.1 Hz), 1.20 (3H, t, J=7.5 Hz), 2.71 (2H, q, J=7.5 Hz), 2.88 (3H, br s), 3.29 (3H, br s), 4.00 (2H, q, J=7.1 Hz), 6.90 (1H, d, J=11.4 Hz), 7.76 (1H, s), 8.02 (1H, br s)

Step 17

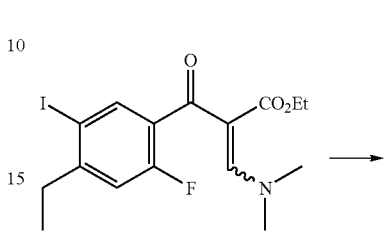

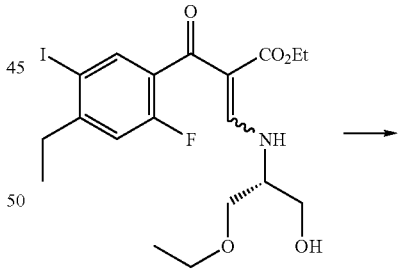

Triethylamine (349 μl, 2.51 mmol) and the crude product (312 mg) obtained in Step 9 were dissolved in chloroform, the compound (700 mg, 1.67 mmol) obtained in Step 16 was added, and the mixture was stirred at room temperature for 1.5 hr. The reaction mixture was concentrated under reduced pressure. The obtained residue was dissolved in ethyl acetate, washed with water (twice) and saturated brine in this order, and dried over sodium sulfate. After filtration, the filtrate was concentrated under reduced pressure to give a crude product (898 mg) as a pale-yellow oil.

Step 18

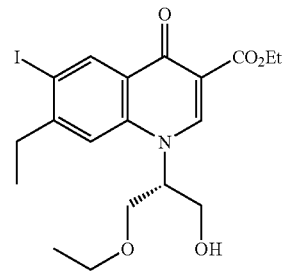

The crude product (898 mg) obtained in Step 17 was dissolved in dimethylformamide (8 ml), potassium carbonate (692 mg, 5.01 mmol) was added, and the mixture was stirred under heating at 80° C. for 21 hr. After allowing to cool, water and ethyl acetate were added to the reaction mixture, the layers were separated, and the aqueous layer was extracted with ethyl acetate. The organic layer was washed with water (three times) and saturated brine in this order, and dried over sodium sulfate. After filtration, the filtrate was concentrated under reduced pressure to give a crude product (758 mg) as a white solid.

$^1$H NMR (CDCl$_3$ 400 MHz) (δ) ppm: 1.17 (3H, t, J=6.9 Hz), 1.31 (3H, t, J=7.5 Hz), 1.40 (3H, t, J=7.2 Hz), 2.84-3.01 (2H, m), 3.50-3.62 (2H, m), 3.97-4.08 (2H, m), 4.11-4.18 (1H, m), 4.26-4.41 (3H, m), 4.81-4.88 (1H, m), 5.62 (1H, t, J=6.9 Hz), 7.37 (1H, s), 7.98 (1H, s), 8.61 (1H, s)

Step 19

Step 20

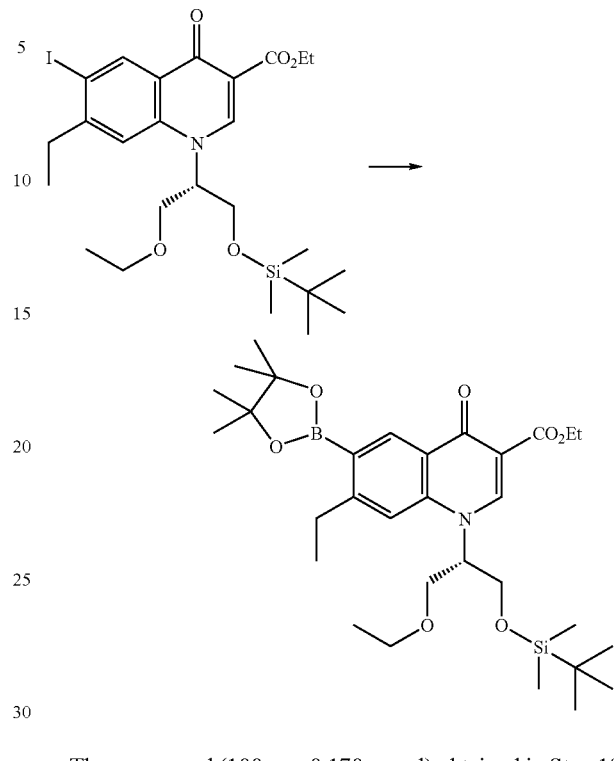

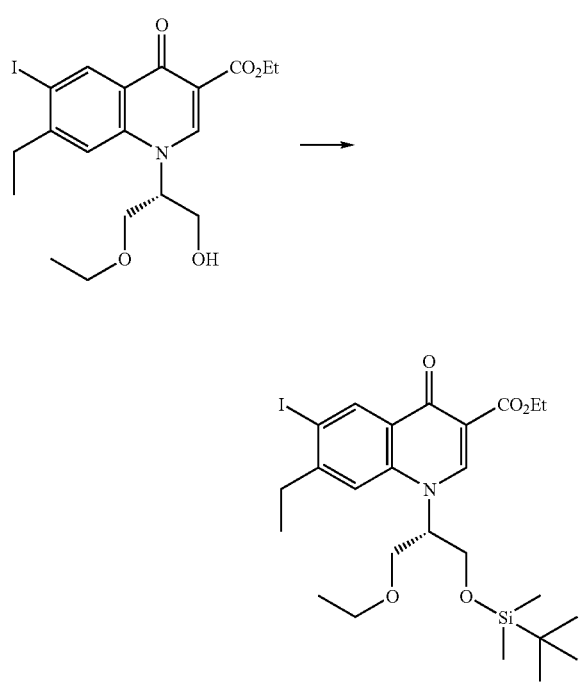

The compound (100 mg, 0.170 mmol) obtained in Step 19 was dissolved in 1,4-dioxane (1 ml), palladium(II) acetate (2 mg, 0.0085 mmol), 2-(dicyclohexylphosphino)biphenyl (12 mg, 0.034 mmol), triethylamine (95 μl, 0.68 mmol) and a 1N solution of pinacolborane in tetrahydrofuran (511 μl, 0.511 mmol) were added in this order, and the mixture was stirred under heating at 80° C. for 1 hr. After allowing to cool, saturated aqueous ammonium chloride solution and ethyl acetate were added to the reaction mixture, the layers were separated, and the aqueous layer was extracted with ethyl acetate. The organic layer was washed with water (three times) and saturated brine in this order, and dried over sodium sulfate. After filtration, the filtrate was concentrated under reduced pressure, and the obtained residue was purified by silica gel chromatography (hexane:ethyl acetate=1:2) to give the object compound (70 mg, yield 70%) as a colorless oil.

$^1$H NMR (CDCl$_3$ 400 MHz) (δ) ppm: −0.02 (6H, s), 0.83 (9H, s), 1.20 (3H, t, J=7.1 Hz), 1.24 (3H, t, J=7.4 Hz), 1.35 (12H, s), 1.40 (3H, t, J=7.2 Hz), 3.03 (2H, dq, J=1.6, 7.4 Hz), 3.54 (2H, q, J=7.1 Hz), 3.90 (2H, d, J=5.6 Hz), 4.00-4.08 (2H, m), 4.37 (2H, dq, J=2.0, 7.2 Hz), 4.79-4.85 (1H, m), 7.28 (1H, s), 8.70 (1H, s), 8.95 (1H, s)

Step 21

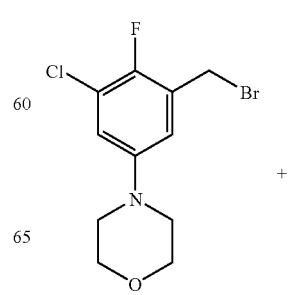

The crude product (758 mg) obtained in Step 18 was dissolved in dimethylformamide (8 ml), imidazole (171 mg, 2.51 mmol) and tert-butyldimethylsilyl chloride (302 mg, 2.00 mmol) were added, and the mixture was stirred at room temperature for 1 hr. Water and ethyl acetate were added to the reaction mixture, the layers were separated, and the aqueous layer was extracted with ethyl acetate. The organic layer was washed with water (three times) and saturated brine in this order, and dried over sodium sulfate. After filtration, the filtrate was concentrated under reduced pressure, and the obtained residue was purified by silica gel chromatography (hexane:ethyl acetate=2:3) to give the object compound (820 mg, yield 84%, 3 steps) as a colorless oil.

$^1$H NMR (CDCl$_3$ 400 MHz) (δ) ppm: −0.02 (3H, s), −0.01 (3H, s), 0.82 (9H, s), 1.20 (3H, t, J=7.0 Hz), 1.28 (3H, t, J=7.5 Hz), 1.40 (3H, t, J=7.2 Hz), 2.85 (2H, q, J=7.5 Hz), 3.54 (2H, q, J=7.0 Hz), 3.89 (2H, d, J=5.3 Hz), 4.04 (2H, d, J=4.9 Hz), 4.34-4.42 (2H, m), 4.75-4.81 (1H, m), 7.38 (1H, s), 8.74 (1H, s), 8.95 (1H, s)

+

-continued

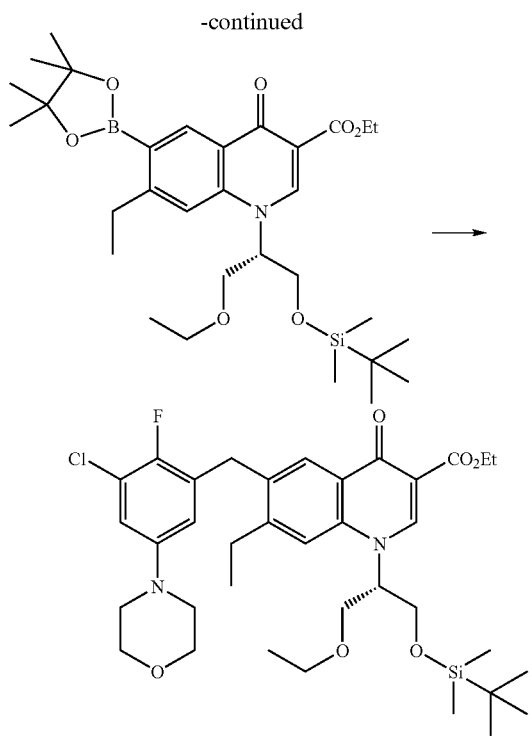

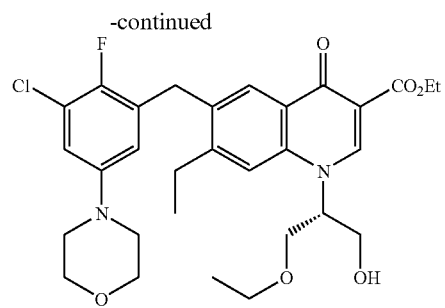

The compound (70 mg, 0.119 mmol) obtained in Step 20 and the compound (44 mg, 0.143 mmol) obtained in Step 6 were dissolved in 1,2-dimethoxyethane (1.5 ml), tetrakis(triphenylphosphine)palladium(0) (7 mg, 0.006 mmol) and 2M aqueous sodium carbonate solution (240 μl, 0.480 mmol) were added, and the mixture was stirred under heating at 80° C. for 50 min. After allowing to cool, water and ethyl acetate were added to the reaction mixture, and the layers were separated. The organic layer was washed with water (three times) and saturated brine in this order, and dried over sodium sulfate. After filtration, the filtrate was concentrated under reduced pressure, and the obtained residue was purified by preparative thin layer chromatography (PTLC)(hexane:ethyl acetate=1:3) to give the object compound (66 mg as a crudely purified product) as a colorless oil.

$^1$H NMR (CDCl$_3$ 400 MHz) (δ) ppm: −0.03 (3H, s), −0.02 (3H, s), 0.82 (9H, s), 1.21 (3H, t, J=7.0 Hz), 1.23 (3H, t, J=7.6 Hz), 1.40 (3H, t, J=7.0 Hz), 2.73 (2H, q, J=7.6 Hz), 2.96 (4H, t, J=4.9 Hz), 3.56 (2H, q, J=7.0 Hz), 3.76 (4H, t, J=4.9 Hz), 3.91 (2H, d, J=5.3 Hz), 4.05 (2H, d, J=4.9 Hz), 4.09 (2H, s), 4.35-4.42 (2H, m), 4.80-4.87 (1H, m), 6.40-6.42 (1H, m), 6.74-6.76 (1H, m), 7.36 (1H, s), 8.31 (1H, s), 8.74 (1H, s)

Step 22

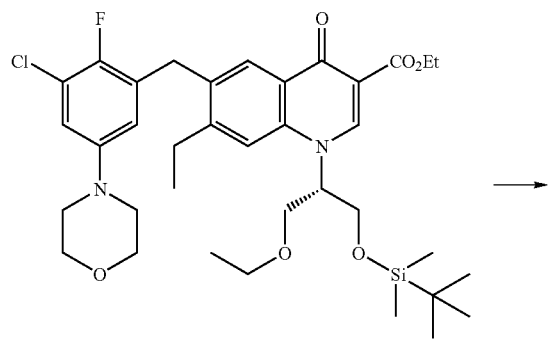

The compound (66 mg) obtained in Step 21 was dissolved in tetrahydrofuran (1 ml), a 1.0 M solution of tetrabutylammonium fluoride in tetrahydrofuran (144 μl, 0.144 mmol) was added, and the mixture was stirred at room temperature for 40 min. Water and ethyl acetate were added to the reaction mixture, the layers were separated, and the aqueous layer was extracted with ethyl acetate. The organic layer was washed with water (three times) and saturated brine in this order, and dried over sodium sulfate. After filtration, the filtrate was concentrated under reduced pressure, and the obtained residue was purified by PTLC (chloroform:methanol=15:1) to give the object compound (53 mg, yield 77%, 2 steps) as a colorless oil.

$^1$H NMR (CDCl$_3$ 400 MHz) (δ) ppm: 1.21 (3H, t, J=7.2 Hz), 1.22 (3H, t, J=7.5 Hz), 1.41 (3H, t, J=7.1 Hz), 2.63-2.81 (2H, m), 2.88 (4H, t, J=4.7 Hz), 3.56-3.63 (2H, m), 3.72 (4H, t, J=4.7 Hz), 3.98-4.02 (1H, m), 4.06-4.18 (4H, m), 4.28-4.43 (3H, m), 4.54-4.69 (1H, m), 4.86-4.92 (1H, m), 6.15-6.18 (1H, m), 6.71-6.73 (1H, m), 7.37 (1H, s), 7.66 (1H, s), 8.68 (1H, s)

Step 23

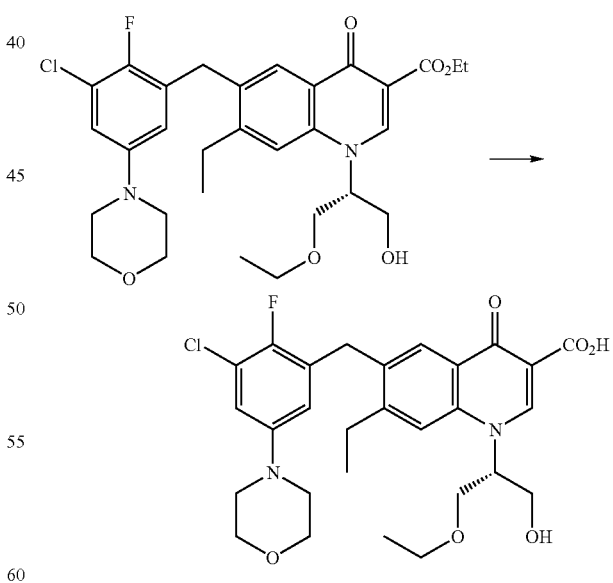

The compound (53 mg, 0.092 mmol) obtained in Step 22 was dissolved in a mixed solvent of tetrahydrofuran (1 ml) and water (0.2 ml), lithium hydroxide monohydrate (8 mg, 0.2 mmol) was added, and the mixture was stirred at room temperature for 3 hr. The reaction mixture was acidified with an aqueous citric acid solution. The precipitated solid was collected by filtration, washed with water and dried under reduced pressure to give the object compound (46 mg, yield 91%) as a white solid.

$^1$H NMR (DMSO-$d_6$ 400 MHz) (δ) ppm: 1.03 (3H, t, J=7.0 Hz), 1.26 (3H, t, J=7.5 Hz), 2.91 (2H, q, J=7.5 Hz), 3.08 (4H, t, J=4.9 Hz), 3.46 (2H, q, J=7.0 Hz), 3.71 (4H, t, J=4.9 Hz), 3.85-4.01 (4H, m), 4.20 (2H, s), 5.27 (1H, t, J=5.4 Hz), 5.33-5.41 (1H, m), 6.91-6.93 (1H, m), 7.03-7.05 (1H, m), 7.96 (1H, s), 8.02 (1H, s), 8.90 (1H, s), 15.21 (1H, s)

MS (ESI): M+ 547

Example 2

Step 1

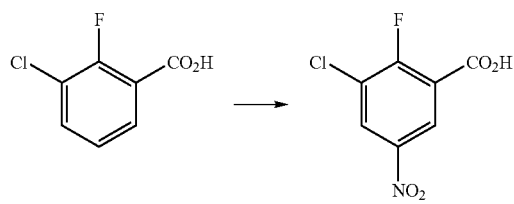

3-Chloro-2-fluorobenzoic acid (5.00 g, 28.64 mmol) was dissolved in concentrated sulfuric acid (15 ml), nitric acid (1.50 ml, 31.50 mmol) was added dropwise under ice-cooling, and the mixture was stirred at room temperature for 19 hr. The reaction mixture was poured into ice water (about 200 ml) and, after stirring, the precipitated solid was collected by filtration and washed with water. The obtained solid was dissolved in ethyl acetate, washed with water, and dried over magnesium sulfate. After filtration, the filtrate was concentrated under reduced pressure to give the object compound (4.81 g, yield 76%) as a pale-orange solid.

$^1$H NMR (DMSO-$d_6$ 400 MHz) (δ) ppm: 8.54 (1H, dd, J=5.7, 2.9 Hz), 8.74 (1H, dd, J=5.8, 2.8 Hz), 14.25 (1H, br s)

Step 2

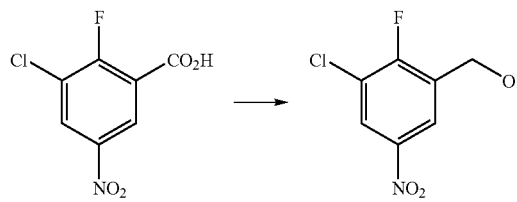

The compound (500 mg, 2.28 mmol) obtained in Step 1 was dissolved in tetrahydrofuran (5 ml), triethylamine (0.317 ml, 2.28 mmol) and isobutyl chlorocarbonate (0.296 ml, 2.28 mmol) were added dropwise under ice-cooling under an argon stream, and the mixture was stirred at the same temperature for 25 min. The reaction mixture was filtered, and washed with tetrahydrofuran (5 ml). The filtrate was ice-cooled, sodium borohydride (129 mg, 3.42 mmol) and water (1.5 ml) were added, and the mixture was stirred at the same temperature for 25 min. Saturated aqueous ammonium chloride solution and saturated brine were added to the reaction mixture, the layers were separated, and the organic layer was washed with saturated brine and dried over magnesium sulfate. After filtration, the filtrate was concentrated under reduced pressure, and the obtained residue was purified by silica gel chromatography (hexane:ethyl acetate=4:1) to give the object compound (357 mg, yield 76%) as a pale-brown oil.

$^1$H NMR (CDCl$_3$ 400 MHz) (δ) ppm: 2.06 (1H, t, J=6.4 Hz), 4.88 (2H, d, J=6.0 Hz), 8.27 (1H, dd, J=6.2, 2.9 Hz), 8.36 (1H, dd, J=5.5, 2.9 Hz)

Step 3

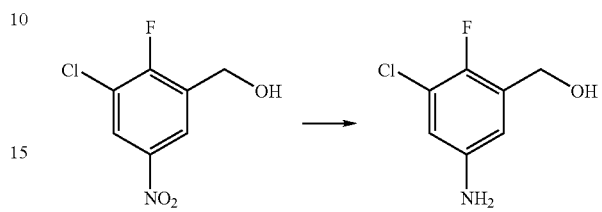

To a mixture of ethanol (10 ml) and water (5 ml) were added reduced iron (486 mg, 8.70 mmol) and ammonium chloride (465 mg, 8.70 mmol). A solution of the compound (357 mg, 1.74 mmol) obtained in Step 2 in tetrahydrofuran (10 ml) was added dropwise at 80° C., and the mixture was stirred under heating at the same temperature for 20 min. After allowing to cool, the reaction mixture was filtered through celite, and washed with ethyl acetate. The filtrate was washed with water, saturated aqueous sodium hydrogen carbonate solution and saturated brine in this order, and dried over magnesium sulfate. After filtration, the filtrate was concentrated under reduced pressure to give a crude product (287 mg) as a yellow solid.

$^1$H NMR (DMSO-$d_6$ 400 MHz) (δ) ppm: 4.44 (2H, d, J=5.8 Hz), 5.20 (2H, br s), 5.23 (1H, t, J=5.8 Hz), 6.53 (1H, dd, J=6.0, 2.8 Hz), 6.61 (1H, dd, J=5.6, 2.8 Hz)

Step 4

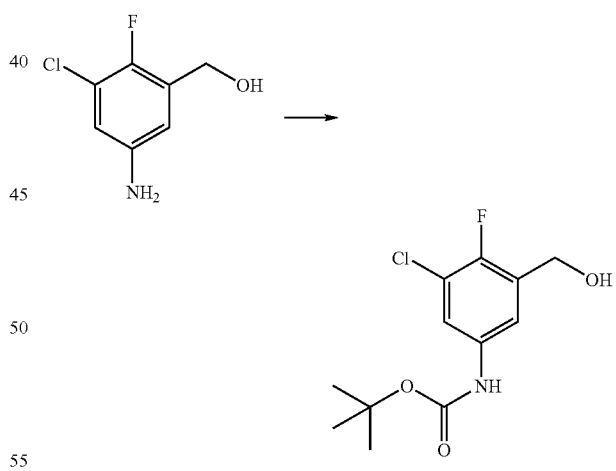

The crude product (287 mg) obtained in Step 3 was dissolved in tetrahydrofuran (3 ml), di-tert-butyl dicarbonate (418 mg, 1.91 mmol) was added, and the mixture was heated under reflux for 6 hr. The reaction mixture was concentrated under reduced pressure, and the obtained residue was purified by silica gel chromatography (hexane:ethyl acetate=4:1) to give the object compound (320 mg, yield 67%, 2 steps) as a white solid.

$^1$H NMR (CDCl$_3$ 400 MHz) (δ) ppm: 1.53 (9H, s), 1.89 (1H, t, J=6.3 Hz), 4.75 (2H, d, J=6.3 Hz), 6.46 (1H, s), 7.26-7.28 (4H, m)), 7.51 (1H, dd, J=6.3, 2.6 Hz)

Step 5

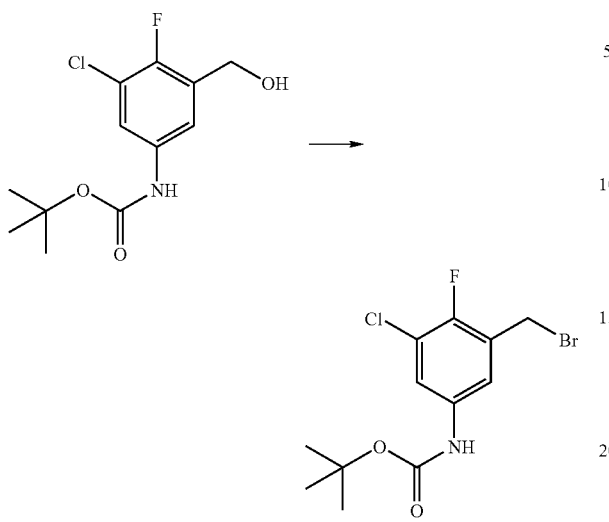

The compound (608 mg, 2.21 mmol) obtained in Step 4 was dissolved in chloroform (12 ml), 3 mmol/g triphenylphosphine resin (1.11 g, 3.32 mmol) and N-bromosuccinimide (471 mg, 2.65 mmol) were added in this order under ice-cooling, and the mixture was stirred at room temperature for 1.5 hr. Ethanol (26 μl) was added to the reaction mixture, and the mixture was filtered and washed with chloroform. The filtrate was concentrated under reduced pressure. The obtained residue was dissolved in ethyl acetate, washed with water and saturated brine in this order, and dried over magnesium sulfate. After filtration, the filtrate was concentrated under reduced pressure, and the obtained residue was purified by silica gel chromatography (hexane:ethyl acetate=4:1) to give the object compound (369 mg, yield 49%) as a pale-yellow solid.

$^1$H NMR (CDCl$_3$ 400 MHz) (δ) ppm: 1.52 (9H, s), 4.46 (2H, d, J=1.2 Hz), 6.45 (1H, br s), 7.31 (1H, dd, J=5.8, 3.0 Hz), 7.46 (1H, dd, J=6.1, 2.4 Hz)

Step 6

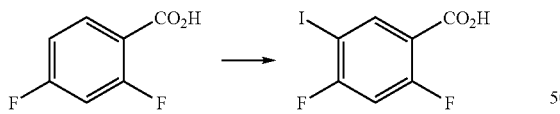

2,4-Difluorobenzoic acid (600.00 g, 3.80 mol) was dissolved in concentrated sulfuric acid (2400 ml), and N-iodosuccinimide (854.40 g, 3.60 mol) was portionwise added at 5° C. or below. After completion of the addition, the mixture was stirred at the same temperature for 3 hr. The reaction mixture was poured into ice water (about 10 L), 10% aqueous sodium sulfite solution (40 ml) was added, and the mixture was stirred for 30 min. The precipitated solid was collected by filtration, suspended in water (about 3 L), and slurry washing was repeated until the pH became 3 or above. The obtained wet crystals (1677 g) were recrystallized from 50% EtOH/water (3000 ml) to give the object compound (824.70 g, yield 76%) as a white solid.

$^1$H NMR (CDCl$_3$ 300 MHz) (δ) ppm: 6.94 (1H, dd, J=10.3, 10.3 Hz), 8.46 (1H, d, J=7.5 Hz)

Step 7

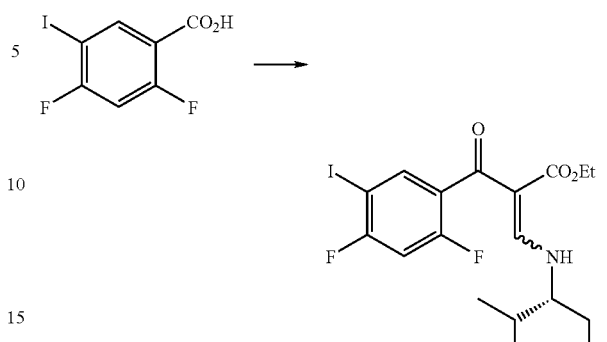

The compound (650.57 g, 2.29 mol) obtained in Step 6 was dissolved in toluene (1300 ml), thionyl chloride (184 ml, 2.52 mol) and dimethylformamide (catalytic amount) were added, and the mixture was stirred at 90° C. for 2 hr. After allowing to cool, the reaction mixture was concentrated under reduced pressure, and subjected to azeotropic distillation with toluene (330 ml) twice. The residue was dissolved in toluene (690 ml) and the solution was added dropwise to a solution of ethyl 3-(dimethylamino)acrylate (361.52 g, 2.525 mol) and diisopropylethylamine (480 ml, 2.75 mol) in toluene (690 ml), and the mixture was stirred under heating at 90° C. for 3 hr. After allowing to cool, (S)-(+)-valinol (260.00 g, 2.52 mol) was added to the reaction mixture, and the mixture was stirred at room temperature for 1 hr. Water (2600 ml) was added to the reaction mixture, the layers were separated, and the aqueous layer was extracted with toluene (680 ml). The organic layer was washed twice with water (2000 ml), and dried over sodium sulfate. After filtration, the filtrate was concentrated under reduced pressure to give a crude product (1180 g) as a brown oil.

Step 8

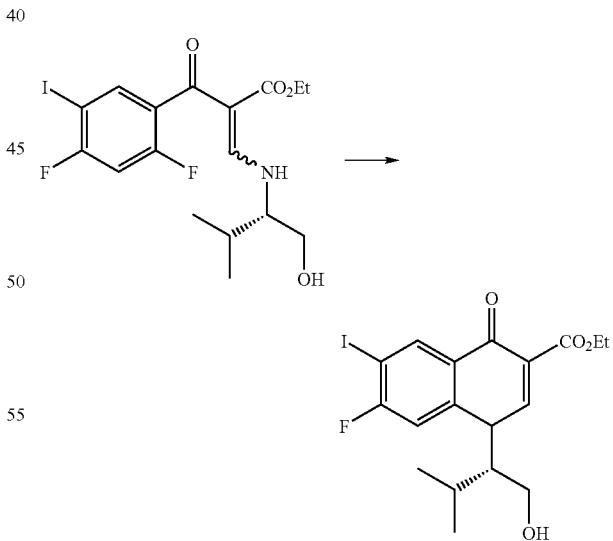

The crude product (1180 g) obtained in Step 7 was dissolved in dimethylformamide (2500 ml), pulverized potassium carbonate (292.00 g, 1.06 mol) was added, and the mixture was stirred at room temperature for 22 hr. The reaction mixture was added to ice water (about 10 L), and the mixture was stirred for 30 min. The precipitated solid was collected by filtration, and washed with water (2000 ml). The obtained solid was dried under reduced pressure, suspended in ethyl acetate (5000 ml) and subjected to slurry-washing. After filtration, the filtrate was dried under reduced pressure to give the object compound (774.63 g, yield 82%) as a yellow-white solid.

$^1$H NMR (DMSO-$d_6$ 300 MHz) (δ) ppm: 0.72 (3H, d, J=6.6 Hz), 1.10 (3H, d, J=6.6 Hz), 1.28 (3H, t, J=7.0 Hz), 2.27 (1H, br), 3.77 (1H, br), 3.86 (1H, br), 4.23 (2H, q, J=7.0 Hz), 4.56 (1H, br), 5.12 (1H, t, J=4.9 Hz), 8.09 (1H, d, J=11.1 Hz), 8.62 (1H, d, J=7.5 Hz), 8.68 (1H, s)

Step 9

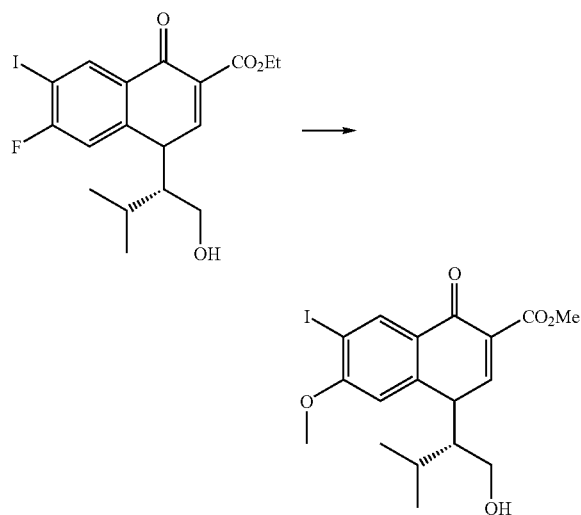

The compound (25.00 g, 55.90 mmol) obtained in Step 8 was dissolved in methanol (250 ml), a 28% solution of sodium methoxide in methanol (12.5 ml, 61.49 mol) was added, and the mixture was heated under reflux for 3 hr. After allowing to cool, the reaction mixture was concentrated under reduced pressure. The obtained residue was dissolved in dimethylformamide (125 ml), potassium carbonate (7.72 g, 55.90 mmol) and iodomethane (3.48 ml, 55.90 mmol) were added, and the mixture was stirred at room temperature for 2 hr. The reaction mixture was poured into ice water containing 6N hydrochloric acid (12 ml), and extracted twice with ethyl acetate. The organic layer was washed with water (three times) and saturated brine in this order, and dried over sodium sulfate. After filtration, the filtrate was concentrated under reduced pressure to give a yellow amorphous crude product (24.94 g).

Step 10

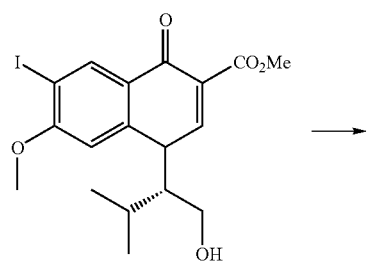

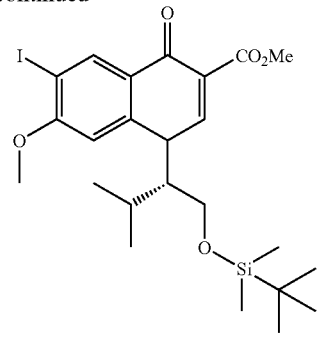

The crude product (24.94 g) obtained in Step 9 was dissolved in dimethylformamide (125 ml), imidazole (4.95 g, 72.66 mmol) and tert-butyldimethylsilyl chloride (10.10 g, 67.07 mmol) were added, and the mixture was stirred at room temperature for 15 hr. Water was added to the reaction mixture, and the mixture was extracted twice with ethyl acetate. The organic layer was washed four times with saturated brine, and dried over sodium sulfate. After filtration, the filtrate was concentrated under reduced pressure, and the obtained residue was purified by silica gel chromatography (hexane:ethyl acetate=1:1 to 1:2) to give the object compound (21.86 g, yield 70%, 2 steps) as a pale-yellow solid.

$^1$H NMR (CDCl$_3$ 300 MHz) (δ) ppm: −0.07 (3H, s), −0.04 (3H, s), 0.78 (9H, s), 0.84 (3H, d, J=6.8 Hz), 1.19 (3H, d, J=6.8 Hz), 2.38-2.49 (1H, m), 3.91 (3H, s), 3.99-4.16 (6H, m), 6.76 (1H, s), 8.66 (1H, s), 8.95 (1H, s)

Step 11

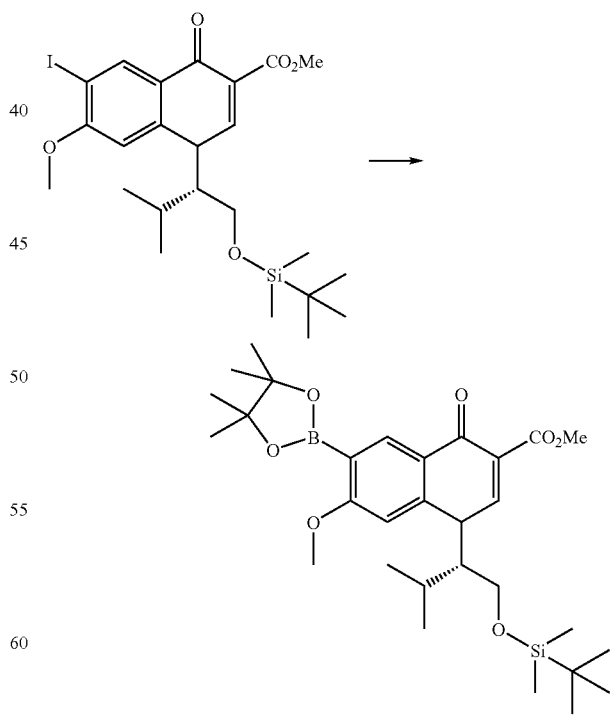

The compound (3.50 g, 6.26 mmol) obtained in Step 10 was suspended in dimethyl sulfoxide (25 ml), bis(pinacolato)diboron (1.75 g, 6.89 mmol), potassium acetate (1.84 g, 18.78 mmol) and [1,1'-bis(diphenylphosphino)ferrocene]dichloropalladium(II) dichloromethane (1:1) complex (153 mg, 0.188 mmol) were added under an argon stream, and the mixture was stirred under heating at 80° C. for 1.5 hr. After allowing to cool, water and ethyl acetate were added to the reaction mixture, the layers were separated, and the aqueous layer was extracted with ethyl acetate. The organic layer was washed with water (three times) and saturated brine in this order, and dried over magnesium sulfate. After filtration, the filtrate was concentrated under reduced pressure to give a brown amorphous crude product (3.45 g).

$^1$H NMR (CDCl$_3$ 300 MHz) (δ) ppm: −0.07 (3H, s), −0.05 (3H, s), 0.78 (9H, s), 0.82 (3H, d, J=6.4 Hz), 1.18 (3H, d, J=6.4 Hz), 1.35 (12H, s), 2.36-2.51 (1H, m), 3.88 (3H, s), 3.93 (3H, s), 4.03-4.23 (3H, m), 6.73 (1H, s), 8.64 (1H, s), 8.85 (1H, s)

Step 12

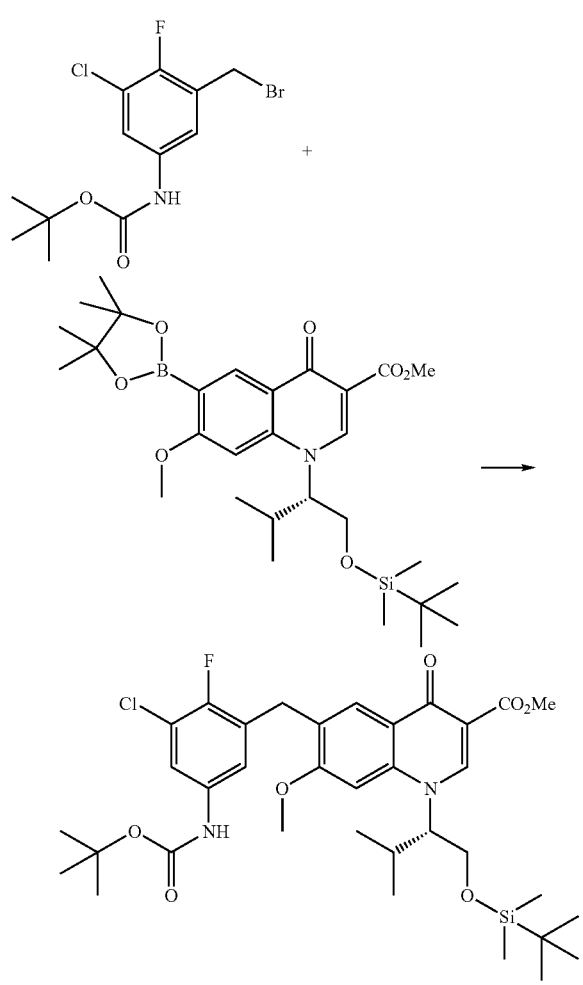

The crude product (1.07 g) obtained in Step 11 and the compound (433 mg, 1.28 mmol) obtained in Step 5 were dissolved in 1,2-dimethoxyethane,
tetrakis(triphenylphosphine)palladium(0) (44 mg, 0.038 mmol) and 2M aqueous sodium carbonate solution (2.60 ml, 5.12 mmol) were added, and the mixture was stirred under heating at 80° C. for 30 min. After allowing to cool, saturated aqueous ammonium chloride solution and ethyl acetate were added to the reaction mixture, and the layers were separated. The organic layer was washed with water and saturated brine in this order, and dried over magnesium sulfate. After filtration, the filtrate was concentrated under reduced pressure, and the obtained residue was purified by silica gel chromatography (hexane:ethyl acetate=1:1) to give the yellow amorphous object compound (1.21 g, yield 71%).

$^1$H NMR (CDCl$_3$ 400 MHz) (δ) ppm: 0.00 (6H, s), 0.77 (9H, s), 0.85 (3H, d, J=6.7 Hz), 1.19 (3H, d, J=6.5 Hz), 1.47 (9H, s), 2.40-2.50 (1H, m), 3.90 (3H, s), 3.91 (3H, s), 3.95 (1H, dd, J=11.0, 2.7 Hz), 4.02 (2H, s), 4.03-4.06 (1H, m), 4.16-4.21 (1H, m), 6.29 (1H, s), 6.72 (1H, dd, J=5.4, 2.7 Hz), 6.78 (1H, s), 7.53-7.58 (1H, m), 8.29 (1H, s), 8.65 (1H, s)

Step 13

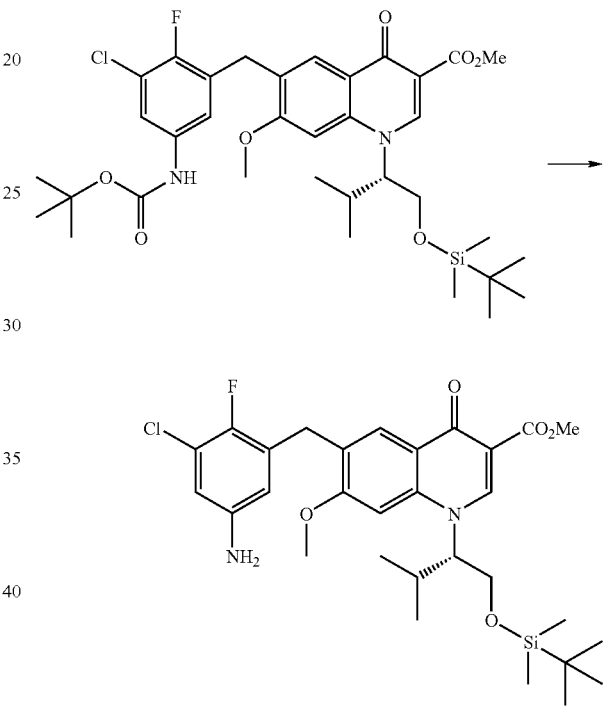

The compound (200 mg, 0.289 mmol) obtained in Step 12 was dissolved in chloroform (1 ml), trifluoroacetic acid (1 ml) was added, and the mixture was stirred at room temperature for 30 min. The reaction mixture was concentrated under reduced pressure, and the obtained residue was dissolved in ethyl acetate. To the solution was added saturated aqueous sodium hydrogen carbonate solution, and the layers were separated. The aqueous layer was extracted with ethyl acetate, and the organic layer was washed with saturated brine and dried over magnesium sulfate. After filtration, the filtrate was concentrated under reduced pressure to give a yellow amorphous crude product (167 mg).

$^1$H NMR (CDCl$_3$ 400 MHz) (δ) ppm: 0.00 (6H, s), 0.77 (9H, s), 0.85 (3H, d, J=6.5 Hz), 1.19 (3H, d, J=6.5 Hz), 2.42-2.48 (1H, m), 3.90 (3H, s), 3.91 (3H, s), 3.93-3.96 (1H, m), 3.98 (2H, s), 4.03-4.07 (1H, m), 4.15-4.21 (1H, m), 6.24 (1H, dd, J=5.4, 2.9 Hz), 6.54 (1H, dd, J=5.7, 2.9 Hz), 6.78 (1H, s), 8.31 (1H, s), 8.65 (1H, s)

Step 14

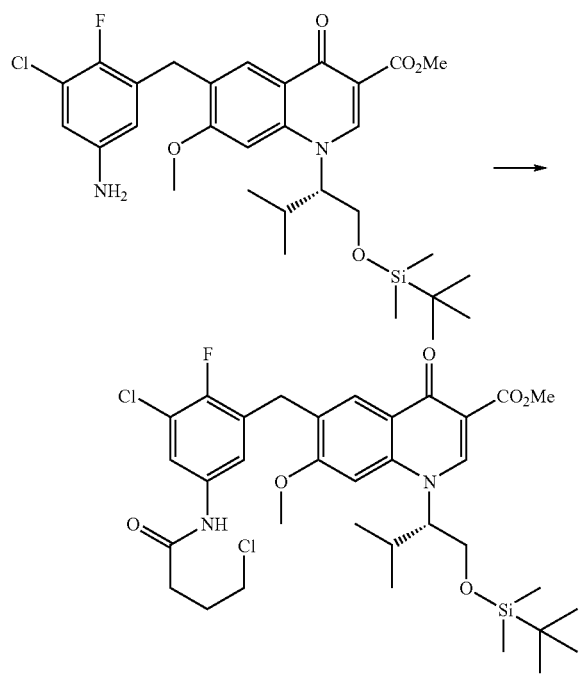

The compound (167 mg) obtained in Step 13 was dissolved in chloroform (1.7 ml), pyridine (46 μl, 0.564 mmol) and 4-chlorobutyryl chloride (38 μl, 0.338 mmol) were added, and the mixture was stirred at room temperature for 15 hr. The reaction mixture was concentrated under reduced pressure, and the obtained residue was dissolved in ethyl acetate. To the solution was added saturated aqueous sodium hydrogen carbonate solution, and the layers were separated. The aqueous layer was extracted with ethyl acetate, and the organic layer was washed with water, saturated aqueous sodium hydrogen carbonate solution and saturated brine in this order, and dried over magnesium sulfate. After filtration, the filtrate was concentrated under reduced pressure, and the obtained residue was purified by silica gel chromatography (chloroform: methanol=95:5) to give the object compound (164 mg, yield 82%, 2 steps) as a pale-yellow gum.

$^1$H NMR (CDCl$_3$ 400 MHz) (δ) ppm: 0.00 (6H, s), 0.77 (9H, s), 0.85 (3H, d, J=6.7 Hz), 1.20 (3H, d, J=6.5 Hz), 2.11-2.18 (1H, m), 2.49 (2H, t, J=7.1 Hz), 3.61 (2H, t, J=6.1 Hz), 3.89 (3H, s), 3.92 (3H, s), 3.93-3.96 (1H, m), 4.03 (2H, s), 4.04-4.08 (1H, m), 4.16-4.22 (1H, m), 6.79 (1H, s), 6.95 (1H, dd, J=5.3, 2.6 Hz), 7.36 (1H, br s), 7.73 (1H, dd, J=6.5, 2.8 Hz), 8.28 (1H, s), 8.67 (1H, s)

Step 15

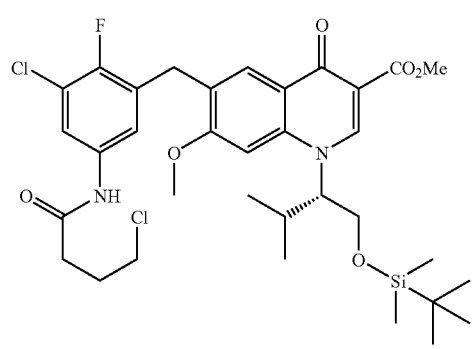

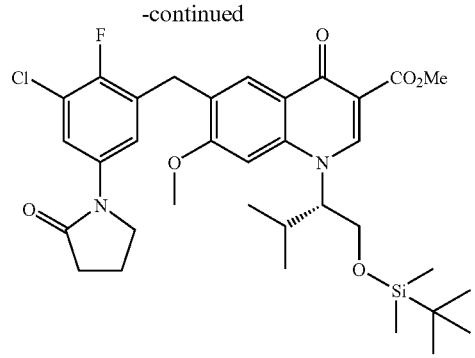

The compound (164 mg, 0.236 mmol) obtained in Step 14 was dissolved in dimethylformamide (1.7 ml), sodium hydride (14 mg, 0.354 mmol) was added at 0° C., and the mixture was stirred at the same temperature for 2 hr. Aqueous ammonium chloride solution and ethyl acetate were added to the reaction mixture, and the layers were separated. The aqueous layer was extracted with ethyl acetate, and the organic layer was washed with water (three times) and saturated brine in this order, and dried over magnesium sulfate. After filtration, the filtrate was concentrated under reduced pressure to give a crude product (152 mg) as a brown gum.

$^1$H NMR (CDCl$_3$ 400 MHz) (δ) ppm: 0.00 (6H, s), 0.77 (9H, s), 0.85 (3H, d, J=6.7 Hz), 1.19 (3H, d, J=6.5 Hz), 2.08-2.15 (2H, m), 2.40-2.50 (1H, m), 2.55 (2H, t, J=8.1 Hz), 3.74 (2H, t, J=7.1 Hz), 3.90 (3H, s), 3.91-3.96 (1H, m), 3.94 (3H, s), 4.03-4.07 (1H, m), 4.07 (2H, s), 4.15-4.21 (1H, m), 6.78 (1H, s), 7.25-7.28 (1H, m), 7.59 (1H, dd, J=6.0, 2.8 Hz), 8.28 (1H, s), 8.65 (1H, s)

Step 16

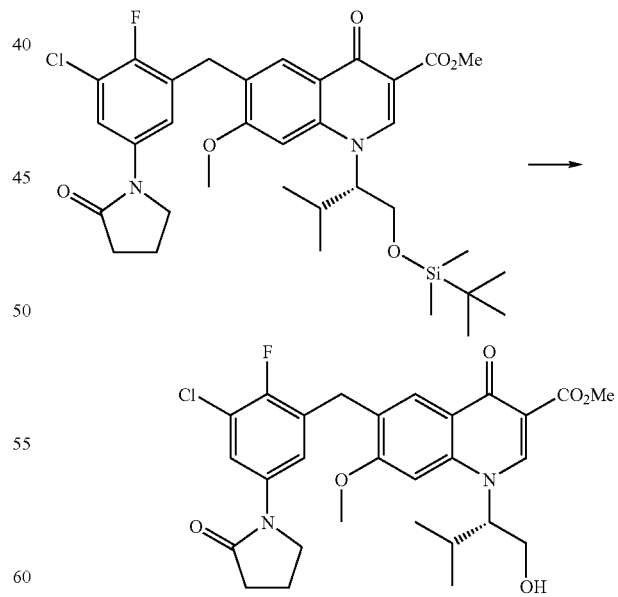

The crude product (152 mg) obtained in Step 15 was dissolved in tetrahydrofuran (3 ml), a 1.0 M solution of tetrabutylammonium fluoride in tetrahydrofuran (700 μl, 0.699 mmol) was added, and the mixture was stirred at room temperature for 1 hr. Water and ethyl acetate were added to the reaction mixture, the layers were separated, and the aqueous layer was extracted with ethyl acetate. The organic layer was washed with water and saturated brine in this order, and dried over magnesium sulfate. After filtration, the filtrate was concentrated under reduced pressure, and the obtained residue was purified by PTLC (chloroform:methanol=9:1) to give the object compound (98 mg, yield 76%, 2 steps) as a pale-yellow oil.

$^1$H NMR (CDCl$_3$ 400 MHz) (δ) ppm: 0.76 (3H, d, J=6.5 Hz), 1.23 (3H, d, J=6.5 Hz), 2.08-2.15 (2H, m), 2.43-2.51 (1H, m), 2.55 (2H, t, J=8.1 Hz), 3.56-3.61 (1H, m), 3.69-3.74 (3H, m), 3.85 (3H, s), 4.03 (3H, s), 4.12-4.27 (3H, m), 4.79-4.90 (1H, m), 6.92 (1H, s), 7.38 (1H, dd, J=5.7, 2.7 Hz), 7.43 (1H, dd, J=6.0, 2.8 Hz), 7.58 (1H, br s), 8.57 (1H, br s)

Step 17

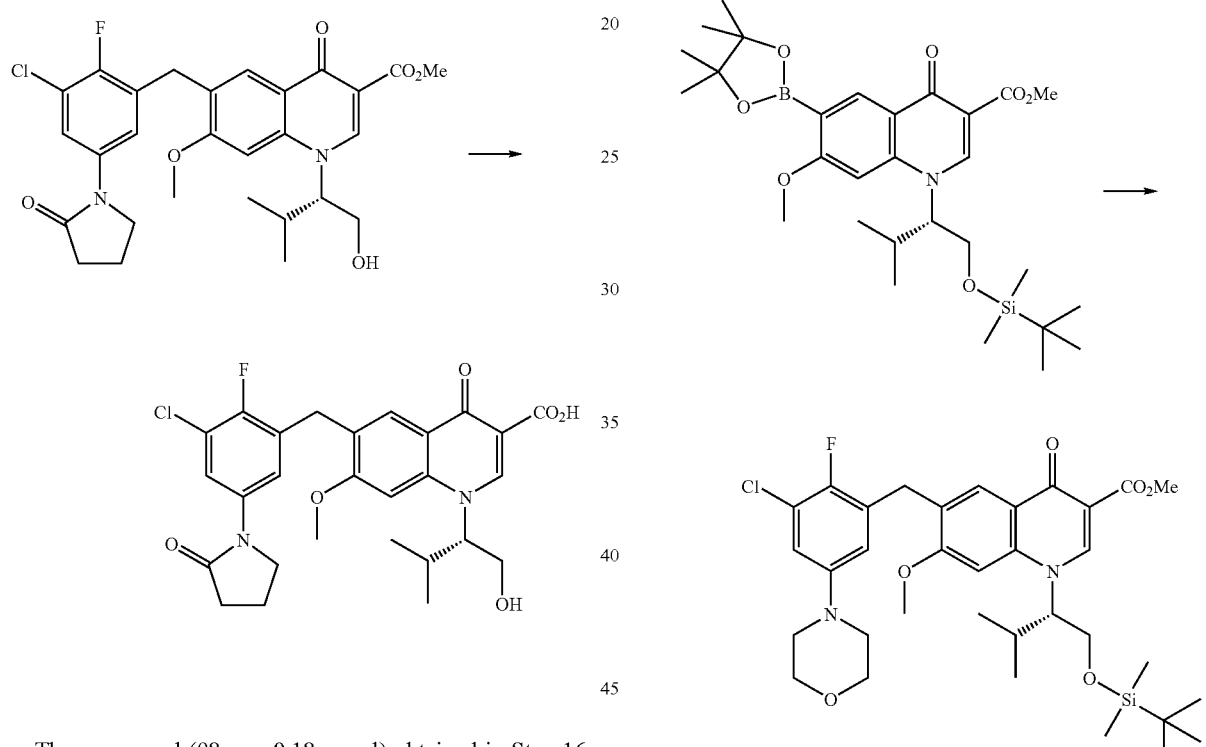

The compound (98 mg, 0.18 mmol) obtained in Step 16 was dissolved in a mixed solvent of tetrahydrofuran (1 ml) and water (0.5 ml), lithium hydroxide monohydrate (15 mg, 0.36 mmol) was added, and the mixture was stirred at room temperature for 3 hr. The reaction mixture was acidified with 1N hydrochloric acid, and extracted with ethyl acetate. The organic layer was washed twice with water, and dried over magnesium sulfate. After filtration, the filtrate was concentrated under reduced pressure, and the obtained residue was recrystallized from acetone-hexane to give the object compound (61 mg, yield 64%) as a pale-yellow solid.

$^1$H NMR (DMSO-d$_6$ 400 MHz) (δ) ppm: 0.72 (3H, d, J=6.6 Hz), 1.16 (3H, d, J=6.4 Hz), 1.99-2.07 (2H, m), 2.31-2.41 (1H, m), 2.46-2.50 (2H, m), 3.75-3.82 (3H, m), 3.95-4.01 (1H, m), 4.05 (3H, s), 4.11 (2H, s), 4.87 (1H, br s), 5.19 (11H, t, J=5.2 Hz), 7.46 (1H, s), 7.62 (1H, dd, J=6.0, 2.6 Hz), 7.82 (1H, dd, J=6.4, 2.6 Hz), 8.03 (1H, s), 8.88 (1H, s), 15.42 (1H, s)

MS (ESI): M+ 531

Example 5

Step 1

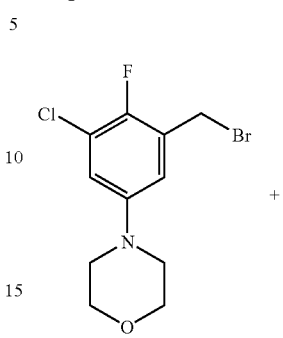

+

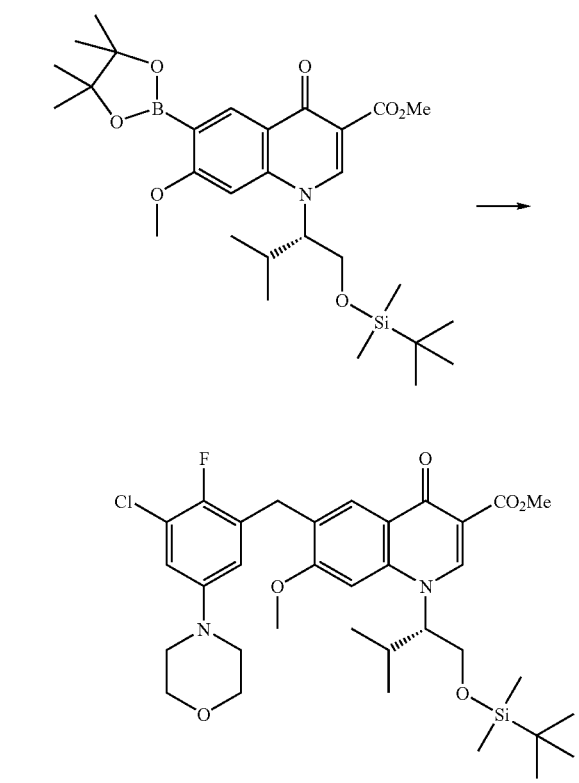

To a solution of the compound (67 mg, 0.22 mmol) obtained in Step 6 of Example 1, the compound (182 mg, 0.33 mmol) obtained in Step 11 of Example 2, tetrakis(triphenylphosphine)palladium(0) (7.5 mg, 0.0065 mmol) in 1,2-dimethoxyethane (2.1 ml) was added 2M aqueous sodium carbonate solution (434 μl 0.87 mmol), and the mixture was stirred under heating at 80° C. for 20 min. After completion of the reaction, ethyl acetate and water were added to the reaction mixture, the layers were separated, and the aqueous layer was extracted with ethyl acetate. The combined organic layer was washed twice with saturated brine, and dried over sodium sulfate. After filtration, the filtrate was concentrated under reduced pressure, and the obtained residue was purified by PTLC (chloroform:acetone=6:1, developed twice) to give a crudely purified product (68 mg) as a pale-brown amorphous solid.

Step 2

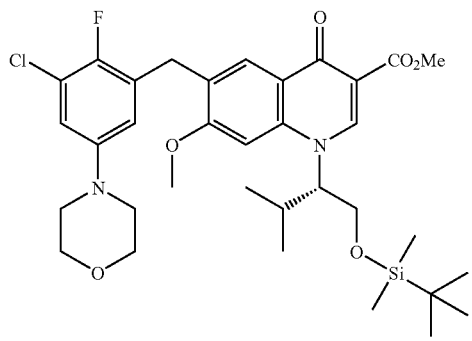

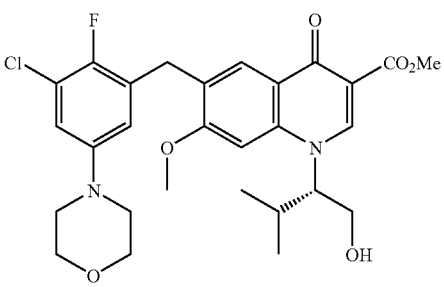

The crudely purified product (68 mg) obtained in Step 1 was stirred in tetrahydrofuran (0.7 ml) with a 1.0 M solution of tetrabutylammonium fluoride in tetrahydrofuran (154 μl, 0.15 mmol) at room temperature for 1.5 hr. Ethyl acetate and brine were added to the reaction mixture, the layers were separated, and the aqueous layer was extracted with ethyl acetate. The combined organic layer was washed four times with saturated brine, and dried over sodium sulfate. After filtration, the filtrate was concentrated under reduced pressure, the obtained residue was treated with ethyl acetate, and the precipitated solid was collected by filtration and dried to give the object compound (30 mg, yield 25%, 2 steps) as a white solid.

$^1$H NMR (CDCl$_3$ 400 MHz) (δ) ppm: 0.76 (3H, d, J=6.7 Hz), 1.24 (3H, d, J=6.5 Hz), 2.42-2.52 (1H, m), 2.92-2.98 (4H, m), 3.57 (1H, d, J=15.0 Hz), 3.73-3.78 (4H, m), 3.87 (3H, s), 3.97 (3H, s), 4.07 (1H, d, J=15.0 Hz), 4.13-4.30 (3H, m), 4.80-4.89 (1H, m), 6.42-6.46 (1H, m), 6.72 (1H, dd, J=5.9, 2.9 Hz), 6.84 (1H, s), 7.61 (1H, s), 8.56 (1H, s)

Step 3

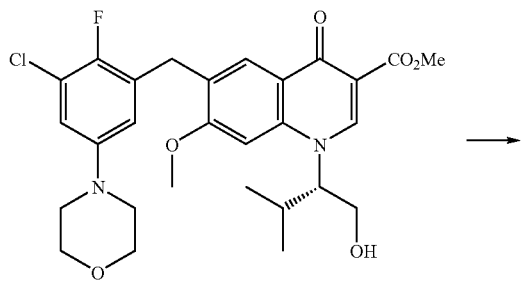

-continued

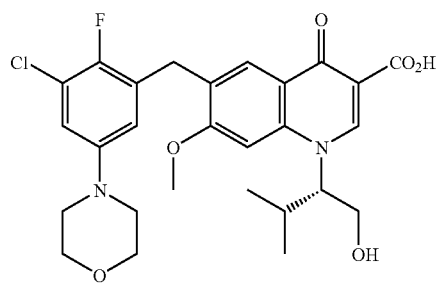

The compound (30 mg, 0.055 mmol) obtained in Step 2 and lithium hydroxide monohydrate (3.5 mg, 0.082 mmol) were stirred in a mixed solvent of tetrahydrofuran (300 μl) and water (150 μl) at room temperature for 4 hr. To the reaction mixture was added a 5% aqueous potassium hydrogen sulfate solution, and the mixture was extracted twice with ethyl acetate. The combined organic layer was washed twice with saturated brine, and dried over sodium sulfate. After filtration, the filtrate was concentrated under reduced pressure, the obtained residue was treated with a mixed solvent of hexane-ethyl acetate, and the precipitated solid was collected by filtration and dried under reduced pressure to give the object compound (28 mg, yield 96%) as a white solid.

$^1$H NMR (DMSO-d$_6$ 400 MHz) (δ) ppm: 0.72 (3H, d, J=6.8 Hz), 1.16 (3H, d, J=6.8 Hz), 2.31-2.43 (1H, m), 3.04-3.10 (4H, m), 3.68-3.73 (4H, m), 3.75-3.82 (1H, m), 3.94-4.03 (1H, m), 4.04 (2H, s), 4.06 (3H, s), 4.83-4.92 (1H m), 5.17-5.23 (1H, m), 6.90-6.95 (1H, m), 6.98-7.03 (1H, m), 7.46 (1H, s), 7.95 (1H, s), 8.87 (1H, s), 15.44 (1H, br s)

MS (ESI): M+ 533

Example 16

Step 1

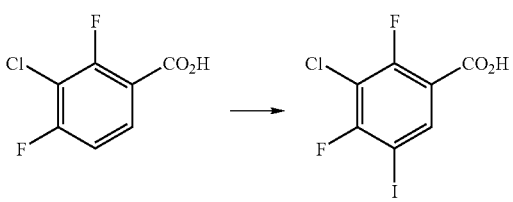

3-Chloro-2,4-difluorobenzoic acid (25 g, 130 mmol) was dissolved in concentrated sulfuric acid (250 ml), and N-iodosuccinimide (30.6 g, 136 mmol) was portionwise added over 10 min under cooling in an ice bath. After completion of the addition, the mixture was stirred at the same temperature for 30 min and at room temperature for 3.5 hr. The reaction mixture was poured into ice water (about 1000 ml) containing sodium sulfite (14.2 g, 136 mmol) and, after stirring, the precipitated solid was collected by filtration and washed with water. The obtained solid was dried under reduced pressure to give the object compound (40.4 g, yield 98%) as a white solid.

$^1$H NMR (DMSO-d$_6$ 400 MHz) (δ) ppm: 8.21-8.27 (1H, m)

Step 2

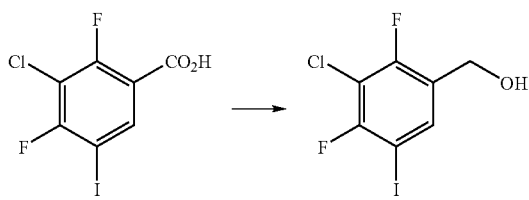

The compound (40.4 t, 127 mmol) obtained in Step 1 was dissolved in tetrahydrofuran (200 ml), and a 1.0 M solution of borane tetrahydrofuran complex in tetrahydrofuran (190 ml, 190 mmol) was added dropwise at 0° C. over 20 min under an argon atmosphere. After completion of the dropwise addition, the mixture was stirred at room temperature for 20 min and then under heating at 50° C. for 1 hr. After allowing to cool, a 1.0 M solution of borane tetrahydrofuran complex in tetrahydrofuran (100 ml, 100 mmol) was added dropwise to the reaction mixture over 5 min under ice-cooling and, after the completion of the dropwise addition, the mixture was stirred at room temperature for 15 min and then under heating at 50° C. for 1 hr. After completion of the reaction, 1N hydrochloric acid (300 ml) was added dropwise under ice-cooling. Ethyl acetate and saturated brine were added to the mixture, the layers were separated, and the aqueous layer was extracted with ethyl acetate. The combined organic layer was washed with saturated brine, saturated aqueous sodium hydrogen carbonate solution and saturated brine in this order, and dried over sodium sulfate. After filtration, the filtrate was concentrated under reduced pressure to give a crude product (40.0 g) as a pale-yellow solid.

Step 3

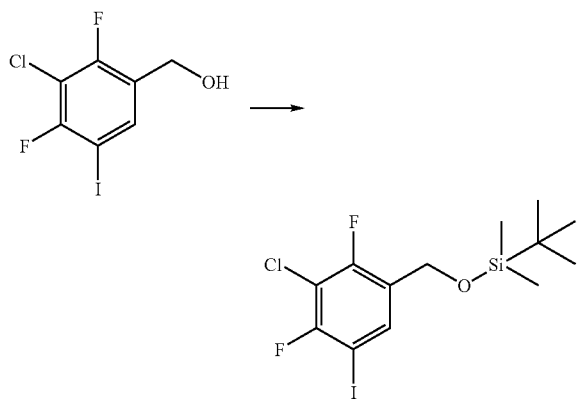

The crude product (40.0 g) obtained in Step 2 was dissolved in dimethylformamide (200 ml), and imidazole (11.2 g, 165 mmol) was added. tert-Butyldimethylsilyl chloride (23.0 g, 152 mmol) was added under cooling in an ice bath, and the mixture was stirred at room temperature for 1.3 hr. Imidazole (1.3 g, 7.9 mmol) and tert-butyldimethylsilyl chloride (1.91 g, 12.5 mmol) were further added, and the mixture was stirred at room temperature for 0.7 hr. Water and ethyl acetate were added to the reaction mixture, the layers were separated, and the aqueous layer was further extracted with ethyl acetate. The combined organic layer was washed four times with saturated brine, and dried over sodium sulfate. After filtration, the filtrate was concentrated under reduced pressure, and the obtained residue was purified by silica gel chromatography (hexane alone) to give the object compound (50.6 g, yield 95%, 2 steps) as a white solid.

$^1$H NMR (CDCl$_3$ 400 MHz) (δ) ppm: 0.12 (6H, s), 0.95 (9H, s), 4.70-4.74 (2H, m), 7.74-7.79 (1H, m)

Step 4

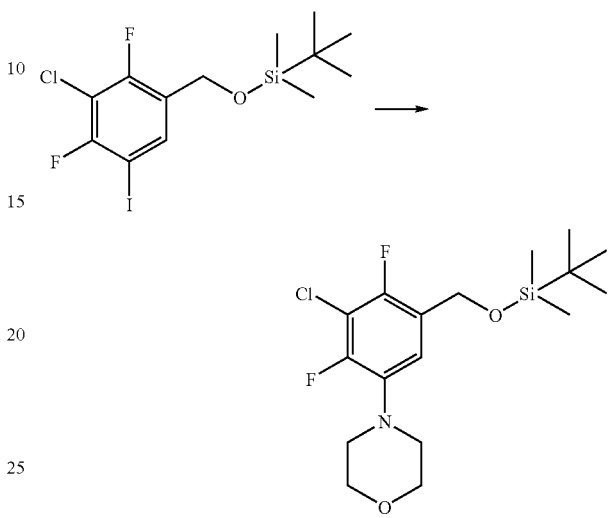

1,4-Dioxane (200 ml) was added to tris(dibenzylideneacetone)dipalladium(0) chloroform (1:1) complex (12.5 g, 12.1 mmol), (±)-2,2'-bis(diphenylphosphino)-1,1'-binaphthyl (15.3 g, 26.6 mmol) and cesium carbonate (66.9 g, 205 mmol), and the mixture was stirred under an argon atmosphere at room temperature for 50 min. Morpholine (14.8 ml, 169 mmol) was added to the mixture, a solution of the compound (50.6 g, 121 mmol) obtained in Step 3 in 1,4-dioxane (300 ml) was added, and the mixture was heated under reflux for 20 hr. After allowing to cool, hexane (400 ml) was added to the reaction mixture and the mixture was stirred. The resulting insoluble material was filtered off through celite and the insoluble material was washed with ethyl acetate. The combined filtrate was washed with water and saturated brine (twice) in this order, and dried over sodium sulfate. After filtration, the filtrate was concentrated under reduced pressure, and the obtained residue was purified by silica gel chromatography (hexane:ethyl acetate=50:1 to 30:1, further 20:1) to give the object compound (22.8 g, yield 50%) as a pale-yellow oil.

$^1$H NMR (CDCl$_3$ 400 MHz) (δ) ppm: 0.12 (6H, s), 0.95 (9H, s), 3.02-3.06 (4H, m), 3.84-3.89 (4H, m), 4.74 (2H, s), 6.99-7.05 (1H, m)

Step 5

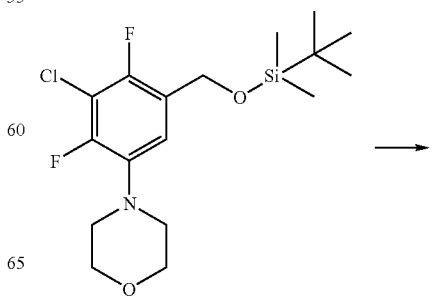

Step 7

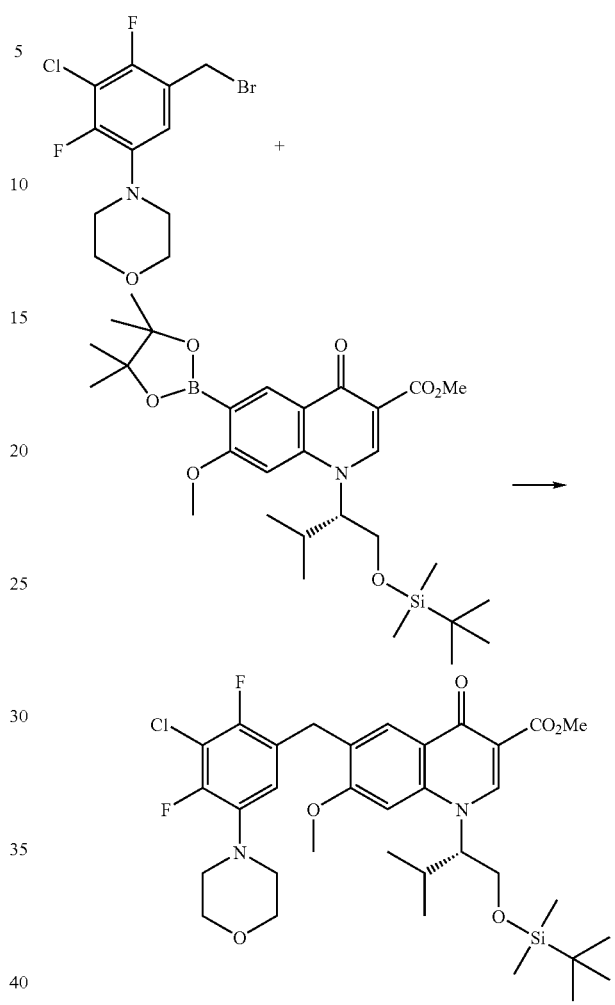

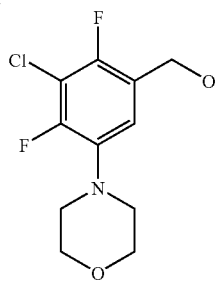

The compound (22.8 g, 60.2 mmol) obtained in Step 4 was dissolved in tetrahydrofuran (220 ml), a 1.0 M solution of tetrabutylammonium fluoride in tetrahydrofuran (90.3 ml, 90.3 mmol) was added, and the mixture was stirred at room temperature for 1 hr. Brine and ethyl acetate were added to the reaction mixture, the layers were separated, and the aqueous layer was extracted with ethyl acetate. The combined organic layer was washed with brine and saturated brine in this order, and dried over sodium sulfate. After filtration, the filtrate was concentrated under reduced pressure, and the obtained residue was purified by silica gel chromatography (hexane:ethyl acetate=2:1 to 1:2) to give the object compound (15.2 g, yield 96%) as a pale-yellow solid.

$^1$H NMR (CDCl$_3$ 400 MHz) (δ) ppm: 1.79-1.84 (1H, m), 3.03-3.09 (4H, m), 3.84-3.89 (4H, m), 4.74 (2H, d, J=6.0 Hz), 6.92-6.99 (1H, m)

Step 6

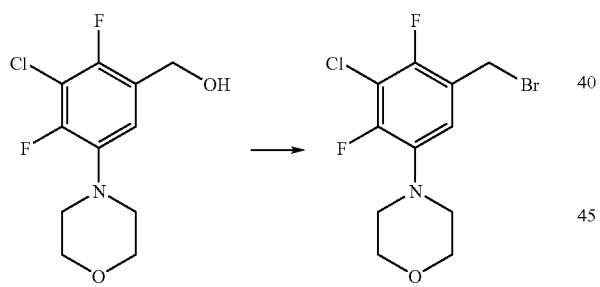

The compound (2 g, 7.6 mmol) obtained in Step 5 was dissolved in chloroform (20 ml), triphenylphosphine (2.39 g, 9.10 mmol) and carbon tetrabromide (3.02 g, 9.10 mmol) were added under ice-cooling, and the mixture was stirred at room temperature for 20 min. Triphenylphosphine (0.597 g, 2.28 mmol) and carbon tetrabromide (0.754 g, 2.27 mmol) were added, and the mixture was stirred at room temperature for 5 min. After completion of the reaction, the mixture was concentrated under reduced pressure, and the obtained residue was purified by silica gel chromatography (hexane:ethyl acetate=50:1 to 2:1) to give the object compound (2.20 g, yield 89%) as a white solid.

$^1$H NMR (CDCl$_3$ 400 MHz) (δ) ppm: 3.02-3.08 (4H, m), 3.83-3.89 (4H, m), 4.46 (2H, s), 6.82-6.88 (1H, m)

To a solution of the compound (55 mg, 0.17 mmol) obtained in Step 6 and the compound (141 mg, 0.25 mmol) obtained in Step 11 of Example 2 in 1,2-dimethoxyethane (1.7 ml) were added tetrakis(triphenylphosphine)palladium (0) (6 mg, 0.005 mmol) and 2M aqueous sodium carbonate solution (337 μl, 0.67 mmol), and the mixture was stirred under an argon atmosphere under heating at 80° C. for 20 min. After completion of the reaction, ethyl acetate and brine were added to the reaction mixture, the layers were separated, and the aqueous layer was extracted with ethyl acetate. The combined organic layer was washed twice with saturated brine, and dried over sodium sulfate. After filtration, the filtrate was concentrated under reduced pressure, and the obtained residue was purified by silica gel chromatography (chloroform: acetone=5:1) to give the object compound (96 mg, yield 84%) as a yellow amorphous solid.

$^1$H NMR (CDCl$_3$ 400 MHz) (δ) ppm: −0.09 (3H, s), −0.05 (3H, s), 0.76 (9H, s), 0.84 (3H, d, J=6.7 Hz), 1.19 (3H, d, J=6.5 Hz), 2.39-2.50 (1H, m), 2.93-2.98 (4H, m), 3.79-3.83 (4H, m), 3.89-4.08 (10H, m), 4.15-4.22 (1H, m), 6.60-6.66 (1H, m), 6.79 (1H, s), 8.27 (1H, s), 8.65 (1H, s)

Step 8

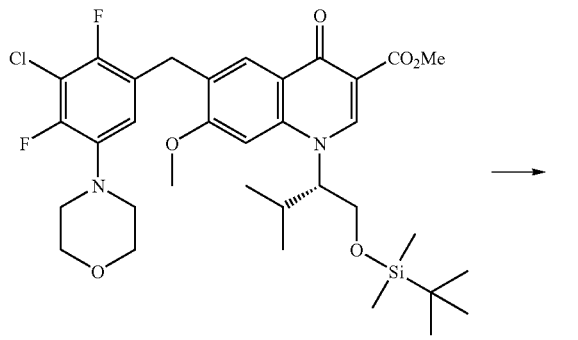

The compound (96 mg, 0.14 mmol) obtained in Step 7 was stirred in tetrahydrofuran (1 ml) with a 1.0 M solution of tetrabutylammonium fluoride in tetrahydrofuran (212 μl, 0.21 mmol), and the mixture was stirred at room temperature for 1.8 hr. Ethyl acetate and brine were added to the reaction mixture, the layers were separated, and the aqueous layer was extracted with ethyl acetate. The combined organic layer was washed twice with saturated brine, and dried over sodium sulfate. After filtration, the filtrate was concentrated under reduced pressure, and the obtained residue was purified by silica gel chromatography (chloroform:acetone=2:1 to chloroform:methanol=10:1) to give the object compound (73 mg, yield 91%) as a pale-yellow solid.

$^1$H NMR (CDCl$_3$ 400 MHz) (δ) ppm: 0.77 (3H, d, J=6.7 Hz), 1.23 (3H, d, J=6.5 Hz), 2.40-2.51 (1H, m), 2.88-2.93 (4H, m), 3.62 (1H, d, J=14.2 Hz), 3.76-3.81 (4H, m), 3.87 (3H, s), 3.96-4.04 (4H, m), 4.15-4.28 (3H, m), 4.52-4.61 (1H, m), 6.49-6.56 (1H, m), 6.86 (1H, s), 7.66 (1H, s), 8.56 (1H, s)

Step 9

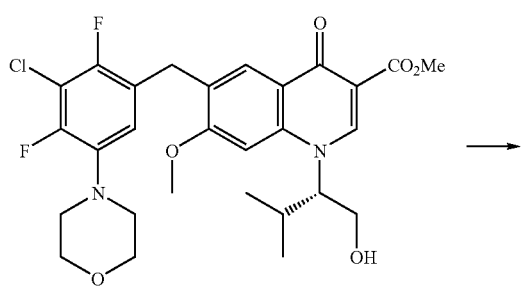

-continued

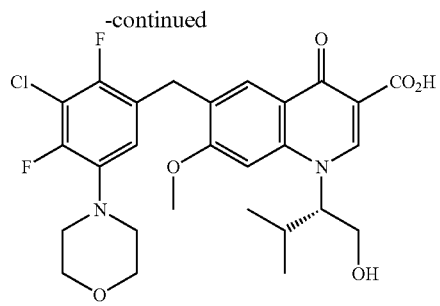

The compound (73 mg, 0.13 mmol) obtained in Step 8 and lithium hydroxide monohydrate (11 mg, 0.26 mmol) were stirred in a mixed solvent of tetrahydrofuran (740 μl) and water (370 μl) at room temperature for 2.3 hr. Ethyl acetate and 5% aqueous potassium hydrogen sulfate solution were added to the reaction mixture, the layers were separated, and the aqueous layer was extracted with ethyl acetate. The combined organic layer was washed twice with saturated brine, and dried over sodium sulfate. After filtration, the filtrate was concentrated under reduced pressure, and the obtained residue was treated with a mixed solvent of hexane-ethyl acetate. The precipitated solid was collected by filtration, and dried to give the object compound (60 mg, yield 84%) as a pale-brown solid.

$^1$H NMR (DMSO-d$_6$ 400 MHz) (δ) ppm: 0.72 (3H, d, J=6.8 Hz), 1.16 (3H, d, J=6.8 Hz), 2.31-2.45 (1H, m), 2.93-3.00 (4H, m), 3.70-3.75 (4H, m), 3.75-3.82 (1H, m), 3.95-4.02 (1H, m), 4.06 (3H, s), 4.07 (2H, s), 4.83-4.92 (1H, m), 5.17-5.23 (1H, m), 7.05-7.11 (1H, m), 7.46 (1H, s), 8.01 (1H, s), 8.88 (1H, s), 15.44 (1H, br s)

MS (ESI): M+ 551

Example 17

Step 1

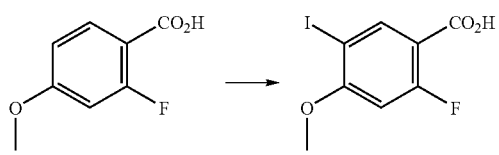

2-Fluoro-4-methoxybenzoic acid (25.0 g, 147 mmol) was dissolved in concentrated sulfuric acid (175 ml), and N-iodosuccinimide (31.4 g, 140 mmol) was portionwise added under ice-cooling over 30 min. After the completion of addition, the ice bath was removed, and the mixture was stirred at room temperature overnight. The reaction mixture was poured into ice water containing sodium sulfite (1.9 g, 15 mmol), and the mixture was stirred for 1 hr. The precipitated solid was collected by filtration and washed with water. The obtained solid was air-dried, and stirred in ethanol (250 ml) at 90° C. for 1 hr. After allowing to cool, the solid was collected by filtration to give the object compound (21.4 g, yield 49%) as a white solid.

$^1$H NMR (DMSO-d$_6$ 400 MHz) (δ) ppm: 3.92 (3H, s), 7.03 (1H, d, J=13.2 Hz), 8.20 (1H, d, J=8.4 Hz), 13.12 (1H, br s)

Step 2

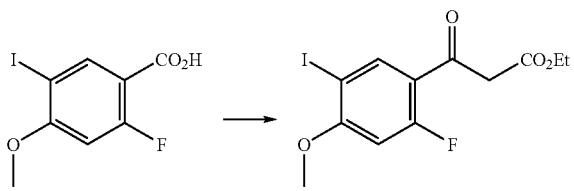

The compound (21.4 g, 72.2 mmol) obtained in Step 1 was suspended in toluene (42 ml), thionyl chloride (15.8 ml, 217 mmol) and dimethylformamide (56 μl, 0.72 mmol) were added, and the mixture was stirred under heating at 75° C. for 2.8 hr under a nitrogen atmosphere. After allowing to cool, the reaction mixture was concentrated under reduced pressure, and subjected to azeotropic distillation with toluene twice to give the residue.

To a mixture of ethyl potassium malonate (24.6 g, 145 mmol) and tetrahydrofuran (125 ml) were added triethylamine (30.2 ml, 217 mmol) and magnesium chloride (1.45 g, 10.14 mmol), and the mixture was stirred under an argon atmosphere at room temperature for 1 hr, and stirred at 70° C. for 3.3 hr. To this mixture was dropwise added a solution of the residue obtained above in tetrahydrofuran (50 ml) at the same temperature over 15 min and then stirred under heating for 30 min. After allowing to cool, 2N hydrochloric acid (175 ml) was added dropwise to the reaction mixture in an ice bath. Toluene was added to the mixture, and the layers were separated. The organic layer was washed with water, aqueous sodium hydrogen carbonate solution (twice) and water in this order. The mixture was concentrated under reduced pressure, and subjected to azeotropic distillation with toluene twice to give the object compound (26.0 g, yield 98%) as a pale-yellow solid.

$^1$H NMR (DMSO-$d_6$ 400 MHz) (δ) ppm: 1.17 (3H, t, J=7.0 Hz), 3.94 (3H, s), 4.00 (2H, d, J=3.3 Hz), 4.11 (2H, q, J=7.0 Hz), 7.09 (1H, d, J=13.7 Hz), 8.20 (1H, d, J=8.4 Hz)

Step 3

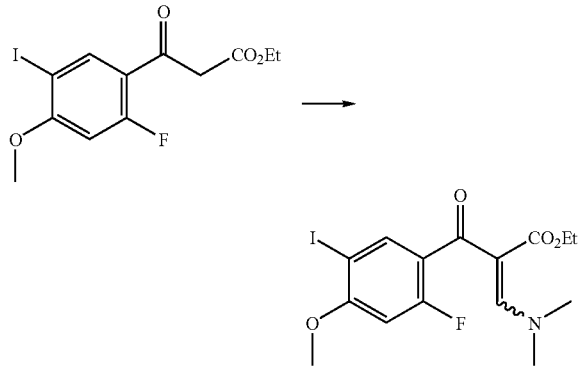

The compound (26.0 g, 71.0=mol) obtained in Step 2 was suspended in toluene (125 ml), dimethylformamide dimethyl acetal (11.3 ml, 85.1 mmol) was added, and the mixture was stirred under heating at 85° C. for 3.8 hr. After allowing to cool, the reaction mixture was concentrated under reduced pressure, and the obtained residue was purified by silica gel chromatography (hexane:ethyl acetate=1:1 to 1:2) to give the object compound (25.0 g, yield 83%) as a pale-yellow solid.

$^1$H NMR (DMSO-$d_6$ 400 MHz) (δ) ppm: 0.95 (3H, t, J=7.1 Hz), 2.73 (3H, br s), 3.29 (3H, br s), 3.84-3.96 (5H, m), 6.93 (1H, d, J=12.8 Hz), 7.70 (1H, s), 7.84 (1H, d, J=8.1 Hz)

Step 4

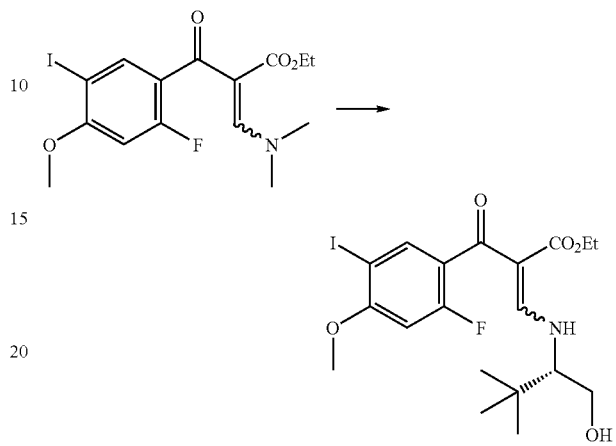

The compound (700 mg, 1.66 mmol) obtained in Step 3 and L-tert-leucinol (234 mg, 1.99 mmol) was stirred in chloroform (7 ml) at room temperature for 2.7 hr. The reaction mixture was concentrated under reduced pressure, ethyl acetate and water were added to the residue, and the layers were separated. The organic layer was washed with water (twice) and brine in this order, and dried over sodium sulfate. After filtration, the filtrate was concentrated under reduced pressure to give a white amorphous crude product (873 mg).

Step 5

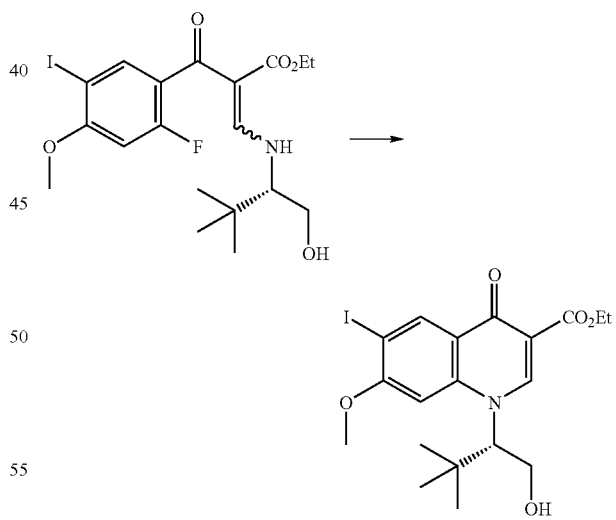

The crude product (873 mg) obtained in Step 4 was stirred with potassium carbonate (689 mg, 4.99 mmol) in dimethylformamide (8 ml) under heating at 80° C. overnight. After completion of the reaction, water and ethyl acetate were added to the reaction mixture, the layers were separated, and the organic layer was washed twice with water. The aqueous layer was extracted again with ethyl acetate, and all the organic layers were combined and washed with brine. The organic layer was dried over sodium sulfate. After filtration, the filtrate was concentrated under reduced pressure to give a crude product (931 mg) as a colorless oil.

Step 6

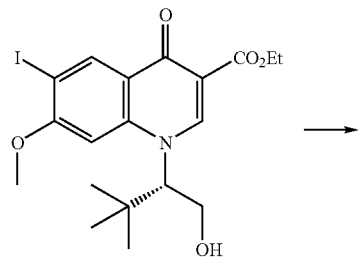 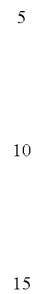 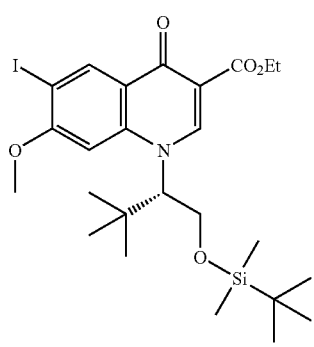

The crude product (931 mg) obtained in Step 5, imidazole (170 mg, 2.49 mmol) and tert-butyldimethylsilyl chloride (301 mg, 1.99 mmol) were stirred in dimethylformamide (5 ml) at room temperature for 1 hr. Water and ethyl acetate were added to the reaction mixture, the layers were separated, and the organic layer was washed with water (twice) and brine in this order, and dried over sodium sulfate. After filtration, the filtrate was concentrated under reduced pressure, and the obtained residue was purified by silica gel chromatography (hexane:ethyl acetate=2:3) to give the object compound (798 mg, yield 82%, 3 steps) as a white solid.

$^1$H NMR (CDCl$_3$ 400 MHz) (δ) ppm: −0.09 (3H, s), 0.00 (3H, s), 0.68 (9H, s), 1.06 (9H, s), 1.41 (3H, t, J=7.1 Hz), 3.99 (3H, s), 4.09-4.20 (2H, m), 4.36-4.44 (2H, m>, 4.52 (1H, dd, J=8.7, 4.5 Hz), 6.86 (1H, s), 8.62 (1H, s), 8.94 (1H, s)

Step 7

-continued

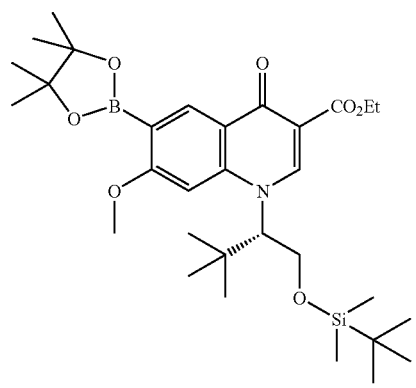

A mixture of the compound (200 mg, 0.340 mmol) obtained in Step 6, bis(pinacolato)diboron (95 mg, 0.37 mmol), potassium acetate (100 mg, 1.02 mmol) and [1,1'-bis(diphenylphosphino)ferrocene]dichloropalladium(II) dichloromethane (1:1) complex (8 mg, 0.01 mmol) in dimethyl sulfoxide (2 ml) was stirred under heating at 80° C. for 1 hr. After allowing to cool, ethyl acetate and water were added to the reaction mixture, the layers were separated, and the organic layer was washed with water (twice) and brine in this order, and dried over sodium sulfate. After filtration, the filtrate was concentrated under reduced pressure to give a black-brown amorphous crude product (241 mg).

Step 8

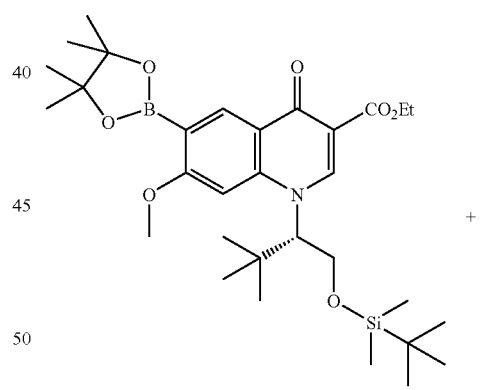

+

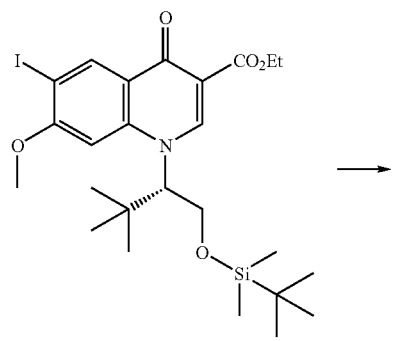 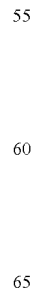 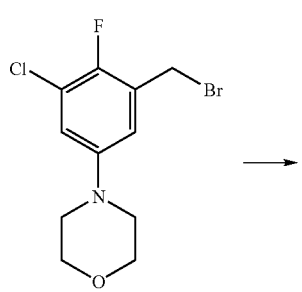

-continued

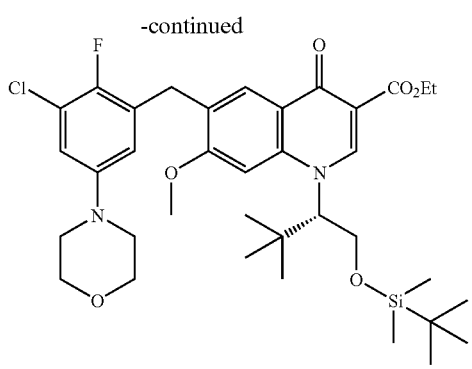

The crude product (241 mg) obtained in Step 7, the compound (126 mg, 0.408 mmol) obtained in Step 6 of Example 1 and tetrakis(triphenylphosphine)palladium(0) (20 mg, 0.017 mmol) were mixed with 1,2-dimethoxyethane (4 ml), 2M aqueous sodium carbonate solution (0.7 ml, 1.4 mmol) was added, and the mixture was stirred under heating at 80° C. for 30 min. After allowing to cool, ethyl acetate and water were added to the reaction mixture, the layers were separated, and the organic layer was washed with water (twice) and brine in this order, and dried over sodium sulfate. After filtration, the filtrate was concentrated under reduced pressure, and the obtained residue was purified by silica gel chromatography (chloroform:acetone=5:1) to give the object compound (217 mg, yield 93%, 2 steps) as a brown oil.

$^1$H NMR (CDCl$_3$ 400 MHz) (δ) ppm: −0.10 (3H, s), 0.00 (3H, s), 0.67 (9H, s), 1.06 (9H, s), 1.41 (3H, t, J=7.2 Hz), 2.96-3.01 (4H, m), 3.76-3.80 (4H, m), 3.91 (3H, s), 3.99 (1H, d, J=15.5 Hz), 4.04 (1H, d, J=15.5 Hz), 4.09-4.20 (2H, m), 4.35-4.43 (2H, m), 4.54 (1H, dd, J=8.8, 4.4 Hz), 6.51 (1H, dd, J=5.5, 2.9 Hz), 6.75 (1H, dd, J=5.8, 2.9 Hz), 6.89 (1H, s), 8.28 (1H, s), 8.62 (1H, s)

Step 9

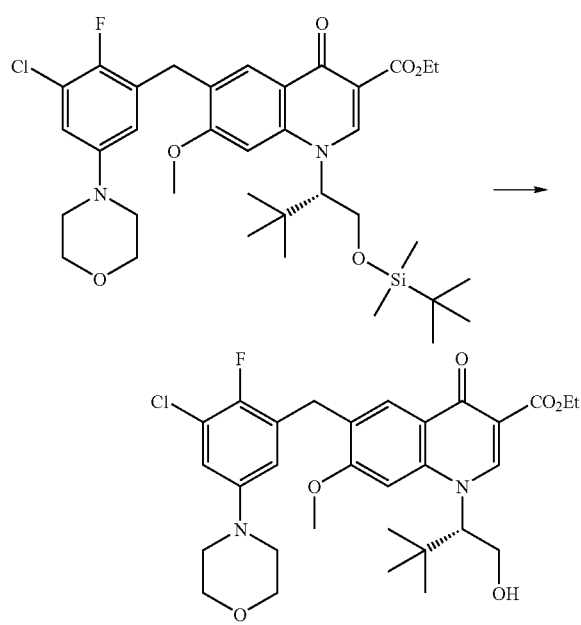

The compound (217 mg, 0.315 mmol) obtained in Step 8 was stirred in tetrahydrofuran (2 ml) with a 1.0 M solution of tetrabutylammonium fluoride in tetrahydrofuran (0.47 ml 0.47 mmol) at room temperature overnight. Water was added to the reaction mixture, ethyl acetate was further added, and the layers were separated. The organic layer was washed with water (twice) and brine in this order, and dried over sodium sulfate. After filtration, the filtrate was concentrated under reduced pressure, and the obtained residue was purified by PTLC (first development; hexane:ethyl acetate=1:5, second development; chloroform:methanol=20:1) to give the object compound (166 mg, yield 92%) as a colorless oil.

$^1$H NMR (CDCl$_3$ 400 MHz) (δ) ppm: 1.00 (9H, s), 1.40 (3H, t, J=6.8 Hz), 2.91-2.97 (4H, m), 3.62 (1H, d, J=14.4 Hz), 3.72-3.80 (4H, m), 3.95 (3H, s), 4.03 (1H, d, J=14.4 Hz), 4.20-4.43 (4H, m), 4.54-4.65 (2H, m), 6.39-6.43 (1H, m), 6.67-6.72 (1H, m), 6.94 (1H, s), 7.77 (1H, s), 8.61 (1H, s)

Step 10

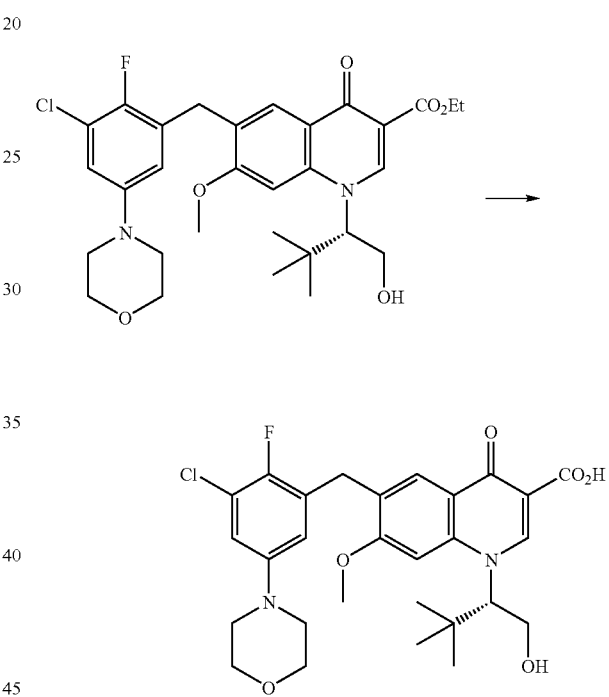

The compound (166 mg, 0.289 mmol) obtained in Step 9 and lithium hydroxide monohydrate (24 mg, 0.58 mmol) were stirred in a mixed solvent of tetrahydrofuran (3 ml) and water (0.6 ml) at room temperature for 4 hr. Aqueous citric acid solution and ethyl acetate were added to the reaction mixture, and the layers were separated. The organic layer was washed with water (twice) and brine in this order, and dried over sodium sulfate. After filtration, the filtrate was concentrated under reduced pressure to give the object compound (146 mg, yield 92%) as a white solid.

$^1$H NMR (DMSO-d$_6$ 400 MHz) (δ) ppm: 0.99 (9H, s), 3.08 (4H, t, J=4.8 Hz), 3.71 (4H, t, J=4.8 Hz), 4.03-4.11 (2H, m), 4.05 (2H, s), 4.08 (3H, s), 5.13 (1H, t, J=4.9 Hz), 5.17-5.20 (1H, m), 6.90-6.92 (1H, m), 7.01-7.03 (1H, m), 7.54 (1H, s), 7.96 (1H, s), 8.79 (1H, s), 15.39 (1H, s)

MS (ESI): M+ 547

Example 25

Step 1

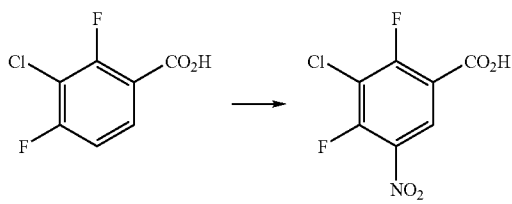

3-Chloro-2,4-difluorobenzoic acid (5.0 g, 26 mmol) was dissolved in concentrated sulfuric acid (15 ml), and fuming nitric acid (1.43 ml, 33.8 mmol) was added dropwise under ice-cooling. After completion of the dropwise addition, the mixture was stirred at room temperature for 1 hr. The reaction mixture was poured into ice water, and the mixture was stirred under ice-cooling. The precipitated solid was collected by filtration and washed with water. The obtained solid was dried under reduced pressure at 50° C. overnight to give the object compound (5.54 g, yield 90%).

$^1$H NMR (CDCl$_3$ 400 MHz) ($\delta$) ppm: 8.78 (1H, dd, J=8.1, 7.2 Hz)

Step 2

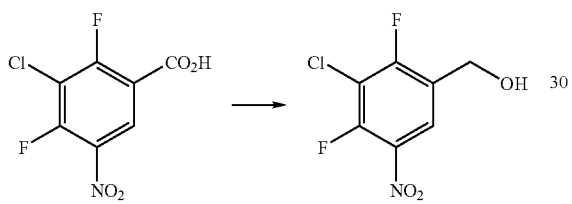

The compound (5.0 g, 21 mmol) obtained in Step 1 was dissolved in tetrahydrofuran (50 ml) and, after ice-cooling, triethylamine (3.08 ml, 22.1 mmol) was added. Isobutyl chlorocarbonate (2.87 ml, 22.1 mmol) was added dropwise, and the mixture was stirred at the same temperature for 40 nm. Sodium borohydride (1.19 g, 31.6 mmol) was added to the obtained mixture, and water (5 ml) was added dropwise over 15 min. The mixture was stirred at the same temperature for 30 min, water was added to the reaction mixture, and the mixture was extracted with ethyl acetate. After partitioning, the aqueous layer was extracted with ethyl acetate. The combined organic layer was washed with saturated aqueous sodium hydrogen carbonate solution and saturated brine and dried over magnesium sulfate. After filtration, the filtrate was concentrated under reduced pressure to give a crude product (2.97 g).

Step 3

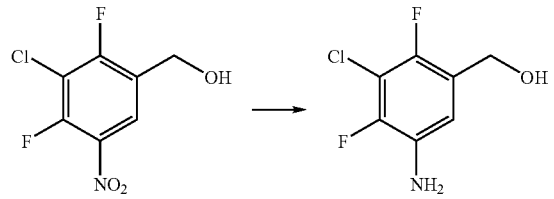

To a mixture of ethanol (15 ml) and water (5 ml) were added reduced iron (3.56 g, 63.7 mmol) and ammonium chloride (3.41 g, 63.7 mmol). To the mixture was dropwise added a solution of the crude product (2.85 g) obtained in Step 2 in tetrahydrofuran (15 ml) at 70° C., and the mixture was stirred under heating at 80° C. for 30 min. After allowing to cool, the reaction mixture was filtered through celite, ethyl acetate and saturated aqueous sodium hydrogen carbonate solution were added to the filtrate, and the layers were separated. The aqueous layer was extracted with ethyl acetate, and the combined organic layer was washed with saturated aqueous sodium hydrogen carbonate solution and saturated brine, and dried over magnesium sulfate. After filtration, the filtrate was concentrated under reduced pressure, and the obtained residue was purified by silica gel chromatography (hexane:ethyl acetate=2:1) to give the object compound (1.50 g, yield 38%, 2 steps).

$^1$H NMR (CDCl$_3$ 400 MHz) ($\delta$) ppm: 1.75 (1H, br s), 3.69 (2H, br s), 4.68 (2H, d, J=3.7 Hz), 6.76 (1H, dd, J=9.3, 7.0 Hz)

Step 4

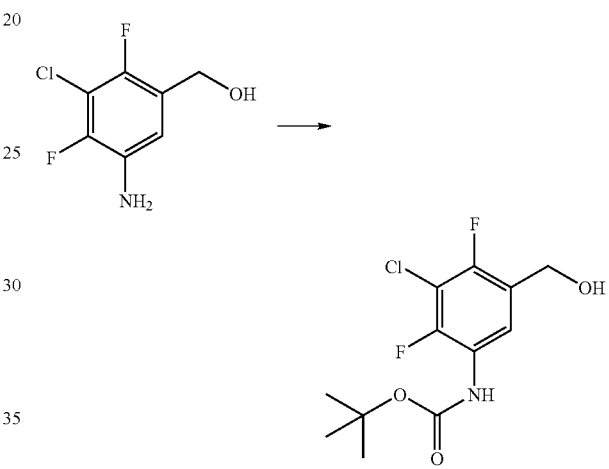

A solution of the compound (1.5 g, 7.8 mmol) obtained in Step 3 and di-tert-butyl dicarbonate (2.54 g, 11.6 mmol) in tetrahydrofuran (10 ml) was heated under reflux for 48 hr. Di-tert-butyl dicarbonate (508 mg, 2.32 mmol) and tetrahydrofuran (2 ml) were added to the reaction mixture, and the mixture was heated under reflux for 30.5 hr. Di-tert-butyl dicarbonate (2.0 g, 9.2 mmol) was added, and the mixture was heated under reflux for 16.5 hr. The reaction mixture was concentrated under reduced pressure and the obtained residue was purified by silica gel chromatography (hexane:ethyl acetate=5:1, 4:1, 3:1 to 2:1) to give the object compound (2.4 g, yield 95%).

$^1$H NMR (CDCl$_3$ 400 MHz) ($\delta$) ppm: 1.53 (9H, s), 1.98 (1H, t, J=6.4 Hz), 4.73 (2H, d, J=6.4 Hz), 6.60 (1H, br s), 8.08 (1H, t, J=7.8 Hz)

Step 5

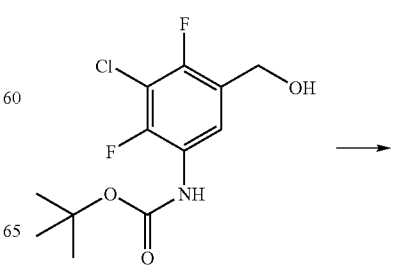

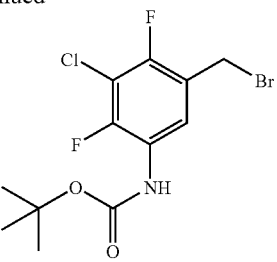

The compound (2.14 g, 7.29 mmol) obtained in Step 4 was dissolved in chloroform (20 ml), triphenylphosphine (2.06 g, 7.87 mmol) and carbon tetrabromide (2.66 g, 8.02 mmol) were added, and the mixture was stirred at room temperature. The reaction mixture was concentrated under reduced pressure, and the obtained residue was purified by silica gel chromatography (hexane:chloroform=1:1) and further treated with hexane. The precipitated solid was collected by filtration and dried under reduced pressure to give the object compound (1.54 g, yield 59%) as a solid.

$^1$H NMR (CDCl$_3$ 400 MHz) (δ) ppm: 1.53 (9H, s), 4.46 (2H, d, J=1.4 Hz), 6.61 (1H, br s), 7.98 (1H, t, J=7.9 Hz)

Step 6

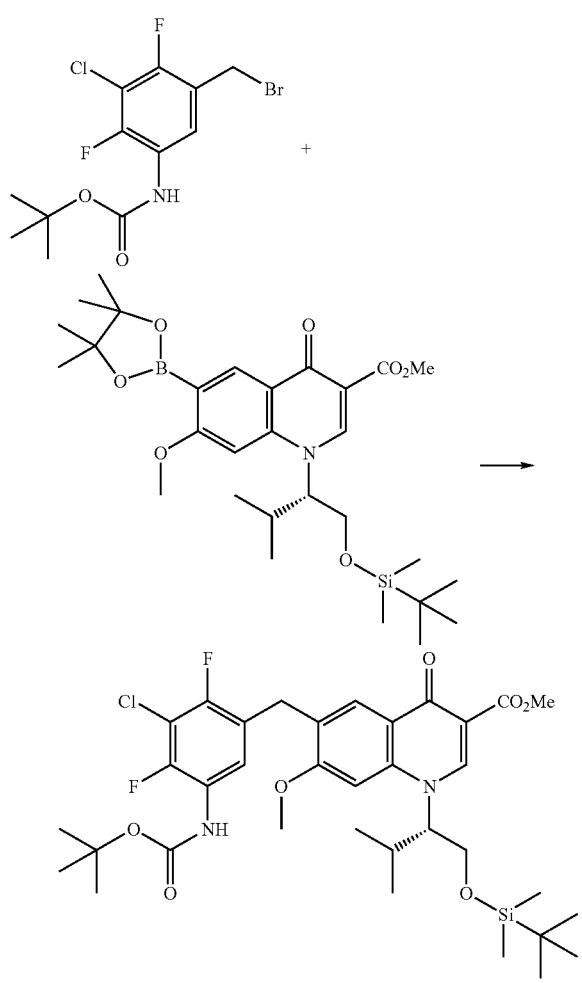

Argon was passed through a solution of the compound (497 mg, 1.39 mmol) obtained in Step 5, the compound (600 mg, 1.07 mmol) obtained in Step 11 of Example 2, tetrakis(triphenylphosphine)palladium(0) (62 mg, 0.054 mmol), and sodium carbonate (340 mg, 3.21 mmol) in a mixture of 1,2-dimethoxyethane (4 ml) and water (2 ml) for 2 min, and the solution was stirred under argon atmosphere under heating at 100° C. for 0.5 hr. Ethyl acetate and saturated aqueous sodium hydrogen carbonate solution were added to the reaction mixture, the layers were separated, and the aqueous layer was extracted with ethyl acetate. The combined organic layer was washed with saturated brine, and dried over sodium sulfate. After filtration, the filtrate was concentrated under reduced pressure, and the obtained residue was purified by silica gel chromatography (hexane:ethyl acetate=2:1 to 1:1) to give the object compound (649 mg, yield 85%).

$^1$H NMR (CDCl$_3$ 400 MHz) (δ) ppm: −0.08 (3H, s), −0.06 (3H, s), 0.77 (9H, s), 0.84 (3H, d, J=6.7 Hz), 1.19 (3H, d, J=6.5 Hz), 1.48 (9H, s), 2.38-2.50 (1H, m), 3.89 (3H, s), 3.92-3.97 (4H, m), 4.00-4.08 (3H, m), 4.14-4.21 (1H, m), 6.50 (1H, br s), 6.73 (1H, s), 7.87 (1H, br s), 8.18 (1H, s), 8.64 (1H, s)

Step 7

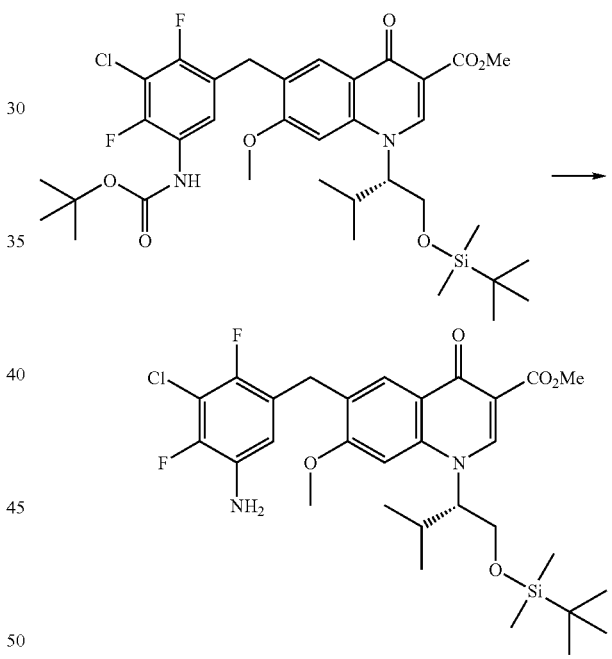

The compound (645 mg, 0.909 mmol) obtained in Step 6 was stirred in a mixed solvent of trifluoroacetic acid (2.5 ml) and chloroform (5 ml) at room temperature for 0.5 hr. The reaction mixture was concentrated under reduced pressure, and ethyl acetate was added to the obtained residue. The organic layer was washed with saturated aqueous sodium hydrogen carbonate solution (twice) and saturated brine in this order, and dried over magnesium sulfate. After filtration, the filtrate was concentrated under reduced pressure, and the obtained residue was purified by silica gel chromatography (chloroform:methanol=10:1) to give the object compound (454 mg, yield 82%).

$^1$H NMR (CDCl$_3$ 400 MHz) (δ) ppm: −0.08 (3H, s), −0.04 (3H, s), 0.77 (9H, s), 0.85 (3H, d, J=6.5 Hz), 1.19 (3H, d, J=6.5 Hz), 2.40-2.51 (1H, m), 3.52 (2H, s), 3.88-3.98 (9H, m), 4.01-4.09 (1H, m), 4.14-4.22 (1H, m), 6.34-6.40 (1H, m), 6.78 (1H, s), 8.30 (1H, s), 8.65 (1H, s)

Step 8

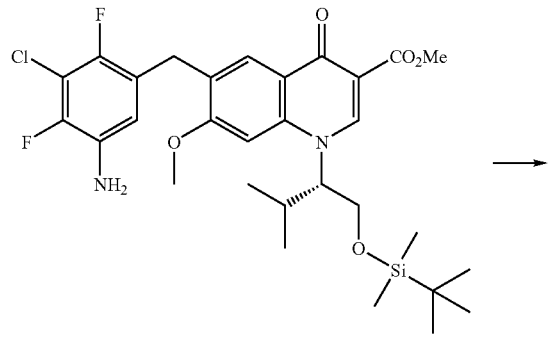

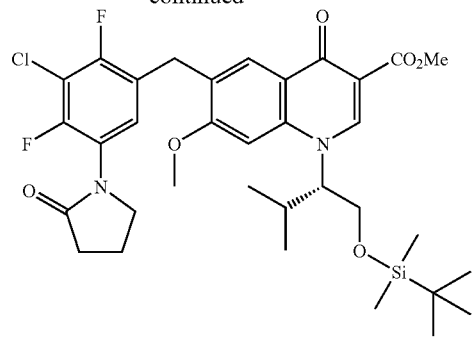

-continued

The crude product (233 mg) obtained in Step 8 was dissolved in dimethylformamide (2 ml), sodium hydride (60%, 19.4 mg, 0.485 mmol) was added at 0° C., and the mixture was stirred at the same temperature for 15 min. Aqueous potassium hydrogen sulfate solution and ethyl acetate were added to the reaction mixture, and the layers were separated. The organic layer was washed with water and saturated brine in this order, and dried over magnesium sulfate. After filtration, the filtrate was concentrated under reduced pressure to give a crude product.

Step 10

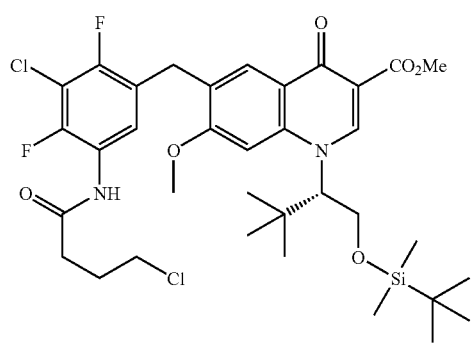

To a solution of the compound (197 mg, 0.323 mmol) obtained in Step 7 and pyridine (53 μl, 0.65 mmol) in chloroform (2 ml) was added 4-chlorobutyryl chloride (44 μl, 0.39 mmol), and the mixture was stirred at room temperature for 4.3 hr. The reaction mixture was concentrated under reduced pressure, ethyl acetate and saturated aqueous sodium hydrogen carbonate solution were added to the obtained residue, and the layers were separated. The organic layer was washed with saturated brine, and dried over magnesium sulfate. After filtration, the filtrate was concentrated under reduced pressure to give a crude product (233 mg).

Step 9

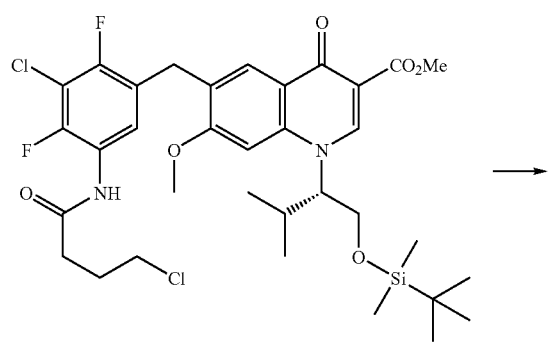

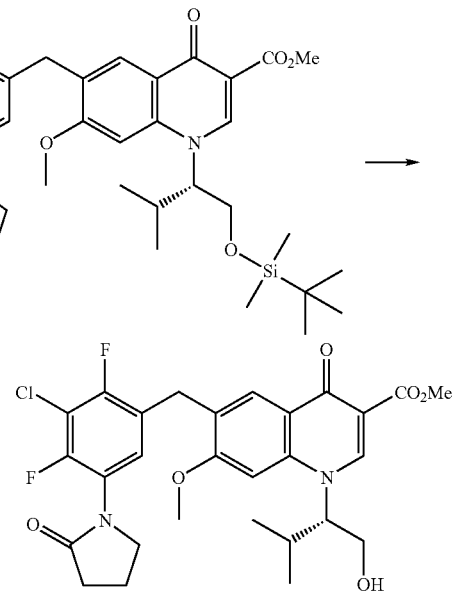

The crude product obtained in Step 9 was stirred in tetrahydrofuran (3 ml) with a 1.0 M solution of tetrabutylammonium fluoride in tetrahydrofuran (485 μl, 0.485 mmol) and acetic acid (55 μl, 0.97 mmol) at room temperature for 5 hr. The reaction mixture was concentrated under reduced pressure, and the obtained residue was purified by silica gel chromatography (chloroform:methanol=15:1) to give the object compound (178 mg, yield 98%, 3 steps).

$^1$H NMR (CDCl$_3$, 400 MHz) (δ) ppm: 0.76 (3H, d, J=6.7 Hz), 1.24 (3H, d, J=6.0 Hz), 2.12-2.21 (2H, m), 2.43-2.53 (2H, m), 3.54 (1H, d, J=14.8 Hz), 3.71 (2H, t, J=7.1 Hz), 3.86 (3H, s), 3.99 (3H, s), 4.08 (1H, d, J=14.8 Hz), 4.14-4.30 (3H, m), 6.87 (1H, s), 6.96-7.02 (1H, m), 7.58 (1H, s), 8.56 (1H, s)

Step 11

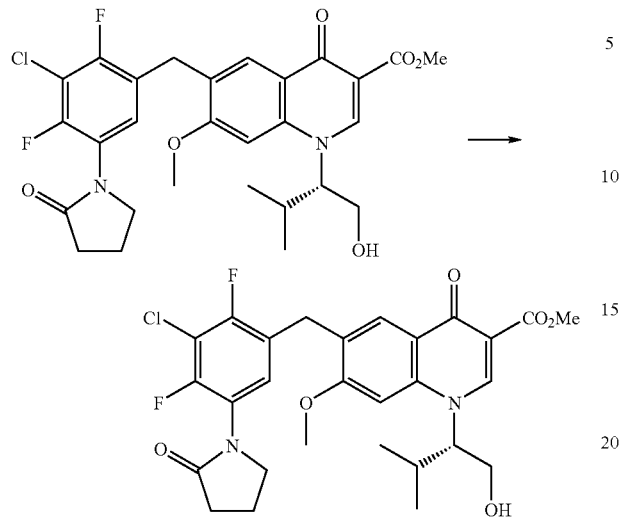

The compound (175 mg, 0.311 mmol) obtained in Step 10 and lithium hydroxide monohydrate (26.1 mg, 0.622 mmol) were stirred in a mixed solvent of tetrahydrofuran (2 ml) and water (1 ml) at room temperature for 1 hr. The reaction mixture was neutralized with 2N hydrochloric acid, and the mixture was extracted with ethyl acetate. The organic layer was washed with saturated brine and dried over sodium sulfate. After filtration, the filtrate was concentrated under reduced pressure, and the obtained residue was treated with a mixed solvent of hexane-ethyl acetate. The precipitated solid was collected by filtration and dried under reduced pressure to give the object compound (92 mg, yield 54%) as a solid.

$^1$H NMR (DMSO-d$_6$ 300 MHz) (δ) ppm: 0.72 (3H, d, J=6.4 Hz), 1.16 (3H, d, J=6.4 Hz), 2.10 (2H, tt, J=7.4, 7.4 Hz), 2.42 (2H, t, J=7.4 Hz), 2.31-2.44 (1H, m), 3.74 (2H, t, J=7.4 Hz), 3.73-3.83 (1H, m), 3.95-4.06 (1H, m), 4.03 (3H, s), 4.10 (2H, s), 4.83-4.91 (1H, m), 5.19 (1H, t, J=5.0 Hz), 7.45 (1H, dd, J=7.6, 7.6 Hz), 7.45 (1H, s), 8.12 (1H, s), 8.88 (1H, s), 15.45 (1H, s)

MS (ESI): M+ 549

Example 49

Step 1

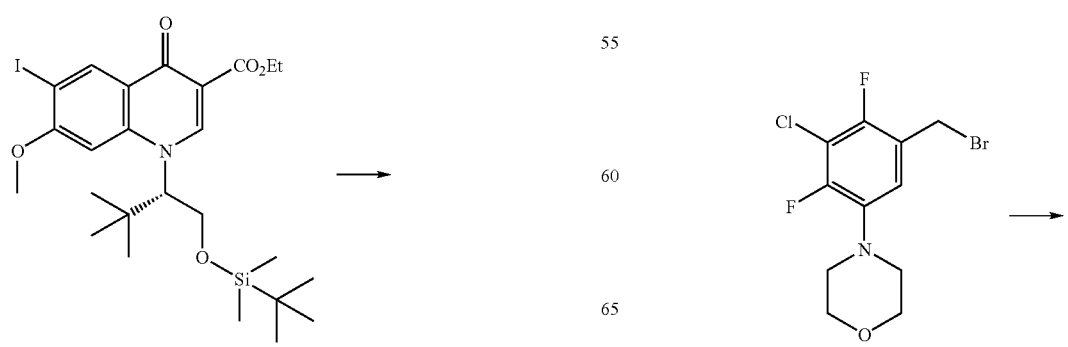

-continued

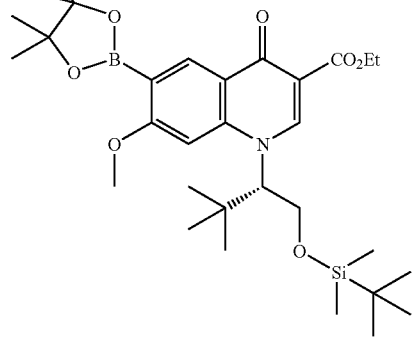

A mixture of the compound (217 mg, 0.369 mmol) obtained in Step 6 of Example 17, bis(pinacolato)diboron (103 mg, 0.406 mmol), potassium acetate (109 mg, 1.11 mmol) and [1,1'-bis(diphenylphosphino)ferrocene]dichloropalladium(II) dichloromethane (1:1) complex (60 mg, 0.074 mmol) in dimethyl sulfoxide (1.6 ml) was stirred under an argon atmosphere under heating at 80° C. for 2 hr. After allowing to cool, ethyl acetate and brine were added to the reaction mixture, and the mixture was stirred at room temperature. The resulting insoluble material was filtered off through celite. The layers of the filtrate were separated, and the organic layer was washed four times with saturated brine and dried over sodium sulfate. After filtration, the filtrate was concentrated under reduced pressure to give a brown amorphous crude product (230 mg).

Step 2

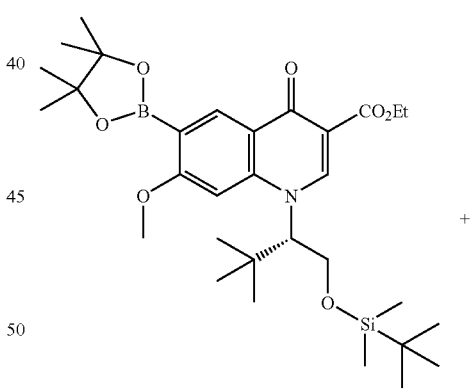

-continued

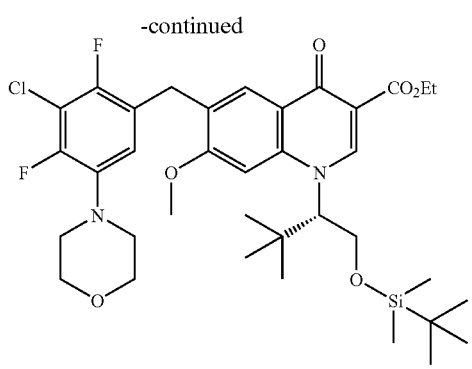

The crude product (230 mg) obtained in Step 1, the compound (100 mg, 0.306 mmol) obtained in Step 6 of Example 16 and tetrakis(triphenylphosphine)palladium(0) (10.6 mg, 0.0092 mmol) were mixed with 1,2-dimethoxyethane (2 ml). 2M Aqueous sodium carbonate solution (612 μl, 1.22 mmol) was added, and the mixture was stirred under heating at 80° C. for 25 min. After allowing to cool, ethyl acetate and water were added to the reaction mixture, the layers were separated, and the aqueous layer was extracted with ethyl acetate. The combined organic layer was washed twice with brine, and dried over sodium sulfate. After filtration, the filtrate was concentrated under reduced pressure, and the obtained residue was purified twice by silica gel chromatography (hexane:ethyl acetate=1:2 to chloroform:acetone=5:1) to give a brown amorphous crudely purified product (40 mg).

Step 3

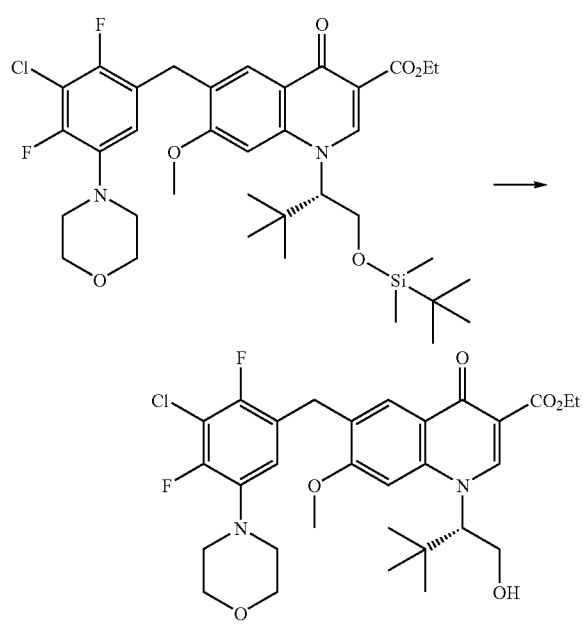

The crudely purified product (40 mg) obtained in Step 2 was stirred in tetrahydrofuran (0.4 ml) with a 1.0 M solution of tetrabutylammonium fluoride in tetrahydrofuran (85 μl, 0.085 mmol) at room temperature for 5 min. Ethyl acetate and brine were added to the reaction mixture, the layers were separated, and the aqueous layer was extracted with ethyl acetate. The combined organic layer was washed twice with saturated brine and dried over sodium sulfate. After filtration, the filtrate was concentrated under reduced pressure, and the obtained residue was purified by PTLC (chloroform:acetone=2:1) to give the object compound (24 mg, yield 13%, 3 steps) as a pale-brown amorphous solid.

$^1$H NMR (CDCl$_3$ 400 MHz) (δ) ppm: 1.02 (9H, s), 1.41 (3H, t, J=7.3 Hz), 2.89-2.93 (4H, m), 3.72 (1H, d, J=14.8 Hz), 3.76-3.82 (5H, m), 3.94-4.00 (4H, m), 4.20-4.44 (4H, m), 4.63 (1H, dd, J=9.4, 3.6 Hz), 6.49-6.55 (1H, m), 6.95 (1H, s), 7.89 (1H, s), 8.60 (1H, s)

Step 4

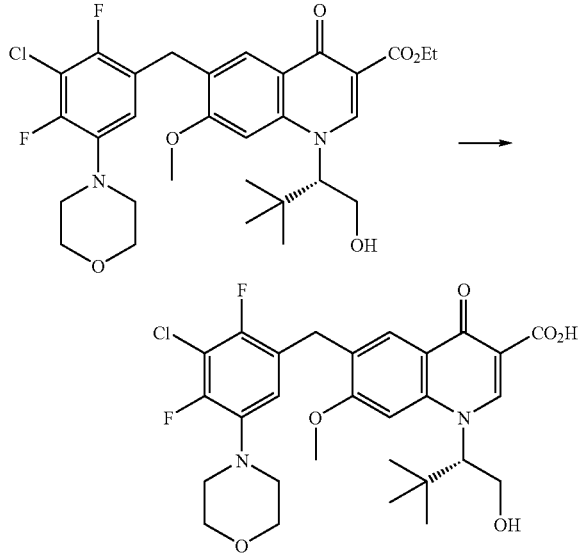

To a mixture of the compound (24 mg, 0.040 mmol) obtained in Step 3, tetrahydrofuran (240 μl) and water (120 μl) was added lithium hydroxide monohydrate (3.4 mg, 0.081 mmol), and the mixture was stirred at room temperature for 2.3 hr. A 5% aqueous potassium hydrogen sulfate solution was added to the reaction mixture, and the mixture was extracted twice with ethyl acetate. The combined organic layer was washed twice with saturated brine and dried over sodium sulfate. After filtration, the filtrate was concentrated under reduced pressure, the obtained residue was treated with a mixed solvent of hexane-ethyl acetate, and the precipitated solid was collected by filtration and dried to give the object compound (20 mg, yield 87%) as a white solid.

$^1$H NMR (DMSO-d$_6$ 400 MHz) (δ) ppm: 0.98 (9H, s), 2.93-2.98 (4H, m), 3.70-3.74 (4H, m), 4.00-4.14 (7H, m), 5.11 (1H, t, J=4.8 Hz), 5.13-5.19 (1H, m), 7.02-7.08 (1H, m), 7.52 (1H, s), 8.01 (1H, s), 8.78 (1H, s), 15.37 (1H, s)

MS (ESI): M+ 565

Example 51

Step 1

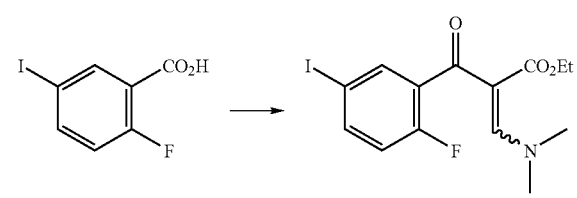

To a suspension of 2-fluoro-5-iodobenzoic acid (4.79 g, 18.0 mmol) and dimethylformamide (69 μl, 0.90 mmol) in toluene (20 ml) was added thionyl chloride (1.57 ml, 21.6 mmol), and the mixture was stirred under heating at 110° C. for 1 hr. The reaction mixture was concentrated under reduced pressure, and subjected to azeotropic distillation with toluene twice. The obtained residue was dissolved in toluene (15 ml), and the solution was added to a solution of ethyl 3-(dimethylamino)acrylate (2.83 g, 19.8 mmol) and diisopropylethylamine (4.07 ml, 23.4 mmol) in toluene (15 ml) at 60° C. over 5 min, and the mixture was stirred under heating at 100° C. for 16 hr. Water and ethyl acetate were added to the reaction mixture, the mixture was stirred, and the layers were separated. The obtained organic layer was washed with water and saturated brine in this order, and dried over sodium sulfate. After filtration, the filtrate was concentrated under reduced pressure, and the obtained residue was purified by silica gel chromatography (hexane:ethyl acetate=3:2 to 1:2) to give the object compound (6.48 g, yield 85%) as a brown oil.

$^1$H NMR (CDCl$_3$ 400 MHz) (δ) ppm: 0.95 (3H, t, J=7.1 Hz), 2.89 (3H, br s), 3.32 (3H, br s), 3.99 (2H, q, J=7.1 Hz), 6.79 (1H, dd, J=10.0, 8.5 Hz), 7.66 (1H, ddd, J=8.5, 4.6, 2.4 Hz), 7.78 (1H, s), 7.87 (1H, dd, J=6.6, 2.4 Hz)

Step 2

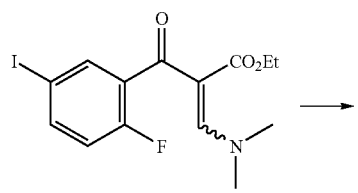

The compound (3.20 g) obtained in Step 1 was dissolved in tetrahydrofuran, L-tert-leucinol (977 mg, 8.34 mmol) was added, and the mixture was stirred at room temperature for 15.5 hr. The reaction mixture was concentrated under reduced pressure, and ethyl acetate and water were added to the residue. The mixture was stirred, and the layers were separated. The organic layer was washed with water and saturated brine in this order, and dried over sodium sulfate. After filtration, the filtrate was concentrated under reduced pressure, and subjected to azeotropic distillation with toluene twice to give a crude product (4.41 g) as a brown oil, which was a mixture of E form/Z form.

$^1$H NMR (CDCl$_3$ 300 MHz) (δ) ppm: 0.87-0.94 (1.6H, m), 0.99-1.06 (10.4H, m), 3.05-3.16 (1H, m), 3.64-3.73 (1H, m), 3.93-4.08 (3H, m), 6.74-6.34 (1H, m), 7.59-7.74 (2H, m), 8.09-8.18 (1H, m)

Step 3

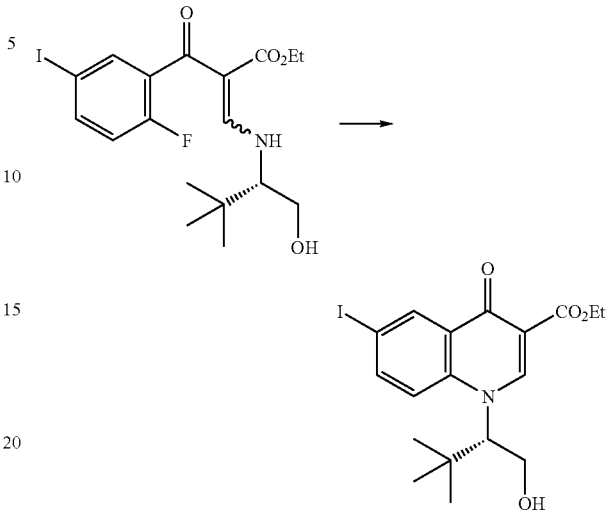

A suspension of the crude product (4.41 g) obtained in Step 2 and potassium carbonate (1.57 g, 11.4 mmol) in dimethylformamide (40 ml) was stirred under heating at 80° C. for 6 hr. Water was added to the reaction mixture under ice-cooling, and the precipitated solid was collected by filtration and washed with water. The obtained solid was air-dried at room temperature and dried under reduced pressure at 60° C. to give a crude product (3.23 g) as a brown solid.

$^1$H NMR (CDCl$_3$ 300 MHz) (δ) ppm: 0.98 (9H, s), 1.41 (3H, t, J=7.2 Hz), 4.22-4.45 (4H, m), 4.68 (1H, dd, J=8.9, 2.8 Hz), 5.14 (1H, br s), 7.46 (1H, d, J=9.3 Hz), 7.89 (1H, dd, J=9.3, 2.2 Hz), 8.07 (1H, d, J=2.2 Hz), 8.69 (1H, s)

Step 4

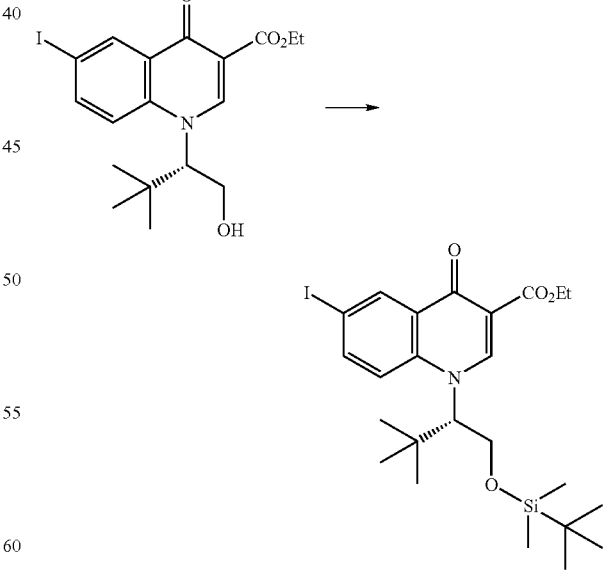

To a solution of the crude product (3.23 g) obtained in Step 3 and imidazole (645 mg 9.48 mmol) in dimethylformamide (30 ml) was added tert-butyldimethylsilyl chloride (1.32 g, 8.75 mmol), and the mixture was stirred at room temperature for 1 hr under an argon atmosphere. Water and ethyl acetate were added to the reaction mixture, the layers were separated, and the organic layer was washed with water (twice) and saturated brine in this order. The aqueous layer was extracted with ethyl acetate, and the obtained organic layer was washed with water and saturated brine. The combined organic layer was dried over sodium sulfate. After filtration, the filtrate was concentrated under reduced pressure, and the obtained residue was purified by silica gel chromatography (hexane:ethyl acetate=3:2 to 2:1) to give the object compound (3.81 g, yield 90%, 3 steps) as a pale-yellow amorphous solid.

$^1$H NMR (CDCl$_3$ 300 MHz) (δ) ppm: −0.10 (3H, s), −0.01 (3H, s), 0.66 (9H, s), 1.04 (9H, s), 1.41 (3H, t, J=7.2 Hz), 4.06-4.19 (2H, m), 4.36-4.45 (2H, m), 4.60 (1H, dd, J=8.7, 4.5 Hz), 7.39 (1H, d, J=9.4 Hz), 7.89 (1H, dd, J=9.4, 2.3 Hz), 8.67 (1H, s), 8.88 (1H, d, J=2.3 Hz)

Step 5

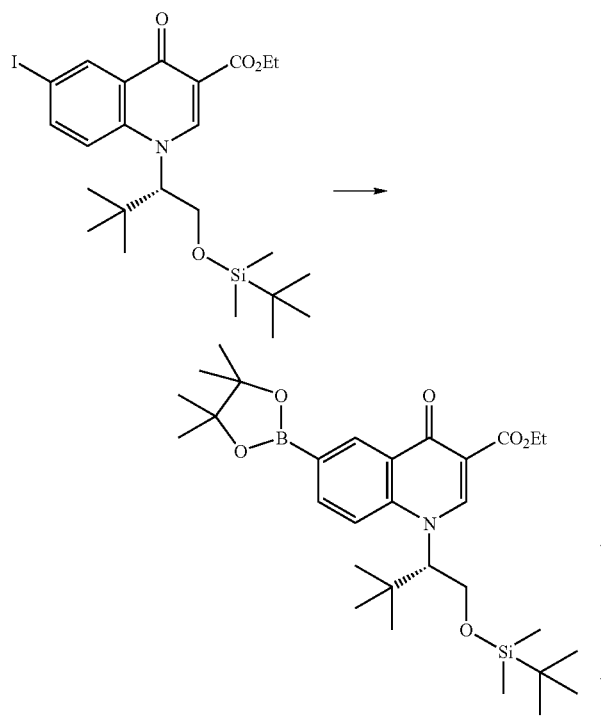

A solution of the compound (300 mg, 0.538 mmol) obtained in Step 4, bis(pinacolato)diboron (150 mg, 0.592 mmol), [1,1'-bis(diphenylphosphino)ferrocene]dichloropalladium(II) dichloromethane (1:1) complex (22 mg, 0.027 mmol) and potassium acetate (158 mg, 1.61 mmol) in dimethyl sulfoxide (3 ml) was stirred under heating at 80° C. for 20 min. After allowing to cool, water and ethyl acetate were added to the reaction mixture, and the resulting insoluble material was filtered off through celite. The layers of the filtrate were separated, and the organic layer was washed with water (three times) and saturated brine in this order, and dried over sodium sulfate. After filtration, the filtrate was concentrated under reduced pressure to give a crude product (366 mg) as a brown amorphous solid.

$^1$H NMR (CDCl$_3$ 400 MHz) (δ) ppm: −0.10 (3H, s), −0.02 (3H, s), 0.65 (9H, s), 1.03 (9H, s), 1.35 (12H, s), 1.41 (3H, t, J=7.1 Hz), 4.09-4.19 (2H, m), 4.36-4.45 (2H, m), 4.71 (1H, dd, J=8.2, 5.0 Hz), 7.59 (1H, d, J=8.8 Hz), 8.01 (1H, dd, J=8.8, 1.63 Hz), 8.67 (1H, s), 9.03 (1H, d, J=1.6 Hz)

Step 6

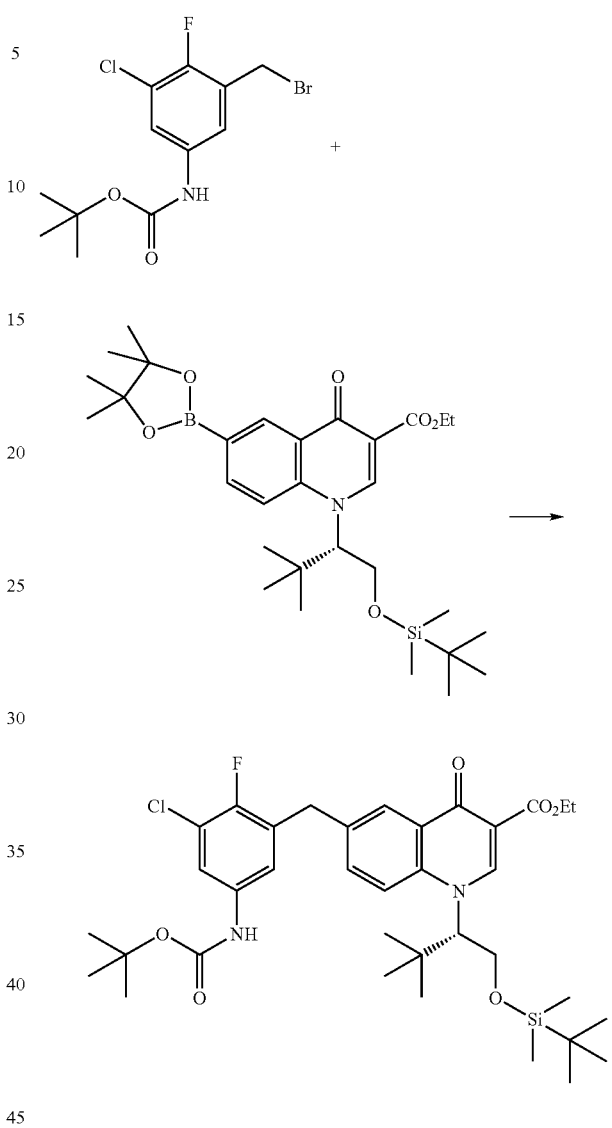

To a solution of the crude product (366 mg) obtained in Step 5, the compound (200 mg, 0.592 mmol) obtained in Step 5 of Example 2 and tetrakis(triphenylphosphine)palladium (0) (31 mg, 0.027 mmol) in 1,2-dimethoxyethane (6 ml) was added 2 M aqueous sodium carbonate solution (1.1 ml, 2.2 mmol), and the mixture was stirred under heating at 80° C. After completion of the reaction, the reaction mixture was allowed to cool and ethyl acetate was added. The layers were separated, and the organic layer was washed with water (three times) and saturated brine in this order, and dried over sodium sulfate. After filtration, the filtrate was concentrated under reduced pressure, and the obtained residue was purified by silica gel chromatography (hexane:ethyl acetate=3:2) to give the object compound (301 mg, yield 81%, 2 steps) as a white amorphous solid.

$^1$H NMR (CDCl$_3$ 400 MHz) (δ) ppm: −0.11 (3H, s), −0.02 (3H, s), 0.64 (9H, s), 1.05 (9H, s), 1.41 (3H, t, J=7.2 Hz), 1.48 (9H, s), 4.02-4.18 (4H, m), 4.36-4.44 (2H, m), 4.64 (1H, dd, J=8.5, 4.5 Hz), 6.34 (1H, s), 6.84 (1H, dd, J=5.6, 2.8 Hz), 7.47 (1H, dd, J=8.9, 2.1 Hz), 7.52-7.59 (2H, m), 8.41 (1H, d, J=2.1 Hz), 8.69 (1H, s)

Step 7

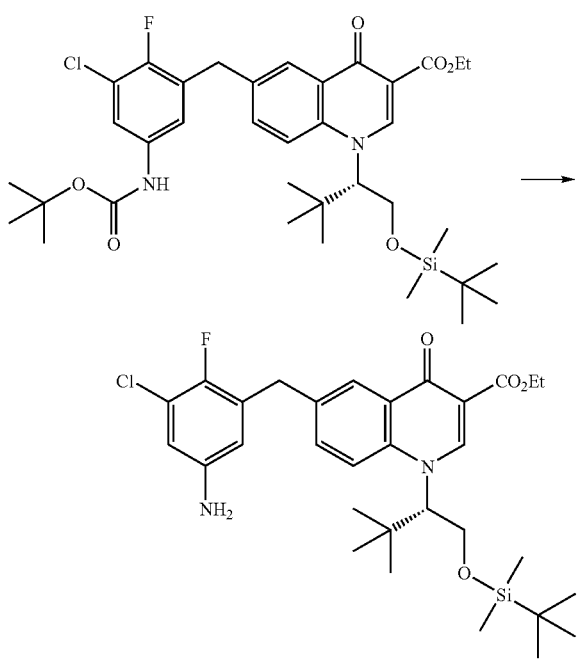

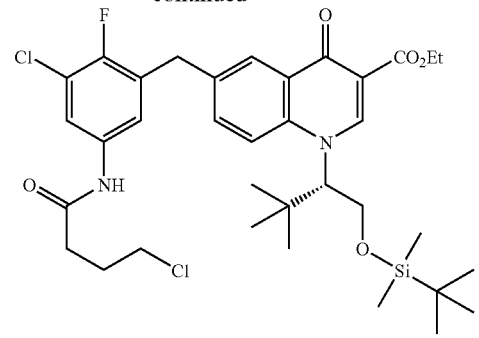

To a solution of the compound (100 mg, 0.170 mmol) obtained in Step 7 and pyridine (27 μl, 0.34 mmol) in chloroform (1 ml) was added 4-chlorobutyryl chloride (44 μl, 0.39 mmol), and the mixture was stirred at room temperature for 20 min. Ethyl acetate was added to the reaction mixture, and the mixture was washed with water (twice) and saturated brine in this order. The organic layer was dried over sodium sulfate. After filtration, the filtrate was concentrated under reduced pressure to give a white amorphous crude product (122 mg).

Step 9

A solution of the compound (301 mg, 0.437 mmol) obtained in Step 6 in a mixture of trifluoroacetic acid (3 ml) and chloroform (3 ml) was stirred at room temperature for 1 hr. The reaction mixture was concentrated under reduced pressure, and subjected to azeotropic distillation with toluene. Aqueous sodium hydrogen carbonate solution and ethyl acetate were added to the obtained residue, and the layers were separated. The organic layer was washed with water (twice) and saturated brine in this order, and dried over sodium sulfate. After filtration, the filtrate was concentrated under reduced pressure, and the obtained residue was purified by silica gel chromatography (hexane:ethyl acetate=1:3 to chloroform:methanol=10:1) to give the object compound (196 mg, yield 76%) as an amorphous solid.

$^1$H NMR (CDCl$_3$ 400 MHz) (δ) ppm: −0.11 (3H, s), −0.02 (3H, s), 0.64 (9H, s), 1.05 (9H, s), 1.41 (3H, t, J=7.1 Hz), 3.50 (2H, br s), 3.96-4.18 (4H, m), 4.36-4.45 (2H, m), 4.64 (1H, dd, J=8.2, 4.9 Hz), 6.32 (1H, dd, J=5.4, 2.8 Hz), 6.56 (1H, dd, J=5.6, 2.8 Hz), 7.48 (1H, dd, J=9.0, 2.3 Hz), 7.56 (1H, d, J=9.0 Hz), 8.42 (1H, d, J=2.3 Hz), 8.69 (1H, s)

Step 8

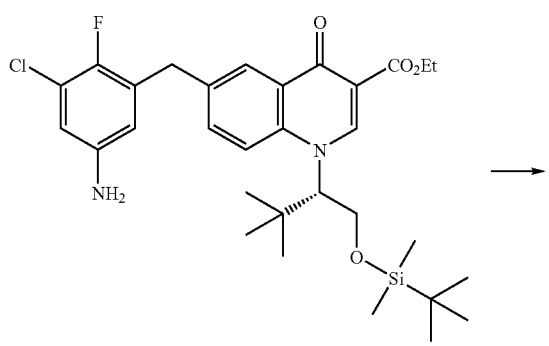

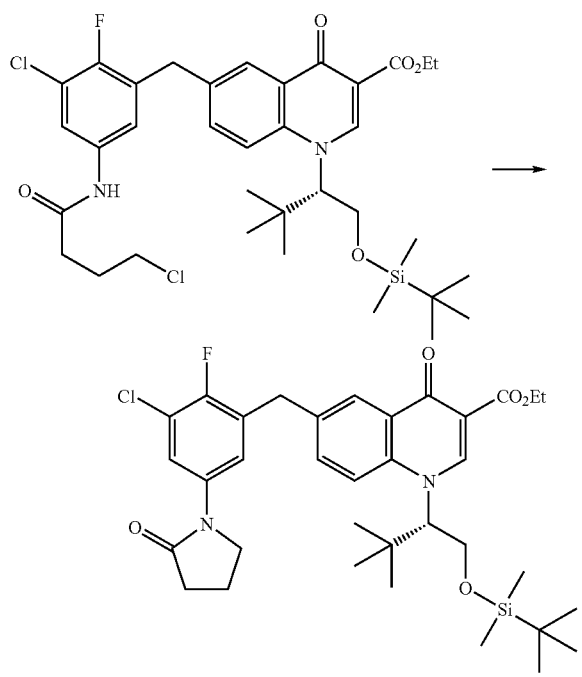

The crude product (122 mg) obtained in Step 8 was dissolved in dimethylformamide (1 ml), sodium hydride (60%, 10 mg, 0.25 mmol) was added at 0° C., and the mixture was stirred at the same temperature for 40 min. An aqueous ammonium chloride solution was added to the reaction mixture, and the mixture was extracted with ethyl acetate. The organic layer was washed with water (three times) and saturated brine in this order, and dried over magnesium sulfate. After filtration, the filtrate was concentrated under reduced pressure, and the obtained residue was purified by silica gel chromatography (hexane:ethyl acetate=1:9 to chloroform:methanol=10:1) to give the object compound (98 mg, yield 88%) as a white amorphous solid.

¹H NMR (CDCl₃ 400 MHz) (δ) ppm: −0.11 (3H, s), −0.02 (3H, s), 0.64 (s, 9H), 1.05 (9H, s), 1.41 (3H, t, J=7.1 Hz), 2.09-2.18 (2H, m), 2.57 (2H, t. J=8.2 Hz), 3.73-3.79 (2H, m), 4.07-4.18 (4H, m), 4.36-4.44 (2H, m), 4.61-4.67 (1H, m), 7.23-7.29 (1H, m), 7.48-7.53 (1H, m), 7.57 (1H, d, J=9.2 Hz), 7.70 (1H, dd, J=6.3, 2.8 Hz), 8.40 (1H, d, J=2.2 Hz), 8.68 (1H, s)

Step 10

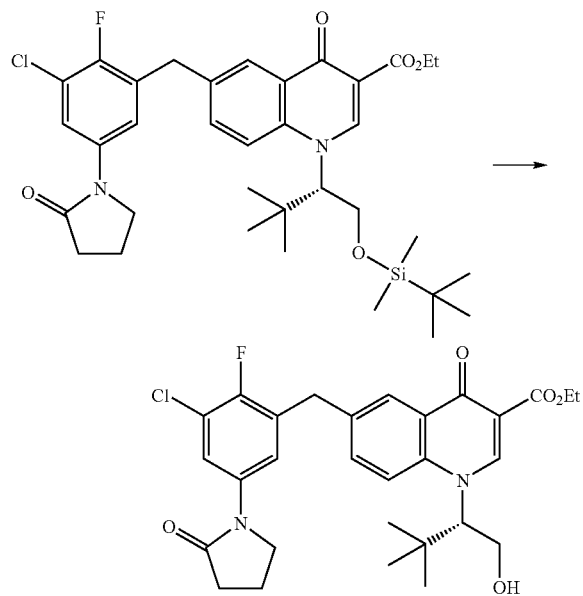

The compound (98 mg, 0.15 mmol) obtained in Step 9 was stirred in tetrahydrofuran (1 ml) with a 1.0 M solution of tetrabutylammonium fluoride in tetrahydrofuran (224 μl, 0.224 mmol), and the mixture was stirred at room temperature for 10 min. Water was added to the reaction mixture, and the mixture was extracted with ethyl acetate. The organic layer was washed with water (three times) and saturated brine in this order, and dried over sodium sulfate. After filtration, the filtrate was concentrated under reduced pressure, and the obtained residue was purified by PTLC (chloroform:methanol=15:1) to quantitatively give the object compound (88 mg) as a white solid.

¹H NMR (CDCl₃ 400 MHz) (δ) ppm: 1.00 (9H, s), 1.40 (3H, t, J=7.2 Hz), 2.08-2.19 (2H, m), 2.57 (2H, t. J=8.1 Hz), 3.76 (2H, t, J=7.5 Hz), 3.83 (1H, d, J=14.4 Hz), 3.96 (1H, d, J=14.4 Hz), 4.16-4.27 (2H, m), 4.27-4.43 (3H, m), 4.69-4.76 (1H, m), 7.29 (1H, dd, J=5.8, 2.8 Hz), 7.42 (1H, dd, J=8.9, 2.3 Hz), 7.60-7.66 (2H, m), 7.89 (1H, d, J=2.3 Hz), 8.68 (1H, s)

Step 11

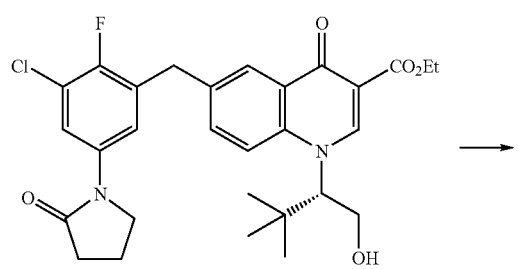

-continued

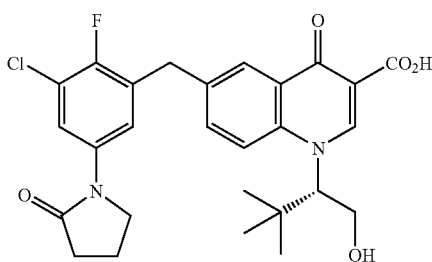

The compound (83 mg, 0.15 mmol) obtained in Step 10 and lithium hydroxide monohydrate (13 mg, 0.31 mmol) were stirred in a mixed solvent of tetrahydrofuran (1.5 ml) and water (0.3 ml) at room temperature for 2.7 hr. An aqueous citric acid solution was added to the reaction mixture, and the mixture was extracted with ethyl acetate. The organic layer was washed with water (three times) and saturated brine in this order, and dried over sodium sulfate. After filtration, the filtrate was concentrated under reduced pressure, and the obtained residue was treated with a mixed solvent of hexane-ethyl acetate. The precipitated solid was collected by filtration and dried under reduced pressure to give the object compound (60 mg, yield 76%) as a white solid.

¹H NMR (DMSO-d₆ 400 MHz) (δ) ppm: 0.96 (9H, s), 2.05 (2H, quint., J=7.5 Hz), 2.45-2.55 (2H, m), 3.82 (2H, t, J=7.1 Hz), 4.00-4.12 (2H, m), 4.26 (2H, s), 5.06-5.13 (2H, m), 7.70 (1H, dd, J=6.1, 2.7 Hz), 7.83 (1H, dd, J=9.2, 2.2 Hz), 7.87 (1H, dd, J=6.4, 2.7 Hz), 8.22 (1H, d, J=2.2 Hz), 8.37 (1H, d, J=9.2 Hz), 8.82 (1H, s), 15.17 (1H, br s)

MS (ESI): M+ 515

Example 53

Step 1

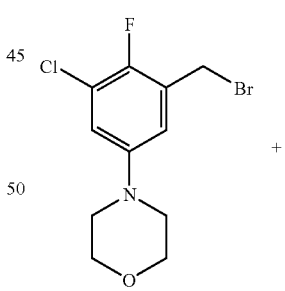

+

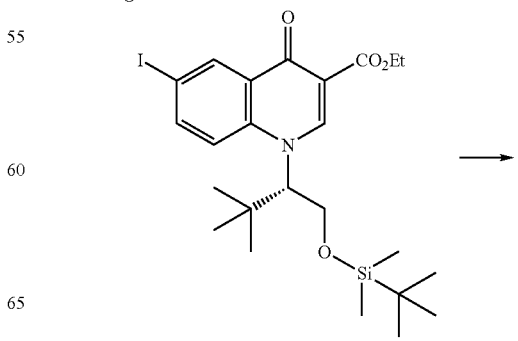

-continued

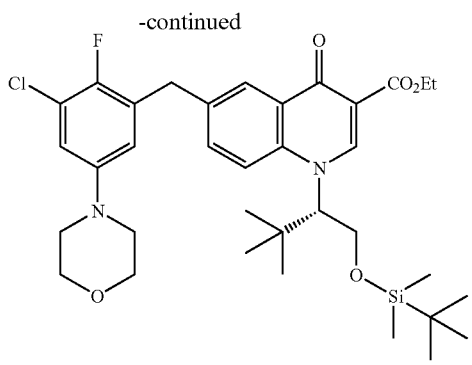

To a suspension of a zinc powder (0.793 g, 12.1 mmol) in tetrahydrofuran (10 ml) were added 1,2-dibromoethane (0.09 ml, 1.0 mmol) and trimethylsilyl chloride (0.27 ml, 2.1 mmol) under heating at 80° C. in an oil bath, and the mixture was stirred at the same temperature for 10 min. After allowing to cool, a solution of the compound (2.88 g, 9.33 mmol) obtained in Step 6 of Example 1 in tetrahydrofuran (20 ml) was added over 10 min under cooling in a water bath, and the mixture was stirred at room temperature for 20 min. To this mixture were added bis(triphenylphosphine)dichloropalladium(II) (252 mg, 0.359 mmol), and a solution of the compound (4.0 g, 7.2 mmol) obtained in Step 4 of Example 51 in tetrahydrofuran (10 ml) in this order, and the mixture was stirred under heating at 80° C. for 15 min. After completion of the reaction, the reaction mixture was allowed to cool, and aqueous ammonium chloride solution and ethyl acetate were added. The resulting insoluble material was filtered off through celite. The layers of the filtrate were separated, and the organic layer was washed with water (twice) and saturated brine in this order, and dried over sodium sulfate. After filtration, the filtrate was concentrated under reduced pressure, and the obtained residue was purified by silica gel chromatography (hexane:ethyl acetate=2:3 to 1:2) to give the object compound (4.71 g, yield 99%) as a pale yellowish-white amorphous solid.

$^1$H NMR (CDCl$_3$ 400 MHz) (δ) ppm: −0.11 (3H, s), −0.02 (3H, s), 0.64 (9H, s), 1.05 (9H, s), 1.41 (3H, t, J=7.1 Hz), 2.99-3.05 (4H, m), 3.77-3.83 (4H, m), 4.02-4.18 (4H, m), 4.34-4.46 (2H, m), 4.64 (1H, dd, J=8.5, 4.8 Hz), 6.59 (1H, dd, J=5.5, 3.1 Hz), 6.76 (1H, dd, J=6.0, 3.1 Hz), 7.49 (11H, dd, J=9.1, 2.1 Hz), 7.57 (1H, d, J=9.1 Hz), 8.42 (1H, d, J=2.1 Hz), 8.68 (1H, s)

Step 2

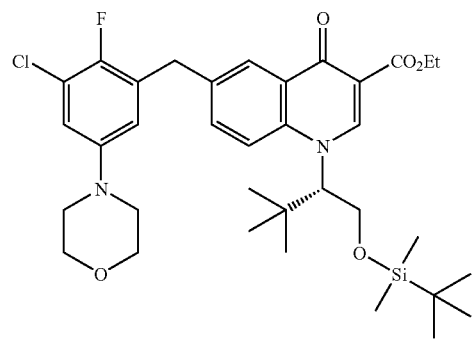

-continued

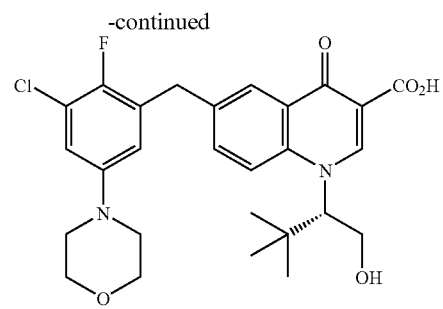

The compound (5.51 g, 8.35 mmol) obtained in Step 1 was dissolved in ethanol (16 ml), 4N aqueous sodium hydroxide solution (8 ml, 32 mmol) was added, and the mixture was stirred under heating at 80° C. for 2 hr. After allowing to cool, a 10% aqueous citric acid solution was added to the reaction mixture, and the mixture was extracted with ethyl acetate. The organic layer was washed with water (three times) and saturated brine in this order, sodium sulfate and activated carbon were added, and the mixture was diluted with chloroform. The mixture was stirred under heating at 45° C. for 15 min. After allowing to cool, the mixture was filtered through celite and concentrated under reduced pressure. The obtained residue was treated with a mixed solvent of hexane-ethyl acetate, and the precipitated solid was collected by filtration and dried under reduced pressure to give the object compound (3.86 g, yield 89%) as a white solid.

$^1$H NMR (DMSO-d$_6$ 400 MHz) (δ) ppm: 0.96 (9H, s), 3.07-3.12 (4H, m), 3.69-3.74 (4H, m), 4.00-4.12 (2H, m), 4.18 (2H, s), 5.05-5.13 (2H, m), 6.97 (1H, dd, J=5.8, 3.0 Hz), 7.08 (1H, dd, J=5.7, 3.0 Hz), 7.88 (1H, dd, J=9.2, 2.1 Hz), 8.23 (1H, d, J=2.1 Hz), 8.36 (1H, d, J=9.2 Hz), 8.82 (1H, s), 15.18 (1H, br s)

MS (ESI): M+ 517

Example 56

Step 1

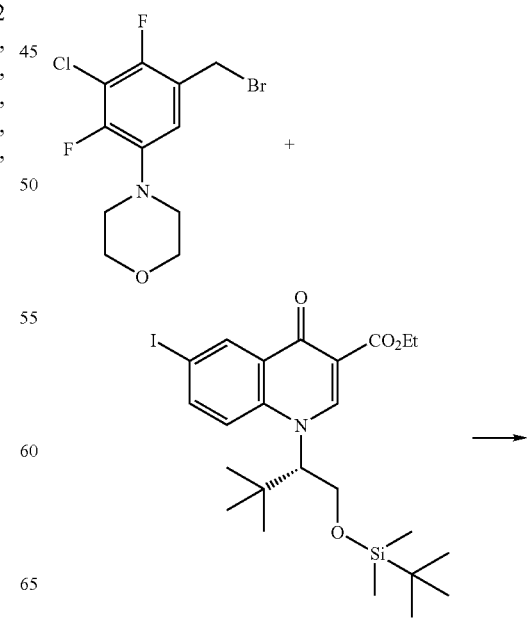

-continued

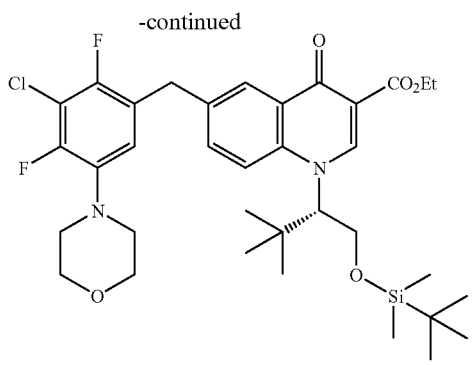

To a suspension of a zinc powder (0.572 g, 8.76 mmol) in tetrahydrofuran (7.5 ml) were added 1,2-dibromoethane (65 μl, 0.75 mmol) and trimethylsilyl chloride (195 μl, 1.54 mmol) under an argon atmosphere under heating at 80° C. in an oil bath, and the mixture was stirred at the same temperature for 5 min. After allowing to cool, a solution of the compound (2.20 g, 6.74 mmol) obtained in Step 6 of Example 16 in tetrahydrofuran (15 ml) was added over 10 min under cooling in a water bath, and the mixture was stirred at room temperature for 15 min. To this mixture were added bis(triphenylphosphine)dichloropalladium(II) (182 mg, 0.259 mmol), and a solution of the compound (2.89 g, 5.18 mmol) obtained in Step 4 of Example 51 in tetrahydrofuran (7.5 ml) in this order, and the mixture was stirred under heating at 80° C. for 15 min. After completion of the reaction, the reaction mixture was allowed to cool, and aqueous ammonium chloride solution and ethyl acetate were added. The resulting insoluble material was filtered off through celite. The layers of the filtrate were separated, and the aqueous layer was extracted with ethyl acetate. The combined organic layer was washed with brine and saturated brine in this order, and dried over sodium sulfate. After filtration, the filtrate was concentrated under reduced pressure, and the obtained residue was purified by silica gel chromatography (hexane:ethyl acetate=3:4 to 3:5, further 1:2) to give the object crudely purified product (3.39 g) as a pale-yellow amorphous solid.

$^1$H NMR (CDCl$_3$ 400 MHz) (δ) ppm: −0.11 (3H, s), −0.02 (3H, s), 0.63 (9H, s), 1.05 (9H, s), 1.41 (3H, t, J=7.2 Hz), 2.94-2.99 (4H, m), 3.79-3.84 (4H, m), 4.02-4.18 (4H, m), 4.34-4.46 (2H, m), 4.65 (1H, dd, J=8.5, 4.5 Hz), 6.60-6.65 (1H, m), 7.47 (1H, dd, J=8.9, 2.1 Hz), 7.58 (1H, d, J=8.9 Hz), 8.40 (1H, d, J=2.1 Hz), 8.69 (1H, s)

Step 2

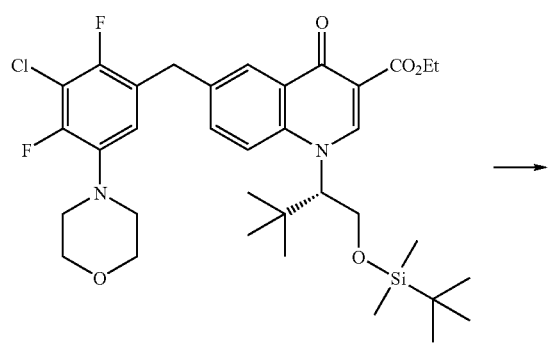

-continued

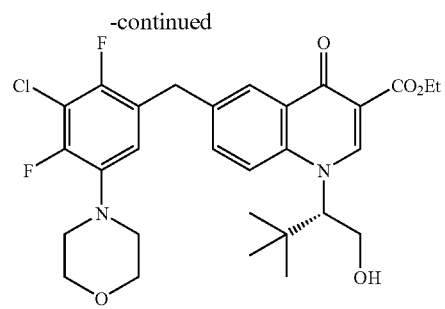

The crudely purified product (3.39 g) obtained in Step 1 was dissolved in tetrahydrofuran (34 ml), a 1.0 M solution of tetrabutylammonium fluoride in tetrahydrofuran (7.5 ml, 7.5 mmol) was added, and the mixture was stirred at room temperature for 5 min. To the reaction mixture was added brine, and the mixture was extracted twice with ethyl acetate. The combined organic layer was washed with brine (twice) and saturated brine in this order, and dried over sodium sulfate. After filtration, the filtrate was concentrated under reduced pressure, and the obtained residue was purified by silica gel chromatography (hexane:ethyl acetate=1:3 to chloroform:acetone=3:2) to give the object compound (2.81 g, yield 96%, 2 steps) as a pale-brown amorphous solid.

$^1$H NMR (CDCl$_3$ 400 MHz) (δ) ppm: 1.00 (9H, s), 1.41 (3H, t, J=7.1 Hz), 2.93-3.00 (4H, m), 3.78-3.86 (6H, m), 3.95 (1H, d, J=15.3 Hz), 4.20-4.45 (4H, m), 4.73 (1H, dd, J=9.4, 4.1 Hz), 6.54-6.60 (1H, m), 7.42 (1H, dd, J=8.9, 1.9 Hz), 7.63 (1H, d, J=8.9 Hz), 7.96 (1H, d, J=1.9 Hz), 8.67 (1H, s)

Step 3

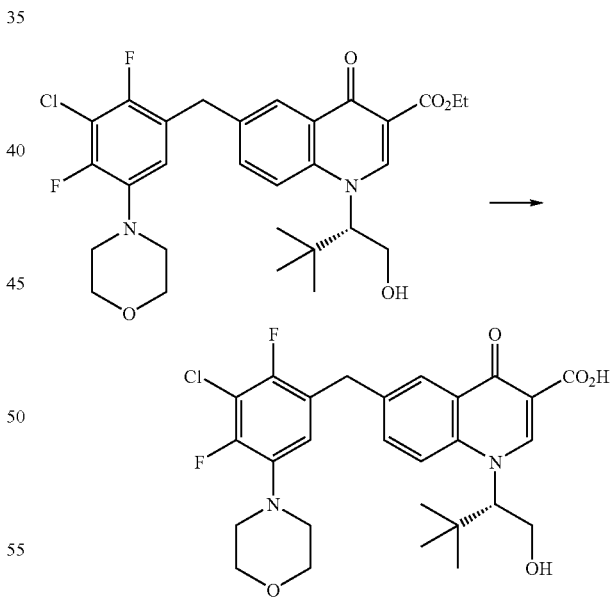

The compound (2.81 g, 4.99 mmol) obtained in Step 2 was dissolved in a mixed solvent of tetrahydrofuran (1.5 ml) and water (0.3 ml), lithium hydroxide monohydrate (418 mg, 9.98 mmol) was added, and the mixture was stirred at room temperature for 2 hr. A 5% aqueous potassium hydrogen sulfate solution was added to the reaction mixture, and the mixture was extracted twice with ethyl acetate. The combined organic layer was washed with brine (twice) and saturated brine in this order, and dried over sodium sulfate. After filtration, the filtrate was concentrated under reduced pressure, and the obtained residue was treated with a mixed solvent of hexane-ethyl acetate. The precipitated solid was collected by filtration and dried under reduced pressure to give the object compound (2.43 g, yield 91%) as a white solid.

$^1$H NMR (DMSO-$d_6$ 400 MHz) (δ) ppm: 0.96 (9H, s), 2.97-3.01 (4H, m), 3.71-3.76 (4H, m), 4.00-4.12 (2H, m), 4.21 (2H, s), 5.06-5.13 (2H, m), 7.24 (1H, dd, J=7.7, 7.7 Hz), 7.83 (1H, dd, J=9.2, 2.1 Hz), 8.24 (1H, d, J=1.9 Hz), 8.36 (1H, d, J=9.3 Hz), 8.81 (1H, s), 15.19 (1H, br s)

MS (ESI): M+ 535

In the same manner as in the above-mentioned Examples, and according to other conventional methods where necessary, the compounds of Examples 3, 4, 6-15, 18-24, 26-29, 32, 34-37, 38-48, 50, 52, 54, 55 and 57-59 were obtained. The chemical structural formulas of these compounds are shown in Tables 1-7. In addition, the compounds of Reference examples 30, 31 and 33 shown in Table 4 can also be produced in the same manner as in the above-mentioned Examples, and according to other conventional methods where necessary.

TABLE 1

| Ex. | structural formula |
|---|---|
| 1 | |
| 2 | |
| 3 | |
| 4 | |
| 5 | |
| 6 | |
| 7 | |
| 8 | |

TABLE 1-continued

| Ex. | structural formula |
|---|---|
| 9 | (structure) |
| 10 | (structure) |

TABLE 2

| Ex. | structural formula |
|---|---|
| 11 | (structure) |
| 12 | (structure) |

TABLE 2-continued

| Ex. | structural formula |
|---|---|
| 13 | (structure) |
| 14 | (structure) |
| 15 | (structure) |
| 16 | (structure) |
| 17 | (structure) |

TABLE 2-continued

| Ex. | structural formula |
|---|---|
| 18 | (structure) |
| 19 | (structure) |
| 20 | (structure) |

TABLE 3

| Ex. | structural formula |
|---|---|
| 21 | (structure) |
| 22 | (structure) |

TABLE 3-continued

| Ex. | structural formula |
|---|---|
| 23 | (structure) |
| 24 | (structure) |
| 25 | (structure) |
| 26 | (structure) |
| 27 | (structure) |

TABLE 3-continued
| Ex. | structural formula |
|---|---|
| 28 | 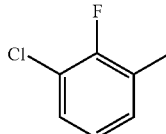 |
| 29 | |
TABLE 4
| Ex. | structural formula |
|---|---|
| 30 | |
| 31 | |
| 32 | |
TABLE 4-continued
| Ex. | structural formula |
|---|---|
| 33 | 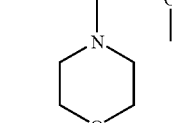 |
| 34 | |
| 35 | |
| 36 | |
| 37 | |

TABLE 5

| Ex. | structural formula |
|---|---|
| 38 | (structure) |
| 39 | (structure) |
| 40 | (structure) |
| 41 | (structure) |
| 42 | (structure) |

TABLE 5-continued

| Ex. | structural formula |
|---|---|
| 43 | (structure) |
| 44 | (structure) |
| 45 | (structure) |
| 46 | (structure) |
| 47 | (structure) |

TABLE 6

| Ex. | structural formula |
|---|---|
| 48 | (structure) |
| 49 | (structure) |
| 50 | (structure) |
| 51 | (structure) |
| 52 | (structure) |

TABLE 6-continued

| Ex. | structural formula |
|---|---|
| 53 | (structure) |
| 54 | (structure) |
| 55 | (structure) |
| 56 | (structure) |
| 57 | (structure) |

TABLE 7

| Ex. | structural formula |
|---|---|
| 58 | |
| 59 | |

The NMR and MS data of the Example compounds are described in the following.

Example 3

$^1$H NMR (DMSO-d$_6$ 400 MHz) (δ) ppm: 0.73 (3H, d, J=6.5 Hz), 1.17 (3H, d, J=6.5 Hz), 1.94 (4H, t, J=6.6 Hz), 2.33-2.42 (1H, m), 3.16-3.20 (4H, m), 3.76-3.83 (1H, m), 3.96-4.01 (1H, m), 4.03 (2H, s), 4.08 (3H, s), 4.90 (1H, s), 5.20 (1H, t, J=5.0 Hz), 6.45 (1H, dd, J=5.4, 2.9 Hz), 6.53 (1H, dd, J=5.7, 2.9 Hz), 7.47 (1H, s), 7.97 (1H, s), 8.89 (1H, s), 15.44 (1H, s)

MS (ESI): M+ 517

Example 4

$^1$H NMR (DMSO-d$_6$ 400 MHz) (δ) ppm: 0.72 (3H, d, J=6.4 Hz), 1.15 (3H, d, J=6.6 Hz), 2.33-2.37 (1H, m), 3.78-3.80 (1H, m), 3.96-4.04 (6H, m), 4.11 (2H, s), 4.42 (2H, dd, J=8.8, 7.1 Hz), 4.85-4.87 (1H, m), 5.19-5.20 (1H, m), 7.45 (1H, s), 7.55 (1H, dd, J=5.7, 2.9 Hz), 7.68 (1H, dd, J=6.1, 2.8 Hz), 8.04 (1H, s), 8.86 (1H, s), 15.43 (1H, s)

MS (ESI): M+ 533

Example 5

$^1$H NMR (DMSO-d$_6$ 400 MHz) (δ) ppm: 0.72 (3H, d, J=6.8 Hz), 1.16 (3H, d, J=6.8 Hz), 2.31-2.43 (1H, m), 3.04-3.10 (4H, m), 3.68-3.73 (4H, m), 3.75-3.82 (1H, m), 3.94-4.03 (1H, m), 4.04 (2H, s), 4.06 (3H, s), 4.83-4.92 (1H, m), 5.17-5.23 (1H, m), 6.90-6.95 (1H, m), 6.98-7.03 (1H, m), 7.46 (1H, s), 7.95 (1H, s), 8.87 (1H, s), 15.44 (1H, br s)

MS (ESI): M+ 533

Example 6

$^1$H NMR (DMSO-d$_6$ 400 MHz) (δ) ppm: 0.72 (3H, d, J=6.7 Hz), 1.16 (3H, d, J=6.7 Hz), 1.46-1.63 (6H, m), 2.31-2.44 (1H, m), 3.05-3.12 (4H, m), 3.75-3.83 (1H, m), 3.95-4.02 (1H, m), 4.02 (2H, s), 4.06 (3H, s), 4.83-4.92 (1H, m), 5.17-5.23 (1H, m), 6.86-6.90 (1H, m), 6.93-6.97 (1H, m), 7.46 (1H, s), 7.96 (1H, s), 8.87 (1H, s), 15.44 (1H, br s)

MS (ESI): M+ 531

Example 7

$^1$H NMR (DMSO-d$_6$ 400 MHz) (δ) ppm: 0.72 (3H, d, J=6.5 Hz), 1.16 (3H, d, J=6.5 Hz), 1.80-1.83 (4H, m), 2.33-2.39 (3H, m), 3.57 (2H, t, J=5.6 Hz), 3.77-3.80 (1H, m), 3.98-3.99 (1H, m), 4.03 (3H, s), 4.10 (2H, s), 4.86-4.88 (1H, m), 5.20 (1H, t, J=5.1 Hz), 7.23 (1H, dd, J=6.1, 2.4 Hz), 7.45-7.47 (2H, m), 8.09 (1H, s), 8.88 (1H, s), 15.46 (1H, s)

MS (ESI): M+ 545

Example 8

$^1$H NMR (DMSO-d$_6$ 400 MHz) (δ) ppm: 0.72 (3H, d, J=6.8 Hz), 1.16 (3H, d, J=6.8 Hz), 1.82-1.91 (1H, m), 1.96-2.07 (1H, m), 2.31-2.43 (1H, m), 2.98-3.03 (1H, m), 3.17-3.38 (3H, m), 3.75-3.83 (1H, m), 3.94-4.02 (1H, m), 4.02 (2H, s), 4.07 (3H, s), 4.33-4.40 (1H, m), 4.84-4.92 (1H, m), 4.96 (1H, d, J=3.7 Hz), 5.17-5.23 (1H, m), 6.39-6.44 (1H, m), 6.48-6.52 (1H, m), 7.46 (1H, s), 7.96 (1H, s), 8.87 (1H, s), 15.44 (1H, br s)

MS (ESI): M+ 533

Example 9

$^1$H NMR (DMSO-d$_6$ 400 MHz) (δ) ppm: 0.72 (3H, d, J=6.8 Hz), 1.16 (3H, d, J=6.8 Hz), 1.82-1.91 (1H, m), 1.96-2.07 (1H, m), 2.30-2.43 (1H, m), 2.97-3.04 (1H, m), 3.17-3.38 (3H, m), 3.74-3.83 (1H, m), 3.94-4.02 (1H, m), 4.02 (2H, s), 4.07 (3H, s), 4.33-4.40 (1H, m), 4.84-4.92 (1H, m), 4.96 (1H, d, J=3.9 Hz), 5.17-5.23 (1H, m), 6.40-6.44 (1H, m), 6.48-6.52 (1H, m), 7.46 (1H, s), 7.96 (1H, s), 8.87 (1H, s), 15.44 (1H, br s)

MS (EST): M+ 533

Example 10

$^1$H NMR (DMSO-d$_6$ 300 MHz) (δ) ppm: 0.72 (3H, d, J=6.8 Hz), 1.15 (3H, d, J=6.4 Hz), 2.43-2.53 (3H, m), 2.89 (3H, s), 3.75-3.80 (3H, m), 3.96-4.03 (4H, m), 4.10 (2H, s), 4.85-4.87 (1H, m), 5.18-5.19 (1H, m), 6.87 (1H, dd, J=5.5, 2.8 Hz), 7.05 (1H, dd, J=6.0, 3.0 Hz), 7.45 (1H, s), 8.09 (1H, s), 8.87 (1H, s), 15.44 (1H, s)

MS (ESI): M+ 546

Example 11

$^1$H NMR (DMSO-d$_6$ 400 MHz) (δ) ppm: 0.72 (3H, d, J=6.5 Hz), 1.16 (3H, d, J=6.5 Hz), 2.02 (3H, s), 2.31-2.46 (1H, m), 3.04-3.10 (2H, m), 3.11-3.16 (2H, m), 3.51-3.58 (4H, m), 3.75-3.83 (1H, m), 3.94-4.03 (1H, m), 4.04 (2H, s), 4.06 (3H, s), 4.84-4.92 (1H, m), 5.17-5.23 (1H, m), 6.92-6.97 (1H, m), 7.00-7.05 (1H, m), 7.46 (1H, s), 7.96 (1H, s), 8.88 (1H, s), 15.44 (1H, br s)

MS (ESI): M+ 574

Example 12

$^1$H NMR (DMSO-d$_6$ 400 MHz) (δ) ppm: 0.72 (3H, d, J=6.5 Hz), 1.16 (3H, d, J=6.5 Hz), 2.34-2.37 (1H, m), 2.49-2.52 (2H, m), 3.44 (2H, t, J=7.1 Hz), 3.67 (2H, t, J=13.2 Hz), 3.77-3.80 (1H, m), 3.99-4.04 (3H, m), 4.07 (3H, s), 4.87-4.89

(1H, m), 5.20 (1H, t, J=5.2 Hz), 6.57 (1H, dd, J=5.6, 3.0 Hz), 6.69 (1H, dd, J=5.7, 2.9 Hz), 7.46 (1H, s), 7.95 (1H, s), 8.88 (1H, s), 15.43 (1H, s)
MS (ESI): M+ 553

Example 13

$^1$H NMR (DMSO-$d_6$ 300 MHz) (δ) ppm: 0.72 (3H, d, J=6.8 Hz), 1.16 (3H, d, J=6.4 Hz), 2.18-2.35 (3H, m), 3.28-3.58 (4H, m), 3.75-3.81 (1H, m), 3.97-4.02 (3H, m), 4.07 (3H, s), 4.86-4.89 (1H, m), 5.20 (1H, t, J=5.1 Hz), 5.33-5.51 (1H, m), 6.50 (1H, dd, J=5.7, 3.0 Hz), 6.60 (1H, dd, J=5.8, 2.8 Hz), 7.46 (1H, s), 7.96 (1H, s), 8.87 (1H, s), 15.43 (1H, s)
MS (ESI): M+ 535

Example 14

$^1$H NMR (DMSO-$d_6$ 300 MHz) (δ) ppm: 0.72 (3H, d, J=6.4 Hz), 1.16 (3H, d, J=6.4 Hz), 2.20-2.31 (3H, m), 3.34-3.51 (4H, m), 3.76-3.82 (1H, m), 3.96-4.03 (3H, m), 4.07 (3H, s), 4.88-4.89 (1H, m), 5.20 (1H, t, J=4.7 Hz), 5.34-5.52 (1H, m), 6.50 (1H, dd, J=5.5, 2.8 Hz), 6.60 (1H, dd, J=5.8, 3.2 Hz), 7.46 (1H, s), 7.96 (1H, s), 8.87 (1H, s), 15.43 (1H, s)
MS (ESI): M+ 535

Example 15

$^1$H NMR (DMSO-$d_6$ 300 MHz) (δ) ppm: 1.18 (3H, d, J=6.0 Hz), 3.07 (4H, t, J=4.7 Hz), 3.21 (3H, s), 3.71 (4H, t, J=4.7 Hz), 3.85-4.04 (8H, m), 5.18-5.23 (2H, m), 6.91 (1H, dd, J=5.8, 2.8 Hz), 7.00 (1H, dd, J=5.7, 3.0 Hz), 7.44 (1H, s), 7.95 (1H, s), 8.94 (1H, s), 15.41 (1H, s)
MS (ESI): M+ 549

Example 16

$^1$H NMR (DMSO-$d_6$ 400 MHz) (δ) ppm: 0.72 (3H, d, J=6.8 Hz), 1.16 (3H, d, J=6.8 Hz), 2.31-2.45 (1H, m), 2.93-3.00 (4H, m), 3.70-3.75 (4H, m), 3.75-3.82 (1H, m), 3.95-4.02 (1H, m), 4.06 (3H, s), 4.07 (2H, s), 4.83-4.92 (1H, m), 5.17-5.23 (1H, m), 7.05-7.11 (1H, m), 7.46 (1H, s), 8.01 (1H, s), 8.88 (1H, s), 15.44 (1H, br s)
MS (ESI): M+ 551

Example 17

$^1$H NMR (DMSO-$d_6$ 400 MHz) (δ) ppm: 0.99 (9H, s), 3.08 (4H, t, J=4.8 Hz), 3.71 (4H, t, J=4.8 Hz), 4.03-4.11 (2H, m), 4.05 (2H, s), 4.08 (3H, s), 5.13 (1H, t, J=4.9 Hz), 5.17-5.20 (1H, m), 6.90-6.92 (1H, m), 7.01-7.03 (1H, m), 7.54 (1H, s), 7.96 (1H, s), 8.79 (1H, s), 15.39 (1H, s)
MS (ESI): M+ 547

Example 18

$^1$H NMR (DMSO-$d_6$ 400 MHz) (δ) ppm: 0.98 (9H, s), 1.25 (3H, t, J=7.4 Hz), 2.88-2.99 (2H, m), 3.08 (4H, t, J=4.8 Hz), 3.71 (4H, t, J=4.8 Hz), 4.03-4.13 (2H, m), 4.19 (2H, s), 5.14 (1H, t, J=4.9 Hz), 5.18-5.21 (1H, m), 6.89-6.91 (1H, m), 7.03-7.06 (1H, m), 7.94 (1H, s), 8.18 (1H, s), 8.80 (1H, s), 15.22 (1H, s)
MS (ESI): M+ 545

Example 19

$^1$H NMR (DMSO-$d_6$ 300 MHz) (δ) ppm: 1.03 (3H, t, J=7.0 Hz), 3.07 (4H, t, J=4.7 Hz), 3.45 (2H, q, J=6.9 Hz), 3.70 (4H, t, J=4.7 Hz), 3.88-4.00 (9H, m), 5.25 (1H, t, J=5.3 Hz), 5.34-5.39 (1H, m), 6.91 (1H, dd, J=5.7, 3.0 Hz), 7.00 (1H, dd, J=6.0, 3.0 Hz), 7.45 (1H, s), 7.97 (1H, s), 8.85 (1H, s), 15.39 (1H, s)
MS (ESI): M+ 549

Example 20

$^1$H NMR (DMSO-$d_6$ 400 MHz) (δ) ppm: 1.25 (3H, t, J=7.5 Hz), 2.90 (2H, q, J=7.5 Hz), 3.07 (4H, t, J=4.8 Hz), 3.26 (3H, s), 3.70 (4H, t, J=4.8 Hz), 3.80-3.96 (4H, m), 4.18 (2H, s), 5.26 (1H, t, J=5.4 Hz), 5.35-5.42 (1H, m), 6.90-6.92 (1H, m), 7.01-7.04 (1H, m), 7.95 (1H, s), 8.00 (1H, s), 8.86 (1H, s), 15.19 (1H, s)
MS (ESI): M+ 533

Example 21

$^1$H NMR (DMSO-$d_6$ 400 MHz) (δ) ppm: 0.72 (3H, d, J=6.7 Hz), 1.15 (3H, d, J=6.5 Hz), 2.34-2.41 (3H, m), 3.50-3.54 (2H, m), 3.70-3.73 (2H, m), 3.74-3.81 (1H, m), 3.95-4.02 (1H, m), 4.04 (3H, s), 4.10 (2H, s), 4.87 (1H, br s), 5.18-5.20 (1H, m), 7.20 (1H, dd, J=5.7, 2.9 Hz), 7.25 (1H, dd, J=5.9, 2.9 Hz), 7.45 (1H, s), 8.08 (1H, s), 8.88 (1H, s), 15.44 (1H, s)
MS (ESI): M+ 567

Example 22

$^1$H NMR (DMSO-$d_6$ 300 MHz) (δ) ppm: 3.07 (4H, t, J=4.7 Hz), 3.26 (3H, s), 3.70 (4H, t, J=4.7 Hz), 3.83-3.94 (4H, m), 4.02-4.04 (5H, m), 5.27 (1H, t, J=5.5 Hz), 5.38-5.42 (1H, m), 6.91 (1H, dd, J=5.7, 3.0 Hz), 7.00 (1H, dd, J=5.8, 3.2 Hz), 7.45 (1H, s), 7.97 (1H, s), 8.83 (1H, s), 15.40 (1H, s)
MS (ESI): M+ 535

Example 23

$^1$H NMR (CDCl$_3$ 400 MHz) (δ) ppm: 0.83 (3H, d, J=6.5 Hz), 1.23 (3H, d, J=6.5 Hz), 1.31 (3H, t, J=7.6 Hz), 2.41-2.52 (1H, m), 2.83 (2H, q, J=7.6 Hz), 3.00 (4H, t, J=4.9 Hz), 3.07 (1H, br s), 3.77 (4H, t, J=4.9 Hz), 4.12-4.27 (4H, m), 4.54-4.62 (1H, m), 6.44-6.49 (1H, m), 6.79 (1H, dd, J=2.8, 6.0 Hz), 7.58 (1H, s), 8.24 (1H, s), 8.86 (1H, s), 15.25 (1H, br s)
MS (ESI): M+ 531

Example 24

$^1$H NMR (DMSO-$d_6$ 300 MHz) (δ) ppm: 0.72 (3H, d, J=7.0 Hz), 1.15 (3H, d, J=7.0 Hz), 1.25 (3H, t, J=7.4 Hz), 2.03 (2H, tt, J=7.0, 7.0 Hz), 2.31-2.43 (1H, m), 2.47 (2H, t, J=7.0 Hz), 2.90 (2H, q, J=7.4 Hz), 3.75-3.79 (1H, m), 3.79 (2H, t, J=7.0 Hz), 3.95-4.03 (1H, m), 4.26 (2H, s), 4.88-4.95 (1H, m), 5.20 (1H, t, J=5.1 Hz), 7.60 (1H, dd, J=2.8, 6.2 Hz), 7.86 (1H, dd, J=2.8, 6.2 Hz), 7.95 (1H, s), 8.09 (1H, s), 8.91 (1H, s), 15.23 (1H, s)
MS (ESI): M+ 529

Example 25

$^1$H NMR (DMSO-$d_6$ 300 MHz) (δ) ppm: 0.72 (3H, d, J=6.4 Hz), 1.16 (3H, d, J=6.4 Hz), 2.10 (2H, tt, J=7.4, 7.4 Hz), 2.42 (2H, t, J=7.4 Hz), 2.31-2.44 (1H, m), 3.74 (2H, t, J=7.4 Hz), 3.73-3.83 (1H, m), 3.95-4.06 (1H, m), 4.03 (3H, s), 4.10 (2H, s), 4.83-4.91 (1H, m), 5.19 (1H, t, J=5.0 Hz), 7.45 (1H, dd, J=7.6, 7.6 Hz), 7.45 (1H, s), 8.12 (1H, s), 8.88 (1H, s), 15.45 (1H, s)
MS (ESI): M+ 549

Example 26

¹H NMR (DMSO-d$_6$ 400 MHz) (δ) ppm: 0.71 (3H, d, J=6.5 Hz), 1.14 (3H, d, J=6.5 Hz), 1.21 (3H, t, J=7.4 Hz), 2.09 (2H, tt, J=7.4, 7.4 Hz), 2.31-2.43 (3H, m), 2.87 (2H, q, J=7.4 Hz), 3.72 (2H, t, J=7.4 Hz), 3.75-3.81 (1H, m), 3.94-4.02 (1H, m), 4.24 (2H, s), 4.90 (1H, br s), 5.16-5.22 (1H, m), 7.41 (1H, t, J=7.8 Hz), 8.01 (1H, s), 8.08 (1H, s), 8.90 (1H, s), 15.23 (1H, s)

MS (ESI): M+ 547

Example 27

¹H NMR (DMSO-d$_6$ 300 MHz) (δ) ppm: 0.72 (3H, d, J=6.4 Hz), 1.16 (3H, d, J=6.4 Hz), 2.36-2.43 (1H, m), 2.63-2.66 (4H, m), 3.47-3.49 (4H, m), 3.76-3.83 (1H, m), 3.97-3.98 (1H, m), 4.03 (2H, s), 4.06 (3H, s), 4.85-4.90 (1H, m), 5.19 (1H, t, J=5.1 Hz), 6.90 (1H, dd, J=5.7, 3.0 Hz), 6.99 (1H, dd, J=6.0, 3.0 Hz), 7.46 (1H, s), 7.97 (1H, s), 8.88 (1H, s), 15.43 (1H, s)

MS (ESI): M+ 549

Example 28

¹H NMR (CDCl$_3$ 300 MHz) (δ) ppm: 1.21 (3H, d, J=6.4 Hz), 2.76-2.98 (1H, m), 3.03 (4H, t, J=4.5 Hz), 3.43 (3H, s), 3.80 (4H, t, J=4.7 Hz), 3.83-3.93 (1H, m), 3.98 (3H, s), 4.04 (2H, s), 4.19-4.36 (2H, m), 4.64 (1H, br s), 6.57-6.64 (1H, m), 6.74-6.81 (1H, m), 6.98 (1H, s), 8.21 (1H, s), 8.84 (1H, s), 15.25 (1H, br s)

MS (ESI): M+ 549

Example 29

¹H NMR (CDCl$_3$ 300 MHz) (δ) ppm: 2.07-2.21 (1H, m), 2.22-2.37 (1H, m), 3.03 (4H, t, J=4.7 Hz), 3.22-3.31 (5H, m), 3.45-3.54 (1H, m), 3.79 (4H, t, J=4.7 Hz), 3.99 (3H, s), 4.04 (2H, s), 4.08-4.20 (2H, m), 5.09 (1H, br s), 6.56-6.63 (1H, m), 6.75-6.80 (1H, m), 7.22 (1H, s), 8.18 (1H, s), 8.86 (1H, s), 15.46 (1H, br s)

MS (ESI): M+ 549

Example 32

¹H NMR (DMSO-d$_6$ 300 MHz) (δ) ppm: 0.72 (3H, d, J=6.8 Hz), 1.16 (3H, d, J=6.4 Hz), 1.39-1.49 (2H, m), 1.78-1.80 (2H, m), 2.36-2.41 (1H, m), 2.83-2.87 (2H, m), 3.42-3.82 (4H, m), 3.97-3.99 (1H, m), 4.03 (2H, br s), 4.06 (3H, s), 4.84-4.90 (1H, m), 6.88-6.94 (1H, m), 6.97-7.02 (1H, m), 7.46 (1H, br s), 7.97 (1H, br s), 8.87 (1H, s)

MS (ESI): M+ 547

Example 34

¹H NMR (DMSO-d$_6$ 400 MHz) (δ) ppm: 1.17 (3H, d, J=6.2 Hz), 1.24 (3H, t, J=7.4 Hz), 2.90 (2H, q, J=7.4 Hz), 3.06-3.08 (4H, m), 3.19 (3H, s), 3.69-3.72 (4H, m), 3.83-3.90 (1H, m), 3.93-4.01 (2H, m), 4.18 (2H, s), 5.18-5.23 (2H, m), 6.90 (1H, dd, J=5.6, 3.0 Hz), 7.03 (1H, dd, J=6.0, 3.0 Hz), 7.93 (1H, s), 8.02 (1H, s), 8.96 (1H, s), 15.21 (1H, s)

MS (ESI): M+ 547

Example 35

¹H NMR (DMSO-d$_6$ 400 MHz) (δ) ppm: 1.16 (3H, d, J=6.5 Hz), 1.25 (3H, t, J=7.4 Hz), 2.92 (2H, q, J=7.4 Hz), 3.07 (4H, t, J=4.8 Hz), 3.25 (3H, s), 3.70 (4H, t, J=4.8 Hz), 3.78-3.80 (1H, br m), 3.98-4.07 (2H, m), 4.18 (2H, s), 5.12-5.19 (1H, m), 5.17 (1H, t, J=5.1 Hz), 6.92 (1H, dd, J=5.8, 3.0 Hz), 7.03 (1H, dd, J=5.8, 3.0 Hz), 7.94 (1H, s), 8.04 (1H, s), 8.90 (1H, s), 15.18 (1H, s)

MS (ESI): M+ 547

Example 36

¹H NMR (DMSO-d$_6$ 300 MHz) (δ) ppm: 0.73 (3H, d, J=6.4 Hz), 1.16 (3H, d, J=6.4 Hz), 2.34-2.39 (1H, m), 3.78-3.80 (1H, m), 3.98-4.00 (1H, m), 4.05 (3H, s), 4.21 (2H, s), 4.86-4.89 (1H, m), 5.19 (1H, t, J=5.1 Hz), 7.36-7.40 (1H, m), 7.47 (1H, br s), 7.89 (1H, td, J=7.7, 1.5 Hz), 8.01 (1H, d, J=8.3 Hz), 8.07 (1H, t, J=3.2 Hz), 8.09 (1H, br s), 8.19 (1H, dd, J=7.0, 2.1 Hz), 8.63-8.66 (1H, m), 8.88 (1H, s), 15.41 (1H, br s)

MS (ESI): M+ 525

Example 37

¹H NMR (DMSO-d$_6$ 300 MHz) (δ) ppm: 0.73 (3H, d, J=6.4 Hz), 1.16 (3H, d, J=6.8 Hz), 2.33-2.41 (1H, m), 3.76-3.82 (1H, m), 3.99 (1, t, J=7.7 Hz), 4.05 (3H, s), 4.21 (2H, s), 4.84-4.90 (1H, m), 5.19 (1H, t, J=4.7 Hz), 7.48 (1H, br s), 7.84 (1H, d, J=3.0 Hz), 7.90 (1H, dd, J=6.4, 2.3 Hz), 7.93 (1H, d, J=3.4 Hz), 8.02 (1H, dd, J=6.4, 2.3 Hz), 8.13 (1H, s), 8.89 (1H, s), 15.41 (1H, s)

MS (ESI): M+ 531

Example 38

¹H NMR (DMSO-d$_6$ 400 MHz) (δ) ppm: 0.90 (3H, t, J=6.9 Hz), 1.18 (3H, d, J=6.0 Hz), 1.24 (3H, t, J=7.4 Hz), 2.89 (2H, q, J=7.4 Hz), 3.05-3.08 (4H, m), 3.19-3.28 (1H, m), 3.50-3.57 (1H, m), 3.68-3.72 (4H, m), 3.84-3.91 (1H, m), 3.94-4.08 (2H, m), 4.18 (2H, s), 5.15-5.24 (2H, m), 6.88 (1H, dd, J=5.6, 3.0 Hz), 7.03 (1H, dd, J=5.8, 3.0 Hz), 7.93 (1H, s), 8.02 (1H, s), 9.01 (1H, s), 15.21 (1H, s)

MS (ESI): M+ 561

Example 39

¹H NMR (DMSO-d$_6$ 400 MHz) (δ) ppm: 1.03 (3H, t, J=7.0 Hz), 2.03 (2H, tt, J=7.8, 7.5 Hz), 2.48 (2H, t, J=7.8 Hz), 3.41-3.50 (2H, m), 3.79 (2H, t, J=7.5 Hz), 3.83-4.02 (4H, m), 4.03 (3H, s), 4.11 (2H, s), 5.26 (1H, dd, J=5.1, 5.1 Hz), 5.34-5.40 (1H, br m), 7.45 (1H, s), 7.61 (1H, dd, J=6.1, 2.8 Hz), 7.80 (1H, dd, J=6.1, 2.8 Hz), 8.04 (1H, s), 8.86 (1H, s), 15.39 (1H, s)

MS (ESI): M+ 547

Example 40

¹H NMR (DMSO-d$_6$ 400 MHz) (δ) ppm: 0.91 (3H, t, J=7.0 Hz), 1.18 (3H, d, J=6.0 Hz), 1.24 (3H, t, J=7.4 Hz), 2.02 (2H, tt, J=7.5, 7.7 Hz), 2.47 (2H, t, J=7.7 Hz), 2.88 (2H, q, J=7.4 Hz), 3.20-3.29 (1H, m), 3.50-3.58 (1H, m), 3.78 (2H, t, J=7.5 Hz), 3.84-4.09 (3H, m), 4.26 (2H, s), 5.16-5.21 (1H, m), 5.23 (1H, t, J=5.0 Hz), 7.57 (1H, dd, J=6.2, 2.7 Hz), 7.86 (1H, dd, J=6.2, 2.7 Hz), 7.95 (1H, s), 8.03 (1H, s), 9.01 (1H, s), 15.21 (1H, s)

MS (ESI): M+ 559

Example 41

¹H NMR (DMSO-d$_6$ 400 MHz) (δ) ppm: 1.16-1.19 (3H, m), 1.24 (3H, t, J=7.5 Hz), 2.03 (2H, tt, J=7.3, 7.3 Hz), 2.45-2.51 (2H, m), 2.89 (2H, q, J=7.5 Hz), 3.20 (3H, s), 3.79

(2H, t, J=7.3 Hz), 3.83-3.90 (1H, m), 3.93-4.01 (2H, m), 4.25 (2H, s), 5.18-5.25 (2H, m), 7.58 (1H, dd, J=6.4, 2.7 Hz), 7.85 (1H, dd, J=6.4, 2.7 Hz), 7.95 (1H, s), 8.03 (1H, s), 8.96 (1H, s), 15.20 (1H, br s)
MS (ESI): M+ 545

Example 42

$^1$H NMR (DMSO-$d_6$ 400 MHz) (δ) ppm: 0.91 (3H, s), 1.45 (3H, s), 3.04-3.10 (4H, m), 3.14 (3H, s), 3.66-3.75 (4H, m), 3.94-4.05 (1H, m), 4.03 (2H, s), 4.06 (3H, s), 4.11-4.19 (1H, m), 4.95-5.01 (1H, m), 5.17-5.24 (1H, m), 6.88-6.94 (1H, m), 6.98-7.03 (1H, m), 7.49 (1H, s), 7.94 (1H, s), 9.09 (1H, s), 15.38 (1H, br s)
MS (ESI): M+ 563

Example 43

$^1$H NMR (DMSO-$d_6$ 400 MHz) (δ) ppm 0.89 (3H, s), 1.24 (3H, t, J=7.6 Hz), 1.45 (3H, s), 2.85-2.98 (2H, m), 3.04-3.10 (4H, m), 3.14 (3H, s), 3.67-3.74 (4H, m), 3.95-4.05 (1H, m), 4.10-4.20 (1H, m), 4.18 (2H, s), 4.97-5.02 (1H, m), 5.21-5.27 (1H, m), 6.88-6.93 (1H, m), 7.01-7.05 (1H, m), 7.91 (1H, s), 8.14 (1H, s), 9.08 (1H, s), 15.21 (1H, br s)
MS (ESI): M+ 561

Example 44

$^1$H NMR (DMSO-$d_6$ 300 MHz) (δ) ppm: 1.26 (3H, t, J=7.5 Hz), 2.11-2.27 (2H, m), 2.90 (2H, q, J=7.4 Hz), 3.06 (4H, t, J=4.7 Hz), 3.11 (3H, s), 3.19-3.22 (2H, m), 3.37-3.41 (2H, m), 3.70 (4H, t, J=4.7 Hz), 3.81-3.93 (2H, m), 4.18 (2H, s), 5.19-5.31 (1H, m), 5.23 (1H, t, J=5.3 Hz), 6.89 (1H, dd, J=5.8, 2.7 Hz), 7.03 (1H, dd, J=5.8, 2.7 Hz), 7.94 (1H, s), 7.98 (1H, s), 8.91 (1H, s), 15.25 (1H, s)
MS (ESI) M+ 547

Example 45

$^1$H NMR (DMSO-$d_6$ 400 MHz) (δ) ppm: 0.98 (9H, s), 2.03 (2H, tt, J=8.2, 7.2 Hz), 2.46 (2H, t, J=8.2 Hz), 3.79 (2H, t, J=7.2 Hz), 4.02-4.16 (4H, m), 4.05 (3H, s), 5.10 (1H, t, J=4.7 Hz), 5.14-5.18 (1H, m), 7.52 (1H, s), 7.60 (1H, dd, J=6.0, 2.6 Hz), 7.82 (1H, dd, J=6.4, 2.6 Hz), 8.03 (1H, s), 8.78 (1H, s), 15.36 (1H, br s)
MS (ESI): M+ 545

Example 46

$^1$H NMR (DMSO-$d_6$ 400 MHz) (δ) ppm 0.98 (9H, s), 2.10 (2H, tt, J=8.0, 7.1 Hz), 2.41 (2H, t, J=8.0 Hz), 3.73 (2H, t, J=7.1 Hz), 4.03 (3H, s), 4.05-4.11 (4H, m), 5.11 (1H, t, J=4.5 Hz), 5.13-5.17 (1H, m), 7.42 (1H, t, J=7.9 Hz), 7.51 (1H, s), 8.11 (1H, s), 8.79 (1H, s), 15.38 (1H, br s)
MS (ESI): M+ 563

Example 47

$^1$H NMR (DMSO-$d_6$ 400 MHz) (δ) ppm: 1.99-2.07 (2H, m), 2.09-2.26 (2H, m), 2.47 (2H, t, J=7.6 Hz), 3.14 (3H, s), 3.21-3.29 (1H, m), 3.33-3.41 (1H, m), 3.79 (2H, t, J=7.6 Hz), 3.79-3.97 (2H, m), 4.03 (3H, s), 4.12 (2H, s), 5.17-5.26 (1H, m), 5.25 (1H, t, J=5.3 Hz), 7.46 (1H, s), 7.61 (1H, dd, J=6.2, 2.7 Hz), 7.81 (1H, dd, J=6.2, 2.7 Hz), 8.03 (1H, s), 8.90 (1H, s), 15.42 (1H, s)
MS (ESI): M+ 547

Example 48

$^1$H NMR (DMSO-$d_6$ 400 MHz) (δ) ppm: 1.18 (3H, d, J=6.5 Hz), 1.99-2.07 (2H, m), 2.48 (2H, t, J=7.9 Hz), 3.21 (3H, s), 3.79 (2H, t, J=7.1 Hz), 3.84-3.91 (1H, m), 3.93-4.00 (2H, m), 4.03 (3H, s), 4.11 (2H, s), 5.17-5.22 (1H, m), 5.21 (1H, t, J=5.3 Hz), 7.45 (1H, s), 7.61 (1H, dd, J=6.2, 2.8 Hz), 7.81 (1H, dd, J=6.2, 2.8 Hz), 8.03 (1H, s), 8.94 (1H, s), 15.40 (1H, s)
MS (ESI): M+ 547

Example 49

$^1$H NMR (DMSO-$d_6$ 400 MHz) (δ) ppm: 0.98 (9H, s), 2.93-2.98 (4H, m), 3.70-3.74 (4H, m), 4.00-4.14 (7H, m), 5.11 (1H, t, J=4.8 Hz), 5.13-5.19 (1H, m), 7.02-7.08 (1H, m), 7.52 (1H, s), 8.01 (1H, s), 8.78 (1H, s), 15.37 (1H, s)
MS (ESI): M+ 565

Example 50

$^1$H NMR (DMSO-$d_6$ 400 MHz) (δ) ppm: 0.93 (3H, t, J=7.1 Hz), 1.19 (3H, d, J=6.0 Hz), 3.04-3.10 (4H, m), 3.21-3.31 (1H, m), 3.50-3.60 (1H, m), 3.67-3.73 (4H, m), 3.84-4.10 (3H, m), 4.04 (5H, s), 5.14-5.25 (2H, m), 6.88-6.92 (1H, m), 6.98-7.02 (1H, m), 7.44 (1H, s), 7.95 (1H, s), 8.97 (1H, s), 15.40 (1H, br s)
MS (ESI): M+ 563

Example 51

$^1$H NMR (DMSO-$d_6$ 400 MHz) (δ) ppm: 0.96 (9H, s), 2.05 (2H, quint., J=7.5 Hz), 2.45-2.55 (2H, m), 3.82 (2H, t, J=7.1 Hz), 4.00-4.12 (2H, m), 4.26 (2H, s), 5.06-5.13 (2H, m), 7.70 (1H, dd, J=6.1, 2.7 Hz), 7.83 (1H, dd, J=9.2, 2.2 Hz), 7.87 (1H, dd, J=6.4, 2.7 Hz), 8.22 (1H, d, J=2.2 Hz), 8.37 (1H, d, J=9.2 Hz), 8.82 (1H, s), 15.17 (1H, br s)
MS (ESI): M+ 515

Example 52

$^1$H NMR (DMSO-$d_6$ 400 MHz) (δ) ppm: 0.97 (9H, s), 1.24 (3H, t, J=7.50 Hz), 2.03 (2H, tt, J=7.5, 7.5 Hz), 2.45-2.51 (2H, m), 2.88-2.95 (2H, m), 3.78 (2H, t, J=7.5 Hz), 4.03-4.11 (2H, m), 4.26 (2H, s), 5.12 (1H, t, J=5.0 Hz), 5.16-5.22 (1H, m), 7.57 (1H, dd, J=6.4, 2.7 Hz), 7.86 (1H, dd, J=6.4, 2.7 Hz), 7.95 (1H, s), 8.17 (1H, s), 8.80 (1H, s), 15.18 (1H, br s)
MS (ESI): M+ 543

Example 53

$^1$H NMR (DMSO-$d_6$ 400 MHz) (δ) ppm: 0.96 (9H, s), 3.07-3.12 (4H, m), 3.69-3.74 (4H, m), 4.00-4.12 (2H, m), 4.18 (2H, s), 5.05-5.13 (2H, m), 6.97 (1H, dd, J=5.8, 3.0 Hz), 7.08 (1H, dd, J=5.7, 3.0 Hz), 7.88 (1H, dd, J=9.2, 2.1 Hz), 8.23 (1H, d, J=2.1 Hz), 8.36 (1H, d, J=9.2 Hz), 8.82 (1H, s), 15.18 (1H, br s)
MS (ESI): M+ 517

Example 54

$^1$H NMR (DMSO-$d_6$ 400 MHz) (δ) ppm 0.96 (9H, s), 2.12 (2H, tt, J=7.9, 6.9 Hz), 2.43 (2H, t, J=7.9 Hz), 3.75 (2H, t, J=6.9 Hz), 4.00-4.11 (2H, m), 4.24 (2H, s), 5.07-5.12 (2H, m), 7.62 (1H, t, J=7.9 Hz), 7.82 (1H, dd, J=9.1, 2.0 Hz), 8.26 (1H, d, J=2.0 Hz), 8.37 (1H, d, J=9.1 Hz), 8.82 (1H, s), 15.16 (1H, br s)

MS (ESI): M+ 533

Example 55

$^1$H NMR (CHCl$_3$ 400 MHz) (δ) ppm: 1.06 (9H, s) 1.30 (3H, t, J=7.5 Hz), 2.17 (2H, tt, J=7.5, 7.9 Hz), 2.49 (2H, t, J=7.9 Hz), 2.77-2.84 (2H, m), 3.75 (2H, t, J=7.5 Hz), 4.14 (2H, dd, J=16.5, 19.3 Hz), 4.28-4.35 (2H, m), 4.95 (1H, dd, J=9.0, 5.1 Hz), 6.94 (1H, t, J=7.8 Hz), 7.68 (1H, s), 8.25 (1H, s), 8.84 (1H, s), 15.14 (1H, s)

MS (ESI): M+ 561

Example 56

$^1$H NMR (DMSO-d$_6$ 400 MHz) (δ) ppm 0.96 (9H, s), 2.97-3.01 (4H, m), 3.71-3.76 (4H, m), 4.00-4.12 (2H, m), 4.21 (2H, s), 5.06-5.13 (2H, m), 7.24 (1H, dd, J=7.7, 7.7 Hz), 7.83 (1H, dd, J=9.2, 2.1 Hz), 8.24 (1H, d, J=1.9 Hz), 8.36 (1H, d, J=9.3 Hz), 8.81 (1H, s), 15.19 (1H, br s)

MS (ESI): M+ 535

Example 57

$^1$H NMR (DMSO-d$_6$ 300 MHz) (δ) ppm: 0.73 (1H, d, J=6.4 Hz), 1.16 (1H, d, J=6.4 Hz), 2.30-2.46 (1H, m), 2.65 (3H, s), 3.74-3.85 (1H, m), 3.93-4.08 (4H, m), 4.22 (2H, s), 4.82-4.94 (1H, m), 5.19 (1H, t, J=5.3 Hz), 7.47 (1H, s), 7.89 (1H, dd, J=6.4, 2.3 Hz), 8.01 (1H, dd, J=6.8, 2.3 Hz), 8.16 (1H, s), 8.89 (1H, s), 15.41 (1H, s)

MS (ESI): M+ 530

Example 58

$^1$H NMR (DMSO-d$_6$ 300 MHz) (δ) ppm 0.96 (9H, s), 3.70 (2H, t, J=4.9 Hz), 3.98 (2H, t, J=5.3 Hz), 4.01-4.11 (2H, m), 4.24 (4H, s), 5.06-5.15 (2H, m), 7.72 (1H, dd, J=7.9, 7.9 Hz), 7.83 (1H, d, J=9.4 Hz), 8.27 (1H, s), 8.34 (1H, d, J=9.4 Hz), 8.82 (1H, s), 15.19 (1H, br s)

MS (ESI): M+ 549

Example 59

$^1$H NMR (DMSO-d$_6$ 400 MHz) (δ) ppm: 0.96 (9H, s), 2.96-3.02 (4H, m), 3.70-3.76 (4H, m), 4.00-4.12 (2H, m), 4.21 (2H, s), 5.07-5.12 (2H, m) 7.22 (1H, dd, J=7.7, 7.7 Hz), 7.83 (1H, dd, J=9.0, 2.4 Hz), 8.24 (1H, d, J=2.0 Hz), 8.36 (1H, d, J=9.0 Hz), 8.82 (1H, s), 15.18 (1H, br s)

MS (ESI) M+ 535

Experimental Example 1

The following explains evaluation methods of the HIV integrase inhibitory activity of the compound of the present invention.

(i) Construction of Recombinant Integrase Gene Expression System

HIV integrase full length gene (J. Virol., 67, 425-437 (1993)) in which phenylalanine at codon 185 was substituted by histidine, was inserted between the restriction enzyme NdeI and XhoI sites of plasmid pET21a(+) (Novagen), whereby an integrase expression vector pET21a-IN-F185H was constructed.

(ii) Production and Purification of Integrase Protein

*Escherichia coli* recombinant BL21(DE3) transformed with plasmid pET21a-IN-F185H obtained in (i) was shake cultured at 30° C. in a liquid medium containing ampicillin. When the culture reached the logarithmic growth phase, isopropyl-β-D-thiogalactopyranoside was added to promote expression of integrase gene. The culture was continued for 3 hr to promote accumulation of the integrase protein. The recombinant *E. coli* was collected in pellets by centrifugal separation and preserved at −80° C.

The *E. coli* was suspended in Lysis buffer (20 nM HEPES (pH 7.5), 5 mM DTT, 10 mM CHAPS, 10% glycerol) containing 1M sodium chloride and subjected to repeat pressurization and depressurization for rupture, and centrifugal separation at 4° C., 40,000×g, 60 min to recover a water-soluble fraction (supernatant). This was diluted 10-fold with Lysis buffer free of sodium chloride, mixed with SP-Sepharose (GE healthcare Bioscience) and stirred at 4° C. for 60 min to allow adsorption of integrase protein to the resin. The resin was washed with Lysis buffer containing 100 mM sodium chloride and the integrase protein was eluted with Lysis buffer containing 1M sodium chloride.

The eluted integrase protein solution was subjected to a Superdex 75 (GE healthcare Bioscience) column for gel filtration. The protein was eluted with Lysis buffer containing 1M sodium chloride.

The obtained fractions of the integrase protein were collected and preserved at −80° C.

(iii) Preparation of DNA Solution

The following DNA synthesized by Greiner or FASMAC was dissolved in TE buffer (10 mM Tris-hydrochloric acid (pH 8.0), 1 mM EDTA) and mixed with donor DNA, target DNA, and each complementary strand (+ and − strands) to 1 μM. The mixture was heated at 95° C. for 5 min, 80° C. for 10 min, 70° C. for 10 min, 60° C. for 10 min, 50° C. for 10 min and 40° C. for 10 min and kept at 25° C. to give a double stranded DNA, which was used for the test.

```
Donor DNA (- strand having biotin attached to the
5' terminal)
Donor + strand:
                                        (SEQ ID NO: 1)
5'-Biotin-ACC CTT TTA GTC AGT GTG AAA AAT CTC TAG
CA-3'

Donor - strand:
                                        (SEQ ID NO: 2)
5'-ACT GCT AGA GAT TTT CCA CAC TGA CTA AAA G-3'

Target DNA (+, - strands both having digoxigenin
added at 3' terminal)
Target + strand:
                                        (SEQ ID NO: 3)
5'-TGA CCA AGG GCT AAT TCA CT -Dig-3'

Target - strand:
                                        (SEQ ID NO: 4)
5'-AGT GAA TTA GCC CTT GT CA-Dig-3'
```

(iv) Determination of Enzyme (HIV Integrase) Inhibitory Activity

The donor DNA was diluted with TE buffer to 10 nM (or 5 nM), of which 50 μl was added to each well of streptavidin-coated microtiter plate (Roche) and allowed to adsorb at 37° C. for 60 min. The plate was washed with phosphate buffer (Dulbecco's PBS, Sanko Junyaku Co., Ltd.) containing 0.1% Tween 20 and phosphate buffer. Then, an enzyme reaction mixture (70 μl), a test substance (10 μl) diluted with the enzyme reaction mixture and 100 µg/ml (or 64 µg/ml (2 µM)) integrase protein (10 µl) were added to each well and reacted at 37° C. for 60 min.

Composition of the enzyme reaction mixture: 30 mM MOPS (3-morpholinopropanesulfonic acid), 5 mM magnesium chloride, 3 mM DTT (dithiothreitol), 0.1 mg/ml BSA (bovine serum albumin), 5% glycerol, 10% DMSO (dimethyl sulfoxide), 0.01% Tween 20.

Then, 50 nM (or 25 nM) target DNA (10 µl) was added, reacted at 37° C. for 10 min and washed with phosphate buffer containing 0.1% Tween 20 to stop the reaction.

Then, 100 mU/ml peroxidase labeled anti-digoxigenin antibody solution (Roche, 100 µl) was added, and the mixture was reacted at 37° C. for 60 min, followed by washing with phosphate buffer containing 0.1% Tween 20.

A peroxidase color solution (Bio Rad, 100 µl) was added and allowed to react at room temperature for 4 min (or 3 min). The color reaction was stopped by adding IN sulfuric acid (100 µl). The absorbance at 450 nm was measured.

The HIV integrase inhibitory activity ($IC_{50}$) of the compound of the present invention was calculated from the inhibition rate according to the following formula:

inhibition rate (%)=[1−(Object−Blank)/(Control−Blank)]×100

Object; absorbance of well in the presence of test compound
Control; absorbance of well in the absence of test compound
Blank; absorbance of well in the absence of test compound, in the absence of integrase protein The results are shown in Tables 8 and 9, wherein each symbol means that $IC_{50}$ falls within the following range.

A: $1 \, \mu M \leq IC_{50} < 10 \, \mu M$
B: $0.1 \, \mu M \leq IC_{50} < 1 \, \mu M$
C: $0.01 \, \mu M \leq IC_{50} < 0.1 \, \mu M$
D: $IC_{50} < 0.01 \, \mu M$

TABLE 8

| Example No. | HIV integrase inhibitory activity ($IC_{50}$) |
| --- | --- |
| 1 | D |
| 2 | D |
| 3 | D |
| 4 | D |
| 5 | D |
| 6 | D |
| 7 | D |
| 8 | D |
| 9 | D |
| 10 | D |
| 11 | D |
| 12 | D |
| 13 | D |
| 14 | D |
| 15 | D |
| 16 | D |
| 17 | D |
| 18 | D |
| 19 | D |
| 20 | D |
| 21 | D |
| 22 | D |
| 23 | D |
| 24 | C |
| 25 | D |
| 26 | D |
| 27 | D |
| 28 | D |
| 29 | D |

TABLE 9

| Example No. | HIV integrase inhibitory activity ($IC_{50}$) |
| --- | --- |
| 32 | D |
| 34 | D |
| 35 | C |
| 36 | D |
| 37 | C |
| 38 | D |
| 39 | D |
| 40 | C |
| 41 | C |
| 42 | D |
| 43 | D |
| 44 | C |
| 45 | D |
| 46 | D |
| 47 | C |
| 48 | D |
| 49 | D |
| 50 | C |
| 51 | D |
| 52 | C |
| 53 | D |
| 54 | D |
| 55 | C |
| 56 | D |
| 57 | D |
| 59 | C |

Experimental Example 2

Evaluation of Antiviral Activity

The effect of combined use of the compound of the present invention and existent anti-HIV agents can be determined in the following manner.

For example, the effect of combined use of two agents from existent nucleoside reverse transcriptase inhibitors (zidovudine, lamivudine, tenofovir), non-nucleoside reverse transcriptase inhibitors (efavirenz) or protease inhibitors (indinavir, nelfinavir) and test substance A and the like are evaluated using CEM-SS cells infected with HIV-1 IIIB by XTT method.

In addition, the effect of combined use of three agents of test substance A, zidovudine and lamivudine, or test substance A, tenofovir and lamivudine, and the like is evaluated.

Prior to the combined use test, $IC_{50}$ and $CC_{50}$ of each pharmaceutical agent alone are measured. 5 concentrations of pharmaceutical agent A and 9 concentrations of pharmaceutical agent B, determined based on these results, are combined to evaluate the effect of combined use of two agents. For combined use of three agents, a high concentration pharmaceutical agent B and a pharmaceutical agent C are mixed and pharmaceutical agent A and the concentration are combined for evaluation.

The test results of the test substance and combination drug alone or in combination thereof are analyzed based on the programs of Prichard and Shipman MacSynergy II version 2.01 and Deltagraph version 1.5d. A three-dimensional plot is drawn from % inhibition at the concentrations of each combined pharmaceutical agent, obtained from 3 times of tests, with 95% (or 68%, 99%) confidence limits, and the effect of the combined use is evaluated based on the numerical values of $\mu M^2$% calculated therefrom. The criteria of evaluation are shown in the following.

| Definition of interaction | μM² % |
|---|---|
| Strong synergistic action | >100 |
| Slight synergistic action | +51-+100 |
| Additive action | +50--50 |
| Slight antagonistic action | -51--100 |
| Strong antagonistic action | <-100 |

Experimental Example 3

Metabolic Stability Test

Test of Metabolic Stability in Liver Microsome

Human or animal species (rat or monkey) liver microsome (Xenotech LLC (Lenexa, Kans., USA), 20 mg protein/mL, 2.5 μL) and NADPH production system coenzyme solution (β-nicotinamide adenine dinucleotide phosphate: 5.2 mM, D-glucose-6-phosphate: 13.2 mM, magnesium chloride: 13.2 mM, glucose-6-phosphate dehydrogenase: 1.8 U/mL) (50 μL) are suspended in 100 mM potassium phosphate buffer (pH 7.4, 147.5 μL), and mixed with a test substance (2 μL) dissolved in acetonitrile containing 0.5% DMSO. The mixture is incubated at 37° C. for 0, 10 and 60 min, acetonitrile containing formic acid (final concentration 0.1%) is added thereto and the mixture is centrifuged. The test substance (unchanged compound) in the supernatant is measured by high performance liquid chromatography/mass spectrometry (LC/MS). Using the obtained measurement values, the residual ratio (%) is calculated by the following formula:

residual ratio (%)=amount of test substance after incubation (0, 10 or 60 min)/amount of test substance at 0 min on incubation×100

The compound of the present invention preferably shows a residual ratio after 60 min of not less than 40%, more preferably not less than 60%, still more preferably not less than 80%.

Formulation Example is given below. This example is merely for the exemplification purpose and does not limit the invention.

Formulation Example

| (a) compound of Example 1 | 10 g |
|---|---|
| (b) lactose | 50 g |
| (c) corn starch | 15 g |
| (d) sodium carboxymethylcellulose | 44 g |
| (e) magnesium stearate | 1 g |

The entire amounts of (a), (b) and (c) and 30 g of (d) are kneaded with water, dried in vacuo and granulated. The obtained granules are mixed with 14 g of (d) and 1 g of (e) and processed into tablets with a tableting machine to give 1000 tablets each containing 10 mg of (a).

INDUSTRIAL APPLICABILITY

The compounds of the present invention show a high inhibitory activity against HIV integrase.

Therefore, these compounds can be pharmaceutical agents effective for, for example, the prophylaxis or treatment of AIDS, as integrase inhibitors, antiviral agents, anti-HIV agents and the like, having an HIV integrase inhibitory activity. In addition, by a combined use with other anti-HIV agent(s) such as protease inhibitor, reverse transcriptase inhibitor and the like, they can be more effective anti-HIV agents. Furthermore, having high inhibitory activity specific for integrase, they can be pharmaceutical agents safe for human body with a fewer side effects.

This application is based on patent application Nos. 2006-174331, 2006-220082 and 2006-274143 filed in Japan, the contents of which are hereby incorporated by reference.

Sequence Listing Free Text

SEQ ID NO: 1: Donor + strand for determining HIV integrase activity

SEQ ID NO: 2: Donor − strand for determining HIV integrase activity

SEQ ID NO: 3: Target + strand for determining HIV integrase activity

SEQ ID NO: 4: Target − strand for determining HIV integrase activity

The invention claimed is:

1. A compound represented by the following formula [I] or a pharmaceutically acceptable salt thereof, or a solvate thereof:

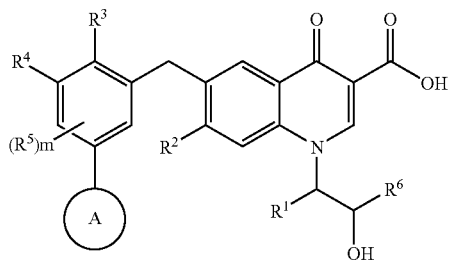

[I]

wherein ring A is a monocyclic heterocyclic group optionally substituted by 1 to 5 substituents selected from the following group A, wherein the monocyclic heterocyclic group contains, besides carbon atom, at least one hetero atom selected from nitrogen atom, oxygen atom and sulfur atom;

group A is a group consisting of halogen atom, $C_{1-4}$ alkyl group, $-(CH_2)_n-OR^{a1}$, $-NR^{a3}R^{a4}$, $-COR^{a2}$ and $-CONR^{a3}R^{a4}$, wherein $R^{a1}$, $R^{a2}$, $R^{a3}$ and $R^{a4}$ are the same or different and each is a hydrogen atom or a $C_{1-4}$ alkyl group, and n is 0 or an integer of 1 to 4;

$R^1$ is a hydrogen atom, a $C_{1-6}$ alkyl group optionally substituted by 1 to 3 substituents selected from the following group B, a $C_{3-10}$ carbon ring group optionally substituted by 1 to 5 substituents selected from the above-mentioned group A, or a heterocyclic group optionally substituted by 1 to 5 substituents selected from the above-mentioned group A, wherein the heterocyclic group contains, besides carbon atom, at least one hetero atom selected from nitrogen atom, oxygen atom and sulfur atom;

group B is a group consisting of a $C_{3-10}$ carbon ring group optionally substituted by 1 to 5 substituents selected from the above-mentioned group A, a heterocyclic group optionally substituted by 1 to 5 substituents selected from the above-mentioned group A, wherein the heterocyclic group is as defined above, halogen atom, cyano group, $-OR^{b1}$, $-SR^{b1}$, $-NR^{b2}R^{b3}$, $-CONR^{b2}R^{b3}$, $-SO_2NR^{b2}R^{b3}$, $-COR^{b1}$, $-NR^{b2}COR^{b1}$, $-SO_2R^{b1}$, $-NR^{b2}SO_2R^{b1}$, $-COOR^{b1}$, $-NR^{b2}COOR^{b1}$ and $-NR^{b4}CO-NR^{b2}R^{b3}$ wherein $R^{b1}$, $R^{b2}$, $R^{b3}$ and $R^{b4}$ are the same or different and each is a hydrogen atom, a $C_{1-4}$ alkyl group, a $C_{3-10}$ carbon ring group optionally substituted by 1 to 5 substituents selected from the above-mentioned group A, or a heterocyclic group optionally substituted by 1 to 5 substituents selected from the above-mentioned group A, wherein the heterocyclic group is as defined above;

$R^2$ is a hydrogen atom, a $C_{1-4}$ alkyl group or $-OR^{11}$, wherein $R^{11}$ is a hydrogen atom or a $C_{1-4}$ alkyl group;

$R^3$ and $R^4$ are the same or different and each is a hydrogen atom, a halogen atom, a $C_{1-4}$ alkyl group or $-OR^{12}$, wherein $R^{12}$ is a hydrogen atom or a $C_{1-4}$ alkyl group;

R⁵ is each independently, a halogen atom, a $C_{1-4}$ alkyl group or —OR R¹³, wherein R¹³ is a hydrogen atom or a $C_{1-4}$ alkyl group;

m is 0, 1 or 2; and

R⁶ is a hydrogen atom, or R¹ and R⁶ form, together with the carbon atoms bonded thereto, a $C_{3-10}$ cycloalkyl group optionally substituted by 1 to 5 substituents selected from the above-mentioned group A.

2. The compound of claim 1, wherein ring A is a monocyclic heterocyclic group containing at least one nitrogen atom, said monocyclic heterocyclic group is optionally substituted by 1 to 5 substituents selected from group A and bonded, via the nitrogen atom, to the benzene ring, or a pharmaceutically acceptable salt thereof, or a solvate thereof.

3. The compound of claim 2, wherein ring A is a heterocyclic group selected from 1-pyrrolidinyl group, 2-oxopyrrolidin-1-yl group, piperidino group, 2-oxopiperidin-1-yl group, 1-piperazinyl group, morpholino group, thiomorpholino group, 3-oxomorpholin-4-yl group, 1,1-dioxoisothiazolidin-2-yl group, 2-oxooxazolidin-3-yl group and 3-oxopyrazolidin-1-yl group, wherein the heterocyclic group is optionally substituted by 1 to 5 substituents selected from group A, or a pharmaceutically acceptable salt thereof, or a solvate thereof.

4. The compound of claim 1, wherein R¹ is a $C_{1-6}$ alkyl group optionally substituted by 1 to 3 substituents selected from group B, and R⁶ is a hydrogen atom, or a pharmaceutically acceptable salt thereof, or a solvate thereof.

5. The compound of claim 1, wherein R² is a $C_{1-4}$ alkyl group or —OR¹¹, wherein R¹¹ is a hydrogen atom or a $C_{1-4}$ alkyl group, or a pharmaceutically acceptable salt thereof, or a solvate thereof.

6. The compound of claim 1, wherein R² is a hydrogen atom, or a pharmaceutically acceptable salt thereof, or a solvate thereof.

7. The compound of claim 1, wherein R³ and R⁴ are the same or different and each is a halogen atom, or a pharmaceutically acceptable salt thereof, or a solvate thereof.

8. The compound of claim 1, wherein m is 1, and R⁵ is a halogen atom, or a pharmaceutically acceptable salt thereof, or a solvate thereof.

9. The compound of claim 1, wherein m is 0, or a pharmaceutically acceptable salt thereof, or a solvate thereof.

10. The compound of claim 1, which is selected from a group consisting of

6-[3-chloro-2-fluoro-5-(morpholin-4-yl)benzyl]-1-((R)-1-ethoxymethyl-2-hydroxyethyl)-7-ethyl-4-oxo-1,4-dihydroquinoline-3-carboxylic acid, 6-[3-chloro-2-fluoro-5-(2-oxopyrrolidin-1-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-(pyrrolidin-1-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-(2-oxooxazolidin-3-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-(morpholin-4-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-(piperidin-1-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-(2-oxopiperidin-1-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-((R)-3-hydroxypyrrolidin-1-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-((S)-3-hydroxypyrrolidin-1-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-(2-methyl-3-oxopyrazolidin-1-yl)benzyl]-1-((S)-1-hydroxymethyl-2-methylpropyl)-7-methoxy-4-oxo-1,4-dihydroquinoline-3-carboxylic acid, 6-[5-(4-acetylpiperazin-1-yl)-3-chloro-2-fluorobenzyl]-1-((S)-1-hydroxymethyl-2-methylpropyl)-7-methoxy-4-oxo-1,4-dihydroquinoline-3-carboxylic acid, 6-[3-chloro-5-(3,3-difluoropyrrolidin-1-yl)-2-fluorobenzyl]-1-((S)-1-hydroxymethyl-2-methylpropyl)-7-methoxy-4-oxo-1,4-dihydroquinoline-3-carboxylic acid, 6-[3-chloro-2-fluoro-5-((R)-3-fluoropyrrolidin-1-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-((S)-3-fluoropyrrolidin-1-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-(morpholin-4-yl)benzyl]-1-((1R,2R)-1-hydroxymethyl-2-methoxypropyl)-7-methoxy-4-oxo-1,4-dihydroquinoline-3-carboxylic acid, 6-[3-chloro-2,4-difluoro-5-(morpholin-4-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-(morpholin-4-yl)benzyl]-1-((S)-1-hydroxymethyl-2,2-dimethylpropyl)-7-methoxy-4-oxo-1,4-dihydroquinoline-3-carboxylic acid, 6-[3-chloro-2-fluoro-5-(morpholin-4-yl)benzyl]-7-ethyl-1-((S)-1-hydroxymethyl-2,2-dimethylpropyl)-4-oxo-1,4-dihydroquinoline-3-carboxylic acid, 6-[3-chloro-2-fluoro-5-(morpholin-4-yl)benzyl]-1-((R)-1-ethoxymethyl-2-hydroxyethyl)-7-methoxy-4-oxo-1,4-dihydroquinoline-3-carboxylic acid, 6-[3-chloro-2-fluoro-5-(morpholin-4-yl)benzyl]-7-ethyl-1-[(R)-2-hydroxy-1-(methoxymethyl)ethyl]-4-oxo-1,4-dihydroquinoline-3-carboxylic acid, 6-[3-chloro-5-(1,1-dioxoisothiazolidin-2-yl)-2-fluorobenzyl]-1-((S)-1-hydroxymethyl-2-methylpropyl)-7-methoxy-4-oxo-1,4-dihydroquinoline-3-carboxylic acid, 6-[3-chloro-2-fluoro-5-(morpholin-4-yl)benzyl]-1-[(R)-2-hydroxy-1-(methoxymethyl)ethyl]-7-methoxy-4-oxo-1,4-dihydroquinoline-3-carboxylic acid, 6-[3-chloro-2-fluoro-5-(morpholin-4-yl)benzyl]-7-ethyl-1-((S)-1-hydroxymethyl-2-methylpropyl)-4-oxo-1,4-dihydroquinoline-3-carboxylic acid, 6-[3-chloro-2-fluoro-5-(2-oxopyrrolidin-1-yl)benzyl]-7-ethyl-1-((S)-1-hydroxymethyl-2-methylpropyl)-4-oxo-1,4-dihydroquinoline-3-carboxylic acid, 6-[3-chloro-2,4-difluoro-5-(2-oxopyrrolidin-1-yl)benzyl]-1-((S)-1-hydroxymethyl-2-methylpropyl)-7-methoxy-4-oxo-1,4-dihydroquinoline-3-carboxylic acid, 6-[3-chloro-2,4-difluoro-5-(2-oxopyrrolidin-1-yl)benzyl]-7-ethyl-1-((S)-1-hydroxymethyl-2-methylpropyl)-4-oxo-1,4-dihydroquinoline-3-carboxylic acid, 6-[3-chloro-2-fluoro-5-(thiomorpholin-4-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-(morpholin-4-yl)benzyl]-1-((1R,2S)-1-hydroxymethyl-2-methoxypropyl)-7-methoxy-4-oxo-1,4-dihydroquinoline-3-carboxylic acid, 6-[3-chloro-2-fluoro-5-(morpholin-4-yl)benzyl]-1-((S)-1-hydroxymethyl-3-methoxypropyl)-7-methoxy-4-oxo-1,4-dihydroquinoline-3-carboxylic acid, 6-[3-chloro-2-fluoro-5-(4-hydroxypiperidin-1-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-(morpholin-4-yl)benzyl]-7-ethyl-1-((1R,2R)-1-hydroxymethyl-2-methoxypropyl)-4-oxo-1,4-dihydroquinoline-3-carboxylic acid, 6-[3-chloro-2-fluoro-5-(morpholin-4-yl)benzyl]-7-ethyl-1-((1R,2S)-1-hydroxymethyl-2-methoxypropyl)-4-oxo-1,4-dihydroquinoline-3-carboxylic acid, 6-[3-chloro-2-fluoro-5-(pyridin-2-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-(thiazol-2-yl)benzyl]-1-((S)-1-hydroxymethyl-2-methylpropyl)-7-methoxy-4-oxo-1,4-dihydroquinoline-3-carboxylic acid, 6-[3-chloro-2-fluoro-5-(morpholin-4-yl)benzyl]-1-[(1R,2R)-2-ethoxy-1-(hydroxymethyl)propyl]-7-ethyl-4-oxo-1,4-dihydroquinoline-3-carboxylic acid, 6-[3-chloro-2-fluoro-5-(2-oxopyrrolidin-1-yl)benzyl]-1-((R)-1-ethoxymethyl-2methoxy-4-oxo-1,4-dihydroquinoline-3-carboxylic acid, 6-[3-chloro-2-fluoro-5-(morpholin-4-yl)benzyl]-1-[(1R,2R)-2-ethoxy-1-(hydroxymethyl)propyl]-7-ethyl-4-oxo-1,4-dihydroquinoline-3-carboxylic acid, 6-[3-chloro-2-fluoro-5-(2-oxopyrrolidin-1-yl)benzyl]-14(R)-1-ethoxymethyl-2-hydroxyethyl)-7-methoxy-4-oxo-1,4-dihydroquinoline-3-carboxylic acid, 6-[3-chloro-2-fluoro-5-(2-oxopyrrolidin-1-yl)benzyl]-1-[(1R,2R)-2-ethoxy-1-(hydroxymethyl)propyl]-7-ethyl-4-oxo-1,4-dihydroquinoline-3-carboxylic acid, 6-[3-chloro-2-fluoro-5-(2-oxopyrrolidin-1-yl)benzyl]-7-ethyl-1-((1R,2R)-1-hydroxymethyl-2-methoxypropyl)-4-oxo-1,4-dihydroquinoline-3-carboxylic acid, 6-[3-chloro-2-fluoro-5-(morpholin-4-yl)benzyl]-1-((R)-1-hydroxymethyl-2-methoxy-2-methylpropyl)-7-methoxy-4-oxo-1,4-dihydroquinoline-3-carboxylic acid, 6-[3-chloro-2-fluoro-5-(morpholin-4-yl)benzyl]-7-ethyl-1-((R)-1-hydroxymethyl-2-methoxy-2-methylpropyl)-4-oxo-1,4-dihydroquinoline-3-carboxylic acid, 6-[3-chloro-2-fluoro-5-(morpholin-4-yl)benzyl]-7-ethyl-1-((S)-1-hydroxymethyl-3-methoxypropyl)-4-oxo-1,4-dihydroquinoline-3-carboxylic acid, 6-[3-chloro-2-fluoro-5-(2-oxopyrrolidin-1-yl)benzyl]-1-((S)-1-hydroxymethyl-2,2-dimethylpropyl)-7-methoxy-4-oxo-1,4-dihydroquinoline-3-carboxylic acid, 6-[3-chloro-2,4-difluoro-5-(2-oxopyrrolidin-1-yl)benzyl]-1-((S)-1-hydroxymethyl-2,2-dimethylpropyl)-7-methoxy-4-oxo-1,4-dihydroquinoline-3-carboxylic acid, 6-[3-chloro-2-fluoro-5-(2-oxopyrrolidin-1-yl)benzyl]-1-((S)-1-hydroxymethyl-3-methoxypropyl)-7-methoxy-4-oxo-1,4-dihydroquinoline-3-carboxylic acid, 6-[3-chloro-2-fluoro-5-(2-oxopyrrolidin-1-yl)benzyl]-1-((1R,2R)-1-hydroxymethyl-2-methoxypropyl)-7-methoxy-4-oxo-1,4-dihydroquinoline-3-carboxylic acid, 6-[3-chloro-2,4-difluoro-5-(morpholin-4-yl)benzyl]-1-((S)-1-hydroxymethyl-2,2-dimethylpropyl)-7-methoxy-4-oxo-1,4-dihydroquinoline-3-carboxylic acid, 6-[3-chloro-2-fluoro-5-(morpholin-4-yl)benzyl]-1-[(1R,2R)-2-ethoxy-1-(hydroxymethyl)propyl]-7-methoxy-4-oxo-1,4-dihydroquinoline-3-carboxylic acid, 6-[3-chloro-2-fluoro-5-(2-oxopyrrolidin-1-yl)benzyl]-1-((S)-1-hydroxymethyl-2,2-dimethylpropyl)-4-oxo-1,4-dihydroquinoline-3-carboxylic acid, 6-[3-chloro-2-fluoro-5-(2-oxopyrrolidin-1-yl)benzyl]-7-ethyl-1-((S)-1-hydroxymethyl-2,2-dimethylpropyl)-4-oxo-1,4-dihydroquinoline-3-carboxylic acid, 6-[3-chloro-2,4-difluoro-5-(2-oxopyrrolidin-1-yl)benzyl]-1-((S)-1-hydroxymethyl-2,2-dimethylpropyl)-4-oxo-1,4-dihydroquinoline-3-carboxylic acid, 6-[3-chloro-2-fluoro-5-(morpholin-4-yl)benzyl]-1-((S)-1-hydroxymethyl-2,2-dimethylpropyl)-4-oxo-1,4-dihydroquinoline-3-carboxylic acid, 6-[3-chloro-2,4-difluoro-5-(2-oxopyrrolidin-1-yl)benzyl]-7-ethyl-1-((S)-1-hydroxymethyl-2,2-dimethylpropyl)-4-oxo-1,4-dihydroquinoline-3-carboxylic acid, 6-[3-chloro-2,4-difluoro-5-(morpholin-4-yl)benzyl]-1-((S)-1-hydroxymethyl-2,2-dimethylpropyl)-4-oxo-1,4-dihydroquinoline-3-carboxylic acid, 6-[3-chloro-2-fluoro-5-(5-methyl-1,2,4-oxadiazol-3-yl)benzyl]-1-((S)-1-hydroxymethyl-2-methylpropyl)-7-methoxy-4-oxo-1,4-dihydroquinoline-3-carboxylic acid, 6-[3-chloro-2,4-difluoro-5-(3-oxomorpholin-4-yl)benzyl]-1-((S)-1-hydroxymethyl-2,2-dimethylpropyl)-4-oxo-1,4-dihydroquinoline-3-carboxylic acid, and 6-[3-chloro-2,4-difluoro-5-(morpholin-4-yl)benzyl]-1-((R)-1-hydroxymethyl-2,2-dimethylpropyl)-4-oxo-1,4-dihydroquinoline-3-carboxylic acid, or a pharmaceutically acceptable salt thereof, or a solvate thereof.

11. A pharmaceutical composition comprising the compound of claim 1 or a pharmaceutically acceptable salt thereof, or a solvate thereof, and a pharmaceutically acceptable carrier.

12. A method for the treatment of an HIV infectious disease in a mammal, which comprises administering an effective amount of the compound of claim 1 or a pharmaceutically acceptable salt thereof, or a solvate thereof, to said mammal.

13. The method of claim 12, which further comprises administering an effective amount of one or more other kinds of anti-HIV active substances to the mammal.

14. A method for inhibiting HIV integrase in a mammal, which comprises administering an effective amount of the compound of claim 1 or a pharmaceutically acceptable salt thereof, or a solvate thereof, to said mammal.

15. A pharmaceutical composition for inhibiting HIV integrase, comprising the compound of claim 1 or a pharmaceutically acceptable salt thereof, or a solvate thereof, and a pharmaceutically acceptable carrier.

16. A compound represented by the following structural formula or a pharmaceutically acceptable salt thereof, or a solvate thereof:

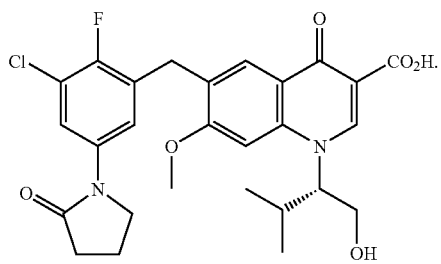

17. A compound represented by the following structural formula or a pharmaceutically acceptable salt thereof, or a solvate thereof:

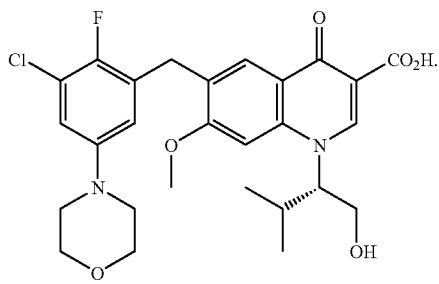

18. A compound represented by the following structural formula or a pharmaceutically acceptable salt thereof, or a solvate thereof:

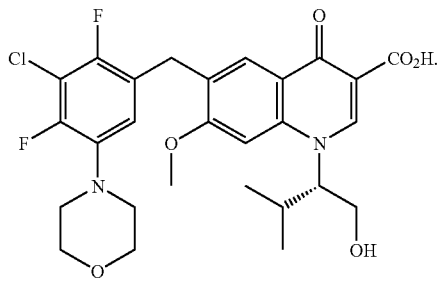

19. A compound represented by the following structural formula or a pharmaceutically acceptable salt thereof, or a solvate thereof:

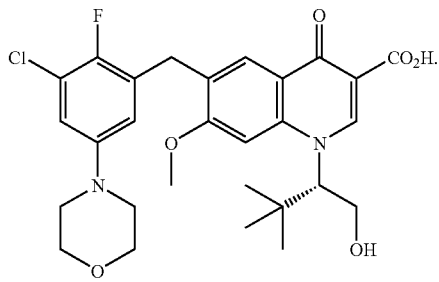

20. A compound represented by the following structural formula or a pharmaceutically acceptable salt thereof, or a solvate thereof:

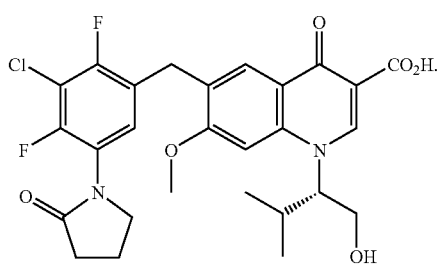

21. A compound represented by the following structural formula or a pharmaceutically acceptable salt thereof, or a solvate thereof:

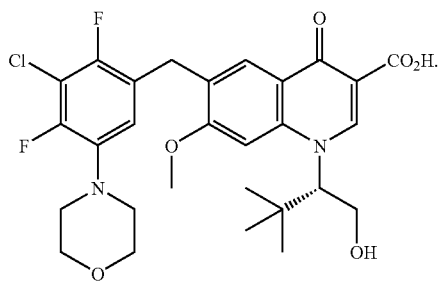

22. A compound represented by the following structural formula or a pharmaceutically acceptable salt thereof, or a solvate thereof:

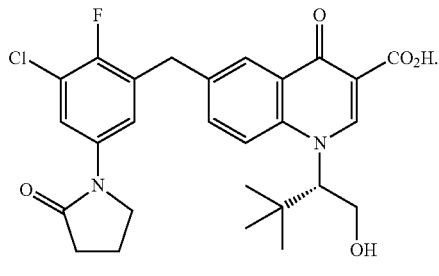

23. A compound represented by the following structural formula or a pharmaceutically acceptable salt thereof, or a solvate thereof:

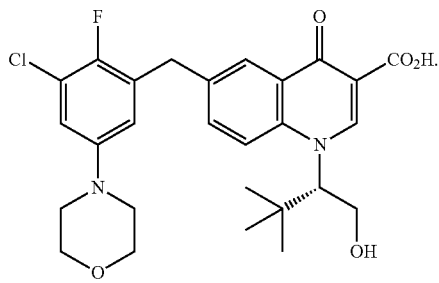

24. A compound represented by the following structural formula or a pharmaceutically acceptable salt thereof, or a solvate thereof:

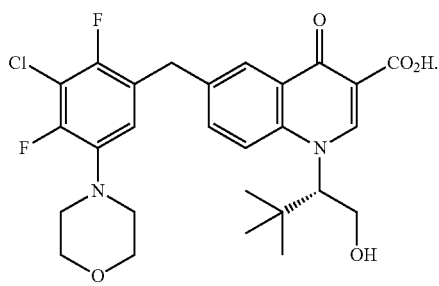

25. A pharmaceutical composition comprising the compound of any one of claims 16-24 or a pharmaceutically acceptable salt thereof, or a solvate thereof, and a pharmaceutically acceptable carrier.

26. A method for the treatment of an HIV infectious disease in a mammal, which comprises administering an effective amount of the compound of any one of claims 16-24 or a pharmaceutically acceptable salt thereof, or a solvate thereof, to said mammal.

27. The method of claim 26, which further comprises administering an effective amount of one or more other kinds of anti-HIV active substances to the mammal.

28. A method for inhibiting HIV integrase in a mammal, which comprises administering an effective amount of the compound of any one of claims 16-24 or a pharmaceutically acceptable salt thereof, or a solvate thereof, to said mammal.

* * * * *

SEQUENCE LISTING

```
<160> NUMBER OF SEQ ID NOS: 4

<210> SEQ ID NO 1
<211> LENGTH: 32
<212> TYPE: DNA
<213> ORGANISM: Artificial
<220> FEATURE:
<223> OTHER INFORMATION: Donor plus strand for activity determination
      of HIV integrase

<400> SEQUENCE: 1 accctttag tcagtgtgga aaatctctag ca                                     32

<210> SEQ ID NO 2
<211> LENGTH: 31
<212> TYPE: DNA
```

-continued

```
<213> ORGANISM: Artificial
<220> FEATURE:
<223> OTHER INFORMATION: Donor minus strand for activity determination
      of HIV integrase

<400> SEQUENCE: 2
actgctagag attttccaca ctgactaaaa g                                   31

<210> SEQ ID NO 3
<211> LENGTH: 20
<212> TYPE: DNA
<213> ORGANISM: Artificial
<220> FEATURE:
<223> OTHER INFORMATION: Target plus strand for activity determination
      of HIV integrase

<400> SEQUENCE: 3
tgaccaaggg ctaattcact                                                20

<210> SEQ ID NO 4
<211> LENGTH: 20
<212> TYPE: DNA
<213> ORGANISM: Artificial
<220> FEATURE:
<223> OTHER INFORMATION: Target minus strand for activity
      determination of HIV integrase

<400> SEQUENCE: 4
agtgaattag cccttggtca                                                20
```